United States Patent [19]

Mitsuhashi et al.

[11] Patent Number: 5,556,749
[45] Date of Patent: Sep. 17, 1996

[54] OLIGOPROBE DESIGNSTATION: A COMPUTERIZED METHOD FOR DESIGNING OPTIMAL DNA PROBES

[75] Inventors: Masato Mitsuhashi, Irvine, Calif.; Allan J. Cooper, Bellvue, Wash.; Michael S. Waterman, Culver City, Calif.; Pavel A. Pevzner, State College, Pa.

[73] Assignee: Hitachi Chemical Research Center, Inc., Irvine, Calif.

[21] Appl. No.: 975,526

[22] Filed: Nov. 12, 1992

[51] Int. Cl.$^6$ ............ C12Q 1/68; G06F 15/16; G06F 17/00
[52] U.S. Cl. ............ 435/6; 364/496; 364/497; 364/498
[58] Field of Search ............ 435/6; 364/496, 364/497, 498, 499; 422/67

[56] References Cited

U.S. PATENT DOCUMENTS

| | | | |
|---|---|---|---|
| 4,908,773 | 3/1990 | Pantoliano et al. | 364/496 |
| 4,912,206 | 3/1990 | Goldgaber et al. | 563/27 |
| 4,917,999 | 4/1990 | Byng et al. | 435/6 |
| 4,942,124 | 7/1990 | Church | 435/6 |
| 4,965,190 | 10/1990 | Woo et al. | 435/6 |
| 4,981,783 | 1/1991 | Augenlicht | 435/6 |
| 4,987,006 | 1/1991 | Williams et al. | 426/53.1 |
| 5,002,867 | 3/1991 | Macevicz | 435/6 |
| 5,015,570 | 5/1991 | Scangos et al. | 435/6 |
| 5,081,584 | 1/1992 | Omichinski et al. | 364/497 |
| 5,082,767 | 1/1992 | Hatfield et al. | 435/6 |
| 5,139,812 | 8/1992 | Lebacq | 427/7 |
| 5,147,778 | 9/1992 | Nietupski et al. | 435/6 |

OTHER PUBLICATIONS

Potera, C. "Hitachi Chemical Offers Probe Design Software and Device" Genetic Engineering News: 13 (18): pp. 1, 22, 1993.
Lowe et al., *Nuc. Acids Res.* 18(7):1757–1761, 1990.
Bonner, T. I., Brenner, D. J., Neufeld, B. R., and Britten, R. J. "Reduction in the Rate of DNA Reassociation by Sequence Divergence," 81 Journal of Molecular Biology 123 (1973).
Bolton, E. T. and McCarthy, B. J. "A General Method for the Isolation of RNA Complementary to DNA," 48 Proceedings of the National Academy of Science 1390 (1962).
Grossi, R. and Luccio, F., "Simple and Efficient String Matching with k Mismatches," 33 Information Processing Letters 113 (Nov. 30, 1989).
Hume, A. and Sunday, D., "Fast String Searching," 21(11) Software–Practice and Experience 1221 (1991).
Itakura, K., Rossi, J. J., and Wallace, R. B., "Synthesis and Use of Synthetic Oligonucleotides," 53 Annual Review of Biochemistry 323 (1984).

(List continued on next page.)

Primary Examiner—W. Gray Jones
Assistant Examiner—Paul L. Tran
Attorney, Agent, or Firm—Wagner & Middlebrook

[57] ABSTRACT

There is disclosed herein an invention which relates to the fields of genetic engineering, microbiology, and computer science, that allows a user, whether they be a molecular biologist or a clinical diagnostician, to calculate and design extremely specific oligonucleotide probes for DNA and mRNA hybridization procedures. The probes designed with this invention may be used for medical diagnostic kits, DNA identification, and potentially continuous monitoring of metabolic processes in human beings. The key features design oligonucleotide probes based on the GenBank database of DNA and mRNA sequences and examine candidate probes for specificity or commonality with respect to a user-selected experimental preparation. Two models are available: a Mismatch Model, that employs hashing and continuous seed filtration, and an H-Site Model, that analyzes candidate probes for their binding specificity relative to some known set of mRNA or DNA sequences. The preferred embodiment of this computerized design tool is written in the Borland® C++ language and runs under Microsoft® Windows™ on IBM® compatible personal computers.

97 Claims, 156 Drawing Sheets

Microfiche Appendix Included
(3 Microfiche, 103 Pages)

OTHER PUBLICATIONS

Landau, G. M. and Vishkin, U. "Efficient String Matching with k Mismatches," 43 Theoretical Computer Science 239 (1986).

Lewis, R. M., "Probfind: A Computer Program for Selecting Oligonucleotide Probes from Peptide Sequences," 14 Nucleic Acids Res. 567 (1986).

Martin, F. H. and Castro, M. M., "Base Pairing Involving Deoxyinosine: Implications for Probe Design," 13 Nucleic Acids Res. 8927 (1985).

Raupach, R. E., "Computer Programs Used in Aid in the Selection of DNA Hybridization Probes," 12 Nucleic Acids Res. 833 (1984).

Southern, E. M., "Detection of Specific Sequences Among DNA Fragments Separated by Gel Electrophoresis," 98 Journal of Molecular Biology 503 (1975).

Ukkonen, E., "Approximate String–Matching with q–Grams and Maximal Matches," 92 Theoretical Computer Science 191 (1992).

Yang, J., Ye, J., and Wallace, D. C., "Computer Selection of Oligonucleotide Probes from Amino Acid Sequences for Use in Gene Library Screening," 12 Nucleic Acids Res. 837 (1984).

Landau, G. M., Vishkin, U., and Nussinov, R., "Locating Alignments with k Differences for Nucleotide and Amino Acids Sequences," 4 Cabios 19 (1988).

Landau, G. M., Vishkin, U., and Nussinov, R., "Fast Alignment of DNA and Protein Sequences," 183 Methods in Enzymology 487 (1990).

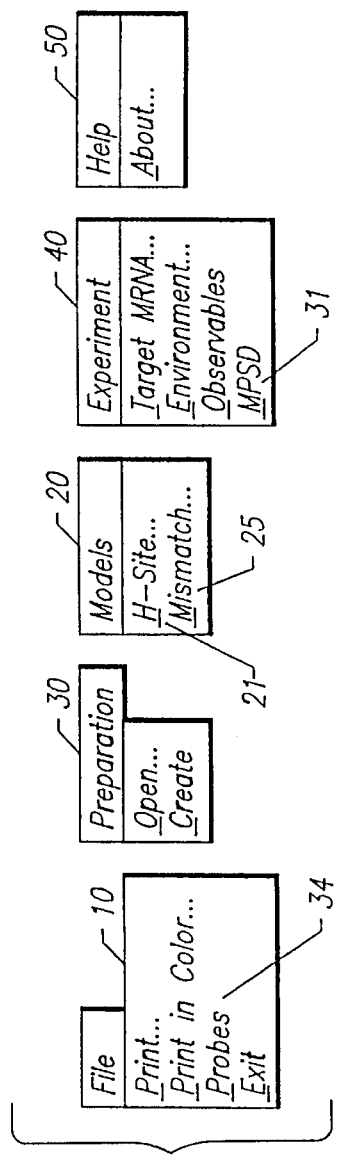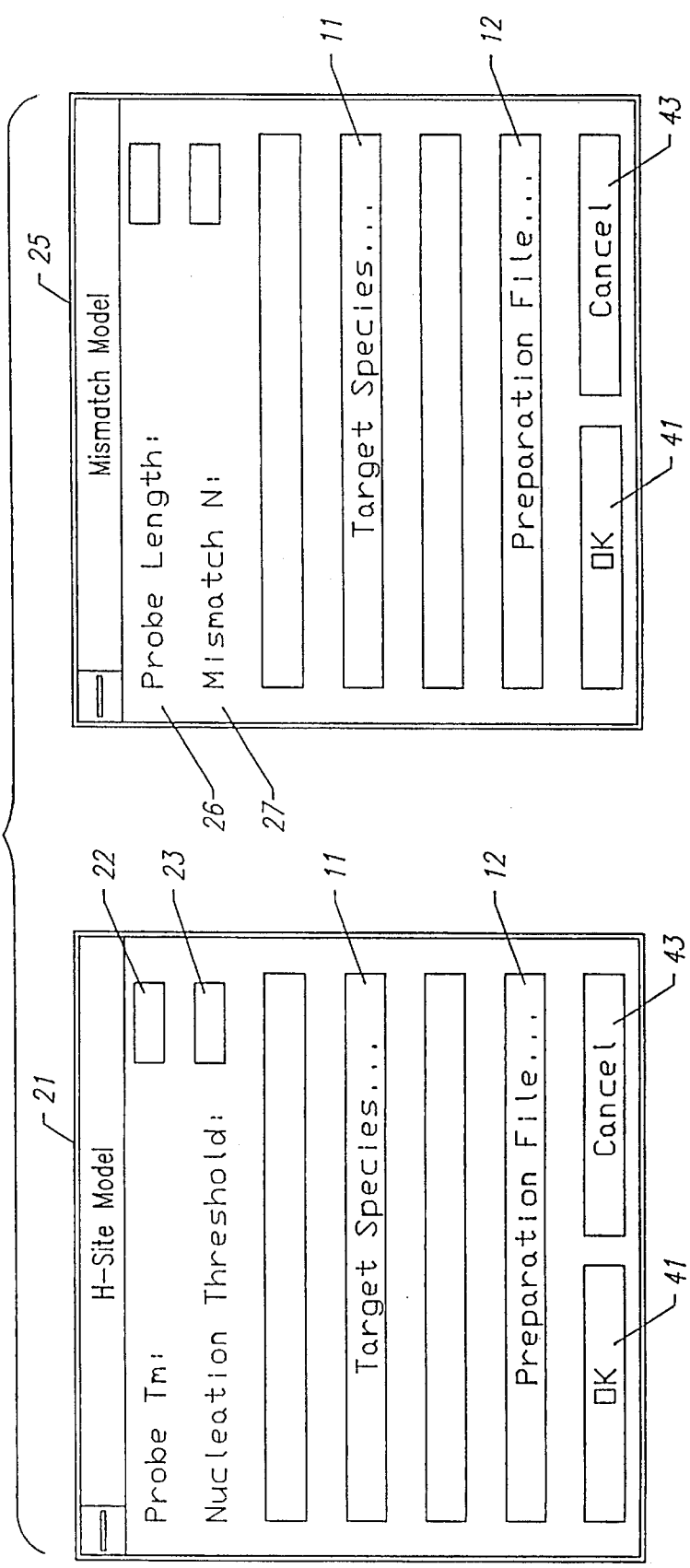
FIG. 2B
FIG. 2C

FIG. 5

Probe Info

PROBE: F:\MILAN\HUMBJUNX.CDS
HYBRIDIZATIONS: F:\MILAN\JUNMIX.PRP

| Locus | Pos | Tm | Length 21 | Hairpin 4 | 1 |
|---|---|---|---|---|---|
| humbjunx | 398 | 0.0 | agggcttcgccgacggctttg | | |
| muscjunx | 398 | 61.7 | -------------------- | | |
| humcjunx | 323 | 50.0 | ----------g--------- | | |
| humdjunx | 323 | 43.0 | ----------g--------- | | |
| humbjunx | 215 | 36.2 | ccctgc--------gccc-- | | |
| humdjunx | 401 | 36.0 | -------g------------ | | |
| musdjunx | 401 | 36.0 | --ag---------g------ | | |
| humdjunx | 100 | 35.7 | --ag---------a------ | | |
| musdjunx | 262 | 34.3 | g----gc-c-------cgc- | | |
| humbjunx | 659 | 30.5 | ct-------gatct-gg--- | | |
| humdjunx | 242 | 29.5 | c----------gt--cacc- | | |
| humdjunx | 343 | 29.5 | --cacc-c------c-gc-- | | |
| humdjunx | 607 | 29.5 | --cca-ca-----agc-ca- | | |
| musbjunx | 230 | 29.5 | --ct-a-ac-------cacc | | |
| musdjunx | 335 | 29.0 | c-ctgcg-c------gccc- | | |
| humcjunx | | | --------------tgcg--c--c--g-- | | |

FIG. 6

```
Probes selected -- JUNMIX.prb                    ─156

File

PROBE:         C:\HITACHI\JUNMIX.PRP
HYBRIDIZATION: C:\HITACHI\HUMBJU
Length = 374   Hairpin = 3  5
Locus      Pos   Tm
humbjunx   374   61.47   ---------------------
musbjunx   365   61.47   ---------------------
humjunx     41   34.82   -------t---------g-g-
humbjunx   182   31.12   -------a---------g+gg
humdjunx   602   31.12   -------c---------c-99

PROBE:         C:\HITACHI\JUNMIX.PRP
HYBRIDIZATION: C:\HITACHI\HUMBJU
Length = 467   Hairpin = 2  13
Locus      Pos   Tm
humbjunx   467   61.7    ---------------------
musbjunx   458   51.6    -----------------c---
humdjunx    32   29.35   tgagcgg--------------
humdjunx    32   29.35   tgagcgg--------------
```

```
PROBE: C:\HITACHI\JUNMIX.PRP
HYBRIDIZATION: C:\HITACHI\HUMBJUNX.CDS
Length = 374  Hairpin = 3 5
Locus      Pos  Tm
humbjunx   374  61.47  ------------------
musbjunx   365  61.47  ------------------
humdjunx   41   34.82  t---------g-g--agt
humbjunx   182  31.12  a---------gtgg--gc
humdjunx   602  31.12  c---------c-ggg-gc
humdjunx   602  31.12  c---------c-ggg-gc PROBE: C:\HITACHI\JUNMIX.PRP
HYBRIDIZATION: C:\HITACHI\HUMBJUNX.CDS
Length = 377  Hairpin = 2 14
Locus      Pos  Tm
humbjunx   377  61.55  ------------------
musbjunx   368  61.55  ------------------
humdjunx   383  28.12  tg-cg-c--g--------
musdjunx   383  28.12  tg-ca-c--g--------
musdjunx   383  28.12  tg-ca-c--g--------

PROBE: C:\HITACHI\JUNMIX.PRP
HYBRIDIZATION: C:\HITACHI\HUMBJUNX.CDS
Length = 389  Hairpin = 3 3
Locus      Pos  Tm
humbjunx   389  61.7   ------------------
muscjunx   314  56.65  -c----------------
musbjunx   380  50.85  ---------------t--g
humcjunx   314  49.35  -t-----------g------
humdjunx   395  33.85  ------------tt-gc--ag
musdjunx   395  33.85  ------------tt-gc--aa
humcjunx   326  32.35  g-ttcgcc----------tg
humdjunx   404  32.35  --ttcgcc----------t-
muscjunx   326  32.35  gcttcgcc----------tg
musdjunx   253  30.85  gacg-gct-ct---------
humbjunx   953  30.65  g---------t--c-cagct-
musdjunx   83   27.3   cc-gcggt-gt---------g
```

FIG. 6A (2)

```
PROBE: C:\HITACHI\JUNMIX.PRP
HYBRIDIZATION: C:\HITACHI\HUMBJUNX.CDS
Length = 397  Hairpin = 4 1
Locus      Pos  Tm
humbjunx   397  61.55  --------------------
muscjunx   322  53.44  ----------------g---
humcjunx   322  45.33  -----g----------g---
musbjunx   388  41.38  --------t--g-----t
humdjunx   214  36.83  ccccctgc------------
humdjunx   99   36.16  cg----gc-c----------
musdjunx   261  34.55  -ct-----------gatct
humdjunx   400  33.27  c---ag----------g---
musdjunx   400  33.27  c---ag----------a---
humcjunx   334  32.28  ----------tgcg--c-
humdjunx   412  32.28  ----------t-a-g-c-
muscjunx   334  32.28  ----------tgcg--c-
humbjunx   658  30.17  cc-cc---------gt---
humdjunx   241  28.95  -c--cacc-c----------
humdjunx   342  28.95  c-cca-ca--------ag
musbjunx   606  28.95  ---ct-a-ac----------
musdjunx   229  28.95  -c-ctgcg-c----------
musdjunx   91   26.67  -gt--------gcc-ccg PROBE: C:\HITACHI\JUNMIX.PRP
HYBRIDIZATION: C:\HITACHI\HUMBJUNX.CDS
Length = 417  Hairpin = 2 15
Locus      Pos  Tm
humbjunx   417  60.08  --------------------
musbjunx   408  55.52  --------------------c----
humdjunx   420  37.3   c-----g---------g---t-a
musbjunx   61   29.0   g---gg---------ca-cctgt-
muscjunx   672  26.27  gc-gc----------a-g--aga--
```

FIG. 6A (3)

```
PROBE: C:\HITACHI\JUNMIX.PRP
HYBRIDIZATION: C:\HITACHI\HUMBJUNX.CDS
Length = 461  Hairpin = 4 9
Locus      Pos  Tm
humbjunx   461  61.63  --------------------
musbjunx   452  61.63  --------------------
musbjunx   452  61.63  --------------------

PROBE: C:\HITACHI\JUNMIX.PRP
HYBRIDIZATION: C:\HITACHI\HUMBJUNX.CDS
Length = 467  Hairpin = 2 13
Locus      Pos  Tm
humbjunx   467  61.7   --------------------
musbjunx   458  51.6   ----------------c-g-
humdjunx   32   29.35  tgagcgg--------gcgg-
humdjunx   32   29.35  tgagcgg--------gcgg- PROBE: C:\HITACHI\JUNMIX.PRP
HYBRIDIZATION: C:\HITACHI\HUMBJUNX.CDS
Length = 477  Hairpin = 2 4
Locus      Pos  Tm
humbjunx   477  61.37  ------------------
humdjunx   489  34.93  c-c---cg----------
humdjunx   489  34.93  c-c---cg----------

PROBE: C:\HITACHI\JUNMIX.PRP
HYBRIDIZATION: C:\HITACHI\HUMBJUNX.CDS
Length = 487  Hairpin = 3 3
Locus      Pos  Tm
humbjunx   487  61.14  ----------------
musdjunx   74   51.0   ct--------------
humdjunx   499  45.64  ----------t---g
humdjunx   527  30.72  cc-c-c----------
musdjunx   97   30.72  ttc-c--------g
musdjunx   580  30.72  -cc---------t-g
musdjunx   637  30.72  cc-cc---------g
musdjunx   637  30.72  cc-cc---------g
```

FIG. 6A (4)

```
PROBE: C:\HITACHI\JUNMIX.PRP
HYBRIDIZATION: C:\HITACHI\HUMBJUNX.CDS
Length = 498  Hairpin = 3 2
Locus     Pos  Tm
humbjunx  498  61.26  ----------------
humbjunx  498  61.26  ----------------

PROBE: C:\HITACHI\JUNMIX.PRP
HYBRIDIZATION: C:\HITACHI\HUMBJUNX.CDS
Length = 504  Hairpin = 3 2
Locus     Pos  Tm
humbjunx  504  61.47  ------------------
musbjunx  495  40.35  c--a------------t-
humdjunx  609  35.29  cg---------cgggg-
humdjunx  609  35.29  cg---------cgggg-
```

FIG. 20A

OligoProbe DesignStation

Probes:    C:\HITACHI\HUMBJUNX.CDS
Datatbase: C:\HITACHI\JUNMIX.SEQ

Mismatch Model, l = 21, k = 4

| Position | length | \multicolumn{5}{c}{Mismatches} | | | | | screensN | | | Probe |
|---|---|---|---|---|---|---|---|---|---|---|---|---|---|
| | | 0 | 1 | 2 | 3 | 4 | 5 | 6 | 7 | 8 | | | |
| 1 | 21 | 1 | 1 | 1 | 1 | 1 | ATGTGCACTAAAATGGAACAG |
| 2 | 21 | 1 | 1 | 1 | 1 | 1 | TGTGCACTAAAATGGAACAGC |
| 3 | 21 | 1 | 1 | 1 | 1 | 1 | GTGCACTAAAATGGAACAGCC |
| 4 | 21 | 1 | 1 | 1 | 1 | 1 | TGCACTAAAATGGAACAGCCC |
| 5 | 21 | 1 | 1 | 1 | 1 | 1 | GCACTAAAATGGAACAGCCCT |
| 6 | 21 | 1 | 1 | 1 | 1 | 1 | CACTAAAATGGAACAGCCCTT |
| 7 | 21 | 1 | 1 | 1 | 1 | 1 | ACTAAAATGGAACAGCCCTTC |
| 8 | 21 | 1 | 1 | 1 | 1 | 1 | CTAAAATGGAACAGCCCTTCT |
| 9 | 21 | 1 | 1 | 1 | 1 | 1 | TAAAATGGAACAGCCCTTCTA |
| 10 | 21 | 1 | 1 | 1 | 1 | 1 | AAAATGGAACAGCCCTTCTAC |
| 11 | 21 | 1 | 1 | 1 | 1 | 1 | AAATGGAACAGCCCTTCTACC |
| 12 | 21 | 1 | 1 | 1 | 1 | 1 | AATGGAACAGCCCTTCTACCA |
| 13 | 21 | 1 | 1 | 1 | 1 | 1 | ATGGAACAGCCCTTCTACCAC |
| 14 | 21 | 1 | 1 | 1 | 1 | 1 | TGGAACAGCCCTTCTACCACG |

FIG. 20B

| | | | | | |
|---|---|---|---|---|---|
| 15 | 21 | 1 | 1 | 1 | 1 | GGAACAGCCCTTCTACCACGA |
| 16 | 21 | 1 | 1 | 1 | 1 | GAACAGCCCCTTCTACCACGAC |
| 17 | 21 | 1 | 1 | 1 | 1 | AACAGCCCTTCTACCACGACG |
| 18 | 21 | 1 | 1 | 1 | 1 | ACAGCCCTTCTACCACGACGA |
| 19 | 21 | 1 | 1 | 1 | 1 | CAGCCCTTCTACCACGACGAC |
| 20 | 21 | 1 | 1 | 1 | 1 | AGCCCTTCTACCACGACGACT |
| 21 | 21 | 1 | 1 | 1 | 1 | GCCCTTCTACCACGACGACTC |
| 22 | 21 | 1 | 1 | 1 | 1 | CCCTTCTACCACGACGACTCA |
| 23 | 21 | 1 | 1 | 1 | 1 | CCTTCTACCACGACGACTCAT |
| 24 | 21 | 1 | 1 | 1 | 1 | CTTCTACCACGACGACTCATA |
| 25 | 21 | 1 | 1 | 1 | 1 | TTCTACCACGACGACTCATAC |
| 26 | 21 | 1 | 1 | 1 | 1 | TCTACCACGACGACTCATACA |
| 27 | 21 | 1 | 1 | 1 | 1 | CTACCACGACGACTCATACAC |
| 28 | 21 | 1 | 1 | 1 | 1 | TACCACGACGACTCATACACA |
| 29 | 21 | 1 | 1 | 1 | 1 | ACCACGACGACTCATACACAG |
| 30 | 21 | 1 | 1 | 1 | 1 | CCACGACGACTCATACACAGC |
| 31 | 21 | 1 | 1 | 1 | 1 | CACGACGACTCATACACAGCT |
| 32 | 21 | 1 | 1 | 1 | 1 | ACGACGACTCATACACAGCTA |
| 33 | 21 | 1 | 1 | 1 | 1 | CGACGACTCATACACAGCTAC |
| 34 | 21 | 1 | 1 | 1 | 1 | GACGACTCATACACAGCTACG |
| 35 | 21 | 1 | 1 | 1 | 1 | ACGACTCATACACAGCTACGG |
| 36 | 21 | 1 | 1 | 1 | 1 | CGACTCATACACAGCTACGGG |

FIG. 20C

| | | | | | |
|---|---|---|---|---|---|
| 37 | 21 | 1 | 1 | 1 | 1 | GACTCATACACAGCTACGGGA |
| 38 | 21 | 1 | 1 | 1 | 1 | ACTCATACACAGCTACGGGAT |
| 39 | 21 | 1 | 1 | 1 | 1 | CTCATACACAGCTACGGGATA |
| 40 | 21 | 1 | 1 | 1 | 1 | TCATACACAGCTACGGGATAC |
| 41 | 21 | 1 | 1 | 1 | 1 | CATACACAGCTACGGGATACG |
| 42 | 21 | 1 | 1 | 1 | 1 | ATACACAGCTACGGGATACGG |
| 43 | 21 | 1 | 1 | 1 | 1 | TACACAGCTACGGGATACGGC |
| 44 | 21 | 1 | 1 | 1 | 1 | ACACAGCTACGGGATACGGCC |
| 45 | 21 | 1 | 1 | 1 | 1 | CACAGCTACGGGATACGGCCG |
| 46 | 21 | 1 | 1 | 1 | 1 | ACAGCTACGGGATACGGCCGG |
| 47 | 21 | 1 | 1 | 1 | 1 | CAGCTACGGGATACGGCCGGG |
| 48 | 21 | 1 | 1 | 1 | 1 | AGCTACGGGATACGGCCGGGC |
| 49 | 21 | 1 | 1 | 1 | 1 | GCTACGGGATACGGCCGGGCC |
| 50 | 21 | 1 | 1 | 1 | 1 | CTACGGGATACGGCCGGGCCC |
| 51 | 21 | 1 | 1 | 1 | 1 | TACGGGATACGGCCGGGCCCC |
| 52 | 21 | 1 | 1 | 1 | 1 | ACGGGATACGGCCGGGCCCCT |
| 53 | 21 | 1 | 1 | 1 | 1 | CGGGATACGGCCGGGCCCCTG |

FIG. 20D

| | | | | | |
|---|---|---|---|---|---|
| 54 | 21 | 1 | 1 | 1 | 1 | GGGATACGGCCGGGCCCCTGG |
| 55 | 21 | 1 | 1 | 1 | 1 | GGATACGGCCGGGCCCCTGGT |
| 56 | 21 | 1 | 1 | 1 | 1 | GATACGGCCGGGCCCCTGGTG |
| 57 | 21 | 1 | 1 | 1 | 1 | ATACGGCCGGGCCCCTGGTGG |
| 58 | 21 | 1 | 1 | 1 | 1 | TACGGCCGGGCCCCTGGTGGC |
| 59 | 21 | 1 | 1 | 1 | 1 | ACGGCCGGGCCCCTGGTGGCC |
| 60 | 21 | 1 | 1 | 1 | 1 | CGGCCGGGCCCCTGGTGGCCT |
| 61 | 21 | 1 | 1 | 1 | 1 | GGCCGGGCCCCTGGTGGCCTC |
| 62 | 21 | 1 | 1 | 1 | 1 | GCCGGGCCCCTGGTGGCCTCT |
| 63 | 21 | 1 | 1 | 1 | 1 | CCGGGCCCCTGGTGGCCTCTC |
| 64 | 21 | 1 | 1 | 1 | 1 | CGGGCCCCTGGTGGCCTCTCT |
| 65 | 21 | 1 | 1 | 1 | 1 | GGGCCCCTGGTGGCCTCTCTC |
| 66 | 21 | 1 | 1 | 1 | 1 | GGCCCCTGGTGGCCTCTCTCT |
| 67 | 21 | 1 | 1 | 1 | 1 | GCCCCTGGTGGCCTCTCTCTA |
| 68 | 21 | 1 | 1 | 1 | 1 | CCCCTGGTGGCCTCTCTCTAC |
| 69 | 21 | 1 | 1 | 1 | 1 | CCCTGGTGGCCTCTCTCTACA |
| 70 | 21 | 1 | 1 | 1 | 1 | CCTGGTGGCCTCTCTCTACAC |
| 71 | 21 | 1 | 1 | 1 | 1 | CTGGTGGCCTCTCTCTACACG |
| 72 | 21 | 1 | 1 | 1 | 1 | TGGTGGCCTCTCTCTACACGA |
| 73 | 21 | 1 | 1 | 1 | 1 | GGTGGCCTCTCTCTACACGAC |
| 74 | 21 | 1 | 1 | 1 | 1 | GTGGCCTCTCTCTACACGACT |

FIG. 20E

| | | | | | |
|---|---|---|---|---|---|
| 75 | 21 | 1 | 1 | 1 | 1 | TGGCCTCTCTCTACACGACTA |
| 76 | 21 | 1 | 1 | 1 | 1 | GGCCTCTCTCTACACGACTAC |
| 77 | 21 | 1 | 1 | 1 | 1 | GCCTCTCTCTACACGACTACA |
| 78 | 21 | 1 | 1 | 1 | 1 | CCTCTCTCTACACGACTACAA |
| 79 | 21 | 1 | 1 | 1 | 1 | CTCTCTCTACACGACTACAAA |
| 80 | 21 | 1 | 1 | 1 | 1 | TCTCTCTACACGACTACAAAC |
| 81 | 21 | 1 | 1 | 1 | 1 | CTCTCTACACGACTACAAACT |
| 82 | 21 | 1 | 1 | 1 | 1 | TCTCTACACGACTACAAACTC |
| 83 | 21 | 1 | 1 | 1 | 1 | CTCTACACGACTACAAACTCC |
| 84 | 21 | 1 | 1 | 1 | 1 | TCTACACGACTACAAACTCCT |
| 85 | 21 | 1 | 1 | 1 | 1 | CTACACGACTACAAACTCCTG |
| 86 | 21 | 1 | 1 | 1 | 1 | TACACGACTACAAACTCCTGA |
| 87 | 21 | 1 | 1 | 1 | 1 | ACACGACTACAAACTCCTGAA |
| 88 | 21 | 1 | 1 | 1 | 1 | CACGACTACAAACTCCTGAAA |
| 89 | 21 | 1 | 1 | 1 | 1 | ACGACTACAAACTCCTGAAAC |
| 90 | 21 | 1 | 1 | 1 | 1 | CGACTACAAACTCCTGAAACC |
| 91 | 21 | 1 | 1 | 1 | 1 | GACTACAAACTCCTGAAACCG |
| 92 | 21 | 1 | 1 | 1 | 1 | ACTACAAACTCCTGAAACCGA |
| 93 | 21 | 1 | 1 | 1 | 1 | CTACAAACTCCTGAAACCGAG |
| 94 | 21 | 1 | 1 | 1 | 1 | TACAAACTCCTGAAACCGAGC |
| 95 | 21 | 1 | 1 | 1 | 1 | ACAAACTCCTGAAACCGAGCC |

FIG. 20F

| | | | | | |
|---|---|---|---|---|---|
| 96 | 21 | 1 | 1 | 1 | CAAACTCCTGAAACCGAGCCT |
| 97 | 21 | 1 | 1 | 1 | AAACTCCTGAAACCGAGCCTG |
| 98 | 21 | 1 | 1 | 1 | AACTCCTGAAACCGAGCCTGG |
| 99 | 21 | 1 | 1 | 1 | ACTCCTGAAACCGAGCCTGGC |
| 100 | 21 | 1 | 1 | 1 | CTCCTGAAACCGAGCCTGGCG |
| 101 | 21 | 1 | 1 | 1 | TCCTGAAACCGAGCCTGGCGG |
| 102 | 21 | 1 | 1 | 1 | CCTGAAACCGAGCCTGGCGGT |
| 103 | 21 | 1 | 1 | 1 | CTGAAACCGAGCCTGGCGGTC |
| 104 | 21 | 1 | 1 | 1 | TGAAACCGAGCCTGGCGGTCA |
| 105 | 21 | 1 | 1 | 1 | GAAACCGAGCCTGGCGGTCAA |
| 106 | 21 | 1 | 1 | 1 | AAACCGAGCCTGGCGGTCAAC |
| 107 | 21 | 1 | 1 | 1 | AACCGAGCCTGGCGGTCAACC |
| 108 | 21 | 1 | 1 | 1 | ACCGAGCCTGGCGGTCAACCT |
| 109 | 21 | 1 | 1 | 1 | CCGAGCCTGGCGGTCAACCTG |
| 110 | 21 | 1 | 1 | 1 | CGAGCCTGGCGGTCAACCTGG |
| 111 | 21 | 1 | 1 | 1 | GAGCCTGGCGGTCAACCTGGC |
| 112 | 21 | 1 | 1 | 1 | AGCCTGGCGGTCAACCTGGCC |
| 113 | 21 | 1 | 1 | 1 | GCCTGGCGGTCAACCTGGCCG |
| 114 | 21 | 1 | 1 | 1 | CCTGGCGGTCAACCTGGCCGA |
| 115 | 21 | 1 | 1 | 1 | CTGGCGGTCAACCTGGCCGAC |
| 116 | 21 | 1 | 1 | 1 | TGGCGGTCAACCTGGCCGACC |

FIG. 20G

| | | | | | |
|---|---|---|---|---|---|
| 117 | 21 | 1 | 1 | 1 | GGCGGTCAACCTGGCCGACCC |
| 118 | 21 | 1 | 1 | 1 | GCGGTCAACCTGGCCGACCCC |
| 119 | 21 | 1 | 1 | 1 | CGGTCAACCTGGCCGACCCCT |
| 120 | 21 | 1 | 1 | 1 | GGTCAACCTGGCCGACCCCTA |
| 121 | 21 | 1 | 1 | 1 | GTCAACCTGGCCGACCCCTAC |
| 122 | 21 | 1 | 1 | 1 | TCAACCTGGCCGACCCCTACC |
| 123 | 21 | 1 | 1 | 1 | CAACCTGGCCGACCCCTACCG |
| 124 | 21 | 1 | 1 | 1 | AACCTGGCCGACCCCTACCGG |
| 125 | 21 | 1 | 1 | 1 | ACCTGGCCGACCCCTACCGGA |
| 126 | 21 | 1 | 1 | 1 | CCTGGCCGACCCCTACCGGAG |
| 127 | 21 | 1 | 1 | 1 | CTGGCCGACCCCTACCGGAGT |
| 128 | 21 | 1 | 1 | 1 | TGGCCGACCCCTACCGGAGTC |
| 129 | 21 | 1 | 1 | 1 | GGCCGACCCCTACCGGAGTCT |
| 130 | 21 | 1 | 1 | 1 | GCCGACCCCTACCGGAGTCTC |
| 131 | 21 | 1 | 1 | 1 | CCGACCCCTACCGGAGTCTCA |
| 132 | 21 | 1 | 1 | 1 | CGACCCCTACCGGAGTCTCAA |
| 133 | 21 | 1 | 1 | 1 | GACCCCTACCGGAGTCTCAAA |
| 134 | 21 | 1 | 1 | 1 | ACCCCTACCGGAGTCTCAAAG |
| 135 | 21 | 1 | 1 | 1 | CCCCTACCGGAGTCTCAAAGC |
| 136 | 21 | 1 | 1 | 1 | CCCTACCGGAGTCTCAAAGCG |
| 137 | 21 | 1 | 1 | 1 | CCTACCGGAGTCTCAAAGCGC |

FIG. 20H

| | | | | | |
|---|---|---|---|---|---|
| 138 | 21 | 1 | 1 | 1 | 1 | CTACCGGAGTCTCAAAGCGCC |
| 139 | 21 | 1 | 1 | 1 | 1 | TACCGGAGTCTCAAAGCGCCT |
| 140 | 21 | 1 | 1 | 1 | 1 | ACCGGAGTCTCAAAGCGCCTG |
| 141 | 21 | 1 | 1 | 1 | 1 | CCGGAGTCTCAAAGCGCCTGG |
| 142 | 21 | 1 | 1 | 1 | 1 | CGGAGTCTCAAAGCGCCTGGG |
| 143 | 21 | 1 | 1 | 1 | 1 | GGAGTCTCAAAGCGCCTGGGG |
| 144 | 21 | 1 | 1 | 1 | 1 | GAGTCTCAAAGCGCCTGGGGC |
| 145 | 21 | 1 | 1 | 1 | 1 | AGTCTCAAAGCGCCTGGGGCT |
| 146 | 21 | 1 | 1 | 1 | 1 | GTCTCAAAGCGCCTGGGGCTC |
| 147 | 21 | 1 | 1 | 1 | 1 | TCTCAAAGCGCCTGGGGCTCG |
| 148 | 21 | 1 | 1 | 1 | 1 | CTCAAAGCGCCTGGGGCTCGC |
| 149 | 21 | 1 | 1 | 1 | 1 | TCAAAGCGCCTGGGGCTCGCG |
| 150 | 21 | 1 | 1 | 1 | 1 | CAAAGCGCCTGGGGCTCGCGG |
| 151 | 21 | 1 | 1 | 1 | 1 | AAAGCGCCTGGGGCTCGCGGA |
| 152 | 21 | 1 | 1 | 1 | 1 | AAGCGCCTGGGGCTCGCGGAC |
| 153 | 21 | 1 | 1 | 1 | 1 | AGCGCCTGGGGCTCGCGGACC |
| 154 | 21 | 1 | 1 | 1 | 1 | GCGCCTGGGGCTCGCGGACCC |
| 155 | 21 | 1 | 1 | 1 | 1 | CGCCTGGGGCTCGCGGACCCG |
| 156 | 21 | 1 | 1 | 1 | 1 | GCCTGGGGCTCGCGGACCCGG |
| 157 | 21 | 1 | 1 | 1 | 1 | CCTGGGGCTCGCGGACCCGGC |
| 158 | 21 | 1 | 1 | 1 | 1 | CTGGGGCTCGCGGACCCGGCC |

FIG. 20I

| | | | | | | |
|---|---|---|---|---|---|---|
| 159 | 21 | 1 | 1 | 1 | 1 | TGGGCTCGCGGACCCGGCCC |
| 160 | 21 | 1 | 1 | 1 | 1 | GGGGCTCGCGGACCCGGCCCA |
| 161 | 21 | 1 | 1 | 1 | 1 | GGGCTCGCGGACCCGGCCCAG |
| 162 | 21 | 1 | 1 | 1 | 1 | GGCTCGCGGACCCGGCCCAGA |
| 163 | 21 | 1 | 1 | 1 | 1 | GCTCGCGGACCCGGCCCAGAG |
| 164 | 21 | 1 | 1 | 1 | 1 | CTCGCGGACCCGGCCCAGAGG |
| 165 | 21 | 1 | 1 | 1 | 1 | TCGCGGACCCGGCCCAGAGGG |
| 166 | 21 | 1 | 1 | 1 | 1 | CGCGGACCCGGCCCAGAGGGC |
| 167 | 21 | 1 | 1 | 1 | 1 | GCGGACCCGGCCCAGAGGGCG |
| 168 | 21 | 1 | 1 | 1 | 1 | CGGACCCGGCCCAGAGGGCGG |
| 169 | 21 | 1 | 1 | 1 | 1 | GGACCCGGCCCAGAGGGCGGC |
| 170 | 21 | 1 | 1 | 1 | 1 | GACCCGGCCCAGAGGGCGGCG |
| 171 | 21 | 1 | 1 | 1 | 1 | ACCCGGCCCAGAGGGCGGCGG |
| 172 | 21 | 1 | 1 | 1 | 1 | CCCGGCCCAGAGGGCGGCGGT |
| 173 | 21 | 1 | 1 | 1 | 1 | CCGGCCCAGAGGGCGGCGGTG |
| 174 | 21 | 1 | 1 | 1 | 1 | CGGCCCAGAGGGCGGCGGTGG |
| 175 | 21 | 1 | 1 | 1 | 1 | GGCCCAGAGGGCGGCGGTGGC |
| 176 | 21 | 1 | 1 | 1 | 1 | GCCCAGAGGGCGGCGGTGGCG |
| 177 | 21 | 1 | 1 | 1 | 1 | CCCAGAGGGCGGCGGTGGCGG |
| 178 | 21 | 1 | 1 | 1 | 1 | CCAGAGGGCGGCGGTGGCGGC |
| 179 | 21 | 1 | 1 | 1 | 1 | CAGAGGGCGGCGGTGGCGGCA |
| 180 | 21 | 1 | 1 | 1 | 1 | AGAGGGCGGCGGTGGCGGCAG |

FIG. 20J

| | | | | | |
|---|---|---|---|---|---|
| 181 | 21 | 1 | 1 | 1 | 1 | GAGGGCGGCGGTGGCGGCAGC |
| 182 | 21 | 1 | 1 | 1 | 1 | AGGGCGGCGGTGGCGGCAGCT |
| 183 | 21 | 1 | 1 | 1 | 1 | GGGCGGCGGTGGCGGCAGCTA |
| 184 | 21 | 1 | 1 | 1 | 1 | GGCGGCGGTGGCGGCAGCTAC |
| 185 | 21 | 1 | 1 | 1 | 1 | GCGGCGGTGGCGGCAGCTACT |
| 186 | 21 | 1 | 1 | 1 | 1 | CGGCGGTGGCGGCAGCTACTT |
| 187 | 21 | 1 | 1 | 1 | 1 | GGCGGTGGCGGCAGCTACTTT |
| 188 | 21 | 1 | 1 | 1 | 1 | GCGGTGGCGGCAGCTACTTTT |
| 189 | 21 | 1 | 1 | 1 | 1 | CGGTGGCGGCAGCTACTTTTC |
| 190 | 21 | 1 | 1 | 1 | 1 | GGTGGCGGCAGCTACTTTTCT |
| 191 | 21 | 1 | 1 | 1 | 1 | GTGGCGGCAGCTACTTTTCTG |
| 192 | 21 | 1 | 1 | 1 | 1 | TGGCGGCAGCTACTTTTCTGG |
| 193 | 21 | 1 | 1 | 1 | 1 | GGCGGCAGCTACTTTTCTGGT |
| 194 | 21 | 1 | 1 | 1 | 1 | GCGGCAGCTACTTTTCTGGTC |
| 195 | 21 | 1 | 1 | 1 | 1 | CGGCAGCTACTTTTCTGGTCA |
| 196 | 21 | 1 | 1 | 1 | 1 | GGCAGCTACTTTTCTGGTCAG |
| 197 | 21 | 1 | 1 | 1 | 1 | GCAGCTACTTTTCTGGTCAGG |
| 198 | 21 | 1 | 1 | 1 | 1 | CAGCTACTTTTCTGGTCAGGG |
| 199 | 21 | 1 | 1 | 1 | 1 | AGCTACTTTTCTGGTCAGGGC |
| 200 | 21 | 1 | 1 | 1 | 1 | GCTACTTTTCTGGTCAGGGCT |
| 201 | 21 | 1 | 1 | 1 | 1 | CTACTTTTCTGGTCAGGGCTC |

FIG. 20K

| | | | | | |
|---|---|---|---|---|---|
| 202 | 21 | 1 | 1 | 1 | 1 | TACTTTCTGGTCAGGGCTCG |
| 203 | 21 | 1 | 1 | 1 | 1 | ACTTTCTGGTCAGGGCTCGG |
| 204 | 21 | 1 | 1 | 1 | 1 | CTTTCTGGTCAGGGCTCGGA |
| 205 | 21 | 1 | 1 | 1 | 1 | TTTCTGGTCAGGGCTCGGAC |
| 206 | 21 | 1 | 1 | 1 | 1 | TTCTGGTCAGGGCTCGGACA |
| 207 | 21 | 1 | 1 | 1 | 1 | TCTGGTCAGGGCTCGGACAC |
| 208 | 21 | 1 | 1 | 1 | 1 | TCTGGTCAGGGCTCGGACAC |
| 209 | 21 | 1 | 1 | 1 | 1 | CTGGTCAGGGCTCGGACACC |
| 210 | 21 | 1 | 1 | 1 | 1 | TGGTCAGGGCTCGGACACCG |
| 211 | 21 | 1 | 1 | 1 | 1 | GGTCAGGGCTCGGACACCGG |
| 212 | 21 | 1 | 1 | 1 | 1 | GTCAGGGCTCGGACACCGGC |
| 213 | 21 | 1 | 1 | 1 | 1 | TCAGGGCTCGGACACCGGCG |
| 214 | 21 | 1 | 1 | 1 | 1 | CAGGGCTCGGACACCGGCGC |
| 215 | 21 | 1 | 1 | 1 | 1 | AGGGCTCGGACACCGGCGCG |
| 216 | 21 | 1 | 1 | 1 | 1 | GGGCTCGGACACCGGCGCGT |
| 217 | 21 | 1 | 1 | 1 | 1 | GGCTCGGACACCGGCGCGTC |
| 218 | 21 | 1 | 1 | 1 | 1 | GCTCGGACACCGGCGCGTCT |
| 219 | 21 | 1 | 1 | 1 | 1 | CTCGGACACCGGCGCGTCTC |
| 220 | 21 | 1 | 1 | 1 | 1 | TCGGACACCGGCGCGTCTCT |
| 221 | 21 | 1 | 1 | 1 | 1 | CGGACACCGGCGCGTCTCTC |
| 222 | 21 | 1 | 1 | 1 | 1 | GGACACCGGCGCGTCTCTCA |
| | | | | | | GACACCGGCGCGTCTCTCAA |

FIG. 20L

| | | | | | |
|---|---|---|---|---|---|
|223|21|1|1|1|1|GACACCGGCGCGTCTCTCAAG|
|224|21|1|1|1|1|ACACCGGCGCGTCTCTCAAGC|
|225|21|1|1|1|1|CACCGGCGCGTCTCTCAAGCT|
|226|21|1|1|1|1|ACCGGCGCGTCTCTCAAGCTC|
|227|21|1|1|1|1|CCGGCGCGTCTCTCAAGCTCG|
|228|21|1|1|1|1|CGGCGCGTCTCTCAAGCTCGC|
|229|21|1|1|1|1|GGCGCGTCTCTCAAGCTCGCC|
|230|21|1|1|1|1|GCGCGTCTCTCAAGCTCGCCT|
|231|21|1|1|1|1|CGCGTCTCTCAAGCTCGCCTC|
|232|21|1|1|1|1|GCGTCTCTCAAGCTCGCCCTCT|
|233|21|1|1|1|1|CGTCTCTCAAGCTCGCCCTCT|
|234|21|1|1|1|1|GTCTCTCAAGCTCGCCCTCTT|
|235|21|1|1|1|1|TCTCTCAAGCTCGCCCTCTTC|
|236|21|1|1|1|1|CTCTCAAGCTCGCCCTCTTCG|
|237|21|1|1|1|1|TCTCAAGCTCGCCCTCTTCGG|
|238|21|1|1|1|1|CTCAAGCTCGCCCTCTTCGGA|
|239|21|1|1|1|1|TCAAGCTCGCCCTCTTCGGAG|
|240|21|1|1|1|1|CAAGCTCGCCCTCTTCGGAGC|
|241|21|1|1|1|1|AAGCTCGCCCTCTTCGGAGCT|
|242|21|1|1|1|1|AGCTCGCCCTCTTCGGAGCTG|
|243|21|1|1|1|1|GCTCGCCCTCTTCGGAGCTGG|
|244|21|1|1|1|1|CTCGCCCTCTTCGGAGCTGGA|

FIG. 20M

| | | | | | |
|---|---|---|---|---|---|
| 245 | 21 | 1 | 1 | 1 | 1 | TCGCCTCTTCGGAGCTGGAAC |
| 246 | 21 | 1 | 1 | 1 | 1 | CGCCTCTTCGGAGCTGGAACG |
| 247 | 21 | 1 | 1 | 1 | 1 | GCCTCTTCGGAGCTGGAACGC |
| 248 | 21 | 1 | 1 | 1 | 1 | CCTCTTCGGAGCTGGAACGCC |
| 249 | 21 | 1 | 1 | 1 | 1 | CTCTTCGGAGCTGGAACGCCT |
| 250 | 21 | 1 | 1 | 1 | 1 | TCTTCGGAGCTGGAACGCCTG |
| 251 | 21 | 1 | 1 | 1 | 1 | CTTCGGAGCTGGAACGCCTGA |
| 252 | 21 | 1 | 1 | 1 | 1 | TTCGGAGCTGGAACGCCTGAT |
| 253 | 21 | 1 | 1 | 1 | 1 | TCGGAGCTGGAACGCCTGATT |
| 254 | 21 | 1 | 1 | 1 | 1 | CGGAGCTGGAACGCCTGATTG |
| 255 | 21 | 1 | 1 | 1 | 1 | GGAGCTGGAACGCCTGATTGT |
| 256 | 21 | 1 | 1 | 1 | 1 | GAGCTGGAACGCCTGATTGTC |
| 257 | 21 | 1 | 1 | 1 | 1 | AGCTGGAACGCCTGATTGTCC |
| 258 | 21 | 1 | 1 | 1 | 1 | GCTGGAACGCCTGATTGTCCC |
| 259 | 21 | 1 | 1 | 1 | 1 | CTGGAACGCCTGATTGTCCCC |
| 260 | 21 | 1 | 1 | 1 | 1 | TGGAACGCCTGATTGTCCCCA |
| 261 | 21 | 1 | 1 | 1 | 1 | GGAACGCCTGATTGTCCCCAA |
| 262 | 21 | 1 | 1 | 1 | 1 | GAACGCCTGATTGTCCCCAAC |
| 263 | 21 | 1 | 1 | 1 | 1 | AACGCCTGATTGTCCCCAACA |
| 264 | 21 | 1 | 1 | 1 | 1 | ACGCCTGATTGTCCCCAACAG |
| 265 | 21 | 1 | 1 | 1 | 1 | CGCCTGATTGTCCCCAACAGC |

FIG. 20N

| | | | | | |
|---|---|---|---|---|---|
| 266 | 21 | 1 | 1 | 1 | 1 | GCCTGATTGTCCCCAACAGCA |
| 267 | 21 | 1 | 1 | 1 | 1 | CCTGATTGTCCCCAACAGCAA |
| 268 | 21 | 1 | 1 | 1 | 1 | CTGATTGTCCCCAACAGCAAC |
| 269 | 21 | 1 | 1 | 1 | 1 | TGATTGTCCCCAACAGCAACG |
| 270 | 21 | 1 | 1 | 1 | 1 | GATTGTCCCCAACAGCAACGG |
| 271 | 21 | 1 | 1 | 1 | 1 | ATTGTCCCCAACAGCAACGGC |
| 272 | 21 | 1 | 1 | 1 | 1 | TTGTCCCCAACAGCAACGGCG |
| 273 | 21 | 1 | 1 | 1 | 1 | TGTCCCCAACAGCAACGGCGT |
| 274 | 21 | 1 | 1 | 1 | 1 | GTCCCCAACAGCAACGGCGTG |
| 275 | 21 | 1 | 1 | 1 | 1 | TCCCCAACAGCAACGGCGTGA |
| 276 | 21 | 1 | 1 | 1 | 1 | CCCCAACAGCAACGGCGTGAT |
| 277 | 21 | 1 | 1 | 1 | 1 | CCCAACAGCAACGGCGTGATC |
| 278 | 21 | 1 | 1 | 1 | 1 | CCAACAGCAACGGCGTGATCA |
| 279 | 21 | 1 | 1 | 1 | 1 | CAACAGCAACGGCGTGATCAC |
| 280 | 21 | 1 | 1 | 1 | 1 | AACAGCAACGGCGTGATCACG |
| 281 | 21 | 1 | 1 | 1 | 1 | ACAGCAACGGCGTGATCACGA |
| 282 | 21 | 1 | 1 | 1 | 1 | CAGCAACGGCGTGATCACGAC |
| 283 | 21 | 1 | 1 | 1 | 1 | AGCAACGGCGTGATCACGACG |
| 284 | 21 | 1 | 1 | 1 | 1 | GCAACGGCGTGATCACGACGA |
| 285 | 21 | 1 | 1 | 1 | 1 | CAACGGCGTGATCACGACGAC |
| 286 | 21 | 1 | 1 | 1 | 1 | AACGGCGTGATCACGACGACG |

FIG. 200

| | | | | | |
|---|---|---|---|---|---|
|287|21|1|1|1|1|ACGGCGTGATCACGACGACGC|
|288|21|1|1|1|1|CGGCGTGATCACGACGACGCC|
|289|21|1|1|1|1|GGCGTGATCACGACGACGCCT|
|290|21|1|1|1|1|GCGTGATCACGACGACGCCTA|
|291|21|1|1|1|1|CGTGATCACGACGACGCCTAC|
|292|21|1|1|1|1|GTGATCACGACGACGCCTACA|
|293|21|1|1|1|1|TGATCACGACGACGCCTACAC|
|294|21|1|1|1|1|GATCACGACGACGCCTACACC|
|295|21|1|1|1|1|ATCACGACGACGCCTACACCC|
|296|21|1|1|1|1|TCACGACGACGCCTACACCCC|
|297|21|1|1|1|1|CACGACGACGCCTACACCCCC|
|298|21|1|1|1|1|ACGACGACGCCTACACCCCCC|
|299|21|1|1|1|1|CGACGACGCCTACACCCCCCG|
|300|21|1|1|1|1|GACGACGCCTACACCCCCCGG|
|301|21|1|1|1|1|ACGACGCCTACACCCCCCGGG|
|302|21|1|1|1|1|CGACGCCTACACCCCCCGGGA|
|303|21|1|1|1|1|GACGCCTACACCCCCCGGGAC|
|304|21|1|1|1|1|ACGCCTACACCCCCCGGGACA|
|305|21|1|1|1|1|CGCCTACACCCCCCGGGACAG|
|306|21|1|1|1|1|GCCTACACCCCCCGGGACAGT|
|307|21|1|1|1|1|CCTACACCCCCCGGGACAGTA|
|308|21|1|1|1|1|CTACACCCCCCGGGACAGTACT|

FIG. 20P

| | | | | | |
|---|---|---|---|---|---|
|309|21|1|1|1|1|TACACCCCCGGGACAGTACTT|
|310|21|1|1|1|1|ACACCCCCGGGACAGTACTTT|
|311|21|1|1|1|1|CACCCCCGGGACAGTACTTTT|
|312|21|1|1|1|1|ACCCCCGGGACAGTACTTTTA|
|313|21|1|1|1|1|CCCCCGGGACAGTACTTTTAC|
|314|21|1|1|1|1|CCCCGGGACAGTACTTTTACC|
|315|21|1|1|1|1|CCCGGGACAGTACTTTTACCC|
|316|21|1|1|1|1|CCGGGACAGTACTTTTACCCC|
|317|21|1|1|1|1|CGGGACAGTACTTTTACCCCC|
|318|21|1|1|1|1|GGGACAGTACTTTTACCCCCG|
|319|21|1|1|1|1|GGACAGTACTTTTACCCCCGC|
|320|21|1|1|1|1|GACAGTACTTTTACCCCCGCG|
|321|21|1|1|1|1|ACAGTACTTTTACCCCCGCGG|
|322|21|1|1|1|1|CAGTACTTTTACCCCCGCGGG|
|323|21|1|1|1|1|AGTACTTTTACCCCCGCGGGG|
|324|21|1|1|1|1|GTACTTTTACCCCCGCGGGGT|
|325|21|1|1|1|1|TACTTTTACCCCCGCGGGGTG|
|326|21|1|1|1|1|ACTTTTACCCCCGCGGGGTGG|
|327|21|1|1|1|1|CTTTTACCCCCGCGGGGTGGC|
|328|21|1|1|1|1|TTTTACCCCCGCGGGGTGGCA|
|329|21|1|1|1|1|TTTACCCCCGCGGGGTGGCA|

FIG. 20Q

| | | | | | |
|---|---|---|---|---|---|
| 330 | 21 | 1 | 1 | 1 | 1 | TTACCCCGCGGGGTGGCAG |
| 331 | 21 | 1 | 1 | 1 | 1 | TACCCCGCGGGGTGGCAGC |
| 332 | 21 | 1 | 1 | 1 | 1 | ACCCCGCGGGGTGGCAGCG |
| 333 | 21 | 1 | 1 | 1 | 1 | CCCCCGCGGGGTGGCAGCGG |
| 334 | 21 | 1 | 1 | 1 | 1 | CCCCGCGGGGTGGCAGCGGT |
| 335 | 21 | 1 | 1 | 1 | 1 | CCCGCGGGGTGGCAGCGGTG |
| 336 | 21 | 1 | 1 | 1 | 1 | CCGCGGGGTGGCAGCGGTGG |
| 337 | 21 | 1 | 1 | 1 | 1 | CGCGGGGTGGCAGCGGTGGA |
| 338 | 21 | 1 | 1 | 1 | 1 | GCGGGGTGGCAGCGGTGGAG |
| 339 | 21 | 1 | 1 | 1 | 1 | CGGGGTGGCAGCGGTGGAGG |
| 340 | 21 | 1 | 1 | 1 | 1 | GGGGTGGCAGCGGTGGAGGT |
| 341 | 21 | 1 | 1 | 1 | 1 | GGGTGGCAGCGGTGGAGGTG |
| 342 | 21 | 1 | 1 | 1 | 1 | GGTGGCAGCGGTGGAGGTGC |
| 343 | 21 | 1 | 1 | 1 | 1 | GTGGCAGCGGTGGAGGTGCA |
| 344 | 21 | 1 | 1 | 1 | 1 | TGGCAGCGGTGGAGGTGCAG |
| 345 | 21 | 1 | 1 | 1 | 1 | GGCAGCGGTGGAGGTGCAGG |
| 346 | 21 | 1 | 1 | 1 | 1 | GCAGCGGTGGAGGTGCAGGG |
| 347 | 21 | 1 | 1 | 1 | 1 | CAGCGGTGGAGGTGCAGGGG |
| 348 | 21 | 1 | 1 | 1 | 1 | AGCGGTGGAGGTGCAGGGGC |
| 349 | 21 | 1 | 1 | 1 | 1 | GCGGTGGAGGTGCAGGGGCG |
| 350 | 21 | 1 | 1 | 1 | 1 | CGGTGGAGGTGCAGGGGGCG |

FIG. 20R

| | | | | | | |
|---|---|---|---|---|---|---|
| 351 | 21 | 1 | 1 | 1 | 1 | CGGTGGAGGTGCAGGGGCGC |
| 352 | 21 | 1 | 1 | 1 | 1 | GGTGGAGGTGCAGGGGCGCA |
| 353 | 21 | 1 | 1 | 1 | 1 | GTGGAGGTGCAGGGGCGCAG |
| 354 | 21 | 1 | 1 | 1 | 1 | TGGAGGTGCAGGGGCGCAGG |
| 355 | 21 | 1 | 1 | 1 | 1 | GGAGGTGCAGGGGCGCAGGG |
| 356 | 21 | 1 | 1 | 1 | 1 | GAGGTGCAGGGGCGCAGGGG |
| 357 | 21 | 1 | 1 | 1 | 1 | AGGTGCAGGGGCGCAGGGGG |
| 358 | 21 | 1 | 1 | 1 | 1 | GGTGCAGGGGCGCAGGGGGC |
| 359 | 21 | 1 | 1 | 1 | 1 | GTGCAGGGGCGCAGGGGGCG |
| 360 | 21 | 1 | 1 | 1 | 1 | TGCAGGGGCGCAGGGGGCGG |
| 361 | 21 | 1 | 1 | 1 | 1 | GCAGGGGCGCAGGGGGCGGC |
| 362 | 21 | 1 | 1 | 1 | 1 | CAGGGGCGCAGGGGGCGGCG |
| 363 | 21 | 1 | 1 | 1 | 1 | AGGGGCGCAGGGGGCGGCGT |
| 364 | 21 | 1 | 1 | 1 | 1 | GGGGCGCAGGGGGCGGCGTC |
| 365 | 21 | 1 | 1 | 1 | 1 | GGGCGCAGGGGGCGGCGTCA |
| 366 | 21 | 1 | 1 | 1 | 1 | GGCGCAGGGGGCGGCGTCAC |
| 367 | 21 | 1 | 1 | 1 | 1 | GCGCAGGGGGCGGCGTCACC |
| 368 | 21 | 1 | 1 | 1 | 2 | CGCAGGGGGCGGCGTCACCG |
| 369 | 21 | 1 | 2 | 2 | 2 | GCAGGGGGCGGCGTCACCGA |
| 370 | 21 | 2 | 2 | 2 | 2 | CAGGGGGCGGCGTCACCGAG |
| 371 | 21 | 2 | 2 | 2 | 2 | AGGGGGCGGCGTCACCGAGG |
| 372 | 21 | 2 | 2 | 2 | 2 | GGGGGCGGCGTCACCGAGGA |

FIG. 20S

| | | | | | |
|---|---|---|---|---|---|
| 373 | 21 | 2 | 2 | 2 | 2 | GGGGGCGGCCGTCACCGAGGAG |
| 374 | 21 | 2 | 2 | 2 | 2 | GGGGCGGCCGTCACCGAGGAGC |
| 375 | 21 | 2 | 2 | 2 | 2 | GGGCGGCCGTCACCGAGGAGCA |
| 376 | 21 | 2 | 2 | 2 | 2 | GGCGGCCGTCACCGAGGAGCAG |
| 377 | 21 | 2 | 2 | 2 | 2 | GCGGCCGTCACCGAGGAGCAGG |
| 378 | 21 | 2 | 2 | 2 | 2 | CGGCCGTCACCGAGGAGCAGGA |
| 379 | 21 | 2 | 2 | 2 | 2 | GGCCGTCACCGAGGAGCAGGAG |
| 380 | 21 | 2 | 2 | 2 | 2 | GCCGTCACCGAGGAGCAGGAGG |
| 381 | 21 | 2 | 2 | 2 | 2 | CCGTCACCGAGGAGCAGGAGGG |
| 382 | 21 | 2 | 2 | 2 | 2 | CGTCACCGAGGAGCAGGAGGGC |
| 383 | 21 | 2 | 2 | 2 | 3 | GTCACCGAGGAGCAGGAGGGCT |
| 384 | 21 | 1 | 3 | 3 | 3 | TCACCGAGGAGCAGGAGGGCTT |
| 385 | 21 | 1 | 3 | 3 | 3 | CACCGAGGAGCAGGAGGGCTTC |
| 386 | 21 | 1 | 3 | 3 | 3 | ACCGAGGAGCAGGAGGGCTTCG |
| 387 | 21 | 1 | 2 | 2 | 2 | CCGAGGAGCAGGAGGGCTTCGC |
| 388 | 21 | 1 | 2 | 2 | 2 | CGAGGAGCAGGAGGGCTTCGCC |
| 389 | 21 | 1 | 2 | 2 | 2 | GAGGAGCAGGAGGGCTTCGCCC |
| 390 | 21 | 1 | 2 | 2 | 2 | AGGAGCAGGAGGGCTTCGCCCG |
| 391 | 21 | 1 | 2 | 2 | 2 | GGAGCAGGAGGGCTTCGCCCGA |
| 392 | 21 | 1 | 2 | 2 | 2 | GAGCAGGAGGGCTTCGCCCGAC |
| 393 | 21 | 1 | 2 | 2 | 2 | AGCAGGAGGGCTTCGCCCGACG |
| | | | | | | GCAGGAGGGCTTCGCCCGACGG |

FIG. 20T

| | | | | | | |
|---|---|---|---|---|---|---|
| 394 | 21 | 1 | 2 | 2 | 2 | 2 | CAGGAGGGCTTCGCCCGACGGC |
| 395 | 21 | 1 | 2 | 2 | 2 | 2 | AGGAGGGCTTCGCCCGACGGCT |
| 396 | 21 | 1 | 2 | 2 | 2 | 2 | GGAGGGCTTCGCCCGACGGCTT |
| 397 | 21 | 1 | 1 | 1 | 1 | 1 | GAGGGCTTCGCCCGACGGCTTT |
| 398 | 21 | 1 | 1 | 1 | 1 | 1 | AGGGCTTCGCCCGACGGCTTTG |
| 399 | 21 | 1 | 1 | 1 | 1 | 1 | GGGCTTCGCCCGACGGCTTTGT |
| 400 | 21 | 1 | 1 | 1 | 1 | 1 | GGCTTCGCCCGACGGCTTTGTC |
| 401 | 21 | 1 | 1 | 1 | 1 | 1 | GCTTCGCCCGACGGCTTTGTCA |
| 402 | 21 | 1 | 1 | 1 | 1 | 1 | CTTCGCCCGACGGCTTTGTCAA |
| 403 | 21 | 1 | 1 | 1 | 1 | 1 | TTCGCCCGACGGCTTTGTCAAA |
| 404 | 21 | 1 | 1 | 1 | 1 | 1 | TCGCCCGACGGCTTTGTCAAAG |
| 405 | 21 | 1 | 1 | 1 | 1 | 1 | CGCCCGACGGCTTTGTCAAAGC |
| 406 | 21 | 1 | 1 | 1 | 1 | 1 | GCCCGACGGCTTTGTCAAAGCC |
| 407 | 21 | 1 | 1 | 1 | 1 | 1 | CCCGACGGCTTTGTCAAAGCCC |
| 408 | 21 | 1 | 1 | 1 | 1 | 1 | CCGACGGCTTTGTCAAAGCCCT |
| 409 | 21 | 1 | 2 | 2 | 2 | 2 | CGACGGCTTTGTCAAAGCCCTG |
| 410 | 21 | 1 | 2 | 2 | 2 | 2 | GACGGCTTTGTCAAAGCCCTGG |
| 411 | 21 | 1 | 2 | 2 | 2 | 2 | ACGGCTTTGTCAAAGCCCTGGA |
| 412 | 21 | 1 | 2 | 2 | 2 | 2 | CGGCTTTGTCAAAGCCCTGGAC |
| 413 | 21 | 1 | 2 | 2 | 2 | 2 | GGCTTTGTCAAAGCCCTGGACG |
| 414 | 21 | 1 | 2 | 2 | 2 | 2 | GCTTTGTCAAAGCCCTGGACGA |
| | | | | | | | CTTTGTCAAAGCCCTGGACGA |

FIG. 20U

| | | | | | |
|---|---|---|---|---|---|
| 415 | 21 | 1 | 2 | 2 | 2 | TTTGTCAAAGCCCTGGACGAT |
| 416 | 21 | 1 | 2 | 2 | 2 | TTGTCAAAGCCCTGGACGATC |
| 417 | 21 | 1 | 2 | 2 | 2 | TGTCAAAGCCCTGGACGATCT |
| 418 | 21 | 1 | 2 | 2 | 2 | GTCAAAGCCCTGGACGATCTG |
| 419 | 21 | 1 | 2 | 2 | 2 | TCAAAGCCCTGGACGATCTGC |
| 420 | 21 | 1 | 2 | 2 | 2 | CAAAGCCCTGGACGATCTGCA |
| 421 | 21 | 1 | 2 | 2 | 2 | AAAGCCCTGGACGATCTGCAC |
| 422 | 21 | 1 | 2 | 2 | 2 | AAGCCCTGGACGATCTGCACA |
| 423 | 21 | 1 | 2 | 2 | 2 | AGCCCTGGACGATCTGCACAA |
| 424 | 21 | 1 | 2 | 2 | 2 | GCCCTGGACGATCTGCACAAG |
| 425 | 21 | 1 | 2 | 2 | 2 | CCCTGGACGATCTGCACAAGA |
| 426 | 21 | 1 | 2 | 2 | 2 | CCTGGACGATCTGCACAAGAT |
| 427 | 21 | 1 | 2 | 2 | 2 | CTGGACGATCTGCACAAGATG |
| 428 | 21 | 1 | 2 | 2 | 2 | TGGACGATCTGCACAAGATGA |
| 429 | 21 | 1 | 2 | 2 | 2 | GGACGATCTGCACAAGATGAA |
| 430 | 21 | 1 | 2 | 2 | 2 | GACGATCTGCACAAGATGAAC |
| 431 | 21 | 1 | 2 | 2 | 2 | ACGATCTGCACAAGATGAACC |
| 432 | 21 | 1 | 2 | 2 | 2 | CGATCTGCACAAGATGAACCA |
| 433 | 21 | 1 | 2 | 2 | 2 | GATCTGCACAAGATGAACCAC |
| 434 | 21 | 1 | 2 | 2 | 2 | ATCTGCACAAGATGAACCACG |
| 435 | 21 | 1 | 2 | 2 | 2 | TCTGCACAAGATGAACCACGT |
| 436 | 21 | 2 | 2 | 2 | 2 | CTGCACAAGATGAACCACGTG |

FIG. 20V

| | | | | | |
|---|---|---|---|---|---|
| 437 | 21 | 2 | 2 | 2 | 2 | TGCACAAGATGAACCACGTGA |
| 438 | 21 | 2 | 2 | 2 | 2 | GCACAAGATGAACCACGTGAC |
| 439 | 21 | 1 | 2 | 2 | 2 | CACAAGATGAACCACGTGACA |
| 440 | 21 | 1 | 2 | 2 | 2 | ACAAGATGAACCACGTGACAC |
| 441 | 21 | 1 | 2 | 2 | 2 | CAAGATGAACCACGTGACACC |
| 442 | 21 | 1 | 2 | 2 | 2 | AAGATGAACCACGTGACACCC |
| 443 | 21 | 1 | 2 | 2 | 2 | AGATGAACCACGTGACACCCC |
| 444 | 21 | 1 | 2 | 2 | 2 | GATGAACCACGTGACACCCCC |
| 445 | 21 | 1 | 2 | 2 | 2 | ATGAACCACGTGACACCCCCC |
| 446 | 21 | 1 | 2 | 2 | 2 | TGAACCACGTGACACCCCCCA |
| 447 | 21 | 1 | 2 | 2 | 2 | GAACCACGTGACACCCCCCAA |
| 448 | 21 | 1 | 2 | 2 | 2 | AACCACGTGACACCCCCCAAC |
| 449 | 21 | 1 | 2 | 2 | 2 | ACCACGTGACACCCCCCAACG |
| 450 | 21 | 1 | 2 | 2 | 2 | CCACGTGACACCCCCCAACGT |
| 451 | 21 | 1 | 2 | 2 | 2 | CACGTGACACCCCCCAACGTG |
| 452 | 21 | 1 | 2 | 2 | 2 | ACGTGACACCCCCCAACGTGT |
| 453 | 21 | 1 | 2 | 2 | 2 | CGTGACACCCCCCAACGTGTC |
| 454 | 21 | 1 | 2 | 2 | 2 | GTGACACCCCCCAACGTGTCC |
| 455 | 21 | 1 | 2 | 2 | 2 | TGACACCCCCCAACGTGTCCC |
| 456 | 21 | 1 | 2 | 2 | 2 | GACACCCCCCAACGTGTCCCT |
| 457 | 21 | 1 | 2 | 2 | 2 | ACACCCCCCAACGTGTCCCTG |

FIG. 20W

| | | | | | | |
|---|---|---|---|---|---|---|
| 458 | 21 | 1 | 2 | 2 | 2 | CACCCCCAACGTGTCCCTGG |
| 459 | 21 | 1 | 2 | 2 | 2 | ACCCCCAACGTGTCCCTGGG |
| 460 | 21 | 2 | 2 | 2 | 2 | CCCCCAACGTGTCCCTGGGC |
| 461 | 21 | 2 | 2 | 2 | 2 | CCCCAACGTGTCCCTGGGCG |
| 462 | 21 | 2 | 2 | 2 | 2 | CCCAACGTGTCCCTGGGCGC |
| 463 | 21 | 1 | 2 | 2 | 2 | CCAACGTGTCCCTGGGCGCT |
| 464 | 21 | 1 | 2 | 2 | 2 | CAACGTGTCCCTGGGCGCTA |
| 465 | 21 | 1 | 1 | 1 | 1 | AACGTGTCCCTGGGCGCTAC |
| 466 | 21 | 1 | 1 | 1 | 1 | ACGTGTCCCTGGGCGCTACC |
| 467 | 21 | 1 | 1 | 1 | 1 | CGTGTCCCTGGGCGCTACCG |
| 468 | 21 | 1 | 1 | 1 | 1 | GTGTCCCTGGGCGCTACCGG |
| 469 | 21 | 1 | 1 | 1 | 1 | TGTCCCTGGGCGCTACCGGG |
| 470 | 21 | 1 | 1 | 1 | 1 | GTCCCTGGGCGCTACCGGGG |
| 471 | 21 | 1 | 1 | 1 | 1 | TCCCTGGGCGCTACCGGGGG |
| 472 | 21 | 1 | 1 | 1 | 1 | CCCTGGGCGCTACCGGGGGG |
| 473 | 21 | 1 | 1 | 1 | 1 | CCTGGGCGCTACCGGGGGGC |
| 474 | 21 | 1 | 1 | 1 | 1 | CTGGGCGCTACCGGGGGGCC |
| 475 | 21 | 1 | 1 | 1 | 1 | TGGGCGCTACCGGGGGGCCC |
| 476 | 21 | 1 | 1 | 1 | 1 | GGGCGCTACCGGGGGGCCCC |
| 477 | 21 | 1 | 1 | 1 | 1 | GGCGCTACCGGGGGGCCCCC |
| 478 | 21 | 1 | 1 | 1 | 1 | GCGCTACCGGGGGGCCCCCG |

FIG. 20X

| | | | | |
|---|---|---|---|---|
| 479 | 21 | 1 | 1 | 1 | 1 | GCGCTACCGGGGGGCCCCCGG |
| 480 | 21 | 1 | 1 | 1 | 1 | CGCTACCGGGGGGCCCCCGGC |
| 481 | 21 | 1 | 1 | 1 | 1 | GCTACCGGGGGGCCCCCGGCT |
| 482 | 21 | 1 | 1 | 1 | 1 | CTACCGGGGGGCCCCCGGCTG |
| 483 | 21 | 1 | 1 | 1 | 1 | TACCGGGGGGCCCCCGGCTGG |
| 484 | 21 | 1 | 1 | 1 | 1 | ACCGGGGGGCCCCCGGCTGGG |
| 485 | 21 | 1 | 1 | 1 | 1 | CCGGGGGGCCCCCGGCTGGGC |
| 486 | 21 | 1 | 1 | 1 | 1 | CGGGGGGCCCCCGGCTGGGCC |
| 487 | 21 | 1 | 1 | 1 | 1 | GGGGGGCCCCCGGCTGGGCCC |
| 488 | 21 | 1 | 1 | 1 | 1 | GGGGGCCCCCGGCTGGGCCCC |
| 489 | 21 | 1 | 1 | 1 | 1 | GGGGCCCCCGGCTGGGCCCCG |
| 490 | 21 | 1 | 1 | 1 | 1 | GGGCCCCCGGCTGGGCCCCGG |
| 491 | 21 | 1 | 1 | 1 | 1 | GGCCCCCGGCTGGGCCCCGGG |
| 492 | 21 | 1 | 1 | 1 | 1 | GCCCCCGGCTGGGCCCCGGGG |
| 493 | 21 | 1 | 1 | 1 | 1 | CCCCCGGCTGGGCCCCGGGGG |
| 494 | 21 | 1 | 1 | 1 | 1 | CCCCGGCTGGGCCCCGGGGGC |
| 495 | 21 | 1 | 1 | 1 | 1 | CCCGGCTGGGCCCCGGGGGCG |
| 496 | 21 | 1 | 1 | 1 | 1 | CCGGCTGGGCCCCGGGGGCGT |
| 497 | 21 | 1 | 1 | 1 | 1 | CGGCTGGGCCCCGGGGGCGTC |
| 498 | 21 | 1 | 1 | 1 | 1 | GGCTGGGCCCCGGGGGCGTCT |
| 499 | 21 | 1 | 1 | 1 | 1 | GCTGGGCCCCGGGGGCGTCTA |
| 500 | 21 | 1 | 1 | 1 | 1 | CTGGGCCCCGGGGGCGTCTAC |

FIG. 20Y

| | | | | | | |
|---|---|---|---|---|---|---|
| 501 | 21 | 1 | 1 | 1 | 1 | TGGGCCCGGGGGCGTCTACGC |
| 502 | 21 | 1 | 1 | 1 | 1 | GGGCCCGGGGGCGTCTACGCC |
| 503 | 21 | 1 | 1 | 1 | 1 | GGCCCGGGGGCGTCTACGCCG |
| 504 | 21 | 1 | 1 | 1 | 1 | GCCCGGGGGCGTCTACGCCGG |
| 505 | 21 | 1 | 1 | 1 | 1 | CCCGGGGGCGTCTACGCCGGC |
| 506 | 21 | 1 | 1 | 1 | 1 | CCGGGGGCGTCTACGCCGGCC |
| 507 | 21 | 1 | 1 | 1 | 1 | CGGGGGCGTCTACGCCGGCCC |
| 508 | 21 | 1 | 1 | 1 | 1 | GGGGGCGTCTACGCCGGCCCG |
| 509 | 21 | 1 | 1 | 1 | 1 | GGGGCGTCTACGCCGGCCCCG |
| 510 | 21 | 1 | 1 | 1 | 1 | GGGCGTCTACGCCGGCCCCGA |
| 511 | 21 | 1 | 1 | 1 | 1 | GGCGTCTACGCCGGCCCCGGAG |
| 512 | 21 | 1 | 1 | 1 | 1 | GCGTCTACGCCGGCCCCGGAGC |
| 513 | 21 | 1 | 1 | 1 | 1 | CGTCTACGCCGGCCCCGGAGCC |
| 514 | 21 | 1 | 1 | 1 | 1 | GTCTACGCCGGCCCCGGAGCCA |
| 515 | 21 | 1 | 1 | 1 | 1 | TCTACGCCGGCCCCGGAGCCAC |
| 516 | 21 | 1 | 1 | 1 | 1 | CTACGCCGGCCCCGGAGCCACC |
| 517 | 21 | 1 | 1 | 1 | 1 | TACGCCGGCCCCGGAGCCACCT |
| 518 | 21 | 1 | 1 | 1 | 1 | ACGCCGGCCCGGAGCCACCTC |
| 519 | 21 | 1 | 1 | 1 | 1 | CGCCGGCCCGGAGCCACCTCC |
| 520 | 21 | 1 | 1 | 1 | 1 | GCCGGCCCGGAGCCACCTCCC |
| 521 | 21 | 1 | 1 | 1 | 1 | CCGGCCCGGAGCCACCTCCCG |

FIG. 20Z

| | | | | | |
|---|---|---|---|---|---|
| 522 | 21 | 1 | 1 | 1 | 1 | CGGCCCGGAGCCACCTCCCGT |
| 523 | 21 | 1 | 1 | 1 | 1 | GGCCCGGAGCCACCTCCCGTT |
| 524 | 21 | 1 | 1 | 1 | 1 | GCCCGGAGCCACCTCCCGTTT |
| 525 | 21 | 1 | 1 | 1 | 1 | CCCGGAGCCACCTCCCGTTTA |
| 526 | 21 | 1 | 1 | 1 | 1 | CCGGAGCCACCTCCCGTTTAC |
| 527 | 21 | 1 | 1 | 1 | 1 | CGGAGCCACCTCCCGTTTACA |
| 528 | 21 | 1 | 1 | 1 | 1 | GGAGCCACCTCCCGTTTACAC |
| 529 | 21 | 1 | 1 | 1 | 1 | GAGCCACCTCCCGTTTACACC |
| 530 | 21 | 1 | 1 | 1 | 1 | AGCCACCTCCCGTTTACACCA |
| 531 | 21 | 1 | 1 | 1 | 1 | GCCACCTCCCGTTTACACCAA |
| 532 | 21 | 1 | 1 | 1 | 1 | CCACCTCCCGTTTACACCAAC |
| 533 | 21 | 1 | 1 | 1 | 1 | CACCTCCCGTTTACACCAACC |
| 534 | 21 | 1 | 1 | 1 | 2 | ACCTCCCGTTTACACCAACCT |
| 535 | 21 | 2 | 2 | 2 | 2 | CCTCCCGTTTACACCAACCTC |
| 536 | 21 | 2 | 2 | 2 | 2 | CTCCCGTTTACACCAACCTCA |
| 537 | 21 | 2 | 2 | 2 | 2 | TCCCGTTTACACCAACCTCAG |
| 538 | 21 | 2 | 2 | 2 | 2 | CCCGTTTACACCAACCTCAGC |
| 539 | 21 | 2 | 2 | 2 | 2 | CCGTTTACACCAACCTCAGCA |
| 540 | 21 | 2 | 2 | 2 | 1 | CGTTTACACCAACCTCAGCAG |
| 541 | 21 | 1 | 1 | 1 | 1 | GTTTACACCAACCTCAGCAGC |
| 542 | 21 | 1 | 1 | 1 | 1 | TTTACACCAACCTCAGCAGCT |

FIG. 20A-1

| | | | | | |
|---|---|---|---|---|---|
| 543 | 21 | 1 | 1 | 1 | 1 | TTACACCAACCTCAGCAGCTA |
| 544 | 21 | 1 | 2 | 2 | 2 | TACACCAACCTCAGCAGCTAC |
| 545 | 21 | 1 | 2 | 2 | 2 | ACACCAACCTCAGCAGCTACT |
| 546 | 21 | 1 | 2 | 2 | 2 | CACCAACCTCAGCAGCTACTC |
| 547 | 21 | 1 | 1 | 1 | 1 | ACCAACCTCAGCAGCTACTCC |
| 548 | 21 | 1 | 1 | 1 | 1 | CCAACCTCAGCAGCTACTCCC |
| 549 | 21 | 1 | 1 | 1 | 1 | CAACCTCAGCAGCTACTCCCC |
| 550 | 21 | 1 | 1 | 1 | 1 | AACCTCAGCAGCTACTCCCCA |
| 551 | 21 | 1 | 1 | 1 | 1 | ACCTCAGCAGCTACTCCCCAG |
| 552 | 21 | 1 | 1 | 1 | 1 | CCTCAGCAGCTACTCCCCAGC |
| 553 | 21 | 1 | 1 | 1 | 1 | CTCAGCAGCTACTCCCCAGCC |
| 554 | 21 | 1 | 1 | 1 | 1 | TCAGCAGCTACTCCCCAGCCT |
| 555 | 21 | 1 | 1 | 1 | 1 | CAGCAGCTACTCCCCAGCCTC |
| 556 | 21 | 1 | 1 | 1 | 1 | AGCAGCTACTCCCCAGCCTCT |
| 557 | 21 | 1 | 1 | 1 | 1 | GCAGCTACTCCCCAGCCTCTG |
| 558 | 21 | 1 | 1 | 1 | 1 | CAGCTACTCCCCAGCCTCTGC |
| 559 | 21 | 1 | 1 | 1 | 1 | AGCTACTCCCCAGCCTCTGCG |
| 560 | 21 | 1 | 1 | 1 | 1 | GCTACTCCCCAGCCTCTGCGT |
| 561 | 21 | 1 | 1 | 1 | 1 | CTACTCCCCAGCCTCTGCGTC |
| 562 | 21 | 1 | 1 | 1 | 1 | TACTCCCCAGCCTCTGCGTCC |
| 563 | 21 | 1 | 1 | 1 | 1 | ACTCCCCAGCCTCTGCGTCCT |
| 564 | 21 | 1 | 1 | 1 | 1 | CTCCCCAGCCTCTGCGTCCTC |

FIG. 20A-2

| | | | | | |
|---|---|---|---|---|---|
| 565 | 21 | 1 | 1 | 1 | TCCCCAGCCTCTGCGTCCTCG |
| 566 | 21 | 1 | 1 | 1 | CCCCAGCCCTCTGCGTCCTCGG |
| 567 | 21 | 1 | 1 | 1 | CCAGCCCTCTGCGTCCTCGG |
| 568 | 21 | 1 | 1 | 1 | CCAGCCCTCTGCGTCCTCGGG |
| 569 | 21 | 1 | 1 | 1 | CAGCCCTCTGCGTCCTCGGGA |
| 570 | 21 | 1 | 1 | 1 | AGCCTCTGCGTCCTCGGGAG |
| 571 | 21 | 1 | 1 | 1 | GCCTCTGCGTCCTCGGGAGG |
| 572 | 21 | 1 | 1 | 1 | CCTCTGCGTCCTCGGGAGGC |
| 573 | 21 | 1 | 1 | 1 | CTCTGCGTCCTCGGGAGGCG |
| 574 | 21 | 1 | 1 | 1 | TCTGCGTCCTCGGGAGGCGC |
| 575 | 21 | 1 | 1 | 1 | CTGCGTCCTCGGGAGGCGCC |
| 576 | 21 | 1 | 1 | 1 | TGCGTCCTCGGGAGGCGCCG |
| 577 | 21 | 1 | 1 | 1 | GCGTCCTCGGGAGGCGCCGG |
| 578 | 21 | 1 | 1 | 1 | CGTCCTCGGGAGGCGCCGGG |
| 579 | 21 | 1 | 1 | 1 | GTCCTCGGGAGGCGCCGGGC |
| 580 | 21 | 1 | 1 | 1 | TCCTCGGGAGGCGCCGGGCT |
| 581 | 21 | 1 | 1 | 1 | CCTCGGGAGGCGCCGGGCTG |
| 582 | 21 | 1 | 1 | 1 | CTCGGGAGGCGCCGGGCTGC |
| 583 | 21 | 1 | 1 | 1 | TCGGGAGGCGCCGGGCTGCC |
| 584 | 21 | 1 | 1 | 1 | CGGGAGGCGCCGGGCTGCCG |
| 585 | 21 | 1 | 1 | 1 | GGGAGGCGCCGGGCTGCCGT |

FIG. 20A-3

| | | | | | | |
|---|---|---|---|---|---|---|
| 586 | 21 | 1 | 1 | 1 | 1 | GGAGGGCGCCGGGGCTGCCGTC |
| 587 | 21 | 1 | 1 | 1 | 1 | GAGGCGCCGGGGCTGCCGTCG |
| 588 | 21 | 1 | 1 | 1 | 1 | AGGCGCCGGGGCTGCCGTCGG |
| 589 | 21 | 1 | 1 | 1 | 1 | GGCGCCGGGGCTGCCGTCGGG |
| 590 | 21 | 1 | 1 | 1 | 1 | GCGCCGGGGCTGCCGTCGGGA |
| 591 | 21 | 1 | 1 | 1 | 1 | CGCCGGGGCTGCCGTCGGGAC |
| 592 | 21 | 1 | 1 | 1 | 1 | GCCGGGGCTGCCGTCGGGACC |
| 593 | 21 | 1 | 1 | 1 | 1 | CCGGGGCTGCCGTCGGGACCG |
| 594 | 21 | 1 | 1 | 1 | 1 | CGGGGCTGCCGTCGGGACCGG |
| 595 | 21 | 1 | 1 | 1 | 1 | GGGGCTGCCGTCGGGACCGGG |
| 596 | 21 | 1 | 1 | 1 | 1 | GGGCTGCCGTCGGGACCGGGA |
| 597 | 21 | 1 | 1 | 1 | 1 | GGCTGCCGTCGGGACCGGGAG |
| 598 | 21 | 1 | 1 | 1 | 1 | GCTGCCGTCGGGACCGGGAGC |
| 599 | 21 | 1 | 1 | 1 | 1 | CTGCCGTCGGGACCGGGAGCT |
| 600 | 21 | 1 | 1 | 1 | 1 | TGCCGTCGGGACCGGGAGCTC |
| 601 | 21 | 1 | 1 | 1 | 1 | GCCGTCGGGACCGGGAGCTCG |
| 602 | 21 | 1 | 1 | 1 | 1 | CCGTCGGGACCGGGAGCTCGT |
| 603 | 21 | 1 | 1 | 1 | 1 | CGTCGGGACCGGGAGCTCGTA |
| 604 | 21 | 1 | 1 | 1 | 1 | GTCGGGACCGGGAGCTCGTAC |
| 605 | 21 | 1 | 1 | 1 | 1 | TCGGGACCGGGAGCTCGTACC |
| 606 | 21 | 1 | 1 | 1 | 1 | CGGGACCGGGAGCTCGTACCC |

FIG. 20A-4

| | | | | | |
|---|---|---|---|---|---|
| 607 | 21 | 1 | 1 | 1 | 1 | GGGACCCGGGAGCTCGTACCCG |
| 608 | 21 | 1 | 1 | 1 | 1 | GGACCCGGGAGCTCGTACCCGA |
| 609 | 21 | 1 | 1 | 1 | 1 | GACCCGGGAGCTCGTACCCGAC |
| 610 | 21 | 1 | 1 | 1 | 1 | ACCCGGGAGCTCGTACCCGACG |
| 611 | 21 | 1 | 1 | 1 | 1 | CCCGGGAGCTCGTACCCGACGA |
| 612 | 21 | 1 | 1 | 1 | 1 | CCGGGAGCTCGTACCCGACGAC |
| 613 | 21 | 1 | 1 | 1 | 1 | CGGGAGCTCGTACCCGACGACC |
| 614 | 21 | 1 | 1 | 1 | 1 | GGGAGCTCGTACCCGACGACCA |
| 615 | 21 | 1 | 1 | 1 | 1 | GGAGCTCGTACCCGACGACCAC |
| 616 | 21 | 1 | 1 | 1 | 1 | GAGCTCGTACCCGACGACCACC |
| 617 | 21 | 1 | 1 | 1 | 1 | AGCTCGTACCCGACGACCACCA |
| 618 | 21 | 1 | 1 | 1 | 1 | GCTCGTACCCGACGACCACCAT |
| 619 | 21 | 1 | 1 | 1 | 1 | CTCGTACCCGACGACCACCATC |
| 620 | 21 | 1 | 1 | 1 | 1 | TCGTACCCGACGACCACCATCA |
| 621 | 21 | 2 | 2 | 2 | 2 | CGTACCCGACGACCACCATCAG |
| 622 | 21 | 2 | 2 | 2 | 2 | GTACCCGACGACCACCATCAGC |
| 623 | 21 | 2 | 2 | 2 | 2 | TACCCGACGACCACCATCAGCT |
| 624 | 21 | 2 | 2 | 2 | 2 | ACCCGACGACCACCATCAGCTA |
| 625 | 21 | 2 | 2 | 2 | 2 | CCCGACGACCACCATCAGCTAC |
| 626 | 21 | 2 | 2 | 2 | 2 | CCGACGACCACCATCAGCTACC |
| 627 | 21 | 2 | 2 | 2 | 2 | CGACGACCACCATCAGCTACCT |
| 628 | 21 | 2 | 2 | 2 | 2 | GACGACCACCATCAGCTACCTC |

FIG. 20A-5

| | | | | | | | |
|---|---|---|---|---|---|---|---|
| 629 | 21 | 1 | 2 | 2 | 2 | 2 | CGACCACCATCAGCTACCTCC |
| 630 | 21 | 1 | 2 | 2 | 2 | 2 | GACCACCATCAGCTACCTCCC |
| 631 | 21 | 1 | 2 | 2 | 2 | 2 | ACCACCATCAGCTACCTCCCA |
| 632 | 21 | 2 | 2 | 2 | 2 | 2 | CCACCATCAGCTACCTCCCAC |
| 633 | 21 | 2 | 2 | 2 | 2 | 2 | CACCATCAGCTACCTCCCACA |
| 634 | 21 | 1 | 2 | 2 | 2 | 2 | ACCATCAGCTACCTCCCACAC |
| 635 | 21 | 1 | 2 | 2 | 2 | 2 | CCATCAGCTACCTCCCACACG |
| 636 | 21 | 1 | 2 | 2 | 2 | 2 | CATCAGCTACCTCCCACACGC |
| 637 | 21 | 1 | 1 | 1 | 1 | 1 | ATCAGCTACCTCCCACACGCG |
| 638 | 21 | 1 | 1 | 1 | 1 | 1 | TCAGCTACCTCCCACACGCCG |
| 639 | 21 | 1 | 1 | 1 | 1 | 1 | CAGCTACCTCCCACACGCGCC |
| 640 | 21 | 1 | 1 | 1 | 1 | 1 | AGCTACCTCCCACACGCGCCG |
| 641 | 21 | 1 | 1 | 1 | 1 | 1 | GCTACCTCCCACACGCGCCGC |
| 642 | 21 | 1 | 1 | 1 | 1 | 1 | CTACCTCCCACACGCGCCGCC |
| 643 | 21 | 1 | 1 | 1 | 1 | 1 | TACCTCCCACACGCGCCGCCC |
| 644 | 21 | 1 | 1 | 1 | 1 | 1 | ACCTCCCACACGCGCCGCCCT |
| 645 | 21 | 1 | 1 | 1 | 1 | 1 | CCTCCCACACGCGCCGCCCTT |
| 646 | 21 | 1 | 1 | 1 | 1 | 1 | CTCCCACACGCGCCGCCCTTC |
| 647 | 21 | 1 | 1 | 1 | 1 | 1 | TCCCACACGCGCCGCCCTTCG |
| 648 | 21 | 1 | 1 | 1 | 1 | 1 | CCCACACGCGCCGCCCTTCGC |
| 649 | 21 | 1 | 1 | 1 | 1 | 1 | CCACACGCGCCGCCCTTCGCC |

FIG. 20A-6

| | | | | | |
|---|---|---|---|---|---|
| 650 | 21 | 1 | 1 | 1 | 1 | CACACGGCGCCGCCCTTCGCCCG |
| 651 | 21 | 1 | 1 | 1 | 1 | ACACGGCGCCGCCCTTCGCCCGG |
| 652 | 21 | 1 | 1 | 1 | 1 | CACGGCGCCGCCCTTCGCCCGGT |
| 653 | 21 | 1 | 1 | 1 | 1 | ACGGCGCCGCCCTTCGCCCGGTG |
| 654 | 21 | 1 | 1 | 1 | 1 | CGGCGCCGCCCTTCGCCCGGTGG |
| 655 | 21 | 1 | 1 | 1 | 1 | GGCGCCGCCCTTCGCCCGGTGGC |
| 656 | 21 | 1 | 1 | 1 | 1 | GCGCCGCCCTTCGCCCGGTGGCC |
| 657 | 21 | 1 | 1 | 1 | 1 | CGCCGCCCTTCGCCCGGTGGCCA |
| 658 | 21 | 1 | 1 | 1 | 1 | GCCGCCCTTCGCCCGGTGGCCAC |
| 659 | 21 | 1 | 1 | 1 | 1 | CCGCCCTTCGCCCGGTGGCCACC |
| 660 | 21 | 1 | 1 | 1 | 1 | CGCCCTTCGCCCGGTGGCCACCC |
| 661 | 21 | 1 | 1 | 1 | 1 | GCCCTTCGCCCGGTGGCCACCCG |
| 662 | 21 | 1 | 1 | 1 | 1 | CCCTTCGCCCGGTGGCCACCCGG |
| 663 | 21 | 1 | 1 | 1 | 1 | CCTTCGCCCGGTGGCCACCCGGC |
| 664 | 21 | 1 | 1 | 1 | 1 | CTTCGCCCGGTGGCCACCCGGCG |
| 665 | 21 | 1 | 1 | 1 | 1 | TTCGCCCGGTGGCCACCCGGCGC |
| 666 | 21 | 1 | 1 | 1 | 1 | TCGCCCGGTGGCCACCCGGCGCA |
| 667 | 21 | 1 | 1 | 1 | 1 | CGCCCGGTGGCCACCCGGCGCAG |
| 668 | 21 | 1 | 1 | 1 | 1 | GCCCGGTGGCCACCCGGCGCAGC |
| 669 | 21 | 1 | 1 | 1 | 1 | CCCGGTGGCCACCCGGCGCAGCT |
| 670 | 21 | 1 | 1 | 1 | 1 | GGTGGCCACCCGGCGCAGCTG |

FIG. 20A-7

| | | | | | |
|---|---|---|---|---|---|
| 671 | 21 | 1 | 1 | 1 | GTGGCCACCCGGCGCAGCTGG |
| 672 | 21 | 1 | 1 | 1 | TGGCCACCCGGCGCAGCTGGG |
| 673 | 21 | 1 | 1 | 1 | GGCCACCCGGCGCAGCTGGGC |
| 674 | 21 | 1 | 1 | 1 | GCCACCCGGCGCAGCTGGGCT |
| 675 | 21 | 1 | 1 | 1 | CCACCCGGCGCAGCTGGGCTT |
| 676 | 21 | 1 | 1 | 1 | CACCCGGCGCAGCTGGGCTTG |
| 677 | 21 | 1 | 1 | 1 | ACCCGGCGCAGCTGGGCTTGG |
| 678 | 21 | 1 | 1 | 1 | CCCGGCGCAGCTGGGCTTGGG |
| 679 | 21 | 1 | 1 | 1 | CCGGCGCAGCTGGGCTTGGGC |
| 680 | 21 | 1 | 1 | 1 | CGGCGCAGCTGGGCTTGGGCC |
| 681 | 21 | 1 | 1 | 1 | GGCGCAGCTGGGCTTGGGCCG |
| 682 | 21 | 1 | 1 | 1 | GCGCAGCTGGGCTTGGGCCGC |
| 683 | 21 | 1 | 1 | 1 | CGCAGCTGGGCTTGGGCCGCG |
| 684 | 21 | 1 | 1 | 1 | GCAGCTGGGCTTGGGCCGCGG |
| 685 | 21 | 1 | 1 | 1 | CAGCTGGGCTTGGGCCGCGGC |
| 686 | 21 | 1 | 1 | 1 | AGCTGGGCTTGGGCCGCGGCG |
| 687 | 21 | 1 | 1 | 1 | GCTGGGCTTGGGCCGCGGCGC |
| 688 | 21 | 1 | 1 | 1 | CTGGGCTTGGGCCGCGGCGCC |
| 689 | 21 | 1 | 1 | 1 | TGGGCTTGGGCCGCGGCGCCT |
| 690 | 21 | 1 | 1 | 1 | GGGCTTGGGCCGCGGCGCCTC |
| 691 | 21 | 1 | 1 | 1 | GGCTTGGGCCGCGGCGCCTCC |
| 692 | 21 | 1 | 1 | 1 | GCTTGGGCCGCGGCGCCTCCA |

FIG. 20A-8

| | | | | | |
|---|---|---|---|---|---|
| 693 | 21 | 1 | 1 | 1 | 1 | CTTGGGCCGGCGCGCCTCCAC |
| 694 | 21 | 1 | 1 | 1 | 1 | TTGGGCCGGCGCGCCTCCACC |
| 695 | 21 | 1 | 1 | 1 | 1 | TGGGCCGGCGCGCCTCCACCT |
| 696 | 21 | 1 | 1 | 1 | 1 | GGGCCGGCGCGCCTCCACCTT |
| 697 | 21 | 1 | 1 | 1 | 1 | GGCCGGCGCGCCTCCACCTTC |
| 698 | 21 | 1 | 1 | 1 | 1 | GCCGGCGCGCCTCCACCTTCA |
| 699 | 21 | 1 | 1 | 1 | 1 | CCGGCGCGCCTCCACCTTCAA |
| 700 | 21 | 1 | 1 | 1 | 1 | CGGCGCGCCTCCACCTTCAAG |
| 701 | 21 | 1 | 1 | 1 | 1 | GGCGCGCCTCCACCTTCAAGG |
| 702 | 21 | 1 | 1 | 1 | 1 | GCGCGCCTCCACCTTCAAGGA |
| 703 | 21 | 1 | 1 | 1 | 1 | CGCGCCTCCACCTTCAAGGAG |
| 704 | 21 | 1 | 1 | 1 | 1 | GCGCCTCCACCTTCAAGGAGG |
| 705 | 21 | 1 | 1 | 1 | 1 | CGCCTCCACCTTCAAGGAGGA |
| 706 | 21 | 1 | 1 | 1 | 1 | GCCTCCACCTTCAAGGAGGAA |
| 707 | 21 | 1 | 1 | 1 | 1 | CCTCCACCTTCAAGGAGGAAC |
| 708 | 21 | 1 | 1 | 1 | 1 | CTCCACCTTCAAGGAGGAACC |
| 709 | 21 | 1 | 1 | 1 | 1 | TCCACCTTCAAGGAGGAACCG |
| 710 | 21 | 1 | 1 | 1 | 1 | CCACCTTCAAGGAGGAACCGC |
| 711 | 21 | 1 | 1 | 1 | 1 | CACCTTCAAGGAGGAACCGCA |
| 712 | 21 | 1 | 1 | 1 | 1 | ACCTTCAAGGAGGAACCGCAG |
| 713 | 21 | 1 | 1 | 1 | 1 | CCTTCAAGGAGGAACCGCAGA |

FIG. 20A-9

| | | | | | | |
|---|---|---|---|---|---|---|
|714|21|1|1|1|1|CTTCAAGGAGGAACCGCAGAC|
|715|21|1|1|1|1|TTCAAGGAGGAACCGCAGACC|
|716|21|1|1|1|1|TCAAGGAGGAACCGCAGACCG|
|717|21|1|1|1|1|CAAGGAGGAACCGCAGACCGT|
|718|21|1|1|1|1|AAGGAGGAACCGCAGACCGTG|
|719|21|1|1|1|1|AGGAGGAACCGCAGACCGTGC|
|720|21|1|1|1|1|GGAGGAACCGCAGACCGTGCC|
|721|21|1|1|1|2|GAGGAACCGCAGACCGTGCCG|
|722|21|2|2|2|2|AGGAACCGCAGACCGTGCCGG|
|723|21|2|2|2|2|GGAACCGCAGACCGTGCCGGA|
|724|21|3|3|3|3|GAACCGCAGACCGTGCCGGAG|
|725|21|2|2|2|2|AACCGCAGACCGTGCCGGAGG|
|726|21|2|2|2|2|ACCGCAGACCGTGCCGGAGGC|
|727|21|1|1|1|1|CCGCAGACCGTGCCGGAGGCG|
|728|21|1|1|1|1|CGCAGACCGTGCCGGAGGCGC|
|729|21|1|1|1|1|GCAGACCGTGCCGGAGGCGCG|
|730|21|1|1|1|1|CAGACCGTGCCGGAGGCGCGC|
|731|21|1|1|1|1|AGACCGTGCCGGAGGCGCGCA|
|732|21|1|1|1|1|GACCGTGCCGGAGGCGCGCAG|
|733|21|1|1|1|1|ACCGTGCCGGAGGCGCGCAGC|
|734|21|1|1|1|1|CCGTGCCGGAGGCGCGCAGCC|

FIG. 20A-10

| | | | | | | |
|---|---|---|---|---|---|---|
| 735 | 21 | 1 | 1 | 1 | 1 | CGTGCCGGAGGCGCGCAGCCG |
| 736 | 21 | 1 | 1 | 1 | 1 | GTGCCGGAGGCGCGCAGCCGG |
| 737 | 21 | 1 | 1 | 1 | 1 | TGCCGGAGGCGCGCAGCCGGG |
| 738 | 21 | 1 | 1 | 1 | 1 | GCCGGAGGCGCGCAGCCGGGA |
| 739 | 21 | 1 | 1 | 1 | 1 | CCGGAGGCGCGCAGCCGGGAC |
| 740 | 21 | 1 | 1 | 1 | 1 | CGGAGGCGCGCAGCCGGGACG |
| 741 | 21 | 1 | 1 | 1 | 1 | GGAGGCGCGCAGCCGGGACGC |
| 742 | 21 | 1 | 1 | 1 | 1 | GAGGCGCGCAGCCGGGACGCC |
| 743 | 21 | 1 | 1 | 1 | 1 | AGGCGCGCAGCCGGGACGCCA |
| 744 | 21 | 1 | 1 | 1 | 1 | GGCGCGCAGCCGGGACGCCAC |
| 745 | 21 | 1 | 1 | 1 | 1 | GCGCGCAGCCGGGACGCCACG |
| 746 | 21 | 2 | 2 | 2 | 1 | CGCGCAGCCGGGACGCCACGC |
| 747 | 21 | 2 | 2 | 2 | 1 | GCGCAGCCGGGACGCCACGCC |
| 748 | 21 | 2 | 2 | 2 | 1 | CGCAGCCGGGACGCCACGCCG |
| 749 | 21 | 1 | 1 | 1 | 1 | GCAGCCGGGACGCCACGCCGC |
| 750 | 21 | 1 | 1 | 1 | 1 | CAGCCGGGACGCCACGCCGCC |
| 751 | 21 | 1 | 1 | 1 | 1 | AGCCGGGACGCCACGCCGCCG |
| 752 | 21 | 1 | 1 | 1 | 1 | GCCGGGACGCCACGCCGCCGG |
| 753 | 21 | 1 | 1 | 1 | 1 | CCGGGACGCCACGCCGCCGGT |
| 754 | 21 | 1 | 1 | 1 | 1 | CGGGACGCCACGCCGCCGGTG |
| 755 | 21 | 1 | 1 | 1 | 1 | GGGACGCCACGCCGCCGGTGT |
| 756 | 21 | 1 | 1 | 1 | 1 | GGACGCCACGCCGCCGGTGTC |

FIG. 20A-11

| | | | | | |
|---|---|---|---|---|---|
|757|21|1|2|2|2|GACGCCACGCCGCCGGTGTCC|
|758|21|1|2|2|2|ACGCCACGCCGCCGGTGTCCC|
|759|21|1|2|2|2|CGCCACGCCGCCGGTGTCCCC|
|760|21|1|2|2|2|GCCACGCCGCCGGTGTCCCCC|
|761|21|1|2|2|2|CCACGCCGCCGGTGTCCCCCA|
|762|21|1|2|2|2|CACGCCGCCGGTGTCCCCCAT|
|763|21|1|2|2|2|ACGCCGCCGGTGTCCCCCATC|
|764|21|1|2|2|2|CGCCGCCGGTGTCCCCCATCA|
|765|21|1|2|2|2|GCCGCCGGTGTCCCCCATCAA|
|766|21|1|2|2|2|CCGCCGGTGTCCCCCATCAAC|
|767|21|1|2|2|2|CGCCGGTGTCCCCCATCAACA|
|768|21|1|2|2|2|GCCGGTGTCCCCCATCAACAT|
|769|21|1|2|2|2|CCGGTGTCCCCCATCAACATG|
|770|21|1|2|2|2|CGGTGTCCCCCATCAACATGG|
|771|21|2|2|2|2|GGTGTCCCCCATCAACATGGA|
|772|21|2|2|2|2|GTGTCCCCCATCAACATGGAA|
|773|21|2|2|2|2|TGTCCCCCATCAACATGGAAG|
|774|21|2|2|2|2|GTCCCCCATCAACATGGAAGA|
|775|21|2|2|2|2|TCCCCCATCAACATGGAAGAC|
|776|21|2|2|2|2|CCCCCATCAACATGGAAGACC|
|777|21|2|2|2|2|CCCCATCAACATGGAAGACCA|

FIG. 20A-12

| | | | | | |
|---|---|---|---|---|---|
| 778 | 21 | 1 | 2 | 2 | 2 | CCCATCAACATGGAAGACCAA |
| 779 | 21 | 1 | 2 | 2 | 2 | CCATCAACATGGAAGACCAAG |
| 780 | 21 | 1 | 2 | 2 | 2 | CATCAACATGGAAGACCAAGA |
| 781 | 21 | 1 | 2 | 2 | 2 | ATCAACATGGAAGACCAAGAG |
| 782 | 21 | 1 | 2 | 2 | 2 | TCAACATGGAAGACCAAGAGC |
| 783 | 21 | 1 | 2 | 2 | 2 | CAACATGGAAGACCAAGAGCG |
| 784 | 21 | 1 | 2 | 2 | 2 | AACATGGAAGACCAAGAGCGC |
| 785 | 21 | 1 | 2 | 2 | 2 | ACATGGAAGACCAAGAGCGCA |
| 786 | 21 | 1 | 2 | 2 | 2 | CATGGAAGACCAAGAGCGCAT |
| 787 | 21 | 1 | 2 | 2 | 2 | ATGGAAGACCAAGAGCGCATC |
| 788 | 21 | 1 | 2 | 2 | 2 | TGGAAGACCAAGAGCGCATCA |
| 789 | 21 | 1 | 2 | 2 | 2 | GGAAGACCAAGAGCGCATCAA |
| 790 | 21 | 1 | 2 | 2 | 2 | GAAGACCAAGAGCGCATCAAA |
| 791 | 21 | 1 | 2 | 2 | 2 | AAGACCAAGAGCGCATCAAAG |
| 792 | 21 | 1 | 2 | 2 | 2 | AGACCAAGAGCGCATCAAAGT |
| 793 | 21 | 1 | 2 | 2 | 2 | GACCAAGAGCGCATCAAAGTG |
| 794 | 21 | 1 | 2 | 2 | 2 | ACCAAGAGCGCATCAAAGTGG |
| 795 | 21 | 1 | 2 | 2 | 2 | CCAAGAGCGCATCAAAGTGGA |
| 796 | 21 | 1 | 2 | 2 | 2 | CAAGAGCGCATCAAAGTGGAG |
| 797 | 21 | 1 | 2 | 2 | 2 | AAGAGCGCATCAAAGTGGAGC |
| 798 | 21 | 1 | 2 | 2 | 2 | AGAGCGCATCAAAGTGGAGCG |

FIG. 20A-13

| | | | | | | |
|---|---|---|---|---|---|---|
| 799 | 21 | 1 | 2 | 2 | 2 | 2 | GAGCGCATCAAAGTGGAGCGC |
| 800 | 21 | 1 | 2 | 2 | 2 | 2 | AGCGCATCAAAGTGGAGCGCA |
| 801 | 21 | 1 | 2 | 2 | 2 | 2 | GCGCATCAAAGTGGAGCGCAA |
| 802 | 21 | 1 | 2 | 2 | 2 | 2 | CGCATCAAAGTGGAGCGCAAG |
| 803 | 21 | 1 | 2 | 2 | 2 | 2 | GCATCAAAGTGGAGCGCAAGC |
| 804 | 21 | 1 | 2 | 2 | 2 | 2 | CATCAAAGTGGAGCGCAAGCG |
| 805 | 21 | 1 | 2 | 2 | 2 | 2 | ATCAAAGTGGAGCGCAAGCGG |
| 806 | 21 | 1 | 2 | 2 | 2 | 2 | TCAAAGTGGAGCGCAAGCGGC |
| 807 | 21 | 1 | 2 | 2 | 2 | 2 | CAAAGTGGAGCGCAAGCGGCT |
| 808 | 21 | 1 | 2 | 2 | 2 | 2 | AAAGTGGAGCGCAAGCGGCTG |
| 809 | 21 | 1 | 2 | 2 | 2 | 2 | AAGTGGAGCGCAAGCGGCTGC |
| 810 | 21 | 1 | 2 | 2 | 2 | 2 | AGTGGAGCGCAAGCGGCTGCG |
| 811 | 21 | 1 | 2 | 2 | 2 | 2 | GTGGAGCGCAAGCGGCTGCGG |
| 812 | 21 | 1 | 2 | 2 | 2 | 2 | TGGAGCGCAAGCGGCTGCGGA |
| 813 | 21 | 1 | 2 | 2 | 2 | 2 | GGAGCGCAAGCGGCTGCGGAA |
| 814 | 21 | 1 | 1 | 1 | 1 | 1 | GAGCGCAAGCGGCTGCGGAAC |
| 815 | 21 | 1 | 1 | 1 | 1 | 1 | AGCGCAAGCGGCTGCGGAACC |
| 816 | 21 | 1 | 1 | 1 | 1 | 1 | GCGCAAGCGGCTGCGGAACCG |
| 817 | 21 | 1 | 1 | 1 | 1 | 1 | CGCAAGCGGCTGCGGAACCGG |
| 818 | 21 | 1 | 1 | 1 | 1 | 1 | GCAAGCGGCTGCGGAACCGGC |
| 819 | 21 | 1 | 1 | 1 | 1 | 1 | CAAGCGGCTGCGGAACCGGCT |
| 820 | 21 | 1 | 2 | 2 | 2 | 2 | AAGCGGCTGCGGAACCGGCTG |

FIG. 20A-14

| | | | | | |
|---|---|---|---|---|---|
| 821 | 21 | 1 | 2 | 2 | 2 | AGCGGCTGCGGAACCGGCTGG |
| 822 | 21 | 1 | 2 | 2 | 2 | GCGGCTGCGGAACCGGCTGGC |
| 823 | 21 | 1 | 2 | 2 | 2 | CGGCTGCGGAACCGGCTGGCG |
| 824 | 21 | 1 | 2 | 2 | 2 | GGCTGCGGAACCGGCTGGCGG |
| 825 | 21 | 1 | 2 | 2 | 2 | GCTGCGGAACCGGCTGGCGGC |
| 826 | 21 | 1 | 2 | 2 | 2 | CTGCGGAACCGGCTGGCGGCC |
| 827 | 21 | 1 | 2 | 2 | 2 | TGCGGAACCGGCTGGCGGCCA |
| 828 | 21 | 1 | 2 | 2 | 2 | GCGGAACCGGCTGGCGGCCAC |
| 829 | 21 | 1 | 2 | 2 | 2 | CGGAACCGGCTGGCGGCCACC |
| 830 | 21 | 1 | 2 | 2 | 2 | GGAACCGGCTGGCGGCCACCA |
| 831 | 21 | 1 | 2 | 2 | 2 | GAACCGGCTGGCGGCCACCAA |
| 832 | 21 | 1 | 2 | 2 | 2 | AACCGGCTGGCGGCCACCAAG |
| 833 | 21 | 1 | 2 | 2 | 2 | ACCGGCTGGCGGCCACCAAGT |
| 834 | 21 | 1 | 2 | 2 | 2 | CCGGCTGGCGGCCACCAAGTG |
| 835 | 21 | 2 | 2 | 2 | 2 | CGGCTGGCGGCCACCAAGTGC |
| 836 | 21 | 2 | 2 | 2 | 2 | GGCTGGCGGCCACCAAGTGCC |
| 837 | 21 | 2 | 2 | 2 | 2 | GCTGGCGGCCACCAAGTGCCG |
| 838 | 21 | 2 | 2 | 2 | 2 | CTGGCGGCCACCAAGTGCCGG |
| 839 | 21 | 2 | 2 | 2 | 2 | TGGCGGCCACCAAGTGCCGGA |
| 840 | 21 | 2 | 2 | 2 | 2 | GGCGGCCACCAAGTGCCGGAA |
| 841 | 21 | 2 | 2 | 2 | 2 | GCGGCCACCAAGTGCCGGAAG |

FIG. 20A-15

| | | | | | |
|---|---|---|---|---|---|
| 842 | 21 | 2 | 2 | 2 | 2 | CGGCCACCAAGTGCCGGAAGC |
| 843 | 21 | 2 | 2 | 2 | 2 | GGCCACCAAGTGCCGGAAGCG |
| 844 | 21 | 2 | 2 | 2 | 2 | GCCACCAAGTGCCGGAAGCGG |
| 845 | 21 | 2 | 2 | 2 | 2 | CCACCAAGTGCCGGAAGCGGA |
| 846 | 21 | 2 | 2 | 2 | 2 | CACCAAGTGCCGGAAGCGGAA |
| 847 | 21 | 2 | 2 | 2 | 2 | ACCAAGTGCCGGAAGCGGAAG |
| 848 | 21 | 2 | 2 | 2 | 2 | CCAAGTGCCGGAAGCGGAAGC |
| 849 | 21 | 2 | 2 | 2 | 2 | CAAGTGCCGGAAGCGGAAGCT |
| 850 | 21 | 2 | 2 | 2 | 2 | AAGTGCCGGAAGCGGAAGCTG |
| 851 | 21 | 2 | 2 | 2 | 2 | AGTGCCGGAAGCGGAAGCTGG |
| 852 | 21 | 2 | 2 | 2 | 2 | GTGCCGGAAGCGGAAGCTGGA |
| 853 | 21 | 2 | 2 | 2 | 2 | TGCCGGAAGCGGAAGCTGGAG |
| 854 | 21 | 2 | 2 | 2 | 2 | GCCGGAAGCGGAAGCTGGAGC |
| 855 | 21 | 2 | 2 | 2 | 2 | CCGGAAGCGGAAGCTGGAGCG |
| 856 | 21 | 2 | 2 | 2 | 2 | CGGAAGCGGAAGCTGGAGCGC |
| 857 | 21 | 2 | 2 | 2 | 2 | GGAAGCGGAAGCTGGAGCGCA |
| 858 | 21 | 2 | 2 | 2 | 2 | GAAGCGGAAGCTGGAGCGCAT |
| 859 | 21 | 2 | 2 | 2 | 2 | AAGCGGAAGCTGGAGCGCATC |
| 860 | 21 | 2 | 2 | 2 | 2 | AGCGGAAGCTGGAGCGCATCG |
| 861 | 21 | 2 | 2 | 2 | 2 | GCGGAAGCTGGAGCGCATCGC |
| 862 | 21 | 2 | 2 | 2 | 2 | CGGAAGCTGGAGCGCATCGCG |

FIG. 20A-16

| | | | | | |
|---|---|---|---|---|---|
| 863 | 21 | 2 | 2 | 2 | GGAAGCTGGAGCGCATCGCGC |
| 864 | 21 | 2 | 2 | 2 | GAAGCTGGAGCGCATCGCGCG |
| 865 | 21 | 2 | 2 | 2 | AAGCTGGAGCGCATCGCGCGC |
| 866 | 21 | 2 | 2 | 2 | AGCTGGAGCGCATCGCGCGCC |
| 867 | 21 | 2 | 2 | 2 | GCTGGAGCGCATCGCGCGCCT |
| 868 | 21 | 2 | 2 | 2 | CTGGAGCGCATCGCGCGCCTG |
| 869 | 21 | 2 | 2 | 2 | TGGAGCGCATCGCGCGCCTGG |
| 870 | 21 | 2 | 2 | 2 | GGAGCGCATCGCGCGCCTGGA |
| 871 | 21 | 2 | 2 | 2 | GAGCGCATCGCGCGCCTGGAG |
| 872 | 21 | 2 | 2 | 2 | AGCGCATCGCGCGCCTGGAGG |
| 873 | 21 | 2 | 2 | 2 | GCGCATCGCGCGCCTGGAGGA |
| 874 | 21 | 2 | 2 | 2 | CGCATCGCGCGCCTGGAGGAC |
| 875 | 21 | 2 | 2 | 2 | GCATCGCGCGCCTGGAGGACA |
| 876 | 21 | 2 | 2 | 2 | CATCGCGCGCCTGGAGGACAA |
| 877 | 21 | 2 | 2 | 2 | ATCGCGCGCCTGGAGGACAAG |
| 878 | 21 | 2 | 2 | 2 | TCGCGCGCCTGGAGGACAAGG |
| 879 | 21 | 2 | 2 | 2 | CGCGCGCCTGGAGGACAAGGT |
| 880 | 21 | 2 | 2 | 2 | GCGCGCCTGGAGGACAAGGTG |
| 881 | 21 | 2 | 2 | 2 | CGCGCCTGGAGGACAAGGTGA |
| 882 | 21 | 2 | 2 | 2 | GCGCCTGGAGGACAAGGTGAA |
| 883 | 21 | 2 | 2 | 2 | CGCCTGGAGGACAAGGTGAAG |
| 884 | 21 | 2 | 2 | 2 | GCCTGGAGGACAAGGTGAAGA |

FIG. 20A-17

| | | | | | |
|---|---|---|---|---|---|
| 885 | 21 | 2 | 2 | 2 | 2 | CCTGGAGGACAAGGTGAAGAC |
| 886 | 21 | 1 | 2 | 2 | 2 | CTGGAGGACAAGGTGAAGACG |
| 887 | 21 | 1 | 2 | 2 | 2 | TGGAGGACAAGGTGAAGACGC |
| 888 | 21 | 1 | 2 | 2 | 2 | GGAGGACAAGGTGAAGACGCT |
| 889 | 21 | 1 | 2 | 2 | 2 | GAGGACAAGGTGAAGACGCTC |
| 890 | 21 | 1 | 2 | 2 | 2 | AGGACAAGGTGAAGACGCTCA |
| 891 | 21 | 1 | 2 | 2 | 2 | GGACAAGGTGAAGACGCTCAA |
| 892 | 21 | 1 | 2 | 2 | 2 | GACAAGGTGAAGACGCTCAAG |
| 893 | 21 | 1 | 2 | 2 | 2 | ACAAGGTGAAGACGCTCAAGG |
| 894 | 21 | 1 | 2 | 2 | 2 | CAAGGTGAAGACGCTCAAGGC |
| 895 | 21 | 1 | 1 | 1 | 1 | AAGGTGAAGACGCTCAAGGCC |
| 896 | 21 | 1 | 1 | 1 | 1 | AGGTGAAGACGCTCAAGGCCG |
| 897 | 21 | 1 | 1 | 1 | 1 | GGTGAAGACGCTCAAGGCCGA |
| 898 | 21 | 1 | 1 | 1 | 1 | GTGAAGACGCTCAAGGCCGAG |
| 899 | 21 | 1 | 1 | 1 | 1 | TGAAGACGCTCAAGGCCGAGA |
| 900 | 21 | 1 | 1 | 1 | 1 | GAAGACGCTCAAGGCCGAGAA |
| 901 | 21 | 1 | 1 | 1 | 1 | AAGACGCTCAAGGCCGAGAAC |
| 902 | 21 | 1 | 1 | 1 | 1 | AGACGCTCAAGGCCGAGAACG |
| 903 | 21 | 1 | 1 | 1 | 1 | GACGCTCAAGGCCGAGAACGC |
| 904 | 21 | 1 | 1 | 1 | 1 | ACGCTCAAGGCCGAGAACGCG |
| 905 | 21 | 1 | 1 | 1 | 1 | CGCTCAAGGCCGAGAACGCGG |

FIG. 20A-18

| | | | | | | |
|---|---|---|---|---|---|---|
| 906 | 21 | 1 | 1 | 1 | 1 | GCTCAAGGCCGAGAACGCGGG |
| 907 | 21 | 1 | 2 | 2 | 2 | CTCAAGGCCGAGAACGCGGGG |
| 908 | 21 | 1 | 2 | 2 | 2 | TCAAGGCCGAGAACGCGGGGC |
| 909 | 21 | 1 | 2 | 2 | 2 | CAAGGCCGAGAACGCGGGGCT |
| 910 | 21 | 1 | 2 | 2 | 2 | AAGGCCGAGAACGCGGGGCTG |
| 911 | 21 | 1 | 2 | 2 | 2 | AGGCCGAGAACGCGGGGCTGT |
| 912 | 21 | 1 | 2 | 2 | 2 | GGCCGAGAACGCGGGGCTGTC |
| 913 | 21 | 1 | 2 | 2 | 2 | GCCGAGAACGCGGGGCTGTCG |
| 914 | 21 | 1 | 2 | 2 | 2 | CCGAGAACGCGGGGCTGTCGA |
| 915 | 21 | 1 | 2 | 2 | 2 | CGAGAACGCGGGGCTGTCGAG |
| 916 | 21 | 2 | 2 | 2 | 2 | GAGAACGCGGGGCTGTCGAGT |
| 917 | 21 | 1 | 1 | 1 | 1 | AGAACGCGGGGCTGTCGAGTA |
| 918 | 21 | 1 | 1 | 1 | 1 | GAACGCGGGGCTGTCGAGTAC |
| 919 | 21 | 1 | 1 | 1 | 1 | AACGCGGGGCTGTCGAGTACC |
| 920 | 21 | 1 | 1 | 1 | 1 | ACGCGGGGCTGTCGAGTACCG |
| 921 | 21 | 1 | 1 | 1 | 1 | CGCGGGGCTGTCGAGTACCGC |
| 922 | 21 | 1 | 1 | 1 | 1 | GCGGGGCTGTCGAGTACCGCC |
| 923 | 21 | 1 | 1 | 1 | 1 | CGGGGCTGTCGAGTACCGCCG |
| 924 | 21 | 1 | 1 | 1 | 1 | GGGGCTGTCGAGTACCGCCGG |
| 925 | 21 | 1 | 1 | 1 | 1 | GGGCTGTCGAGTACCGCCGGC |
| 926 | 21 | 1 | 1 | 1 | 1 | GGCTGTCGAGTACCGCCGGCC |

FIG. 20A-19

| | | | | | |
|---|---|---|---|---|---|
| 927 | 21 | 1 | 1 | 1 | 1 | GCTGTCGAGTACCGCCGGCCT |
| 928 | 21 | 1 | 1 | 1 | 1 | CTGTCGAGTACCGCCGGCCTC |
| 929 | 21 | 1 | 1 | 1 | 1 | TGTCGAGTACCGCCGGCCTCC |
| 930 | 21 | 1 | 1 | 1 | 1 | GTCGAGTACCGCCGGCCTCCT |
| 931 | 21 | 1 | 1 | 1 | 1 | TCGAGTACCGCCGGCCTCCTC |
| 932 | 21 | 1 | 1 | 1 | 1 | CGAGTACCGCCGGCCTCCTCC |
| 933 | 21 | 1 | 1 | 1 | 1 | GAGTACCGCCGGCCTCCTCCG |
| 934 | 21 | 1 | 1 | 1 | 1 | AGTACCGCCGGCCTCCTCCGG |
| 935 | 21 | 1 | 1 | 1 | 1 | GTACCGCCGGCCTCCTCCGGG |
| 936 | 21 | 1 | 1 | 1 | 1 | TACCGCCGGCCTCCTCCGGGA |
| 937 | 21 | 1 | 1 | 1 | 1 | ACCGCCGGCCTCCTCCGGGAG |
| 938 | 21 | 1 | 1 | 1 | 1 | CCGCCGGCCTCCTCCGGGAGC |
| 939 | 21 | 1 | 1 | 1 | 1 | CGCCGGCCTCCTCCGGGAGCA |
| 940 | 21 | 1 | 1 | 1 | 1 | GCCGGCCTCCTCCGGGAGCAG |
| 941 | 21 | 1 | 1 | 1 | 1 | CCGGCCTCCTCCGGGAGCAGG |
| 942 | 21 | 1 | 1 | 1 | 1 | CGGCCTCCTCCGGGAGCAGGT |
| 943 | 21 | 1 | 1 | 1 | 1 | GGCCTCCTCCGGGAGCAGGTG |
| 944 | 21 | 1 | 1 | 1 | 1 | GCCTCCTCCGGGAGCAGGTGG |
| 945 | 21 | 1 | 1 | 1 | 1 | CCTCCTCCGGGAGCAGGTGGC |
| 946 | 21 | 1 | 1 | 1 | 1 | CTCCTCCGGGAGCAGGTGGCC |
| 947 | 21 | 1 | 1 | 1 | 1 | TCCTCCGGGAGCAGGTGGCCC |
| 948 | 21 | 1 | 1 | 1 | 1 | CCTCCGGGAGCAGGTGGCCCA |

FIG. 20A-20

| | | | | | |
|---|---|---|---|---|---|
| 949 | 21 | 1 | 1 | 1 | 1 | 1 | CTCCGGGAGCAGGTGGCCCAG |
| 950 | 21 | 1 | 1 | 1 | 1 | 1 | TCCGGGAGCAGGTGGCCCAGC |
| 951 | 21 | 1 | 1 | 1 | 1 | 1 | CCGGGAGCAGGTGGCCCAGCT |
| 952 | 21 | 1 | 1 | 1 | 1 | 1 | CGGGAGCAGGTGGCCCAGCTC |
| 953 | 21 | 1 | 1 | 1 | 1 | 1 | GGGAGCAGGTGGCCCAGCTCA |
| 954 | 21 | 1 | 1 | 1 | 1 | 1 | GGAGCAGGTGGCCCAGCTCAA |
| 955 | 21 | 1 | 2 | 2 | 2 | 2 | GAGCAGGTGGCCCAGCTCAAA |
| 956 | 21 | 1 | 2 | 2 | 2 | 2 | AGCAGGTGGCCCAGCTCAAAC |
| 957 | 21 | 1 | 2 | 2 | 2 | 2 | GCAGGTGGCCCAGCTCAAACA |
| 958 | 21 | 1 | 2 | 2 | 2 | 2 | CAGGTGGCCCAGCTCAAACAG |
| 959 | 21 | 1 | 2 | 2 | 2 | 2 | AGGTGGCCCAGCTCAAACAGA |
| 960 | 21 | 1 | 2 | 2 | 2 | 1 | GGTGGCCCAGCTCAAACAGAA |
| 961 | 21 | 1 | 1 | 1 | 1 | 1 | GTGGCCCAGCTCAAACAGAAG |
| 962 | 21 | 1 | 1 | 1 | 1 | 1 | TGGCCCAGCTCAAACAGAAGG |
| 963 | 21 | 1 | 1 | 1 | 1 | 1 | GGCCCAGCTCAAACAGAAGGT |
| 964 | 21 | 1 | 1 | 1 | 1 | 1 | GCCCAGCTCAAACAGAAGGTC |
| 965 | 21 | 1 | 1 | 1 | 1 | 1 | CCCAGCTCAAACAGAAGGTCA |
| 966 | 21 | 1 | 2 | 2 | 2 | 2 | CCAGCTCAAACAGAAGGTCAT |
| 967 | 21 | 1 | 2 | 2 | 2 | 2 | CAGCTCAAACAGAAGGTCATG |
| 968 | 21 | 1 | 2 | 2 | 2 | 2 | AGCTCAAACAGAAGGTCATGA |
| 969 | 21 | 1 | 2 | 2 | 2 | 2 | GCTCAAACAGAAGGTCATGAC |

FIG. 20A-21

| | | | | | | |
|---|---|---|---|---|---|---|
| 970 | 21 | 1 | 2 | 2 | 2 | 2 | CTCAAACAGAAGGTCATGACC |
| 971 | 21 | 1 | 2 | 2 | 2 | 2 | TCAAACAGAAGGTCATGACCC |
| 972 | 21 | 1 | 2 | 2 | 2 | 2 | CAAACAGAAGGTCATGACCCA |
| 973 | 21 | 1 | 1 | 1 | 1 | 1 | AAACAGAAGGTCATGACCCAC |
| 974 | 21 | 1 | 1 | 1 | 1 | 1 | AACAGAAGGTCATGACCCACG |
| 975 | 21 | 1 | 1 | 1 | 1 | 1 | ACAGAAGGTCATGACCCACGT |
| 976 | 21 | 1 | 2 | 2 | 2 | 2 | CAGAAGGTCATGACCCACGTC |
| 977 | 21 | 1 | 2 | 2 | 2 | 2 | AGAAGGTCATGACCCACGTCA |
| 978 | 21 | 1 | 2 | 2 | 2 | 2 | GAAGGTCATGACCCACGTCAG |
| 979 | 21 | 1 | 2 | 2 | 2 | 2 | AAGGTCATGACCCACGTCAGC |
| 980 | 21 | 1 | 2 | 2 | 2 | 2 | AGGTCATGACCCACGTCAGCA |
| 981 | 21 | 1 | 2 | 2 | 2 | 2 | GGTCATGACCCACGTCAGCAA |
| 982 | 21 | 1 | 2 | 2 | 2 | 2 | GTCATGACCCACGTCAGCAAC |
| 983 | 21 | 1 | 2 | 2 | 2 | 2 | TCATGACCCACGTCAGCAACG |
| 984 | 21 | 1 | 2 | 2 | 2 | 2 | CATGACCCACGTCAGCAACGG |
| 985 | 21 | 1 | 2 | 2 | 2 | 2 | ATGACCCACGTCAGCAACGGC |
| 986 | 21 | 1 | 2 | 2 | 2 | 2 | TGACCCACGTCAGCAACGGCT |
| 987 | 21 | 1 | 2 | 2 | 2 | 2 | GACCCACGTCAGCAACGGCTG |
| 988 | 21 | 1 | 1 | 1 | 1 | 1 | ACCCACGTCAGCAACGGCTGT |
| 989 | 21 | 1 | 1 | 1 | 1 | 1 | CCCACGTCAGCAACGGCTGTC |
| 990 | 21 | 1 | 1 | 1 | 1 | 1 | CCACGTCAGCAACGGCTGTCA |

FIG. 20A-22

| | | | | | |
|---|---|---|---|---|---|
| 991 | 21 | 1 | 1 | 1 | 1 | CACGTCAGCAACGGGCTGTCAG |
| 992 | 21 | 1 | 1 | 1 | 1 | ACGTCAGCAACGGGCTGTCAGC |
| 993 | 21 | 1 | 1 | 1 | 1 | CGTCAGCAACGGGCTGTCAGCT |
| 994 | 21 | 1 | 1 | 1 | 1 | GTCAGCAACGGGCTGTCAGCTG |
| 995 | 21 | 1 | 1 | 1 | 1 | TCAGCAACGGGCTGTCAGCTGC |
| 996 | 21 | 1 | 1 | 1 | 1 | CAGCAACGGGCTGTCAGCTGCT |
| 997 | 21 | 1 | 1 | 1 | 1 | AGCAACGGGCTGTCAGCTGCTG |
| 998 | 21 | 1 | 1 | 1 | 1 | GCAACGGGCTGTCAGCTGCTGC |
| 999 | 21 | 1 | 1 | 1 | 1 | CAACGGGCTGTCAGCTGCTGCT |
| 1000 | 21 | 1 | 1 | 1 | 1 | AACGGGCTGTCAGCTGCTGCTT |
| 1001 | 21 | 1 | 1 | 1 | 1 | ACGGGCTGTCAGCTGCTGCTTG |
| 1002 | 21 | 1 | 1 | 1 | 1 | CGGGCTGTCAGCTGCTGCTTGG |
| 1003 | 21 | 1 | 1 | 1 | 1 | GGGCTGTCAGCTGCTGCTTGGG |
| 1004 | 21 | 1 | 1 | 1 | 1 | GGCTGTCAGCTGCTGCTTGGGG |
| 1005 | 21 | 1 | 1 | 1 | 1 | GCTGTCAGCTGCTGCTTGGGGT |
| 1006 | 21 | 1 | 1 | 1 | 1 | CTGTCAGCTGCTGCTTGGGGTC |
| 1007 | 21 | 1 | 1 | 1 | 1 | TGTCAGCTGCTGCTTGGGGTCA |
| 1008 | 21 | 1 | 1 | 1 | 1 | GTCAGCTGCTGCTTGGGGTCAA |
| 1009 | 21 | 1 | 1 | 1 | 1 | TCAGCTGCTGCTTGGGGTCAAG |
| 1010 | 21 | 1 | 1 | 1 | 1 | CAGCTGCTGCTTGGGGTCAAGG |
| 1011 | 21 | 1 | 1 | 1 | 1 | AGCTGCTGCTTGGGGTCAAGGG |
| 1012 | 21 | 1 | 1 | 1 | 1 | GCTGCTGCTTGGGGTCAAGGGA |

FIG. 20A-23

| | | | | | |
|---|---|---|---|---|---|
| 1013 | 21 | 1 | 2 | 2 | 2 | TGCTGCTTGGGGTCAAGGGAC |
| 1014 | 21 | 1 | 2 | 2 | 2 | GCTGCTTGGGGTCAAGGGACA |
| 1015 | 21 | 1 | 2 | 2 | 2 | CTGCTTGGGGTCAAGGGACAC |
| 1016 | 21 | 1 | 2 | 2 | 2 | TGCTTGGGGTCAAGGGACACG |
| 1017 | 21 | 1 | 2 | 2 | 2 | GCTTGGGGTCAAGGGACACGC |
| 1018 | 21 | 1 | 2 | 2 | 2 | CTTGGGGTCAAGGGACACGCC |
| 1019 | 21 | 1 | 2 | 2 | 2 | TTGGGGTCAAGGGACACGCCT |
| 1020 | 21 | 1 | 2 | 2 | 2 | TGGGGTCAAGGGACACGCCTT |
| 1021 | 21 | 2 | 2 | 2 | 2 | GGGGTCAAGGGACACGCCTTC |
| 1022 | 21 | 2 | 2 | 2 | 2 | GGGTCAAGGGACACGCCTTCT |
| 1023 | 21 | 2 | 2 | 2 | 2 | GGTCAAGGGACACGCCTTCTG |
| 1024 | 21 | 2 | 2 | 2 | 2 | GTCAAGGGACACGCCTTCTGA |

FIG. 24A (1)

OligoProbe DesignStation

Probes:     C:\HITACHI\HUMBJUNX.CDS
Datatbase:  C:\HITACHI\JUNMIX.SEQ

Mismatch Model, l = 21, k = 4

| Position | length | 0 | 1 | Mismatches 2 | 3 | 4 | 5 | 6 | 7 | screensN 8 | Probe |
|---|---|---|---|---|---|---|---|---|---|---|---|
| 1 | 21 | 0 | 0 | 0 | 0 | 0 | | | | | ATGTGCACTAAAATGGAACAG |
| 2 | 21 | 0 | 0 | 0 | 0 | 0 | | | | | TGTGCACTAAAATGGAACAGC |
| 3 | 21 | 0 | 0 | 0 | 0 | 0 | | | | | GTGCACTAAAATGGAACAGCC |
| 4 | 21 | 0 | 0 | 0 | 0 | 0 | | | | | TGCACTAAAATGGAACAGCCC |
| 5 | 21 | 0 | 0 | 0 | 0 | 0 | | | | | GCACTAAAATGGAACAGCCCT |
| 6 | 21 | 0 | 0 | 0 | 0 | 0 | | | | | CACTAAAATGGAACAGCCCTT |
| 7 | 21 | 0 | 0 | 0 | 0 | 0 | | | | | ACTAAAATGGAACAGCCCTTC |
| 8 | 21 | 0 | 0 | 0 | 0 | 0 | | | | | CTAAAATGGAACAGCCCTTCT |
| 9 | 21 | 0 | 0 | 0 | 0 | 0 | | | | | TAAAATGGAACAGCCCTTCTA |
| 10 | 21 | 0 | 0 | 0 | 0 | 0 | | | | | AAAATGGAACAGCCCTTCTAC |

FIG. 24A (2)

| | | | | | |
|---|---|---|---|---|---|
| 11 | 21 | o | o | o | o | o | AAATGGAACAGCCCTTCTACC |
| 12 | 21 | o | o | o | o | o | AATGGAACAGCCCTTCTACCA |
| 13 | 21 | o | o | o | o | o | ATGGAACAGCCCTTCTACCAC |
| 14 | 21 | o | o | o | o | o | TGGAACAGCCCTTCTACCACG |
| 15 | 21 | o | o | o | o | o | GGAACAGCCCTTCTACCACGA |
| 16 | 21 | o | o | o | o | o | GAACAGCCCTTCTACCACGAC |
| 17 | 21 | o | o | o | o | o | AACAGCCCTTCTACCACGACG |
| 18 | 21 | o | o | o | o | o | ACAGCCCTTCTACCACGACGA |
| 19 | 21 | o | o | o | o | o | CAGCCCTTCTACCACGACGAC |
| 20 | 21 | o | o | o | o | o | AGCCCTTCTACCACGACGACT |
| 21 | 21 | o | o | o | o | o | GCCCTTCTACCACGACGACTC |
| 22 | 21 | o | o | o | o | o | CCCTTCTACCACGACGACTCA |
| 23 | 21 | o | o | o | o | o | CCTTCTACCACGACGACTCAT |
| 24 | 21 | o | o | o | o | o | CTTCTACCACGACGACTCATA |
| 25 | 21 | o | o | o | o | o | TTCTACCACGACGACTCATAT |
| 26 | 21 | o | o | o | o | o | TCTACCACGACGACTCATACA |
| 27 | 21 | o | o | o | o | o | CTACCACGACGACTCATACAC |
| 28 | 21 | o | o | o | o | o | TACCACGACGACTCATACACA |
| 29 | 21 | o | o | o | o | o | ACCACGACGACTCATACACAG |
| 30 | 21 | o | o | o | o | o | CCACGACGACTCATACACAGC |
| 31 | 21 | o | o | o | o | o | CACGACGACTCATACACAGCT |

FIG. 24A (3)

| # | | | | |
|---|---|---|---|---|
| 32 21 | 0 | 0 | 0 | ACGGACGACTCATACACAGCTA |
| 33 21 | 0 | 0 | 0 | CGACGACTCATACACAGCTAC |
| 34 21 | 0 | 0 | 0 | GACGACTCATACACAGCTACG |
| 35 21 | 0 | 0 | 0 | ACGACTCATACACAGCTACGG |
| 36 21 | 0 | 0 | 0 | CGACTCATACACAGCTACGGG |
| 37 21 | 0 | 0 | 0 | GACTCATACACAGCTACGGGA |
| 38 21 | 0 | 0 | 0 | ACTCATACACAGCTACGGGAT |
| 39 21 | 0 | 0 | 0 | CTCATACACAGCTACGGGATA |
| 40 21 | 0 | 0 | 0 | TCATACACAGCTACGGGATAC |
| 41 21 | 0 | 0 | 0 | CATACACAGCTACGGGATACG |
| 42 21 | 0 | 0 | 0 | ATACACAGCTACGGGATACGG |
| 43 21 | 0 | 0 | 0 | TACACAGCTACGGGATACGGC |
| 44 21 | 0 | 0 | 0 | ACACAGCTACGGGATACGGCC |
| 45 21 | 0 | 0 | 0 | CACAGCTACGGGATACGGCCG |
| 46 21 | 0 | 0 | 0 | ACAGCTACGGGATACGGCCGG |
| 47 21 | 0 | 0 | 0 | CAGCTACGGGATACGGCCGGG |
| 48 21 | 0 | 0 | 0 | AGCTACGGGATACGGCCGGGC |
| 49 21 | 0 | 0 | 0 | GCTACGGGATACGGCCGGGCC |
| 50 21 | 0 | 0 | 0 | CTACGGGATACGGCCGGGCCC |
| 51 21 | 0 | 0 | 0 | TACGGGATACGGCCGGGCCCC |
| 52 21 | 0 | 0 | 0 | ACGGGATACGGCCGGGCCCCT |
| 53 21 | 0 | 0 | 0 | CGGGATACGGCCGGGCCCCTG |

FIG. 24A (4)

| | | | | | |
|---|---|---|---|---|---|
| 54 | 21 | o | o | o | o | GGGATACGGGCCGGGCCCCTGG |
| 55 | 21 | o | o | o | o | GGATACGGGCCGGGCCCCTGGT |
| 56 | 21 | o | o | o | o | GATACGGGCCGGGCCCCTGGTG |
| 57 | 21 | o | o | o | o | ATACGGGCCGGGCCCCTGGTGG |
| 58 | 21 | o | o | o | o | TACGGGCCGGGCCCCTGGTGGC |
| 59 | 21 | o | o | o | o | ACGGGCCGGGCCCCTGGTGGCC |
| 60 | 21 | o | o | o | o | CGGGCCGGGCCCCTGGTGGCCT |
| 61 | 21 | o | o | o | o | GGGCCGGGCCCCTGGTGGCCTC |
| 62 | 21 | o | o | o | o | GGCCGGGCCCCTGGTGGCCTCT |
| 63 | 21 | o | o | o | o | GCCGGGCCCCTGGTGGCCTCTC |
| 64 | 21 | o | o | o | o | CCGGGCCCCTGGTGGCCTCTCT |
| 65 | 21 | o | o | o | o | CGGGCCCCTGGTGGCCTCTCTC |
| 66 | 21 | o | o | o | o | GGGCCCCTGGTGGCCTCTCTCT |
| 67 | 21 | o | o | o | o | GGCCCCTGGTGGCCTCTCTCTA |
| 68 | 21 | o | o | o | o | GCCCCTGGTGGCCTCTCTCTAC |
| 69 | 21 | o | o | o | o | CCCCTGGTGGCCTCTCTCTACA |
| 70 | 21 | o | o | o | o | CCCTGGTGGCCTCTCTCTACAC |
| 71 | 21 | o | o | o | o | CCTGGTGGCCTCTCTCTACACG |
| 72 | 21 | o | o | o | o | CTGGTGGCCTCTCTCTACACGA |
| 73 | 21 | o | o | o | o | TGGTGGCCTCTCTCTACACGAC |
| 74 | 21 | o | o | o | o | GGTGGCCTCTCTCTACACGACT |

FIG. 24A (5)

| # | | | | | Sequence |
|---|---|---|---|---|---|
| 75 | 21 | 0 | 0 | 0 | 0 | TGGCCTCTCTCTACACGACTA |
| 76 | 21 | 0 | 0 | 0 | 0 | GGCCTCTCTCTACACGACTAC |
| 77 | 21 | 0 | 0 | 0 | 0 | GCCTCTCTCTACACGACTACA |
| 78 | 21 | 0 | 0 | 0 | 0 | CCTCTCTCTACACGACTACAA |
| 79 | 21 | 0 | 0 | 0 | 0 | CTCTCTCTACACGACTACAAA |
| 80 | 21 | 0 | 0 | 0 | 0 | TCTCTCTACACGACTACAAAC |
| 81 | 21 | 0 | 0 | 0 | 0 | CTCTCTACACGACTACAAACT |
| 82 | 21 | 0 | 0 | 0 | 0 | TCTCTACACGACTACAAACTC |
| 83 | 21 | 0 | 0 | 0 | 0 | CTCTACACGACTACAAACTCC |
| 84 | 21 | 0 | 0 | 0 | 0 | TCTACACGACTACAAACTCCT |
| 85 | 21 | 0 | 0 | 0 | 0 | CTACACGACTACAAACTCCTG |
| 86 | 21 | 0 | 0 | 0 | 0 | TACACGACTACAAACTCCTGA |
| 87 | 21 | 0 | 0 | 0 | 0 | ACACGACTACAAACTCCTGAA |
| 88 | 21 | 0 | 0 | 0 | 0 | CACGACTACAAACTCCTGAAA |
| 89 | 21 | 0 | 0 | 0 | 0 | ACGACTACAAACTCCTGAAAC |
| 90 | 21 | 0 | 0 | 0 | 0 | CGACTACAAACTCCTGAAACC |
| 91 | 21 | 0 | 0 | 0 | 0 | GACTACAAACTCCTGAAACCG |
| 92 | 21 | 0 | 0 | 0 | 0 | ACTACAAACTCCTGAAACCGA |
| 93 | 21 | 0 | 0 | 0 | 0 | CTACAAACTCCTGAAACCGAG |
| 94 | 21 | 0 | 0 | 0 | 0 | TACAAACTCCTGAAACCGAGC |
| 95 | 21 | 0 | 0 | 0 | 0 | ACAAACTCCTGAAACCGAGCC |

FIG. 24A (6)

| | | | | | |
|---|---|---|---|---|---|
| 96 21 | o | o | o | o | CAAACTCCTGAAACCGAGCCT |
| 97 21 | o | o | o | o | AAACTCCTGAAACCGAGCCTG |
| 98 21 | o | o | o | o | AACTCCTGAAACCGAGCCTGG |
| 99 21 | o | o | o | o | ACTCCTGAAACCGAGCCTGGC |
| 100 21 | o | o | o | o | CTCCTGAAACCGAGCCTGGCG |
| 101 21 | o | o | o | o | TCCTGAAACCGAGCCTGGCGG |
| 102 21 | o | o | o | o | CCTGAAACCGAGCCTGGCGGT |
| 103 21 | o | o | o | o | CTGAAACCGAGCCTGGCGGTC |
| 104 21 | o | o | o | o | TGAAACCGAGCCTGGCGGTCA |
| 105 21 | o | o | o | o | GAAACCGAGCCTGGCGGTCAA |
| 106 21 | o | o | o | o | AAACCGAGCCTGGCGGTCAAC |
| 107 21 | o | o | o | o | AACCGAGCCTGGCGGTCAACC |
| 108 21 | o | o | o | o | ACCGAGCCTGGCGGTCAACCT |
| 109 21 | o | o | o | o | CCGAGCCTGGCGGTCAACCTG |
| 110 21 | o | o | o | o | CGAGCCTGGCGGTCAACCTGG |
| 111 21 | o | o | o | o | GAGCCTGGCGGTCAACCTGGC |
| 112 21 | o | o | o | o | AGCCTGGCGGTCAACCTGGCC |
| 113 21 | o | o | o | o | GCCTGGCGGTCAACCTGGCCG |
| 114 21 | o | o | o | o | CCTGGCGGTCAACCTGGCCGA |
| 115 21 | o | o | o | o | CTGGCGGTCAACCTGGCCGAC |

FIG. 24A (7)

| | | | | | |
|---|---|---|---|---|---|
| 116 | 21 | 0 | 0 | 0 | 0 | 0 | TGGCGGTCAACCTGGCCGACC |
| 117 | 21 | 0 | 0 | 0 | 0 | 0 | GGCGGTCAACCTGGCCGACCC |
| 118 | 21 | 0 | 0 | 0 | 0 | 0 | GCGGTCAACCTGGCCGACCCC |
| 119 | 21 | 0 | 0 | 0 | 0 | 0 | CGGTCAACCTGGCCGACCCCT |
| 120 | 21 | 0 | 0 | 0 | 0 | 0 | GGTCAACCTGGCCGACCCCTA |
| 121 | 21 | 0 | 0 | 0 | 0 | 0 | GTCAACCTGGCCGACCCCTAC |
| 122 | 21 | 0 | 0 | 0 | 0 | 0 | TCAACCTGGCCGACCCCTACC |
| 123 | 21 | 0 | 0 | 0 | 0 | 0 | CAACCTGGCCGACCCCTACCG |
| 124 | 21 | 0 | 0 | 0 | 0 | 0 | AACCTGGCCGACCCCTACCGG |
| 125 | 21 | 0 | 0 | 0 | 0 | 0 | ACCTGGCCGACCCCTACCGGA |
| 126 | 21 | 0 | 0 | 0 | 0 | 0 | CCTGGCCGACCCCTACCGGAG |
| 127 | 21 | 0 | 0 | 0 | 0 | 0 | CTGGCCGACCCCTACCGGAGT |
| 128 | 21 | 0 | 0 | 0 | 0 | 0 | TGGCCGACCCCTACCGGAGTC |
| 129 | 21 | 0 | 0 | 0 | 0 | 0 | GGCCGACCCCTACCGGAGTCT |
| 130 | 21 | 0 | 0 | 0 | 0 | 0 | GCCGACCCCTACCGGAGTCTC |
| 131 | 21 | 0 | 0 | 0 | 0 | 0 | CCGACCCCTACCGGAGTCTCA |
| 132 | 21 | 0 | 0 | 0 | 0 | 0 | CGACCCCTACCGGAGTCTCAA |
| 133 | 21 | 0 | 0 | 0 | 0 | 0 | GACCCCTACCGGAGTCTCAAA |
| 134 | 21 | 0 | 0 | 0 | 0 | 0 | ACCCCTACCGGAGTCTCAAAG |
| 135 | 21 | 0 | 0 | 0 | 0 | 0 | CCCCTACCGGAGTCTCAAAGC |
| 136 | 21 | 0 | 0 | 0 | 0 | 0 | CCCTACCGGAGTCTCAAAGCG |

FIG. 24A (8)

| | | | | | |
|---|---|---|---|---|---|
| 137 | 21 | 0 | 0 | 0 | 0 | CCTACCGGAGTCTCAAAGCGC |
| 138 | 21 | 0 | 0 | 0 | 0 | CTACCGGAGTCTCAAAGCGCC |
| 139 | 21 | 0 | 0 | 0 | 0 | TACCGGAGTCTCAAAGCGCCT |
| 140 | 21 | 0 | 0 | 0 | 0 | ACCGGAGTCTCAAAGCGCCTG |
| 141 | 21 | 0 | 0 | 0 | 0 | CCGGAGTCTCAAAGCGCCTGG |
| 142 | 21 | 0 | 0 | 0 | 0 | CGGAGTCTCAAAGCGCCTGGG |
| 143 | 21 | 0 | 0 | 0 | 0 | GGAGTCTCAAAGCGCCTGGGG |
| 144 | 21 | 0 | 0 | 0 | 0 | GAGTCTCAAAGCGCCTGGGGC |
| 145 | 21 | 0 | 0 | 0 | 0 | AGTCTCAAAGCGCCTGGGGCT |
| 146 | 21 | 0 | 0 | 0 | 0 | GTCTCAAAGCGCCTGGGGCTC |
| 147 | 21 | 0 | 0 | 0 | 0 | TCTCAAAGCGCCTGGGGCTCG |
| 148 | 21 | 0 | 0 | 0 | 0 | CTCAAAGCGCCTGGGGCTCGC |
| 149 | 21 | 0 | 0 | 0 | 0 | TCAAAGCGCCTGGGGCTCGCG |
| 150 | 21 | 0 | 0 | 0 | 0 | CAAAGCGCCTGGGGCTCGCGG |
| 151 | 21 | 0 | 0 | 0 | 0 | AAAGCGCCTGGGGCTCGCGGA |
| 152 | 21 | 0 | 0 | 0 | 0 | AAGCGCCTGGGGCTCGCGGAC |
| 153 | 21 | 0 | 0 | 0 | 0 | AGCGCCTGGGGCTCGCGGACC |
| 154 | 21 | 0 | 0 | 0 | 0 | GCGCCTGGGGCTCGCGGACCC |
| 155 | 21 | 0 | 0 | 0 | 0 | CGCCTGGGGCTCGCGGACCCG |
| 156 | 21 | 0 | 0 | 0 | 0 | GCCTGGGGCTCGCGGACCCGG |
| 157 | 21 | 0 | 0 | 0 | 0 | CCTGGGGCTCGCGGACCCGGC |

FIG. 24A (9)

| | | | | | |
|---|---|---|---|---|---|
| 158 | 21 | o | o | o | o | o | CTGGGGCTCGCGGACCCCGGCC |
| 159 | 21 | o | o | o | o | o | TGGGGCTCGCGGACCCCGGCCC |
| 160 | 21 | o | o | o | o | o | GGGGCTCGCGGACCCCGGCCCA |
| 161 | 21 | o | o | o | o | o | GGGCTCGCGGACCCCGGCCCAG |
| 162 | 21 | o | o | o | o | o | GGCTCGCGGACCCCGGCCCAGA |
| 163 | 21 | o | o | o | o | o | GCTCGCGGACCCCGGCCCAGAG |
| 164 | 21 | o | o | o | o | o | CTCGCGGACCCCGGCCCAGAGG |
| 165 | 21 | o | o | o | o | o | TCGCGGACCCCGGCCCAGAGGG |
| 166 | 21 | o | o | o | o | o | CGCGGACCCCGGCCCAGAGGGC |
| 167 | 21 | o | o | o | o | o | GCGGACCCCGGCCCAGAGGGCG |
| 168 | 21 | o | o | o | o | o | CGGACCCCGGCCCAGAGGGCGG |
| 169 | 21 | o | o | o | o | o | GGACCCCGGCCCAGAGGGCGGC |
| 170 | 21 | o | o | o | o | o | GACCCCGGCCCAGAGGGCGGCG |
| 171 | 21 | o | o | o | o | o | ACCCCGGCCCAGAGGGCGGCGG |
| 172 | 21 | o | o | o | o | o | CCCCGGCCCAGAGGGCGGCGGT |
| 173 | 21 | o | o | o | o | o | CCCGGCCCAGAGGGCGGCGGTG |
| 174 | 21 | o | o | o | o | o | CCGGCCCAGAGGGCGGCGGTGG |
| 175 | 21 | o | o | o | o | o | CGGCCCAGAGGGCGGCGGTGGC |
| 176 | 21 | o | o | o | o | o | GGCCCAGAGGGCGGCGGTGGCG |
| 177 | 21 | o | o | o | o | o | GCCCAGAGGGCGGCGGTGGCGG |
| 178 | 21 | o | o | o | o | o | CCCAGAGGGCGGCGGTGGCGGC |

FIG. 24A (10)

| | | | | | |
|---|---|---|---|---|---|
| 179 | 21 | 0 | 0 | 0 | 0 | CAGAGGGGCGGTGGCGGCA |
| 180 | 21 | 0 | 0 | 0 | 0 | AGAGGGCGGTGGCGGCAG |
| 181 | 21 | 0 | 0 | 0 | 0 | GAGGGCGGTGGCGGCAGC |
| 182 | 21 | 0 | 0 | 0 | 0 | AGGGCGGTGGCGGCAGCT |
| 183 | 21 | 0 | 0 | 0 | 0 | GGGCGGTGGCGGCAGCTA |
| 184 | 21 | 0 | 0 | 0 | 0 | GGCGGTGGCGGCAGCTAC |
| 185 | 21 | 0 | 0 | 0 | 0 | GCGGTGGCGGCAGCTACT |
| 186 | 21 | 0 | 0 | 0 | 0 | CGGTGGCGGCAGCTACTT |
| 187 | 21 | 0 | 0 | 0 | 0 | GGTGGCGGCAGCTACTTT |
| 188 | 21 | 0 | 0 | 0 | 0 | GTGGCGGCAGCTACTTTT |
| 189 | 21 | 0 | 0 | 0 | 0 | TGGCGGCAGCTACTTTTC |
| 190 | 21 | 0 | 0 | 0 | 0 | GGCGGCAGCTACTTTTCT |
| 191 | 21 | 0 | 0 | 0 | 0 | GCGGCAGCTACTTTTCTG |
| 192 | 21 | 0 | 0 | 0 | 0 | CGGCAGCTACTTTTCTGG |
| 193 | 21 | 0 | 0 | 0 | 0 | GGCAGCTACTTTTCTGGT |
| 194 | 21 | 0 | 0 | 0 | 0 | GCAGCTACTTTTCTGGTC |
| 195 | 21 | 0 | 0 | 0 | 0 | CAGCTACTTTTCTGGTCA |
| 196 | 21 | 0 | 0 | 0 | 0 | GGCAGCTACTTTTCTGGTCAG |
| 197 | 21 | 0 | 0 | 0 | 0 | GCAGCTACTTTTCTGGTCAGG |
| 198 | 21 | 0 | 0 | 0 | 0 | CAGCTACTTTTCTGGTCAGGG |
| 199 | 21 | 0 | 0 | 0 | 0 | AGCTACTTTTCTGGTCAGGGC |

FIG. 24A (11)

| | | | | | |
|---|---|---|---|---|---|
| 200 | 21 | 0 | 0 | 0 | 0 | GCTACTTTTCTGGTCAGGGCT |
| 201 | 21 | 0 | 0 | 0 | 0 | CTACTTTTCTGGTCAGGGCTC |
| 202 | 21 | 0 | 0 | 0 | 0 | TACTTTTCTGGTCAGGGCTCG |
| 203 | 21 | 0 | 0 | 0 | 0 | ACTTTTCTGGTCAGGGCTCGG |
| 204 | 21 | 0 | 0 | 0 | 0 | CTTTTCTGGTCAGGGCTCGGA |
| 205 | 21 | 0 | 0 | 0 | 0 | TTTTCTGGTCAGGGCTCGGAC |
| 206 | 21 | 0 | 0 | 0 | 0 | TTTCTGGTCAGGGCTCGGACA |
| 207 | 21 | 0 | 0 | 0 | 0 | TTCTGGTCAGGGCTCGGACAC |
| 208 | 21 | 0 | 0 | 0 | 0 | TCTGGTCAGGGCTCGGACACC |
| 209 | 21 | 0 | 0 | 0 | 0 | CTGGTCAGGGCTCGGACACCG |
| 210 | 21 | 0 | 0 | 0 | 0 | TGGTCAGGGCTCGGACACCGG |
| 211 | 21 | 0 | 0 | 0 | 0 | GGTCAGGGCTCGGACACCGGC |
| 212 | 21 | 0 | 0 | 0 | 0 | GTCAGGGCTCGGACACCGGCG |
| 213 | 21 | 0 | 0 | 0 | 0 | TCAGGGCTCGGACACCGGCGC |
| 214 | 21 | 0 | 0 | 0 | 0 | CAGGGCTCGGACACCGGCGCG |
| 215 | 21 | 0 | 0 | 0 | 0 | AGGGCTCGGACACCGGCGCGT |
| 216 | 21 | 0 | 0 | 0 | 0 | GGGCTCGGACACCGGCGCGTC |
| 217 | 21 | 0 | 0 | 0 | 0 | GGCTCGGACACCGGCGCGTCT |
| 218 | 21 | 0 | 0 | 0 | 0 | GCTCGGACACCGGCGCGTCTC |
| 219 | 21 | 0 | 0 | 0 | 0 | CTCGGACACCGGCGCGTCTCT |
| 220 | 21 | 0 | 0 | 0 | 0 | TCGGACACCGGCGCGTCTCTC |

FIG. 24A (12)

| | | | | | |
|---|---|---|---|---|---|
| 221 | 21 | o | o | o | o | CGGACACCGGCGCGTCTCTCA |
| 222 | 21 | o | o | o | o | GGACACCGGCGCGTCTCTCAA |
| 223 | 21 | o | o | o | o | GACACCGGCGCGTCTCTCAAG |
| 224 | 21 | o | o | o | o | ACACCGGCGCGTCTCTCAAGC |
| 225 | 21 | o | o | o | o | CACCGGCGCGTCTCTCAAGCT |
| 226 | 21 | o | o | o | o | ACCGGCGCGTCTCTCAAGCTC |
| 227 | 21 | o | o | o | o | CCGGCGCGTCTCTCAAGCTCG |
| 228 | 21 | o | o | o | o | CGGCGCGTCTCTCAAGCTCGC |
| 229 | 21 | o | o | o | o | GGCGCGTCTCTCAAGCTCGCC |
| 230 | 21 | o | o | o | o | GCGCGTCTCTCAAGCTCGCCT |
| 231 | 21 | o | o | o | o | CGCGTCTCTCAAGCTCGCCTC |
| 232 | 21 | o | o | o | o | GCGTCTCTCAAGCTCGCCTCT |
| 233 | 21 | o | o | o | o | CGTCTCTCAAGCTCGCCTCTT |
| 234 | 21 | o | o | o | o | GTCTCTCAAGCTCGCCTCTTC |
| 235 | 21 | o | o | o | o | TCTCTCAAGCTCGCCTCTTCG |
| 236 | 21 | o | o | o | o | CTCTCAAGCTCGCCTCTTCGG |
| 237 | 21 | o | o | o | o | TCTCAAGCTCGCCTCTTCGGA |
| 238 | 21 | o | o | o | o | CTCAAGCTCGCCTCTTCGGAG |
| 239 | 21 | o | o | o | o | TCAAGCTCGCCTCTTCGGAGC |
| 240 | 21 | o | o | o | o | CAAGCTCGCCTCTTCGGAGCT |
| 241 | 21 | o | o | o | o | AAGCTCGCCTCTTCGGAGCTG |

FIG. 24A (13)

| | | | | | |
|---|---|---|---|---|---|
| 242 | 21 | o | o | o | o | AGCTCGCCTCTTCGGAGCTGG |
| 243 | 21 | o | o | o | o | GCTCGCCCTCTTCGGAGCTGGA |
| 244 | 21 | o | o | o | o | CTCGCCCTCTTCGGAGCTGGA |
| 245 | 21 | o | o | o | o | TCGCCCTCTTCGGAGCTGGAA |
| 246 | 21 | o | o | o | o | CGCCCTCTTCGGAGCTGGAAC |
| 247 | 21 | o | o | o | o | GCCCTCTTCGGAGCTGGAACG |
| 248 | 21 | o | o | o | o | CCCTCTTCGGAGCTGGAACGC |
| 249 | 21 | o | o | o | o | CCTCTTCGGAGCTGGAACGCC |
| 250 | 21 | o | o | o | o | CTCTTCGGAGCTGGAACGCCT |
| 251 | 21 | o | o | o | o | TCTTCGGAGCTGGAACGCCCT |
| 252 | 21 | o | o | o | o | CTTCGGAGCTGGAACGCCCTG |
| 253 | 21 | o | o | o | o | TTCGGAGCTGGAACGCCCTGA |
| 254 | 21 | o | o | o | o | TCGGAGCTGGAACGCCCTGAT |
| 255 | 21 | o | o | o | o | CGGAGCTGGAACGCCCTGATT |
| 256 | 21 | o | o | o | o | GGAGCTGGAACGCCCTGATTG |
| 257 | 21 | o | o | o | o | GAGCTGGAACGCCCTGATTGT |
| 258 | 21 | o | o | o | o | AGCTGGAACGCCCTGATTGTC |
| 259 | 21 | o | o | o | o | GCTGGAACGCCCTGATTGTCC |
| 260 | 21 | o | o | o | o | CTGGAACGCCCTGATTGTCCC |
| 261 | 21 | o | o | o | o | TGGAACGCCCTGATTGTCCCA |
| 262 | 21 | o | o | o | o | GGAACGCCCTGATTGTCCCCA |
| 263 | 21 | o | o | o | o | GAACGCCCTGATTGTCCCCAAC |

FIG. 24A (14)

| | | | | | |
|---|---|---|---|---|---|
| 263 | 21 | 0 | 0 | 0 | 0 | AACGCCTGATTGTCCCCAACA |
| 264 | 21 | 0 | 0 | 0 | 0 | ACGCCTGATTGTCCCCAACAG |
| 265 | 21 | 0 | 0 | 0 | 0 | CGCCTGATTGTCCCCAACAGC |
| 266 | 21 | 0 | 0 | 0 | 0 | GCCTGATTGTCCCCAACAGCA |
| 267 | 21 | 0 | 0 | 0 | 0 | CCTGATTGTCCCCAACAGCAA |
| 268 | 21 | 0 | 0 | 0 | 0 | CTGATTGTCCCCAACAGCAAC |
| 269 | 21 | 0 | 0 | 0 | 0 | TGATTGTCCCCAACAGCAACG |
| 270 | 21 | 0 | 0 | 0 | 0 | GATTGTCCCCAACAGCAACGG |
| 271 | 21 | 0 | 0 | 0 | 0 | ATTGTCCCCAACAGCAACGGC |
| 272 | 21 | 0 | 0 | 0 | 0 | TTGTCCCCAACAGCAACGGCG |
| 273 | 21 | 0 | 0 | 0 | 0 | TGTCCCCAACAGCAACGGCGT |
| 274 | 21 | 0 | 0 | 0 | 0 | GTCCCCAACAGCAACGGCGTG |
| 275 | 21 | 0 | 0 | 0 | 0 | TCCCCAACAGCAACGGCGTGA |
| 276 | 21 | 0 | 0 | 0 | 0 | CCCCAACAGCAACGGCGTGAT |
| 277 | 21 | 0 | 0 | 0 | 0 | CCCAACAGCAACGGCGTGATC |
| 278 | 21 | 0 | 0 | 0 | 0 | CCAACAGCAACGGCGTGATCA |
| 279 | 21 | 0 | 0 | 0 | 0 | CAACAGCAACGGCGTGATCAC |
| 280 | 21 | 0 | 0 | 0 | 0 | AACAGCAACGGCGTGATCACG |
| 281 | 21 | 0 | 0 | 0 | 0 | ACAGCAACGGCGTGATCACGA |
| 282 | 21 | 0 | 0 | 0 | 0 | CAGCAACGGCGTGATCACGAC |
| 283 | 21 | 0 | 0 | 0 | 0 | AGCAACGGCGTGATCACGACG |

FIG. 24A (15)

| # | | | | | | Sequence |
|---|---|---|---|---|---|---|
| 284 | 21 | o | o | o | o | GCAACGGCGTGATCACGACGA |
| 285 | 21 | o | o | o | o | CAACGGCGTGATCACGACGAC |
| 286 | 21 | o | o | o | o | AACGGCGTGATCACGACGACG |
| 287 | 21 | o | o | o | o | ACGGCGTGATCACGACGACGC |
| 288 | 21 | o | o | o | o | CGGCGTGATCACGACGACGCC |
| 289 | 21 | o | o | o | o | GGCGTGATCACGACGACGCCT |
| 290 | 21 | o | o | o | o | GCGTGATCACGACGACGCCTA |
| 291 | 21 | o | o | o | o | CGTGATCACGACGACGCCTAC |
| 292 | 21 | o | o | o | o | GTGATCACGACGACGCCTACA |
| 293 | 21 | o | o | o | o | TGATCACGACGACGCCTACAC |
| 294 | 21 | o | o | o | o | GATCACGACGACGCCTACACC |
| 295 | 21 | o | o | o | o | ATCACGACGACGCCTACACCC |
| 296 | 21 | o | o | o | o | TCACGACGACGCCTACACCCC |
| 297 | 21 | o | o | o | o | CACGACGACGCCTACACCCCC |
| 298 | 21 | o | o | o | o | ACGACGACGCCTACACCCCCG |
| 299 | 21 | o | o | o | o | CGACGACGCCTACACCCCCGG |
| 300 | 21 | o | o | o | o | GACGACGCCTACACCCCCGGG |
| 301 | 21 | o | o | o | o | ACGACGCCTACACCCCCGGGA |
| 302 | 21 | o | o | o | o | CGACGCCTACACCCCCGGGAC |
| 303 | 21 | o | o | o | o | GACGCCTACACCCCCGGGACA |
| 304 | 21 | o | o | o | o | ACGCCTACACCCCCGGGACAG |

FIG. 24A (16)

| | | | | | |
|---|---|---|---|---|---|
| 305 | 21 | 0 | 0 | 0 | 0 | CGCCTACACCCCCGGGACAGT |
| 306 | 21 | 0 | 0 | 0 | 0 | GCCTACACCCCCGGGACAGTA |
| 307 | 21 | 0 | 0 | 0 | 0 | CCTACACCCCCGGGACAGTAC |
| 308 | 21 | 0 | 0 | 0 | 0 | CTACACCCCCGGGACAGTACT |
| 309 | 21 | 0 | 0 | 0 | 0 | TACACCCCCGGGACAGTACTT |
| 310 | 21 | 0 | 0 | 0 | 0 | ACACCCCCGGGACAGTACTTT |
| 311 | 21 | 0 | 0 | 0 | 0 | CACCCCCGGGACAGTACTTTT |
| 312 | 21 | 0 | 0 | 0 | 0 | ACCCCCGGGACAGTACTTTTA |
| 313 | 21 | 0 | 0 | 0 | 0 | CCCCCGGGACAGTACTTTTAC |
| 314 | 21 | 0 | 0 | 0 | 0 | CCCCGGGACAGTACTTTTACC |
| 315 | 21 | 0 | 0 | 0 | 0 | CCCGGGACAGTACTTTTACCC |
| 316 | 21 | 0 | 0 | 0 | 0 | CCGGGACAGTACTTTTACCCC |
| 317 | 21 | 0 | 0 | 0 | 0 | CGGGACAGTACTTTTACCCCC |
| 318 | 21 | 0 | 0 | 0 | 0 | GGGACAGTACTTTTACCCCCG |
| 319 | 21 | 0 | 0 | 0 | 0 | GGACAGTACTTTTACCCCCGC |
| 320 | 21 | 0 | 0 | 0 | 0 | GACAGTACTTTTACCCCCGCG |
| 321 | 21 | 0 | 0 | 0 | 0 | ACAGTACTTTTACCCCCGCGG |
| 322 | 21 | 0 | 0 | 0 | 0 | CAGTACTTTTACCCCCGCGGG |
| 323 | 21 | 0 | 0 | 0 | 0 | AGTACTTTTACCCCCGCGGGG |
| 324 | 21 | 0 | 0 | 0 | 0 | GTACTTTTACCCCCGCGGGGG |
| 325 | 21 | 0 | 0 | 0 | 0 | TACTTTTACCCCCGCGGGGGT |

FIG. 24A (17)

| # | | | | | Sequence |
|---|---|---|---|---|---|
| 326 21 | 0 | 0 | 0 | 0 | ACTTTTACCCCCGCGGGGGTG |
| 327 21 | 0 | 0 | 0 | 0 | CTTTTACCCCCGCGGGGGTGG |
| 328 21 | 0 | 0 | 0 | 0 | TTTTACCCCCGCGGGGGTGGC |
| 329 21 | 0 | 0 | 0 | 0 | TTTACCCCCGCGGGGGTGGCA |
| 330 21 | 0 | 0 | 0 | 0 | TTACCCCCGCGGGGGTGGCAG |
| 331 21 | 0 | 0 | 0 | 0 | TACCCCCGCGGGGGTGGCAGC |
| 332 21 | 0 | 0 | 0 | 0 | ACCCCCGCGGGGGTGGCAGCG |
| 333 21 | 0 | 0 | 0 | 0 | CCCCCGCGGGGGTGGCAGCGG |
| 334 21 | 0 | 0 | 0 | 0 | CCCCGCGGGGGTGGCAGCGGT |
| 335 21 | 0 | 0 | 0 | 0 | CCCGCGGGGGTGGCAGCGGTG |
| 336 21 | 0 | 0 | 0 | 0 | CCGCGGGGGTGGCAGCGGTGG |
| 337 21 | 0 | 0 | 0 | 0 | CGCGGGGGTGGCAGCGGTGGA |
| 338 21 | 0 | 0 | 0 | 0 | GCGGGGGTGGCAGCGGTGGAG |
| 339 21 | 0 | 0 | 0 | 0 | CGGGGGTGGCAGCGGTGGAGG |
| 340 21 | 0 | 0 | 0 | 0 | GGGGGTGGCAGCGGTGGAGGT |
| 341 21 | 0 | 0 | 0 | 0 | GGGGTGGCAGCGGTGGAGGTG |
| 342 21 | 0 | 0 | 0 | 0 | GGGTGGCAGCGGTGGAGGTGC |
| 343 21 | 0 | 0 | 0 | 0 | GGTGGCAGCGGTGGAGGTGCA |
| 344 21 | 0 | 0 | 0 | 0 | GTGGCAGCGGTGGAGGTGCAG |
| 345 21 | 0 | 0 | 0 | 0 | TGGCAGCGGTGGAGGTGCAGG |
| 346 21 | 0 | 0 | 0 | 0 | GGCAGCGGTGGAGGTGCAGGG |

FIG. 24A (18)

| | | | | | |
|---|---|---|---|---|---|
| 347 | 21 | 0 | 0 | 0 | 0 | GCAGCGGTGGAGGTGCAGGGG |
| 348 | 21 | 0 | 0 | 0 | 0 | CAGCGGTGGAGGTGCAGGGGG |
| 349 | 21 | 0 | 0 | 0 | 0 | AGCGGTGGAGGTGCAGGGGGC |
| 350 | 21 | 0 | 0 | 0 | 0 | GCGGTGGAGGTGCAGGGGGCG |
| 351 | 21 | 0 | 0 | 0 | 0 | CGGTGGAGGTGCAGGGGGCGC |
| 352 | 21 | 0 | 0 | 0 | 0 | GGTGGAGGTGCAGGGGGCGCA |
| 353 | 21 | 0 | 0 | 0 | 0 | GTGGAGGTGCAGGGGGCGCAG |
| 354 | 21 | 0 | 0 | 0 | 0 | TGGAGGTGCAGGGGGCGCAGG |
| 355 | 21 | 0 | 0 | 0 | 0 | GGAGGTGCAGGGGGCGCAGGG |
| 356 | 21 | 0 | 0 | 0 | 0 | GAGGTGCAGGGGGCGCAGGGG |
| 357 | 21 | 0 | 0 | 0 | 0 | AGGTGCAGGGGGCGCAGGGGG |
| 358 | 21 | 0 | 0 | 0 | 0 | GGTGCAGGGGGCGCAGGGGGC |
| 359 | 21 | 0 | 0 | 0 | 0 | GTGCAGGGGGCGCAGGGGGCG |
| 360 | 21 | 0 | 0 | 0 | 0 | TGCAGGGGGCGCAGGGGGCGG |
| 361 | 21 | 0 | 0 | 0 | 0 | GCAGGGGGCGCAGGGGGCGGC |
| 362 | 21 | 0 | 0 | 0 | 0 | CAGGGGGCGCAGGGGGCGGCG |
| 363 | 21 | 0 | 0 | 0 | 0 | AGGGGGCGCAGGGGGCGGCGT |
| 364 | 21 | 0 | 0 | 0 | 0 | GGGGGCGCAGGGGGCGGCGTC |
| 365 | 21 | 0 | 0 | 0 | 0 | GGGGCGCAGGGGGCGGCGTCA |
| 366 | 21 | 0 | 0 | 0 | 0 | GGGCGCAGGGGGCGGCGTCAC |
| 367 | 21 | 0 | 0 | 0 | 0 | GGCGCAGGGGGCGGCGTCACC |

FIG. 24A (19)

| | | | | | |
|---|---|---|---|---|---|
| 368 | 21 | 0 | 0 | 0 | 0 | 0 | GCGCAGGGGGCGGCGTCACCG |
| 369 | 21 | 0 | 0 | 0 | 0 | 0 | CGCAGGGGGCGGCGTCACCGA |
| 370 | 21 | 0 | 0 | 0 | 0 | 0 | GCAGGGGGCGGCGTCACCGAG |
| 371 | 21 | 0 | 0 | 0 | 0 | 0 | CAGGGGGCGGCGTCACCGAGG |
| 372 | 21 | 0 | 0 | 0 | 0 | 0 | AGGGGGCGGCGTCACCGAGGA |
| 373 | 21 | 0 | 0 | 0 | 0 | 0 | GGGGGCGGCGTCACCGAGGAG |
| 374 | 21 | 0 | 0 | 0 | 0 | 0 | GGGGCGGCGTCACCGAGGAGC |
| 375 | 21 | 0 | 0 | 0 | 0 | 0 | GGGCGGCGTCACCGAGGAGCA |
| 376 | 21 | 0 | 0 | 0 | 0 | 0 | GGCGGCGTCACCGAGGAGCAG |
| 377 | 21 | 0 | 0 | 0 | 0 | 0 | GCGGCGTCACCGAGGAGCAGG |
| 378 | 21 | 0 | 0 | 0 | 0 | 0 | CGGCGTCACCGAGGAGCAGGA |
| 379 | 21 | 0 | 0 | 0 | 0 | 0 | GGCGTCACCGAGGAGCAGGAG |
| 380 | 21 | 0 | 0 | 0 | 0 | 0 | GCGTCACCGAGGAGCAGGAGG |
| 381 | 21 | 0 | 0 | 0 | 0 | 0 | CGTCACCGAGGAGCAGGAGGG |
| 382 | 21 | 0 | 0 | 0 | 0 | 0 | GTCACCGAGGAGCAGGAGGGC |
| 383 | 21 | 0 | 0 | 0 | 0 | 0 | TCACCGAGGAGCAGGAGGGCT |
| 384 | 21 | 0 | 0 | 0 | 0 | 0 | CACCGAGGAGCAGGAGGGCTT |
| 385 | 21 | 0 | 0 | 0 | 0 | 0 | ACCGAGGAGCAGGAGGGCTTC |
| 386 | 21 | 0 | 0 | 0 | 0 | 0 | CCGAGGAGCAGGAGGGCTTCG |
| 387 | 21 | 0 | 0 | 0 | 0 | 0 | CGAGGAGCAGGAGGGCTTCGC |
| 388 | 21 | 0 | 0 | 0 | 0 | 0 | GAGGAGCAGGAGGGCTTCGCC |

FIG. 24A (20)

| | | | | | |
|---|---|---|---|---|---|
| 389 | 21 | 0 | 0 | 0 | 0 | AGGAGCAGGAGGGCTTCGCCG |
| 390 | 21 | 0 | 0 | 0 | 0 | GGAGCAGGAGGGCTTCGCCGA |
| 391 | 21 | 0 | 0 | 0 | 0 | GAGCAGGAGGGCTTCGCCGAC |
| 392 | 21 | 0 | 0 | 0 | 0 | AGCAGGAGGGCTTCGCCGACG |
| 393 | 21 | 0 | 0 | 0 | 0 | GCAGGAGGGCTTCGCCGACGG |
| 394 | 21 | 0 | 0 | 0 | 0 | CAGGAGGGCTTCGCCGACGGC |
| 395 | 21 | 0 | 0 | 0 | 0 | AGGAGGGCTTCGCCGACGGCT |
| 396 | 21 | 0 | 0 | 0 | 0 | GGAGGGCTTCGCCGACGGCTT |
| 397 | 21 | 0 | 0 | 0 | 0 | GAGGGCTTCGCCGACGGCTTT |
| 398 | 21 | 0 | 0 | 0 | 0 | AGGGCTTCGCCGACGGCTTTG |
| 399 | 21 | 0 | 0 | 0 | 0 | GGGCTTCGCCGACGGCTTTGT |
| 400 | 21 | 0 | 0 | 0 | 0 | GGCTTCGCCGACGGCTTTGTC |
| 401 | 21 | 0 | 0 | 0 | 0 | GCTTCGCCGACGGCTTTGTCA |
| 402 | 21 | 0 | 0 | 0 | 0 | CTTCGCCGACGGCTTTGTCAA |
| 403 | 21 | 0 | 0 | 0 | 0 | TTCGCCGACGGCTTTGTCAAA |
| 404 | 21 | 0 | 0 | 0 | 0 | TCGCCGACGGCTTTGTCAAAG |
| 405 | 21 | 0 | 0 | 0 | 0 | CGCCGACGGCTTTGTCAAAGC |
| 406 | 21 | 0 | 0 | 0 | 0 | GCCGACGGCTTTGTCAAAGCC |
| 407 | 21 | 0 | 0 | 0 | 0 | CCGACGGCTTTGTCAAAGCCC |
| 408 | 21 | 0 | 0 | 0 | 0 | CGACGGCTTTGTCAAAGCCCT |
| 409 | 21 | 0 | 0 | 0 | 0 | GACGGCTTTGTCAAAGCCCTG |

FIG. 24A (21)

| | | | | | |
|---|---|---|---|---|---|
| 410 | 21 | 0 | 0 | 0 | 0 | ACGGCTTTGTCAAAGCCCTGG |
| 411 | 21 | 0 | 0 | 0 | 0 | CGGCTTTGTCAAAGCCCTGGA |
| 412 | 21 | 0 | 0 | 0 | 0 | GGCTTTGTCAAAGCCCTGGAC |
| 413 | 21 | 0 | 0 | 0 | 0 | GCTTTGTCAAAGCCCTGGACG |
| 414 | 21 | 0 | 0 | 0 | 0 | CTTTGTCAAAGCCCTGGACGA |
| 415 | 21 | 0 | 0 | 0 | 0 | TTTGTCAAAGCCCTGGACGAT |
| 416 | 21 | 0 | 0 | 0 | 0 | TTGTCAAAGCCCTGGACGATC |
| 417 | 21 | 0 | 0 | 0 | 0 | TGTCAAAGCCCTGGACGATCT |
| 418 | 21 | 0 | 0 | 0 | 0 | GTCAAAGCCCTGGACGATCTG |
| 419 | 21 | 0 | 0 | 0 | 0 | TCAAAGCCCTGGACGATCTGC |
| 420 | 21 | 0 | 0 | 0 | 0 | CAAAGCCCTGGACGATCTGCA |
| 421 | 21 | 0 | 0 | 0 | 0 | AAAGCCCTGGACGATCTGCAC |
| 422 | 21 | 0 | 0 | 0 | 0 | AAGCCCTGGACGATCTGCACA |
| 423 | 21 | 0 | 0 | 0 | 0 | AGCCCTGGACGATCTGCACAA |
| 424 | 21 | 0 | 0 | 0 | 0 | GCCCTGGACGATCTGCACAAG |
| 425 | 21 | 0 | 0 | 0 | 0 | CCCTGGACGATCTGCACAAGA |
| 426 | 21 | 0 | 0 | 0 | 0 | CCTGGACGATCTGCACAAGAT |
| 427 | 21 | 0 | 0 | 0 | 0 | CTGGACGATCTGCACAAGATG |
| 428 | 21 | 0 | 0 | 0 | 0 | TGGACGATCTGCACAAGATGA |
| 429 | 21 | 0 | 0 | 0 | 0 | GGACGATCTGCACAAGATGAA |
| 430 | 21 | 0 | 0 | 0 | 0 | GACGATCTGCACAAGATGAAC |

FIG. 24A (22)

| | | | | | |
|---|---|---|---|---|---|
| 431 | 21 | 0 | 0 | 0 | 0 | ACGATCTGCACAAGATGAACC |
| 432 | 21 | 0 | 0 | 0 | 0 | CGATCTGCACAAGATGAACCA |
| 433 | 21 | 0 | 0 | 0 | 0 | GATCTGCACAAGATGAACCAC |
| 434 | 21 | 0 | 0 | 0 | 0 | ATCTGCACAAGATGAACCACG |
| 435 | 21 | 0 | 0 | 0 | 0 | TCTGCACAAGATGAACCACGT |
| 436 | 21 | 0 | 0 | 0 | 0 | CTGCACAAGATGAACCACGTG |
| 437 | 21 | 0 | 0 | 0 | 0 | TGCACAAGATGAACCACGTGA |
| 438 | 21 | 0 | 0 | 0 | 0 | GCACAAGATGAACCACGTGAC |
| 439 | 21 | 0 | 0 | 0 | 0 | CACAAGATGAACCACGTGACA |
| 440 | 21 | 0 | 0 | 0 | 0 | ACAAGATGAACCACGTGACAC |
| 441 | 21 | 0 | 0 | 0 | 0 | CAAGATGAACCACGTGACACC |
| 442 | 21 | 0 | 0 | 0 | 0 | AAGATGAACCACGTGACACCC |
| 443 | 21 | 0 | 0 | 0 | 0 | AGATGAACCACGTGACACCCC |
| 444 | 21 | 0 | 0 | 0 | 0 | GATGAACCACGTGACACCCCC |
| 445 | 21 | 0 | 0 | 0 | 0 | ATGAACCACGTGACACCCCCC |
| 446 | 21 | 0 | 0 | 0 | 0 | TGAACCACGTGACACCCCCCA |
| 447 | 21 | 0 | 0 | 0 | 0 | GAACCACGTGACACCCCCCAA |
| 448 | 21 | 0 | 0 | 0 | 0 | AACCACGTGACACCCCCCAAC |
| 449 | 21 | 0 | 0 | 0 | 0 | ACCACGTGACACCCCCCAACG |
| 450 | 21 | 0 | 0 | 0 | 0 | CCACGTGACACCCCCCAACGT |
| 451 | 21 | 0 | 0 | 0 | 0 | CACGTGACACCCCCCAACGTG |

FIG. 24A (23)

| | | | | | |
|---|---|---|---|---|---|
| 452 | 21 | o o o o o | o o o o o | o o o o o | o | ACGTGACACCCCCAACGTGT |
| 453 | 21 | o o o o o | o o o o o | o o o o o | o | CGTGACACCCCCAACGTGTC |
| 454 | 21 | o o o o o | o o o o o | o o o o o | o | GTGACACCCCCAACGTGTCC |
| 455 | 21 | o o o o o | o o o o o | o o o o o | o | TGACACCCCCAACGTGTCCC |
| 456 | 21 | o o o o o | o o o o o | o o o o o | o | GACACCCCCAACGTGTCCCT |
| 457 | 21 | o o o o o | o o o o o | o o o o o | o | ACACCCCCAACGTGTCCCTG |
| 458 | 21 | o o o o o | o o o o o | o o o o o | o | CACCCCCAACGTGTCCCTGG |
| 459 | 21 | o o o o o | o o o o o | o o o o o | o | ACCCCCAACGTGTCCCTGGG |
| 460 | 21 | o o o o o | o o o o o | o o o o o | o | CCCCCAACGTGTCCCTGGGC |
| 461 | 21 | o o o o o | o o o o o | o o o o o | o | CCCCAACGTGTCCCTGGGCG |
| 462 | 21 | o o o o o | o o o o o | o o o o o | o | CCCAACGTGTCCCTGGGCGC |
| 463 | 21 | o o o o o | o o o o o | o o o o o | o | CCAACGTGTCCCTGGGCGCT |
| 464 | 21 | o o o o o | o o o o o | o o o o o | o | CAACGTGTCCCTGGGCGCTA |
| 465 | 21 | o o o o o | o o o o o | o o o o o | o | AACGTGTCCCTGGGCGCTAC |
| 466 | 21 | o o o o o | o o o o o | o o o o o | o | ACGTGTCCCTGGGCGCTACC |
| 467 | 21 | o o o o o | o o o o o | o o o o o | o | CGTGTCCCTGGGCGCTACCG |
| 468 | 21 | o o o o o | o o o o o | o o o o o | o | GTGTCCCTGGGCGCTACCGG |
| 469 | 21 | o o o o o | o o o o o | o o o o o | o | TGTCCCTGGGCGCTACCGGG |
| 470 | 21 | o o o o o | o o o o o | o o o o o | o | GTCCCTGGGCGCTACCGGGG |
| 471 | 21 | o o o o o | o o o o o | o o o o o | o | TCCCTGGGCGCTACCGGGGG |
| 472 | 21 | o o o o o | o o o o o | o o o o o | o | CCCTGGGCGCTACCGGGGGG |

FIG. 24A (24)

| | | | | | |
|---|---|---|---|---|---|
| 473 | 21 | o | o | o | o | o | CCCTGGGCGCTACCGGGGGC |
| 474 | 21 | o | o | o | o | o | CCTGGGCGCTACCGGGGGCC |
| 475 | 21 | o | o | o | o | o | CTGGGCGCTACCGGGGGCCC |
| 476 | 21 | o | o | o | o | o | TGGGCGCTACCGGGGGCCCC |
| 477 | 21 | o | o | o | o | o | GGGCGCTACCGGGGGCCCCC |
| 478 | 21 | o | o | o | o | o | GGCGCTACCGGGGGCCCCCG |
| 479 | 21 | o | o | o | o | o | GCGCTACCGGGGGCCCCCGG |
| 480 | 21 | o | o | o | o | o | CGCTACCGGGGGCCCCCGGC |
| 481 | 21 | o | o | o | o | o | GCTACCGGGGGCCCCCGGCT |
| 482 | 21 | o | o | o | o | o | CTACCGGGGGCCCCCGGCTG |
| 483 | 21 | o | o | o | o | o | TACCGGGGGCCCCCGGCTGG |
| 484 | 21 | o | o | o | o | o | ACCGGGGGCCCCCGGCTGGG |
| 485 | 21 | o | o | o | o | o | CCGGGGGCCCCCGGCTGGGC |
| 486 | 21 | o | o | o | o | o | CGGGGGCCCCCGGCTGGGCC |
| 487 | 21 | o | o | o | o | o | GGGGGCCCCCGGCTGGGCCC |
| 488 | 21 | o | o | o | o | o | GGGGCCCCCGGCTGGGCCCG |
| 489 | 21 | o | o | o | o | o | GGGCCCCCGGCTGGGCCCGG |
| 490 | 21 | o | o | o | o | o | GGCCCCCGGCTGGGCCCGGG |
| 491 | 21 | o | o | o | o | o | GCCCCCGGCTGGGCCCGGGG |
| 492 | 21 | o | o | o | o | o | CCCCCGGCTGGGCCCGGGGG |
| 493 | 21 | o | o | o | o | o | CCCCGGCTGGGCCCGGGGGC |

FIG. 24A (25)

| | | | | | |
|---|---|---|---|---|---|
| 494 | 21 | 0 | 0 | 0 | 0 | 0 | CCCCGGCTGGGCCCGGGGGCG |
| 495 | 21 | 0 | 0 | 0 | 0 | 0 | CCCGGCTGGGCCCGGGGGCGT |
| 496 | 21 | 0 | 0 | 0 | 0 | 0 | CCGGCTGGGCCCGGGGGCGTC |
| 497 | 21 | 0 | 0 | 0 | 0 | 0 | CGGCTGGGCCCGGGGGCGTCT |
| 498 | 21 | 0 | 0 | 0 | 0 | 0 | GGCTGGGCCCGGGGGCGTCTA |
| 499 | 21 | 0 | 0 | 0 | 0 | 0 | GCTGGGCCCGGGGGCGTCTAC |
| 500 | 21 | 0 | 0 | 0 | 0 | 0 | CTGGGCCCGGGGGCGTCTACG |
| 501 | 21 | 0 | 0 | 0 | 0 | 0 | TGGGCCCGGGGGCGTCTACGC |
| 502 | 21 | 0 | 0 | 0 | 0 | 0 | GGGCCCGGGGGCGTCTACGCC |
| 503 | 21 | 0 | 0 | 0 | 0 | 0 | GGCCCGGGGGCGTCTACGCCG |
| 504 | 21 | 0 | 0 | 0 | 0 | 0 | GCCCGGGGGCGTCTACGCCGG |
| 505 | 21 | 0 | 0 | 0 | 0 | 0 | CCCGGGGGCGTCTACGCCGGC |
| 506 | 21 | 0 | 0 | 0 | 0 | 0 | CCGGGGGCGTCTACGCCGGCC |
| 507 | 21 | 0 | 0 | 0 | 0 | 0 | CGGGGGCGTCTACGCCGGCCC |
| 508 | 21 | 0 | 0 | 0 | 0 | 0 | GGGGGCGTCTACGCCGGCCCG |
| 509 | 21 | 0 | 0 | 0 | 0 | 0 | GGGGCGTCTACGCCGGCCCGG |
| 510 | 21 | 0 | 0 | 0 | 0 | 0 | GGGCGTCTACGCCGGCCCGGA |
| 511 | 21 | 0 | 0 | 0 | 0 | 0 | GGCGTCTACGCCGGCCCGGAG |
| 512 | 21 | 0 | 0 | 0 | 0 | 0 | GCGTCTACGCCGGCCCGGAGC |
| 513 | 21 | 0 | 0 | 0 | 0 | 0 | CGTCTACGCCGGCCCGGAGCC |
| 514 | 21 | 0 | 0 | 0 | 0 | 0 | GTCTACGCCGGCCCGGAGCCA |

FIG. 24A (26)

| | | | | |
|---|---|---|---|---|
| 515 | 21 | 0 | 0 | 0 | 0 | TCTACGCCCGGCCCGGAGCCAC |
| 516 | 21 | 0 | 0 | 0 | 0 | CTACGCCCGGCCCGGAGCCACC |
| 517 | 21 | 0 | 0 | 0 | 0 | TACGCCCGGCCCGGAGCCACCT |
| 518 | 21 | 0 | 0 | 0 | 0 | ACGCCCGGCCCGGAGCCACCTC |
| 519 | 21 | 0 | 0 | 0 | 0 | CGCCCGGCCCGGAGCCACCTCC |
| 520 | 21 | 0 | 0 | 0 | 0 | GCCCGGCCCGGAGCCACCTCCC |
| 521 | 21 | 0 | 0 | 0 | 0 | CCCGGCCCGGAGCCACCTCCCC |
| 522 | 21 | 0 | 0 | 0 | 0 | CCGGCCCGGAGCCACCTCCCCG |
| 523 | 21 | 0 | 0 | 0 | 0 | CGGCCCGGAGCCACCTCCCCGT |
| 524 | 21 | 0 | 0 | 0 | 0 | GGCCCGGAGCCACCTCCCCGTT |
| 525 | 21 | 0 | 0 | 0 | 0 | GCCCGGAGCCACCTCCCCGTTT |
| 526 | 21 | 0 | 0 | 0 | 0 | CCCGGAGCCACCTCCCCGTTTA |
| 527 | 21 | 0 | 0 | 0 | 0 | CCGGAGCCACCTCCCCGTTTAC |
| 528 | 21 | 0 | 0 | 0 | 0 | CGGAGCCACCTCCCCGTTTACA |
| 529 | 21 | 0 | 0 | 0 | 0 | GGAGCCACCTCCCCGTTTACAC |
| 530 | 21 | 0 | 0 | 0 | 0 | GAGCCACCTCCCCGTTTACACC |
| 531 | 21 | 0 | 0 | 0 | 0 | AGCCACCTCCCCGTTTACACCA |
| 532 | 21 | 0 | 0 | 0 | 0 | GCCACCTCCCCGTTTACACCAA |
| 533 | 21 | 0 | 0 | 0 | 0 | CCACCTCCCCGTTTACACCAAC |
| 534 | 21 | 0 | 0 | 0 | 0 | CACCTCCCCGTTTACACCAACC |
| 535 | 21 | 0 | 0 | 0 | 0 | ACCTCCCCGTTTACACCAACCT |
| | | | | | | CCTCCCCGTTTACACCAACCTC |

FIG. 24A (27)

| | | | | | |
|---|---|---|---|---|---|
| 536 | 21 | 0 | 0 | 0 | 0 | CTCCCGTTTACACCAACCTCA |
| 537 | 21 | 0 | 0 | 0 | 0 | TCCCGTTTACACCAACCTCAG |
| 538 | 21 | 0 | 0 | 0 | 0 | CCCGTTTACACCAACCTCAGC |
| 539 | 21 | 0 | 0 | 0 | 0 | CCGTTTACACCAACCTCAGCA |
| 540 | 21 | 0 | 0 | 0 | 0 | CGTTTACACCAACCTCAGCAG |
| 541 | 21 | 0 | 0 | 0 | 0 | GTTTACACCAACCTCAGCAGC |
| 542 | 21 | 0 | 0 | 0 | 0 | TTTACACCAACCTCAGCAGCT |
| 543 | 21 | 0 | 0 | 0 | 0 | TTACACCAACCTCAGCAGCTA |
| 544 | 21 | 0 | 0 | 0 | 0 | TACACCAACCTCAGCAGCTAC |
| 545 | 21 | 0 | 0 | 0 | 0 | ACACCAACCTCAGCAGCTACT |
| 546 | 21 | 0 | 0 | 0 | 0 | CACCAACCTCAGCAGCTACTC |
| 547 | 21 | 0 | 0 | 0 | 0 | ACCAACCTCAGCAGCTACTCC |
| 548 | 21 | 0 | 0 | 0 | 0 | CCAACCTCAGCAGCTACTCCC |
| 549 | 21 | 0 | 0 | 0 | 0 | CAACCTCAGCAGCTACTCCCC |
| 550 | 21 | 0 | 0 | 0 | 0 | AACCTCAGCAGCTACTCCCCA |
| 551 | 21 | 0 | 0 | 0 | 0 | ACCTCAGCAGCTACTCCCCAG |
| 552 | 21 | 0 | 0 | 0 | 0 | CCTCAGCAGCTACTCCCCAGC |
| 553 | 21 | 0 | 0 | 0 | 0 | CTCAGCAGCTACTCCCCAGCC |
| 554 | 21 | 0 | 0 | 0 | 0 | TCAGCAGCTACTCCCCAGCCT |
| 555 | 21 | 0 | 0 | 0 | 0 | CAGCAGCTACTCCCCAGCCTC |
| 556 | 21 | 0 | 0 | 0 | 0 | AGCAGCTACTCCCCAGCCTCT |

FIG. 24A (28)

| | | | | | |
|---|---|---|---|---|---|
| 557 | 21 | 0 | 0 | 0 | 0 | GCAGCTACTCCCCAGCCTCTG |
| 558 | 21 | 0 | 0 | 0 | 0 | CAGCTACTCCCCAGCCTCTGC |
| 559 | 21 | 0 | 0 | 0 | 0 | AGCTACTCCCCAGCCTCTGCG |
| 560 | 21 | 0 | 0 | 0 | 0 | GCTACTCCCCAGCCTCTGCGT |
| 561 | 21 | 0 | 0 | 0 | 0 | CTACTCCCCAGCCTCTGCGTC |
| 562 | 21 | 0 | 0 | 0 | 0 | TACTCCCCAGCCTCTGCGTCC |
| 563 | 21 | 0 | 0 | 0 | 0 | ACTCCCCAGCCTCTGCGTCCT |
| 564 | 21 | 0 | 0 | 0 | 0 | CTCCCCAGCCTCTGCGTCCTC |
| 565 | 21 | 0 | 0 | 0 | 0 | TCCCCAGCCTCTGCGTCCTCG |
| 566 | 21 | 0 | 0 | 0 | 0 | CCCCAGCCTCTGCGTCCTCGG |
| 567 | 21 | 0 | 0 | 0 | 0 | CCCAGCCTCTGCGTCCTCGGG |
| 568 | 21 | 0 | 0 | 0 | 0 | CCAGCCTCTGCGTCCTCGGGA |
| 569 | 21 | 0 | 0 | 0 | 0 | CAGCCTCTGCGTCCTCGGGAG |
| 570 | 21 | 0 | 0 | 0 | 0 | AGCCTCTGCGTCCTCGGGAGG |
| 571 | 21 | 0 | 0 | 0 | 0 | GCCTCTGCGTCCTCGGGAGGC |
| 572 | 21 | 0 | 0 | 0 | 0 | CCTCTGCGTCCTCGGGAGGCG |
| 573 | 21 | 0 | 0 | 0 | 0 | CTCTGCGTCCTCGGGAGGCGC |
| 574 | 21 | 0 | 0 | 0 | 0 | TCTGCGTCCTCGGGAGGCGCC |
| 575 | 21 | 0 | 0 | 0 | 0 | CTGCGTCCTCGGGAGGCGCCG |
| 576 | 21 | 0 | 0 | 0 | 0 | TGCGTCCTCGGGAGGCGCCGG |
| 577 | 21 | 0 | 0 | 0 | 0 | GCGTCCTCGGGAGGCGCCGGG |

FIG. 24A (29)

| | | | | | |
|---|---|---|---|---|---|
| 578 | 21 | 0 | 0 | 0 | 0 | CGTCCTCGGGAGGCGCCGGGG |
| 579 | 21 | 0 | 0 | 0 | 0 | GTCCTCGGGAGGCGCCGGGGC |
| 580 | 21 | 0 | 0 | 0 | 0 | TCCTCGGGAGGCGCCGGGGCT |
| 581 | 21 | 0 | 0 | 0 | 0 | CCTCGGGAGGCGCCGGGGCTG |
| 582 | 21 | 0 | 0 | 0 | 0 | CTCGGGAGGCGCCGGGGCTGC |
| 583 | 21 | 0 | 0 | 0 | 0 | TCGGGAGGCGCCGGGGCTGCC |
| 584 | 21 | 0 | 0 | 0 | 0 | CGGGAGGCGCCGGGGCTGCCG |
| 585 | 21 | 0 | 0 | 0 | 0 | GGGAGGCGCCGGGGCTGCCGT |
| 586 | 21 | 0 | 0 | 0 | 0 | GGAGGCGCCGGGGCTGCCGTC |
| 587 | 21 | 0 | 0 | 0 | 0 | GAGGCGCCGGGGCTGCCGTCG |
| 588 | 21 | 0 | 0 | 0 | 0 | AGGCGCCGGGGCTGCCGTCGG |
| 589 | 21 | 0 | 0 | 0 | 0 | GGCGCCGGGGCTGCCGTCGGG |
| 590 | 21 | 0 | 0 | 0 | 0 | GCGCCGGGGCTGCCGTCGGGA |
| 591 | 21 | 0 | 0 | 0 | 0 | CGCCGGGGCTGCCGTCGGGAC |
| 592 | 21 | 0 | 0 | 0 | 0 | GCCGGGGCTGCCGTCGGGACC |
| 593 | 21 | 0 | 0 | 0 | 0 | CCGGGGCTGCCGTCGGGACCG |
| 594 | 21 | 0 | 0 | 0 | 0 | CGGGGCTGCCGTCGGGACCGG |
| 595 | 21 | 0 | 0 | 0 | 0 | GGGGCTGCCGTCGGGACCGGG |
| 596 | 21 | 0 | 0 | 0 | 0 | GGGCTGCCGTCGGGACCGGGA |
| 597 | 21 | 0 | 0 | 0 | 0 | GGCTGCCGTCGGGACCGGGAG |
| 598 | 21 | 0 | 0 | 0 | 0 | GCTGCCGTCGGGACCGGGAGC |

FIG. 24A (30)

| | | | | | |
|---|---|---|---|---|---|
| 599 | 21 | o | o | o | o | CTGCCGTCGGGACCGGGAGCT |
| 600 | 21 | o | o | o | o | TGCCGTCGGGACCGGGAGCTC |
| 601 | 21 | o | o | o | o | GCCGTCGGGACCGGGAGCTCG |
| 602 | 21 | o | o | o | o | CCGTCGGGACCGGGAGCTCGT |
| 603 | 21 | o | o | o | o | CGTCGGGACCGGGAGCTCGTA |
| 604 | 21 | o | o | o | o | GTCGGGACCGGGAGCTCGTAC |
| 605 | 21 | o | o | o | o | TCGGGACCGGGAGCTCGTACC |
| 606 | 21 | o | o | o | o | CGGGACCGGGAGCTCGTACCC |
| 607 | 21 | o | o | o | o | GGGACCGGGAGCTCGTACCCG |
| 608 | 21 | o | o | o | o | GGACCGGGAGCTCGTACCCGA |
| 609 | 21 | o | o | o | o | GACCGGGAGCTCGTACCCGAC |
| 610 | 21 | o | o | o | o | ACCGGGAGCTCGTACCCGACG |
| 611 | 21 | o | o | o | o | CCGGGAGCTCGTACCCGACGA |
| 612 | 21 | o | o | o | o | CGGGAGCTCGTACCCGACGAC |
| 613 | 21 | o | o | o | o | GGGAGCTCGTACCCGACGACC |
| 614 | 21 | o | o | o | o | GGAGCTCGTACCCGACGACCA |
| 615 | 21 | o | o | o | o | GAGCTCGTACCCGACGACCAC |
| 616 | 21 | o | o | o | o | AGCTCGTACCCGACGACCACC |
| 617 | 21 | o | o | o | o | GCTCGTACCCGACGACCACCA |
| 618 | 21 | o | o | o | o | CTCGTACCCGACGACCACCAT |
| 619 | 21 | o | o | o | o | TCGTACCCGACGACCACCATC |

FIG. 24A (31)

| | | | | | |
|---|---|---|---|---|---|
| 620 | 21 | 0 | 0 | 0 | 0 | 0 | CGTACCCGACGACCACCATCA |
| 621 | 21 | 0 | 0 | 0 | 0 | 0 | GTACCCGACGACCACCATCAG |
| 622 | 21 | 0 | 0 | 0 | 0 | 0 | TACCCGACGACCACCATCAGC |
| 623 | 21 | 0 | 0 | 0 | 0 | 0 | ACCCGACGACCACCATCAGCT |
| 624 | 21 | 0 | 0 | 0 | 0 | 0 | CCCGACGACCACCATCAGCTA |
| 625 | 21 | 0 | 0 | 0 | 0 | 0 | CCGACGACCACCATCAGCTAC |
| 626 | 21 | 0 | 0 | 0 | 0 | 0 | CGACGACCACCATCAGCTACC |
| 627 | 21 | 0 | 0 | 0 | 0 | 0 | GACGACCACCATCAGCTACCT |
| 628 | 21 | 0 | 0 | 0 | 0 | 0 | ACGACCACCATCAGCTACCTC |
| 629 | 21 | 0 | 0 | 0 | 0 | 0 | CGACCACCATCAGCTACCTCC |
| 630 | 21 | 0 | 0 | 0 | 0 | 0 | GACCACCATCAGCTACCTCCC |
| 631 | 21 | 0 | 0 | 0 | 0 | 0 | ACCACCATCAGCTACCTCCCA |
| 632 | 21 | 0 | 0 | 0 | 0 | 0 | CCACCATCAGCTACCTCCCAC |
| 633 | 21 | 0 | 0 | 0 | 0 | 0 | CACCATCAGCTACCTCCCACA |
| 634 | 21 | 0 | 0 | 0 | 0 | 0 | ACCATCAGCTACCTCCCACAC |
| 635 | 21 | 0 | 0 | 0 | 0 | 0 | CCATCAGCTACCTCCCACACG |
| 636 | 21 | 0 | 0 | 0 | 0 | 0 | CATCAGCTACCTCCCACACGC |
| 637 | 21 | 0 | 0 | 0 | 0 | 0 | ATCAGCTACCTCCCACACGCG |
| 638 | 21 | 0 | 0 | 0 | 0 | 0 | TCAGCTACCTCCCACACGCGC |
| 639 | 21 | 0 | 0 | 0 | 0 | 0 | CAGCTACCTCCCACACGCGCC |
| 640 | 21 | 0 | 0 | 0 | 0 | 0 | AGCTACCTCCCACACGCGCCG |

FIG. 24A (32)

| | | | | | |
|---|---|---|---|---|---|
| 641 | 21 | 0 | 0 | 0 | 0 | GCTACCTCCCACACGCGCCCGC |
| 642 | 21 | 0 | 0 | 0 | 0 | CTACCTCCCACACGCGCCCGCC |
| 643 | 21 | 0 | 0 | 0 | 0 | TACCTCCCACACGCGCCCGCCC |
| 644 | 21 | 0 | 0 | 0 | 0 | ACCTCCCACACGCGCCCGCCCT |
| 645 | 21 | 0 | 0 | 0 | 0 | CCTCCCACACGCGCCCGCCCTT |
| 646 | 21 | 0 | 0 | 0 | 0 | CTCCCACACGCGCCCGCCCTTC |
| 647 | 21 | 0 | 0 | 0 | 0 | TCCCACACGCGCCCGCCCTTCG |
| 648 | 21 | 0 | 0 | 0 | 0 | CCCACACGCGCCCGCCCTTCGC |
| 649 | 21 | 0 | 0 | 0 | 0 | CCACACGCGCCCGCCCTTCGCC |
| 650 | 21 | 0 | 0 | 0 | 0 | CACACGCGCCCGCCCTTCGCCG |
| 651 | 21 | 0 | 0 | 0 | 0 | ACACGCGCCCGCCCTTCGCCGG |
| 652 | 21 | 0 | 0 | 0 | 0 | CACGCGCCCGCCCTTCGCCGGT |
| 653 | 21 | 0 | 0 | 0 | 0 | ACGCGCCCGCCCTTCGCCGGTG |
| 654 | 21 | 0 | 0 | 0 | 0 | CGCGCCCGCCCTTCGCCGGTGG |
| 655 | 21 | 0 | 0 | 0 | 0 | GCGCCCGCCCTTCGCCGGTGGC |
| 656 | 21 | 0 | 0 | 0 | 0 | CGCCCGCCCTTCGCCGGTGGCC |
| 657 | 21 | 0 | 0 | 0 | 0 | GCCCGCCCTTCGCCGGTGGCCA |
| 658 | 21 | 0 | 0 | 0 | 0 | CCCGCCCTTCGCCGGTGGCCAC |
| 659 | 21 | 0 | 0 | 0 | 0 | CCGCCCTTCGCCGGTGGCCACC |
| 660 | 21 | 0 | 0 | 0 | 0 | CGCCCTTCGCCGGTGGCCACCC |
| 661 | 21 | 0 | 0 | 0 | 0 | GCCCTTCGCCGGTGGCCACCCG |

FIG. 24A (33)

| | | | | | |
|---|---|---|---|---|---|
| 662 | 21 | 0 | 0 | 0 | 0 | CCTTCGCCCGGTGGCCACCCGG |
| 663 | 21 | 0 | 0 | 0 | 0 | CTTCGCCCGGTGGCCACCCGGC |
| 664 | 21 | 0 | 0 | 0 | 0 | TTCGCCCGGTGGCCACCCGGCG |
| 665 | 21 | 0 | 0 | 0 | 0 | TCGCCCGGTGGCCACCCGGCGC |
| 666 | 21 | 0 | 0 | 0 | 0 | CGCCCGGTGGCCACCCGGCGCA |
| 667 | 21 | 0 | 0 | 0 | 0 | GCCCGGTGGCCACCCGGCGCAG |
| 668 | 21 | 0 | 0 | 0 | 0 | CCGGTGGCCACCCGGCGCAGC |
| 669 | 21 | 0 | 0 | 0 | 0 | CGGTGGCCACCCGGCGCAGCT |
| 670 | 21 | 0 | 0 | 0 | 0 | GGTGGCCACCCGGCGCAGCTG |
| 671 | 21 | 0 | 0 | 0 | 0 | GTGGCCACCCGGCGCAGCTGG |
| 672 | 21 | 0 | 0 | 0 | 0 | TGGCCACCCGGCGCAGCTGGG |
| 673 | 21 | 0 | 0 | 0 | 0 | GGCCACCCGGCGCAGCTGGGC |
| 674 | 21 | 0 | 0 | 0 | 0 | GCCACCCGGCGCAGCTGGGCT |
| 675 | 21 | 0 | 0 | 0 | 0 | CCACCCGGCGCAGCTGGGCTT |
| 676 | 21 | 0 | 0 | 0 | 0 | CACCCGGCGCAGCTGGGCTTG |
| 677 | 21 | 0 | 0 | 0 | 0 | ACCCGGCGCAGCTGGGCTTGG |
| 678 | 21 | 0 | 0 | 0 | 0 | CCCGGCGCAGCTGGGCTTGGG |
| 679 | 21 | 0 | 0 | 0 | 0 | CCGGCGCAGCTGGGCTTGGGC |
| 680 | 21 | 0 | 0 | 0 | 0 | CGGCGCAGCTGGGCTTGGGCC |
| 681 | 21 | 0 | 0 | 0 | 0 | GGCGCAGCTGGGCTTGGGCCG |
| 682 | 21 | 0 | 0 | 0 | 0 | GCGCAGCTGGGCTTGGGCCGC |

FIG. 24A (34)

| | | | | | | |
|---|---|---|---|---|---|---|
| 683 | 21 | 0 | 0 | 0 | 0 | 0 | CGCAGCTGGGCTTGGGCCGCG |
| 684 | 21 | 0 | 0 | 0 | 0 | 0 | GCAGCTGGGCTTGGGCCGCGG |
| 685 | 21 | 0 | 0 | 0 | 0 | 0 | CAGCTGGGCTTGGGCCGCGGC |
| 686 | 21 | 0 | 0 | 0 | 0 | 0 | AGCTGGGCTTGGGCCGCGGCG |
| 687 | 21 | 0 | 0 | 0 | 0 | 0 | GCTGGGCTTGGGCCGCGGCGC |
| 688 | 21 | 0 | 0 | 0 | 0 | 0 | CTGGGCTTGGGCCGCGGCGCC |
| 689 | 21 | 0 | 0 | 0 | 0 | 0 | TGGGCTTGGGCCGCGGCGCCT |
| 690 | 21 | 0 | 0 | 0 | 0 | 0 | GGGCTTGGGCCGCGGCGCCTC |
| 691 | 21 | 0 | 0 | 0 | 0 | 0 | GGCTTGGGCCGCGGCGCCTCC |
| 692 | 21 | 0 | 0 | 0 | 0 | 0 | GCTTGGGCCGCGGCGCCTCCA |
| 693 | 21 | 0 | 0 | 0 | 0 | 0 | CTTGGGCCGCGGCGCCTCCAC |
| 694 | 21 | 0 | 0 | 0 | 0 | 0 | TTGGGCCGCGGCGCCTCCACC |
| 695 | 21 | 0 | 0 | 0 | 0 | 0 | TGGGCCGCGGCGCCTCCACCT |
| 696 | 21 | 0 | 0 | 0 | 0 | 0 | GGGCCGCGGCGCCTCCACCTT |
| 697 | 21 | 0 | 0 | 0 | 0 | 0 | GGCCGCGGCGCCTCCACCTTC |
| 698 | 21 | 0 | 0 | 0 | 0 | 0 | GCCGCGGCGCCTCCACCTTCA |
| 699 | 21 | 0 | 0 | 0 | 0 | 0 | CCGCGGCGCCTCCACCTTCAA |
| 700 | 21 | 0 | 0 | 0 | 0 | 0 | CGCGGCGCCTCCACCTTCAAG |
| 701 | 21 | 0 | 0 | 0 | 0 | 0 | GCGGCGCCTCCACCTTCAAGG |
| 702 | 21 | 0 | 0 | 0 | 0 | 0 | CGGCGCCTCCACCTTCAAGGA |
| 703 | 21 | 0 | 0 | 0 | 0 | 0 | GGCGCCTCCACCTTCAAGGAG |

FIG. 24A (35)

| | | | | | | |
|---|---|---|---|---|---|---|
| 704 | 21 | o | o | o | o | o | GCGCCTCCACCTTCAAGGAGG |
| 705 | 21 | o | o | o | o | o | CGCCTCCACCTTCAAGGAGGA |
| 706 | 21 | o | o | o | o | o | GCCTCCACCTTCAAGGAGGAA |
| 707 | 21 | o | o | o | o | o | CCTCCACCTTCAAGGAGGAAC |
| 708 | 21 | o | o | o | o | o | CTCCACCTTCAAGGAGGAACC |
| 709 | 21 | o | o | o | o | o | TCCACCTTCAAGGAGGAACCG |
| 710 | 21 | o | o | o | o | o | CCACCTTCAAGGAGGAACCGC |
| 711 | 21 | o | o | o | o | o | CACCTTCAAGGAGGAACCGCA |
| 712 | 21 | o | o | o | o | o | ACCTTCAAGGAGGAACCGCAG |
| 713 | 21 | o | o | o | o | o | CCTTCAAGGAGGAACCGCAGA |
| 714 | 21 | o | o | o | o | o | CTTCAAGGAGGAACCGCAGAC |
| 715 | 21 | o | o | o | o | o | TTCAAGGAGGAACCGCAGACC |
| 716 | 21 | o | o | o | o | o | TCAAGGAGGAACCGCAGACCG |
| 717 | 21 | o | o | o | o | o | CAAGGAGGAACCGCAGACCGT |
| 718 | 21 | o | o | o | o | o | AAGGAGGAACCGCAGACCGTG |
| 719 | 21 | o | o | o | o | o | AGGAGGAACCGCAGACCGTGC |
| 720 | 21 | o | o | o | o | o | GGAGGAACCGCAGACCGTGCC |
| 721 | 21 | o | o | o | o | o | GAGGAACCGCAGACCGTGCCG |
| 722 | 21 | o | o | o | o | o | AGGAACCGCAGACCGTGCCGG |
| 723 | 21 | o | o | o | o | o | GGAACCGCAGACCGTGCCGGA |
| 724 | 21 | o | o | o | o | o | GAACCGCAGACCGTGCCGGAG |

FIG. 24A (36)

| | | | | | |
|---|---|---|---|---|---|
|725|21|o|o|o|o|o|AACCGCAGACCGTGCCCGGAGG|
|726|21|o|o|o|o|o|ACCGCAGACCGTGCCCGGAGGC|
|727|21|o|o|o|o|o|CCGCAGACCGTGCCCGGAGGCG|
|728|21|o|o|o|o|o|CGCAGACCGTGCCCGGAGGCGC|
|729|21|o|o|o|o|o|GCAGACCGTGCCCGGAGGCGCG|
|730|21|o|o|o|o|o|CAGACCGTGCCCGGAGGCGCGC|
|731|21|o|o|o|o|o|AGACCGTGCCCGGAGGCGCGCA|
|732|21|o|o|o|o|o|GACCGTGCCCGGAGGCGCGCAG|
|733|21|o|o|o|o|o|ACCGTGCCCGGAGGCGCGCAGC|
|734|21|o|o|o|o|o|CCGTGCCCGGAGGCGCGCAGCC|
|735|21|o|o|o|o|o|CGTGCCCGGAGGCGCGCAGCCG|
|736|21|o|o|o|o|o|GTGCCCGGAGGCGCGCAGCCGG|
|737|21|o|o|o|o|o|TGCCCGGAGGCGCGCAGCCGGG|
|738|21|o|o|o|o|o|GCCCGGAGGCGCGCAGCCGGGA|
|739|21|o|o|o|o|o|CCCGGAGGCGCGCAGCCGGGAC|
|740|21|o|o|o|o|o|CCGGAGGCGCGCAGCCGGGACG|
|741|21|o|o|o|o|o|CGGAGGCGCGCAGCCGGGACGC|
|742|21|o|o|o|o|o|GGAGGCGCGCAGCCGGGACGCC|
|743|21|o|o|o|o|o|GAGGCGCGCAGCCGGGACGCCA|
|744|21|o|o|o|o|o|AGGCGCGCAGCCGGGACGCCAC|
|745|21|o|o|o|o|o|GGCGCGCAGCCGGGACGCCACG|
|  |  |o|o|o|o|o|GCGCGCAGCCGGGACGCCACG|

FIG. 24A (37)

| | | | | | |
|---|---|---|---|---|---|
| 746 | 21 | 0 | 0 | 0 | 0 | CGCGCAGCCCGGGACGCCACGC |
| 747 | 21 | 0 | 0 | 0 | 0 | GCGCAGCCCGGGACGACCACGCC |
| 748 | 21 | 0 | 0 | 0 | 0 | CGCAGCCCGGGACGCCACGCCG |
| 749 | 21 | 0 | 0 | 0 | 0 | GCAGCCCGGGACGCCACGCCGC |
| 750 | 21 | 0 | 0 | 0 | 0 | CAGCCCGGGACGCCACGCCGCC |
| 751 | 21 | 0 | 0 | 0 | 0 | AGCCCGGGACGCCACGCCGCCG |
| 752 | 21 | 0 | 0 | 0 | 0 | GCCCGGGACGCCACGCCGCCGG |
| 753 | 21 | 0 | 0 | 0 | 0 | CCCGGGACGCCACGCCGCCGGT |
| 754 | 21 | 0 | 0 | 0 | 0 | CCGGGACGCCACGCCGCCGGTG |
| 755 | 21 | 0 | 0 | 0 | 0 | CGGGACGCCACGCCGCCGGTGT |
| 756 | 21 | 0 | 0 | 0 | 0 | GGGACGCCACGCCGCCGGTGTC |
| 757 | 21 | 0 | 0 | 0 | 0 | GGACGCCACGCCGCCGGTGTCC |
| 758 | 21 | 0 | 0 | 0 | 0 | GACGCCACGCCGCCGGTGTCCC |
| 759 | 21 | 0 | 0 | 0 | 0 | ACGCCACGCCGCCGGTGTCCCC |
| 760 | 21 | 0 | 0 | 0 | 0 | CGCCACGCCGCCGGTGTCCCCC |
| 761 | 21 | 0 | 0 | 0 | 0 | GCCACGCCGCCGGTGTCCCCCA |
| 762 | 21 | 0 | 0 | 0 | 0 | CCACGCCGCCGGTGTCCCCCAT |
| 763 | 21 | 0 | 0 | 0 | 0 | CACGCCGCCGGTGTCCCCCATC |
| 764 | 21 | 0 | 0 | 0 | 0 | ACGCCGCCGGTGTCCCCCATCA |
| 765 | 21 | 0 | 0 | 0 | 0 | CGCCGCCGGTGTCCCCCATCAA |
| 766 | 21 | 0 | 0 | 0 | 0 | GCCGCCGGTGTCCCCCATCAAC |

FIG. 24A (38)

| | | | | | |
|---|---|---|---|---|---|
| 767 | 21 | o | o | o | o | o | CGCCGGTGTCCCCATCAACA |
| 768 | 21 | o | o | o | o | o | GCCGGTGTCCCCATCAACAT |
| 769 | 21 | o | o | o | o | o | CCGGTGTCCCCATCAACATG |
| 770 | 21 | o | o | o | o | o | CGGTGTCCCCATCAACATGG |
| 771 | 21 | o | o | o | o | o | GGTGTCCCCATCAACATGGA |
| 772 | 21 | o | o | o | o | o | GTGTCCCCATCAACATGGAA |
| 773 | 21 | o | o | o | o | o | TGTCCCCATCAACATGGAAG |
| 774 | 21 | o | o | o | o | o | GTCCCCATCAACATGGAAGA |
| 775 | 21 | o | o | o | o | o | TCCCCATCAACATGGAAGAC |
| 776 | 21 | o | o | o | o | o | CCCCATCAACATGGAAGACC |
| 777 | 21 | o | o | o | o | o | CCCATCAACATGGAAGACCA |
| 778 | 21 | o | o | o | o | o | CCATCAACATGGAAGACCAA |
| 779 | 21 | o | o | o | o | o | CATCAACATGGAAGACCAAG |
| 780 | 21 | o | o | o | o | o | ATCAACATGGAAGACCAAGA |
| 781 | 21 | o | o | o | o | o | TCAACATGGAAGACCAAGAG |
| 782 | 21 | o | o | o | o | o | CAACATGGAAGACCAAGAGC |
| 783 | 21 | o | o | o | o | o | AACATGGAAGACCAAGAGCG |
| 784 | 21 | o | o | o | o | o | ACATGGAAGACCAAGAGCGC |
| 785 | 21 | o | o | o | o | o | CATGGAAGACCAAGAGCGCA |
| 786 | 21 | o | o | o | o | o | ATGGAAGACCAAGAGCGCAT |
| 787 | 21 | o | o | o | o | o | ATGGAAGACCAAGAGCGCATC |

FIG. 24A (39)

| | | | | | |
|---|---|---|---|---|---|
| 788 | 21 | 0 | 0 | 0 | 0 | TGGAAGACCAAGAGCGCATCA |
| 789 | 21 | 0 | 0 | 0 | 0 | GGAAGACCAAGAGCGCATCAA |
| 790 | 21 | 0 | 0 | 0 | 0 | GAAGACCAAGAGCGCATCAAA |
| 791 | 21 | 0 | 0 | 0 | 0 | AAGACCAAGAGCGCATCAAAG |
| 792 | 21 | 0 | 0 | 0 | 0 | AGACCAAGAGCGCATCAAAGT |
| 793 | 21 | 0 | 0 | 0 | 0 | GACCAAGAGCGCATCAAAGTG |
| 794 | 21 | 0 | 0 | 0 | 0 | ACCAAGAGCGCATCAAAGTGG |
| 795 | 21 | 0 | 0 | 0 | 0 | CCAAGAGCGCATCAAAGTGGA |
| 796 | 21 | 0 | 0 | 0 | 0 | CAAGAGCGCATCAAAGTGGAG |
| 797 | 21 | 0 | 0 | 0 | 0 | AAGAGCGCATCAAAGTGGAGC |
| 798 | 21 | 0 | 0 | 0 | 0 | AGAGCGCATCAAAGTGGAGCG |
| 799 | 21 | 0 | 0 | 0 | 0 | GAGCGCATCAAAGTGGAGCGC |
| 800 | 21 | 0 | 0 | 0 | 0 | AGCGCATCAAAGTGGAGCGCA |
| 801 | 21 | 0 | 0 | 0 | 0 | GCGCATCAAAGTGGAGCGCAA |
| 802 | 21 | 0 | 0 | 0 | 0 | CGCATCAAAGTGGAGCGCAAG |
| 803 | 21 | 0 | 0 | 0 | 0 | GCATCAAAGTGGAGCGCAAGC |
| 804 | 21 | 0 | 0 | 0 | 0 | CATCAAAGTGGAGCGCAAGCG |
| 805 | 21 | 0 | 0 | 0 | 0 | ATCAAAGTGGAGCGCAAGCGG |
| 806 | 21 | 0 | 0 | 0 | 0 | TCAAAGTGGAGCGCAAGCGGC |
| 807 | 21 | 0 | 0 | 0 | 0 | CAAAGTGGAGCGCAAGCGGCT |
| 808 | 21 | 0 | 0 | 0 | 0 | AAAGTGGAGCGCAAGCGGCTG |

FIG. 24A (40)

| | | | | | |
|---|---|---|---|---|---|
| 809 | 21 | 0 | 0 | 0 | 0 | 0 | AAGTGGAGCGCAAGCGGCTGC |
| 810 | 21 | 0 | 0 | 0 | 0 | 0 | AGTGGAGCGCAAGCGGCTGCG |
| 811 | 21 | 0 | 0 | 0 | 0 | 0 | GTGGAGCGCAAGCGGCTGCGG |
| 812 | 21 | 0 | 0 | 0 | 0 | 0 | TGGAGCGCAAGCGGCTGCGGA |
| 813 | 21 | 0 | 0 | 0 | 0 | 0 | GGAGCGCAAGCGGCTGCGGAA |
| 814 | 21 | 0 | 0 | 0 | 0 | 0 | GAGCGCAAGCGGCTGCGGAAC |
| 815 | 21 | 0 | 0 | 0 | 0 | 0 | AGCGCAAGCGGCTGCGGAACC |
| 816 | 21 | 0 | 0 | 0 | 0 | 0 | GCGCAAGCGGCTGCGGAACCG |
| 817 | 21 | 0 | 0 | 0 | 0 | 0 | CGCAAGCGGCTGCGGAACCGG |
| 818 | 21 | 0 | 0 | 0 | 0 | 0 | GCAAGCGGCTGCGGAACCGGC |
| 819 | 21 | 0 | 0 | 0 | 0 | 0 | CAAGCGGCTGCGGAACCGGCT |
| 820 | 21 | 0 | 0 | 0 | 0 | 0 | AAGCGGCTGCGGAACCGGCTG |
| 821 | 21 | 0 | 0 | 0 | 0 | 0 | AGCGGCTGCGGAACCGGCTGG |
| 822 | 21 | 0 | 0 | 0 | 0 | 0 | GCGGCTGCGGAACCGGCTGGC |
| 823 | 21 | 0 | 0 | 0 | 0 | 0 | CGGCTGCGGAACCGGCTGGCG |
| 824 | 21 | 0 | 0 | 0 | 0 | 0 | GGCTGCGGAACCGGCTGGCGG |
| 825 | 21 | 0 | 0 | 0 | 0 | 0 | GCTGCGGAACCGGCTGGCGGC |
| 826 | 21 | 0 | 0 | 0 | 0 | 0 | CTGCGGAACCGGCTGGCGGCC |
| 827 | 21 | 0 | 0 | 0 | 0 | 0 | TGCGGAACCGGCTGGCGGCCA |
| 828 | 21 | 0 | 0 | 0 | 0 | 0 | GCGGAACCGGCTGGCGGCCAC |
| 829 | 21 | 0 | 0 | 0 | 0 | 0 | CGGAACCGGCTGGCGGCCACC |

FIG. 24A (41)

| | | | | | |
|---|---|---|---|---|---|
| 830 | 21 | 0 | 0 | 0 | 0 | 0 | GGAACCGGCTGGGCGGCCACCA |
| 831 | 21 | 0 | 0 | 0 | 0 | 0 | GAACCGGCTGGGCGGCCACCAA |
| 832 | 21 | 0 | 0 | 0 | 0 | 0 | AACCGGCTGGGCGGCCACCAAG |
| 833 | 21 | 0 | 0 | 0 | 0 | 0 | ACCGGCTGGGCGGCCACCAAGT |
| 834 | 21 | 0 | 0 | 0 | 0 | 0 | CCGGCTGGGCGGCCACCAAGTG |
| 835 | 21 | 0 | 0 | 0.0 | 0 | 0 | CGGCTGGGCGGCCACCAAGTGC |
| 836 | 21 | 0 | 0 | 0 | 0 | 0 | GGCTGGGCGGCCACCAAGTGCC |
| 837 | 21 | 0 | 0 | 0 | 0 | 0 | GCTGGGCGGCCACCAAGTGCCG |
| 838 | 21 | 0 | 0 | 0 | 0 | 0 | CTGGGCGGCCACCAAGTGCCGG |
| 839 | 21 | 0 | 0 | 0 | 0 | 0 | TGGGCGGCCACCAAGTGCCGGA |
| 840 | 21 | 0 | 0 | 0 | 0 | 0 | GGGCGGCCACCAAGTGCCGGAA |
| 841 | 21 | 0 | 0 | 0 | 0 | 0 | GGCGGCCACCAAGTGCCGGAAG |
| 842 | 21 | 0 | 0 | 0 | 0 | 0 | GCGGCCACCAAGTGCCGGAAGC |
| 843 | 21 | 0 | 0 | 0 | 0 | 0 | CGGCCACCAAGTGCCGGAAGCG |
| 844 | 21 | 0 | 0 | 0 | 0 | 0 | GGCCACCAAGTGCCGGAAGCGG |
| 845 | 21 | 0 | 0 | 0 | 0 | 0 | GCCACCAAGTGCCGGAAGCGGA |
| 846 | 21 | 0 | 0 | 0 | 0 | 0 | CCACCAAGTGCCGGAAGCGGAA |
| 847 | 21 | 0 | 0 | 0 | 0 | 0 | CACCAAGTGCCGGAAGCGGAAG |
| 848 | 21 | 0 | 0 | 0 | 0 | 0 | ACCAAGTGCCGGAAGCGGAAGC |
| 849 | 21 | 0 | 0 | 0 | 0 | 0 | CCAAGTGCCGGAAGCGGAAGCT |
| 850 | 21 | 0 | 0 | 0 | 0 | 0 | CAAGTGCCGGAAGCGGAAGCTG |

FIG. 24A (42)

| | | | | | |
|---|---|---|---|---|---|
| 851 | 21 | o | o | o | o | o | AGTGCCGGAAGCGGAAGCTGG |
| 852 | 21 | o | o | o | o | o | GTGCCGGAAGCGGAAGCTGGA |
| 853 | 21 | o | o | o | o | o | TGCCGGAAGCGGAAGCTGGAG |
| 854 | 21 | o | o | o | o | o | GCCGGAAGCGGAAGCTGGAGC |
| 855 | 21 | o | o | o | o | o | CCGGAAGCGGAAGCTGGAGCG |
| 856 | 21 | o | o | o | o | o | CGGAAGCGGAAGCTGGAGCGC |
| 857 | 21 | o | o | o | o | o | GGAAGCGGAAGCTGGAGCGCA |
| 858 | 21 | o | o | o | o | o | GAAGCGGAAGCTGGAGCGCAT |
| 859 | 21 | o | o | o | o | o | AAGCGGAAGCTGGAGCGCATC |
| 860 | 21 | o | o | o | o | o | AGCGGAAGCTGGAGCGCATCG |
| 861 | 21 | o | o | o | o | o | GCGGAAGCTGGAGCGCATCGC |
| 862 | 21 | o | o | o | o | o | CGGAAGCTGGAGCGCATCGCG |
| 863 | 21 | o | o | o | o | o | GGAAGCTGGAGCGCATCGCGC |
| 864 | 21 | o | o | o | o | o | GAAGCTGGAGCGCATCGCGCG |
| 865 | 21 | o | o | o | o | o | AAGCTGGAGCGCATCGCGCCG |
| 866 | 21 | o | o | o | o | o | AGCTGGAGCGCATCGCGCCGC |
| 867 | 21 | o | o | o | o | o | GCTGGAGCGCATCGCGCCGCC |
| 868 | 21 | o | o | o | o | o | CTGGAGCGCATCGCGCCGCCT |
| 869 | 21 | o | o | o | o | o | TGGAGCGCATCGCGCCGCCTG |
| 870 | 21 | o | o | o | o | o | GGAGCGCATCGCGCCGCCTGG |
| 871 | 21 | o | o | o | o | o | GAGCGCATCGCGCCGCCTGGA |

FIG. 24A (43)

| | | | | | |
|---|---|---|---|---|---|
| 872 | 21 | 0 | 0 | 0 | 0 | 0 | AGCGGCATCGCGCGCCTGGAGG |
| 873 | 21 | 0 | 0 | 0 | 0 | 0 | GCGCATCGCGCGCCTGGAGGA |
| 874 | 21 | 0 | 0 | 0 | 0 | 0 | CGCATCGCGCGCCTGGAGGAC |
| 875 | 21 | 0 | 0 | 0 | 0 | 0 | GCATCGCGCGCCTGGAGGACA |
| 876 | 21 | 0 | 0 | 0 | 0 | 0 | CATCGCGCGCCTGGAGGACAA |
| 877 | 21 | 0 | 0 | 0 | 0 | 0 | ATCGCGCGCCTGGAGGACAAG |
| 878 | 21 | 0 | 0 | 0 | 0 | 0 | TCGCGCGCCTGGAGGACAAGG |
| 879 | 21 | 0 | 0 | 0 | 0 | 0 | CGCGCGCCTGGAGGACAAGGT |
| 880 | 21 | 0 | 0 | 0 | 0 | 0 | GCGCGCCTGGAGGACAAGGTG |
| 881 | 21 | 0 | 0 | 0 | 0 | 0 | CGCGCCTGGAGGACAAGGTGA |
| 882 | 21 | 0 | 0 | 0 | 0 | 0 | GCGCCTGGAGGACAAGGTGAA |
| 883 | 21 | 0 | 0 | 0 | 0 | 0 | CGCCTGGAGGACAAGGTGAAG |
| 884 | 21 | 0 | 0 | 0 | 0 | 0 | GCCTGGAGGACAAGGTGAAGA |
| 885 | 21 | 0 | 0 | 0 | 0 | 0 | CCTGGAGGACAAGGTGAAGAC |
| 886 | 21 | 0 | 0 | 0 | 0 | 0 | CTGGAGGACAAGGTGAAGACG |
| 887 | 21 | 0 | 0 | 0 | 0 | 0 | TGGAGGACAAGGTGAAGACGC |
| 888 | 21 | 0 | 0 | 0 | 0 | 0 | GGAGGACAAGGTGAAGACGCT |
| 889 | 21 | 0 | 0 | 0 | 0 | 0 | GAGGACAAGGTGAAGACGCTC |
| 890 | 21 | 0 | 0 | 0 | 0 | 0 | AGGACAAGGTGAAGACGCTCA |
| 891 | 21 | 0 | 0 | 0 | 0 | 0 | GGACAAGGTGAAGACGCTCAA |
| 892 | 21 | 0 | 0 | 0 | 0 | 0 | GACAAGGTGAAGACGCTCAAG |

FIG. 24A (44)

| | | | | | |
|---|---|---|---|---|---|
| 893 | 21 | 0 | 0 | 0 | 0 | 0 | ACAAGGTGAAGACGCTCAAGG |
| 894 | 21 | 0 | 0 | 0 | 0 | 0 | CAAGGTGAAGACGCTCAAGGC |
| 895 | 21 | 0 | 0 | 0 | 0 | 0 | AAGGTGAAGACGCTCAAGGCC |
| 896 | 21 | 0 | 0 | 0 | 0 | 0 | AGGTGAAGACGCTCAAGGCCG |
| 897 | 21 | 0 | 0 | 0 | 0 | 0 | GGTGAAGACGCTCAAGGCCGA |
| 898 | 21 | 0 | 0 | 0 | 0 | 0 | GTGAAGACGCTCAAGGCCGAG |
| 899 | 21 | 0 | 0 | 0 | 0 | 0 | TGAAGACGCTCAAGGCCGAGA |
| 900 | 21 | 0 | 0 | 0 | 0 | 0 | GAAGACGCTCAAGGCCGAGAA |
| 901 | 21 | 0 | 0 | 0 | 0 | 0 | AAGACGCTCAAGGCCGAGAAC |
| 902 | 21 | 0 | 0 | 0 | 0 | 0 | AGACGCTCAAGGCCGAGAACG |
| 903 | 21 | 0 | 0 | 0 | 0 | 0 | GACGCTCAAGGCCGAGAACGC |
| 904 | 21 | 0 | 0 | 0 | 0 | 0 | ACGCTCAAGGCCGAGAACGCG |
| 905 | 21 | 0 | 0 | 0 | 0 | 0 | CGCTCAAGGCCGAGAACGCGG |
| 906 | 21 | 0 | 0 | 0 | 0 | 0 | GCTCAAGGCCGAGAACGCGGG |
| 907 | 21 | 0 | 0 | 0 | 0 | 0 | CTCAAGGCCGAGAACGCGGGG |
| 908 | 21 | 0 | 0 | 0 | 0 | 0 | TCAAGGCCGAGAACGCGGGGC |
| 909 | 21 | 0 | 0 | 0 | 0 | 0 | CAAGGCCGAGAACGCGGGGCT |
| 910 | 21 | 0 | 0 | 0 | 0 | 0 | AAGGCCGAGAACGCGGGGCTG |
| 911 | 21 | 0 | 0 | 0 | 0 | 0 | AGGCCGAGAACGCGGGGCTGT |
| 912 | 21 | 0 | 0 | 0 | 0 | 0 | GGCCGAGAACGCGGGGCTGTC |
| 913 | 21 | 0 | 0 | 0 | 0 | 0 | GCCGAGAACGCGGGGCTGTCG |

FIG. 24A (45)

| | | | | | |
|---|---|---|---|---|---|
| 914 21 | 0 | 0 | 0 | 0 | 0 | CCGAGAACGCGGGGCTGTCGA |
| 915 21 | 0 | 0 | 0 | 0 | 0 | CGAGAACGCGGGGCTGTCGAG |
| 916 21 | 0 | 0 | 0 | 0 | 0 | GAGAACGCGGGGCTGTCGAGT |
| 917 21 | 0 | 0 | 0 | 0 | 0 | AGAACGCGGGGCTGTCGAGTA |
| 918 21 | 0 | 0 | 0 | 0 | 0 | GAACGCGGGGCTGTCGAGTAC |
| 919 21 | 0 | 0 | 0 | 0 | 0 | AACGCGGGGCTGTCGAGTACC |
| 920 21 | 0 | 0 | 0 | 0 | 0 | ACGCGGGGCTGTCGAGTACCG |
| 921 21 | 0 | 0 | 0 | 0 | 0 | CGCGGGGCTGTCGAGTACCGC |
| 922 21 | 0 | 0 | 0 | 0 | 0 | GCGGGGCTGTCGAGTACCGCC |
| 923 21 | 0 | 0 | 0 | 0 | 0 | CGGGGCTGTCGAGTACCGCCG |
| 924 21 | 0 | 0 | 0 | 0 | 0 | GGGGCTGTCGAGTACCGCCGG |
| 925 21 | 0 | 0 | 0 | 0 | 0 | GGGCTGTCGAGTACCGCCGGC |
| 926 21 | 0 | 0 | 0 | 0 | 0 | GGCTGTCGAGTACCGCCGGCC |
| 927 21 | 0 | 0 | 0 | 0 | 0 | GCTGTCGAGTACCGCCGGCCT |
| 928 21 | 0 | 0 | 0 | 0 | 0 | CTGTCGAGTACCGCCGGCCTC |
| 929 21 | 0 | 0 | 0 | 0 | 0 | TGTCGAGTACCGCCGGCCTCC |
| 930 21 | 0 | 0 | 0 | 0 | 0 | GTCGAGTACCGCCGGCCTCCT |
| 931 21 | 0 | 0 | 0 | 0 | 0 | TCGAGTACCGCCGGCCTCCTC |
| 932 21 | 0 | 0 | 0 | 0 | 0 | CGAGTACCGCCGGCCTCCTCC |
| 933 21 | 0 | 0 | 0 | 0 | 0 | GAGTACCGCCGGCCTCCTCCG |
| 934 21 | 0 | 0 | 0 | 0 | 0 | AGTACCGCCGGCCTCCTCCGG |

FIG. 24A (46)

| | | | | | |
|---|---|---|---|---|---|
| 935 | 21 | 0 | 0 | 0 | 0 | GTACCGCCGGCCTCCTCCGGG |
| 936 | 21 | 0 | 0 | 0 | 0 | TACCGCCGGCCTCCTCCGGGA |
| 937 | 21 | 0 | 0 | 0 | 0 | ACCGCCGGCCTCCTCCGGGAG |
| 938 | 21 | 0 | 0 | 0 | 0 | CCGCCGGCCTCCTCCGGGAGC |
| 939 | 21 | 0 | 0 | 0 | 0 | CGCCGGCCTCCTCCGGGAGCA |
| 940 | 21 | 0 | 0 | 0 | 0 | GCCGGCCTCCTCCGGGAGCAG |
| 941 | 21 | 0 | 0 | 0 | 0 | CCGGCCTCCTCCGGGAGCAGG |
| 942 | 21 | 0 | 0 | 0 | 0 | CGGCCTCCTCCGGGAGCAGGT |
| 943 | 21 | 0 | 0 | 0 | 0 | GGCCTCCTCCGGGAGCAGGTG |
| 944 | 21 | 0 | 0 | 0 | 0 | GCCTCCTCCGGGAGCAGGTGG |
| 945 | 21 | 0 | 0 | 0 | 0 | CCTCCTCCGGGAGCAGGTGGC |
| 946 | 21 | 0 | 0 | 0 | 0 | CTCCTCCGGGAGCAGGTGGCC |
| 947 | 21 | 0 | 0 | 0 | 0 | TCCTCCGGGAGCAGGTGGCCC |
| 948 | 21 | 0 | 0 | 0 | 0 | CCTCCGGGAGCAGGTGGCCCA |
| 949 | 21 | 0 | 0 | 0 | 0 | CTCCGGGAGCAGGTGGCCCAG |
| 950 | 21 | 0 | 0 | 0 | 0 | TCCGGGAGCAGGTGGCCCAGC |
| 951 | 21 | 0 | 0 | 0 | 0 | CCGGGAGCAGGTGGCCCAGCT |
| 952 | 21 | 0 | 0 | 0 | 0 | CGGGAGCAGGTGGCCCAGCTC |
| 953 | 21 | 0 | 0 | 0 | 0 | GGGAGCAGGTGGCCCAGCTCA |
| 954 | 21 | 0 | 0 | 0 | 0 | GGAGCAGGTGGCCCAGCTCAA |
| 955 | 21 | 0 | 0 | 0 | 0 | GAGCAGGTGGCCCAGCTCAAA |

FIG. 24A (47)

| | | | | | |
|---|---|---|---|---|---|
| 956 | 21 | 0 | 0 | 0 | 0 | AGCAGGTGGCCCAGCTCAAAAC |
| 957 | 21 | 0 | 0 | 0 | 0 | GCAGGTGGCCCAGCTCAAAACA |
| 958 | 21 | 0 | 0 | 0 | 0 | CAGGTGGCCCAGCTCAAAACAG |
| 959 | 21 | 0 | 0 | 0 | 0 | AGGTGGCCCAGCTCAAAACAGA |
| 960 | 21 | 0 | 0 | 0 | 0 | GGTGGCCCAGCTCAAAACAGAA |
| 961 | 21 | 0 | 0 | 0 | 0 | GTGGCCCAGCTCAAAACAGAAG |
| 962 | 21 | 0 | 0 | 0 | 0 | TGGCCCAGCTCAAAACAGAAGG |
| 963 | 21 | 0 | 0 | 0 | 0 | GGCCCAGCTCAAAACAGAAGGT |
| 964 | 21 | 0 | 0 | 0 | 0 | GCCCAGCTCAAAACAGAAGGTC |
| 965 | 21 | 0 | 0 | 0 | 0 | CCCAGCTCAAAACAGAAGGTCA |
| 966 | 21 | 0 | 0 | 0 | 0 | CCAGCTCAAAACAGAAGGTCAT |
| 967 | 21 | 0 | 0 | 0 | 0 | CAGCTCAAAACAGAAGGTCATG |
| 968 | 21 | 0 | 0 | 0 | 0 | AGCTCAAAACAGAAGGTCATGA |
| 969 | 21 | 0 | 0 | 0 | 0 | GCTCAAAACAGAAGGTCATGAC |
| 970 | 21 | 0 | 0 | 0 | 0 | CTCAAAACAGAAGGTCATGACC |
| 971 | 21 | 0 | 0 | 0 | 0 | TCAAAACAGAAGGTCATGACCC |
| 972 | 21 | 0 | 0 | 0 | 0 | CAAAACAGAAGGTCATGACCCA |
| 973 | 21 | 0 | 0 | 0 | 0 | AAAACAGAAGGTCATGACCCAC |
| 974 | 21 | 0 | 0 | 0 | 0 | AAACAGAAGGTCATGACCCACG |
| 975 | 21 | 0 | 0 | 0 | 0 | AACAGAAGGTCATGACCCACGT |
| 976 | 21 | 0 | 0 | 0 | 0 | ACAGAAGGTCATGACCCACGTC |
| | | | | | | CAGAAGGTCATGACCCACGTC |

FIG. 24A (48)

| # | | | | | | Sequence |
|---|---|---|---|---|---|---|
| 977 | 21 | 0 | 0 | 0 | 0 | AGAAGGTCATGACCCACGTCA |
| 978 | 21 | 0 | 0 | 0 | 0 | GAAGGTCATGACCCACGTCAG |
| 979 | 21 | 0 | 0 | 0 | 0 | AAGGTCATGACCCACGTCAGC |
| 980 | 21 | 0 | 0 | 0 | 0 | AGGTCATGACCCACGTCAGCA |
| 981 | 21 | 0 | 0 | 0 | 0 | GGTCATGACCCACGTCAGCAA |
| 982 | 21 | 0 | 0 | 0 | 0 | GTCATGACCCACGTCAGCAAC |
| 983 | 21 | 0 | 0 | 0 | 0 | TCATGACCCACGTCAGCAACG |
| 984 | 21 | 0 | 0 | 0 | 0 | CATGACCCACGTCAGCAACGG |
| 985 | 21 | 0 | 0 | 0 | 0 | ATGACCCACGTCAGCAACGGC |
| 986 | 21 | 0 | 0 | 0 | 0 | TGACCCACGTCAGCAACGGCT |
| 987 | 21 | 0 | 0 | 0 | 0 | GACCCACGTCAGCAACGGCTG |
| 988 | 21 | 0 | 0 | 0 | 0 | ACCCACGTCAGCAACGGCTGT |
| 989 | 21 | 0 | 0 | 0 | 0 | CCCACGTCAGCAACGGCTGTC |
| 990 | 21 | 0 | 0 | 0 | 0 | CCACGTCAGCAACGGCTGTCA |
| 991 | 21 | 0 | 0 | 0 | 0 | CACGTCAGCAACGGCTGTCAG |
| 992 | 21 | 0 | 0 | 0 | 0 | ACGTCAGCAACGGCTGTCAGC |
| 993 | 21 | 0 | 0 | 0 | 0 | CGTCAGCAACGGCTGTCAGCT |
| 994 | 21 | 0 | 0 | 0 | 0 | GTCAGCAACGGCTGTCAGCTG |
| 995 | 21 | 0 | 0 | 0 | 0 | TCAGCAACGGCTGTCAGCTGC |
| 996 | 21 | 0 | 0 | 0 | 0 | CAGCAACGGCTGTCAGCTGCT |
| 997 | 21 | 0 | 0 | 0 | 0 | AGCAACGGCTGTCAGCTGCTG |

FIG. 24A (49)

| | | | | | |
|---|---|---|---|---|---|
| 998 | 21 | | | | | GCAACGGCTGTCAGCTGCTGC |
| 999 | 21 | | | | | CAACGGCTGTCAGCTGCTGCT |
| 1000 | 21 | 0 | 0 | 0 | 0 | AACGGCTGTCAGCTGCTGCTT |
| 1001 | 21 | 0 | 0 | 0 | 0 | ACGGCTGTCAGCTGCTGCTTG |
| 1002 | 21 | 0 | 0 | 0 | 0 | CGGCTGTCAGCTGCTGCTTGG |
| 1003 | 21 | 0 | 0 | 0 | 0 | GGCTGTCAGCTGCTGCTTGGG |
| 1004 | 21 | 0 | 0 | 0 | 0 | GCTGTCAGCTGCTGCTTGGGG |
| 1005 | 21 | 0 | 0 | 0 | 0 | CTGTCAGCTGCTGCTTGGGGT |
| 1006 | 21 | 0 | 0 | 0 | 0 | TGTCAGCTGCTGCTTGGGGTC |
| 1007 | 21 | 0 | 0 | 0 | 0 | GTCAGCTGCTGCTTGGGGTCA |
| 1008 | 21 | 0 | 0 | 0 | 0 | TCAGCTGCTGCTTGGGGTCAA |
| 1009 | 21 | 0 | 0 | 0 | 0 | CAGCTGCTGCTTGGGGTCAAG |
| 1010 | 21 | 0 | 0 | 0 | 0 | AGCTGCTGCTTGGGGTCAAGG |
| 1011 | 21 | 0 | 0 | 0 | 0 | GCTGCTGCTTGGGGTCAAGGG |
| 1012 | 21 | 0 | 0 | 0 | 0 | CTGCTGCTTGGGGTCAAGGGA |
| 1013 | 21 | 0 | 0 | 0 | 0 | TGCTGCTTGGGGTCAAGGGAC |
| 1014 | 21 | 0 | 0 | 0 | 0 | GCTGCTTGGGGTCAAGGGACA |
| 1015 | 21 | 0 | 0 | 0 | 0 | CTGCTTGGGGTCAAGGGACAC |

FIG. 24A (50)

| | | | | | |
|---|---|---|---|---|---|
| 1016 | 21 | 0 | 0 | 0 | 0 | 0 | TGCTTGGGGTCAAGGGACACG |
| 1017 | 21 | 0 | 0 | 0 | 0 | 0 | GCTTGGGGTCAAGGGACACGC |
| 1018 | 21 | 0 | 0 | 0 | 0 | 0 | CTTGGGGTCAAGGGACACGCC |
| 1019 | 21 | 0 | 0 | 0 | 0 | 0 | TTGGGGTCAAGGGACACGCCT |
| 1020 | 21 | 0 | 0 | 0 | 0 | 0 | TGGGGTCAAGGGACACGCCTT |
| 1021 | 21 | 0 | 0 | 0 | 0 | 0 | GGGGTCAAGGGACACGCCTTC |
| 1022 | 21 | 0 | 0 | 0 | 0 | 0 | GGGTCAAGGGACACGCCTTCT |
| 1023 | 21 | 0 | 0 | 0 | 0 | 0 | GGTCAAGGGACACGCCTTCTG |
| 1024 | 21 | 0 | 0 | 0 | 0 | 0 | GTCAAGGGACACGCCTTCTGA |

FIG. 24B (1)

(Partial File -- 10 pages of 190 pages)

OligoProbe DesignStation

Probes:       C:\HITACHI\HUMBJUNX.CDS
Preparation:  C:\HITACHI\JUNMIX.PRP

```
              Locus pos Tm      Locus pos Tm   Locus pos Tm   Locus pos Tm
atgtgcactaaaatggaacagcccttctac
    1 30     1   1   2          2    2   2     2   2   3      4
humbjunx     1   60.76
musbjunx     1   50.03
muscjunx     1   30.07
musdjunx   721   27.84
```

FIG. 24B (2)

```
tgtgcactaaaatggaacagccccttctac
  2 29      1           1         2        2         2          2         2      2      3      4
       humbjunx 65533 60.68
       musbjunx 65533 49.58
       muscjunx 1     29.97
       musdjunx 721   27.66 gtgcactaaaatggaacagcccttctac
  3 28     1           1        2        2        2          2        2      2      3      4
       humbjunx 65533 60.60
       musbjunx 65533 49.10
       muscjunx 1     29.86
       musdjunx 721   27.47
```

FIG. 24B (3)

```
tgcactaaaatggaacagcccttctacc
    4 28   1           1       1    2    2    2    2    2    3    4
    humbjunx 65533 60.60
    musbjunx 65533 46.57
    muscjunx     1 29.86
    musdjunx   729 27.47 gcactaaaatggaacagcccttctacc
    5 27   1           1       1    2    2    2    2    2    3    4
    humbjunx     5 60.51
    musbjunx     5 45.96
    muscjunx     1 29.75
    musdjunx   729 27.26
```

FIG. 24B (4)

```
cactaaatggaacagcccttctaccac
    6 28      1         1    1    2    2    2    2    3         4
         humbjunx 1    60.60
         musbjunx 5    46.42
         muscjunx 1    30.79
         musdjunx 729  27.47 actaaaatggaacagcccttctaccacg
    7 28      1         1    1    2    2    2    3    3         4
         humbjunx 1    60.60
         musbjunx 5    46.42
         muscjunx 1    33.32
         musdjunx 729  27.47 ctaaaaatggaacagcccttctaccacg
    8 27      1         1    1    2    2    2    3    3         4
         humbjunx 1    60.51
         musbjunx 5    45.96
         muscjunx 1    33.33
         musdjunx 729  27.26
```

FIG. 24B (5)

```
taaaatggaacagccccttctctaccacgac
   9 28   1      1      1      2      2      2      2      2      3      3      4
       humbjunx 9   60.60
       musbjunx 5   49.10
       muscjunx 9   34.39
       musdjunx 729  27.47 aaaatggaacagcccttctctaccacgac
  10 27   1      1      1      2      2      2      2      2      3      3      4
       humbjunx 5   60.51
       musbjunx 5   49.70
       muscjunx 9   34.44
       musdjunx 729  27.26 aaatggaacagcccttctctaccacgac
  11 26   1      1      1      2      2      2      2      2      3      3      4
       humbjunx 5   60.42
       musbjunx 5   49.19
       muscjunx 9   34.50
       musdjunx 729  27.04
```

FIG. 24B (6)

```
aatggaacagcccttctaccacgac
   12 25    1              2    2    2    2    3    3    4
         humbjunx 5                           60.32
         musbjunx 5                           48.64
         muscjunx 9                           34.56
         musdjunx 737                         26.80 atggaacagcccttctaccacgac
   13 24    1              2    2    2    2    4    5    6
         humbjunx 13                          60.20
         musbjunx 13                          48.04
         muscjunx 9                           34.62
         musdjunx 1                           32.46
         humdjunx 65533                       30.25
         musdjunx 737                         26.55
```

FIG. 24B (7)

```
tggaacagcccttctaccacgac             1   2   2   2   2   3   5   6
 14 23         1       1
   humbjunx  9        60.08
   musbjunx  9        47.39
   muscjunx  9        33.39
   musdjunx  1        31.14
   humdjunx  65533    28.83
   musdjunx  737      26.27 ggaacagcccttctaccacgacg             2   2   2   2   2   3   5   6
 15 23         1       1
   humbjunx  9        61.86
   musbjunx  9        49.17
   muscjunx  9        32.09
   musdjunx  1        29.83
   humdjunx  65533    28.53
   musdjunx  737      26.27
```

FIG. 24B (8)

```
gaacagcccttctaccacgacga
  16 23           1                    1      2      2   2
       humbjunx   9     60.08           musdjunx 737     26.27
       musbjunx   9     47.39
       muscjunx   9     30.00                                    4
       humdjunx   65533 29.66
       musdjunx   1     27.57
       humbjunx   281   26.27
       musbjunx   281   26.27                                             8 aacagcccttctaccacgacgac
  17 23           1                    1      2      2   2
       humbjunx   17    60.08           musdjunx 737     26.27
       musbjunx   17    47.39
       muscjunx   17    30.00                                    6
       humdjunx   5     29.66
       humbjunx   281   29.35
       musbjunx   281   29.35
       musdjunx   1     27.57                                             8
```

FIG. 24B (9)

```
acagcccttctaccacgagact
   18 23        1          1
        humbjunx  13    60.08
        musbjunx  17    47.39
        muscjunx  17    30.00
        humdjunx   5    29.66
        humbjunx 281    29.35
        musbjunx 281    29.35
        musdjunx   1    27.57

1   2   2   2   2  26.27
                              musdjunx 737

2   2   2   2   2 cagcccttctaccacgacgactc
   19 23        1          1
        humbjunx  13    61.86
        musbjunx  17    49.17
        muscjunx  17    30.00
        humdjunx   5    29.66
        humbjunx 281    29.35
        musbjunx 281    29.35
        musdjunx   1    27.57

```
agcccttctaccacgacgactca
   20 23    1          1   1   2   2   2   2   6   7
         humbjunx 13  60.08
         musbjunx 17  46.08
         muscjunx 17  30.00
         humdjunx  5  29.66
         humbjunx 281 29.35
         musbjunx 281 29.35
         musdjunx  1  27.57 gcccttctaccacgacgactcat
   21 23    1          1   2   2   2   2   6   7
         humbjunx 21  60.08
         musbjunx 17  44.78
         muscjunx 17  30.00
         humdjunx  5  29.66
         humbjunx 281 29.35
         musbjunx 281 29.35
         musdjunx  9  27.57
```

FIG. 24B (11)

```
cccttctaccaccacgacgactcatac
22 24          1           1      1      2     2     2     2    6    7
  humbjunx 17     60.20
  musbjunx 17     43.66
  humbjunx 281    31.67
  muscjunx 17     30.13
  humdjunx 5      29.80
  musbjunx 281    29.50
  musdjunx 5      24.84 ccttctaccaccacgacgactcatacac
23 25            1         1      1      2     2     2     3    5    6
  humbjunx 17     60.32
  musbjunx 17     40.56
  humbjunx 289    35.76
  muscjunx 17     30.24
  musbjunx 289    29.64
  humdjunx 5      27.08
```

FIG. 24B (12)

```
cttctaccacgacgactcatacacag
 24 26    1              1    1    1    2    2    2    2    3    4    4
      humbjunx 17      60.42
      musbjunx 17      44.00
      humbjunx 289     35.65
      musbjunx 289     29.77 ttctaccacgacgactcatacacagc
 25 26    1              1    1    1    2    2    2    2    3    4    4
      humbjunx 25      60.42
      musbjunx 25      46.73
      humbjunx 289     35.65
      musbjunx 289     29.77 tctaccacgacgactcatacacagc
 26 25    1              1    1    1    2    2    2    2    3    4    4
      humbjunx 21      60.32
      musbjunx 25      46.08
      humbjunx 289     35.76
      musbjunx 289     29.64
```

FIG. 24B (13)

```
ctaccacgacgactcatacacagc
  27 24         1           1           1    2    2    2    3    4    4
       humbjunx 21   60.20
       musbjunx 25   45.37
       humbjunx 289  35.87
       musbjunx 289  29.50 taccacgacgactcatacacagctac
  28 26         1           1           1    2    2    2    3    4    4
       humbjunx 21   60.42
       musbjunx 25   42.26
       humbjunx 289  35.65
       musbjunx 289  29.77 accacgacgactcatacacagctac
  29 25         1           1           1    2    2    2    3    4    4
       humbjunx 29   60.32
       musbjunx 25   42.64
       humbjunx 289  35.76
       musbjunx 289  29.64
```

FIG. 24B (14)

```
ccacgacgactcatacacagctac
  30 24      1        1           1    2   2   3   4   4
    humbjunx 25   60.20
    musbjunx 25   43.04
    humbjunx 289  35.87
    musbjunx 289  29.50 cacgacgactcatacacagctacg
  31 24      1        1           1    2   2   3   4   5
    humbjunx 25   60.20
    musbjunx 25   43.04
    humbjunx 297  35.87
    musbjunx 297  29.50
    humdjunx 573  26.55 acgacgactcatacacagctacgg
  32 24      1        1           1    2   2   3   3   5
    humbjunx 25   60.20
    musbjunx 25   42.70
    humbjunx 293  32.92
    humdjunx 573  26.55
    musbjunx 293  26.55
```

FIG. 24B (15)

```
cgacgactcatacacagctacgg
 33 23      1      1      1      1      2      2      2      2      3
     humbjunx 33       60.08
     musbjunx 33       41.82
     humdjunx 573      26.27 gacgactcatacacagctacggg
 34 23      1      1      1      2      2      2      2      3
     humbjunx 29       60.08
     musbjunx 29       41.82
     humdjunx 581      26.27 acgactcatacacagctacgggatac
 35 26      1      2      2      2      2      2      2      3
     humbjunx 29       60.42
     musbjunx 29       44.26
     humdjunx 581      27.04
```

FIG. 24B (16)

```
cgactcatacacagctacgggatac    1    1    2    2    2    2    3
36 25            1       1
     humbjunx 29       60.32
     musbjunx 29       43.52
     humdjunx 581      26.80 gactcatacacagctacgggatacg    1    1    2    2    2    2    3
37 25            1       1
     humbjunx 37       60.32
     musbjunx 37       43.52
     humdjunx 581      26.80 actcatacacagctacgggatacgg    1    1    2    2    2    2    3
38 25            1       1
     humbjunx 33       60.32
     musbjunx 37       43.52
     humdjunx 581      26.80
```

FIG. 24B (17)

```
ctcatacacagctacgggatacgg     1    1    2    2    2    2    3
  39 24       1       1
    humbjunx 33      60.20
    musbjunx 37      42.70
    humdjunx 581     26.55 tcatacacagctacgggatacggc     1    1    2    2    2    2    3
  40 24       1       1
    humbjunx 33      60.20
    musbjunx 37      39.75
    humdjunx 581     26.55 catacacagctacgggatacggc      1    1    2    2    2    2    3
  41 23       1       1
    humbjunx 41      60.08
    musbjunx 37      38.91
    humdjunx 581     26.27
```

FIG. 24B (18)

```
atacacagctacgggatacggcc
  42 23    1      1      1    1   2   2   2   3
       humbjunx 37     60.08
       musbjunx 37     38.91
       humdjunx 589    26.27 tacacagctacgggatacgggccg
  43 23    1      1    2   2   2   2   3
       humbjunx 37     61.86
       musbjunx 37     41.82
       humdjunx 589    26.27 acacagctacgggatacgggccg
  44 22    1      1    2   2   2   2   3
       humbjunx 37     61.81
       musbjunx 37     40.86
       humdjunx 589    25.96
```

FIG. 24B (19)

```
cacagctacggggatacgggccg
45 21     1       1       1       1       2       2       2       2       2       3
  humbjunx  45    61.76
  musbjunx  45    40.00
  humdjunx 589    25.62 acagctacggggatacgggccgg
46 21     1       1       1       1       2       2       2       2       2       3
  humbjunx  41    61.76
  musbjunx  45    43.38
  humdjunx 589    25.62
```

FIG. 24B (20)

```
cagctacgggatacgggccgg
  47 20      1            1      1   2   2   2   2   2   3
         humbjunx 41  61.70
         musbjunx 45  43.90
         humdjunx 589 25.25 agctacgggatacgggcccggg
  48 20      1            1      1   2   2   2   2   3   3
         humbjunx 41  61.70
         musbjunx 45  40.35
         muscjunx 561 31.40
```

FIG. 27

```
LOCUS       HUMBJUNX       1044 bp    DNA              19-DEC-1991
BASE COUNT    195 A      368 C      340 G      141 T
ORIGIN
    1 ATGTGCACTA AAATGGAACA GCCCTTCTAC CACGACGACT CATACACAGC TACGGGATAC
   61 GGCCGGGCCC CTGGTGGCCT CTCTCTACAC GACTACAAAC TCCTGAAACC GAGCCTGGCG
  121 GTCAACCTGG CCGACCCCTA CCGGAGTCTC AAAGCGCCTG GGGCTCGCCG ACCCGGCCCA
  181 GAGGGCGGCG GTGGCGGCAG CTACTTTTCT GGTCAGGGCT CGGACACCGG CGCGTCTCTC
  241 AAGCTCGCCT CTTCGGAGCT GGAACGCCTG ATTGTCCCCA ACAGCAACGG CGTGATCACG
  301 ACGACGCCTA CACCCCGGG ACAGTACTTT TACCCCCGCG CAGGGTGGCAG CGGTGGAGGT
  361 GCAGGGGCGG CAGGGGGCGG CGTCACCGGG GAGCAGGAGG GCTTCGCCGA CGGCTTTGTC
  421 AAAGCCCTGG ACGATCTGCA CAAGATGAAC CCCCCAACGT GTCCCTGGGC
  481 GCTACCGGGG GGCCCCCGGC TGGGCCCCGG CACGTGACAC GCCACCTCCC
  541 GTTTACACCA ACCTCAGCAG CTACTCCCCA GGCGTCTACG CGCCGGGGCT
  601 GCCGTCGGGA CCGGGAGCTC GTACCCGACG GCCTCTGCGT CCTCGGGAGG CGCCGGGCCG
  661 CCCTTCGCCG GTGGCCACCC GGCTTGGGCC ACCACCATCA GCTACCTCCC ACACGCGCCG
  721 GAGGAACCGC AGACCCGTGC AGCCCGGGACG GGCTTGGGCC ACCACCATCA GCTACCTCCC CACCTTCAAG
  781 ATCAACATGG AAGACCAAGA GCGCATCAAA GTGGAGCGCA AGCGGCTGCG GAACCGGCTG
  841 GCGGCCACCA AGTGCCGGAA GCGGAAGCTG GAGCGCATCG CGCGCCTGGA GGACAAGGTG
  901 AAGACGCTCA AGGCCGAGAA CTCAGAGCTG GCGTCCACAG CGGTCTTCTT CGGGAGCAG
  961 GTGGCCCAGC TCAAACAGAA GGTCATGACC TCGAGTACCG ACGTCAGCA GCTGCTGCTT
 1021 GGGGTCAAGG GACACGCCCTT CTGA
//
```

FIG. 28A

```
LOCUS        HUMBJUNX        1044 bp    DNA              19-DEC-1991
BASE COUNT       195 A       368 C      340 G       141 T
ORIGIN
    1 ATGTGCACTA AAATGGAACA GCCCTTCTAC CACGACGACT CATACACAGC TACGGGATAC
   61 GGCCGGCCCC CTGGTGCGCC CTCTCTACAC GACTACAAAC TCCTGAAACC GAGCCTGGCG
  121 GTCAACCTGG CCGACCCCTA CCGGAGTCTC AAAGCGCCTG GGGCTCGCGG ACCCGCCCCA
  181 GAGGGCGGCG GTGGCGGCAG CTACTTTCT GGTCAGGGCT CGGACACCGG CGCGTCTCTC
  241 AAGCTCGCCT CTTCGGAGCT GGAACGCCTG ATTGTCCCCA ACAGCAACGG CGTGATCACG
  301 ACGACGCCTA CACCCCCGGG ACAGTACTTT TACCCCCGCG GGGTGGCAG CGGTGGAGGT
  361 GCAGGGGGCG CAGGGGGCGG CGTCACCGAG GAGCAGGAGG GCTTCGCCGA CGGCTTTGTC
  421 AAAGCCCTGG ACGATCTGCA CAAGATGAAC CACGTGACAC CCCCAACGT GTCCCTGGGC
  481 GCTACCGGGG GCCCCCCGGC GGCGTCTACG GGGCCCCGGA CCGGCCCCGA GCCACCTCCC
  541 GTTTACACCA ACCTCAGCAG CCCTCTGCGT CCTCGGGAGG CGCCCGGGCT
  601 GCCGTCGGGA CCGGAGCTC GTACCCGACG ACCACCATCA GCTACCTCCC ACACGCGCCG
  661 CCCTTCGCCG GTGGCCACCC GGCGCAGCTG GGCTTGGGCC GCGGCCCTC CACCTTCAAG
  721 GAGGAACCGC AGACCGTGCC GGAGGCGCGC AGCCGGGACG CCACGCCCGC GGTGTCCCCC
  781 ATCAACATGG AAGACCAAGA GCGCATCAAA GTGGAGCGCA AGCGGCTGCG GAACCGGCTG
  841 GCGGCCACCA AGTGCCGGAA GCGGAAGCTG GAGCGCATCG CGCCCCTGGA GGACAAGGTG
  901 AAGACGCTCA AGGCCGAGAA CGCCGGGCTG TCGAGTACCG CCGGCCTCCT CCGGGAGCAG
  961 GTGGCCCAGC TCAAACAGAA GGTCATGACC CACGTCAGCA ACGGCTGTCA GCTGCTGCTT
 1021 GGGGTCAAGG GACACGCCCTT CTGA
```

FIG. 28B

```
LOCUS       HUMCJUNX        996 bp    DNA                          19-DEC-1991
BASE COUNT     226 A     342 C     299 G     129 T
ORIGIN
    1 ATGACTGCAA AGATGGAAAC GACCTTCTAT GACGATGCCC TCAACGCCTC GTTCCTCCCG
   61 TCCGAGAGCG GACCTTATGG CTACAGTAAC CCCAAGATCC CCCAAGAAG CATGACCCTG
  121 AACCTGGCCG ACCCAGTGGG GAGCCTGAAG CCGCACCTCC GCGCCAAGAA CTCGGACCTC
  181 CTCACCTCGC CCGACGTGGG GCTGCTCAAG CTGGCGTCGC CCGAGCTGGA GCGCCTGATA
  241 ATCCAGTCCA GCAACGGGCA CATCACCACC ACGCCCGACC CCACCCAGTT CCTGTGCCCC
  301 AAGAACGTGA CAGATGAGCA GGAGGGGTTC GCCGAGGGCT TCGTGCGCGC CCTGGCCGAA
  361 CTGCACAGCC AGAACACGCT GCCCAGCGTC ACGTCGGCGG CGCAGCCGGT CAACGGGCA
  421 GGCATGGTGG CTCCCGCGGT AGCCTCGGTG GCAGGGGGCA GCGGCAGCGG CGGCTTCAGC
  481 GCCAGCCTGC ACAGCGAGCC GCCGGTCTAC GCAAACCTCA GCAACTTCAA CCCAGGCGCG
  541 CTGAGCAGCG GCGGCGGGGC GCCGAGCAGC CCCTCCTAC GGCGCGGCCG CCCTGGCCTT TCCCGCGCAA
  601 CCCCAGCAGC AGCAGCAGG CTGCCCCAGC GCCGCACCAC AGATGCCCGT GCAGCACCCG
  661 CGGCTGCAGG CCCTGAAGGA GGAGCCTCAG ACAGTGCCCG AGATGCCCGG CGAGACACCG
  721 CCCCTGTCCC CCATCGACAT GGAGTCCCAG GAGCGGATCA AGGCGGAGAG GAAGCGCATG
  781 AGGAACCGCA TCGCTGCCTC CAAGTGCCGA AAAAGGAAGC TGGAGAGAAT CGCCCGGCTG
  841 GAGGAAAAAG TGAAAACCTT GAAAGCTCAG AACTCGGAGC TGGCGTCCAC GGCCAACATG
  901 CTCAGGGAAC AGGTGGCACA GCTTAAACAG AAAGTCATGA ACCACGTTAA CAGTGGGTGC
  961 CAACTCATGC TAACGCAGCA GTTGCAAACA TTTTGA
```

FIG. 28C

```
LOCUS       HUMDJUNX    1044 bp  ss-mRNA              PRI      24-MAY-1991
DEFINITION  Human junD mRNA
ACCESSION   X56681
KEYWORDS    jun-D gene; oncogene.
SOURCE      Homo sapiens RNA.
  ORGANISM  Homo sapiens
            Eukaryota; Animalia; Metazoa; Chordata; Vertebrata; Mammalia;
            Theria; Eutheria; Primates; Haplorhini; Catarrhini; Hominidae.
REFERENCE   1 (bases 1 to 1891)
  AUTHORS   Shaul,Y.
  JOURNAL   Unpublished (1990)
  STANDARD  full automatic
REFERENCE   2 (sites)
```

FIG. 28D

```
AUTHORS    Berger,I. and Shaul,Y.
TITLE      Structure and function of human jun-D
JOURNAL    Unpublished (1990)
STANDARD   full staff_review
COMMENT    From EMBL_26  entry HSJUNDR;  dated 18-MAR-1991.
FEATURES              Location/Qualifiers
    mRNA              1..1891
                      /gene="junD"
                      /evidence=EXPERIMENTAL
    CDS               175..1218
                      /product="junD protein"
                      /gene="junD"
                      /codon_start=1
    polyA_site        1891..1891
```

FIG. 28E

```
BASE COUNT     162 A      405 C      360 G      117 T
ORIGIN
    1 ATGGAAACAC CCTTCTACGG CGATGAGGCG CTGAGCGGCC TGGGCGGCGG CGCCAGTGGC
   61 AGCGGCGGCA CGTTCGCGTC CCCGGGCCCG TTGTTCCCCG GGGCGCCCCC GACGGCCGCG
  121 GCCGGCAGCA TGATGAAGAA GGACGCGCTG ACGCTGAGCC TGAGTGAGCA GGTGGCGGCA
  181 GCGCTCAAGC CTGCGCCCGC TACCCCCCTG CCGCCCGACG GCGCCCCCAGC CGCGGCCTCC
  241 GCGGCACCCC CCGACGGCCT GCTCGCCTCT CCCGACCTGG GCTGCTGAA GCTGGCCTCC
  301 CCCGAGCTCG AGCGCCTCAT CATCCAGTCC AACGGGCTGG TCACCACCAC GCCGACGAGC
  361 TCACAGTTCC TCTACCCCAA GGTGGCGGCC AGCGAGGAGC AGGAGTTCGC CGAGGGCTTC
  421 GTCAAGGCCC TGGAGGATTT ACACAAGCAG AACCAGCTCG GCGCGGGCCG GGCCGCTGCC
  481 GCCGCGCCCG CCGCCGCCGG GGGCCCCTCG GGCACGGCCA CGGGCTCCCG GCCCCCCGGC
  541 GAGCTGGCCC CGGCGGCGCC CGCGCCTGAA GCGCCTGTCT ACGCAGCTAC GAGCAGCTAC
  601 GCGGGCGGCG CCGGGGGGCG GGGGGCGCC GCCGACGGTCG CCTTCGCTGC CGAACCTGTG
  661 CCCTTCCCGC CGCCGCCACC CCCAGGCGCG TTGGGCCGCC CGCGCCTGGC TGCGCTCAAG
  721 GACGAGCCAC AGACGGTGCC CGACGTGCCG AGCTTCGGCG AGAGCCCGCC GTTGTCGCCC
  781 ATCGACATGG ACACGCAGGA GCGGCATCAA GCGGAGCGCA AGCGGCTGCG CAACCGCATC
  841 GCCGCCTCCA AGTGCCGCAA GCGCAAGCTG GAGCGGATCG CCGCCCTGGA AGAGAAAGTG
  901 AAGACCCTCA AGAGTCAGAA CTCGGAGCTG GCGTCCACAG CGAGCCTGCT GCGCGAGCAG
  961 GTGGCGCAGC TCAAGCAGAA AGTCCTCAGC CACGTCAACA GCGGCTGCCA GCTGCTGCCC
 1021 CAGCACCAGG TCCCGGCGTA CTGA
```

FIG. 28F

```
LOCUS        MUSBJUNX      1035 bp    DNA              19-DEC-1991
BASE COUNT       210 A      333 C      333 G      159 T
ORIGIN
    1 ATGTGCACGA AAATGGAACA GCCTTTCTAT CACGACGACT CTTACGCAGC GGCGGGATAC
   61 GGTCGGAGCC CTGGCAGCCT GTCTCTACAC GACTACAAAC TCCTGAAACC CACCTTGGCG
  121 CTCAACCTGG CGGATCCCTA TCGGGGTCTC AAGGGTCCTG GGGCGCGGGG TCCAGGCCCG
  181 GAGGCAGTG GGCAGGCAG CTACTTTTCG GGTCAGGGAT CAGACACAGG CGCATCTCTG
  241 AAGCTAGCCT CCACGGAACT GGAGCGCTTG ATCGTCCCCA ACAGCAACGG CGTGATCACG
  301 ACGACGCCCA CGCCTCCGGG ACAGTACTTT TACCCCCGTG GGGTGGCAG CGGTGGAGGT
  361 ACAGGGGGCG GCGTCACCGA GGAGCAGGAG GGCTTTGCGG ACGGTTTTGT CAAAGCCCTG
  421 GACGACCTGC ACAAGATGAA CCACGTGACG CCCCCCAACG TGTCCCTGGG CGCCAGCGGG
  481 GGTCCCCAGG CCGGCCCAGG GGGCGCTCTA T GCTGGTCCGG AGCCGCCTCC CGTCTACACC
  541 AACCTCAGCA GTTACTCTCC CCCTCTGGAG CCCTACCACC CGCCGTCGGG
  601 ACTGGGAGCT CATACCCGAC AGCTACCTCC CACATGCACC ACCCTTTGCG
  661 GGCGGCCACC CGGCACAGCT GGGTTTGAGT CGTGGCGCTT CCGCCTTTAA AGAGGAACCG
  721 CAGACCGTAC CGGAGGCACG CAGCCGCGAC GCCACGCCGC CTGTGTCCCC CATCAACATG
  781 GAAGACCAGG AGCGCATCAA AGTGGAGCGA AAGCGGCTGC GGAACAGGCT GGCGGCCACC
  841 AAGTGCCGGA AGCGGAAGCT GGAGCGCATC GCGCGCCTGG AGGACAAGGT GAAGACACTC
  901 AAGGCTGAGA ACGCGGGGCT GTCGAGTGCT GCCGGGTCTC TAAGGGAGCA AGTGGCGCAG
  961 CTCAAGCAGA AGGTCATGAC CCATGTCAGC AACGGCTGCC AGTTGCTGCT AGGGGTCAAG
 1021 GGACACGCCT TCTGA
```

```
LOCUS       MUSCJUNX     1005 bp    DNA                    19-DEC-1991
BASE COUNT     223 A      334 C      300 G      148 T
ORIGIN
        1 ATGACTGCAA AGATGGAAAC GACCTTCTAC GACGATGCCC TCAACGCCTC GTTCCTCCAG
       61 TCCGAGAGCG GTGCCTACGG CTACAGTAAC CCTAAGATCC TAAAACAGAG CATGACCTTG
      121 AACCTGGCCG ACCCGGTGGG CAGTCTGAAG CCGCACCTCC GCCCAAGAA CTCGGACCTT
      181 CTCACGTCGC CCGACGTCGG GCTGCTCAAG CTGGCGTCGC CGGAGCTGGA GCGCCTGATC
      241 ATCCAGTCCA GCAATGGGCA CATCACCACT ACACCGACCC CACCCAGTT CTTGTGCCCC
      301 AAGAACGTGA CCGACGAGCA GGAGGGCTTC GCCGAGGGCT TCGTGCGCGC CCTGGCTGAA
      361 CTGCATAGCC AGAACACGCT TCCCAGTGTC ACCCTCCGCG GCCAGCCCGT CAGCGGGGCG
      421 GGCATGGTGG CTCCCGCGGT GGCCCTCAGT ACCTTCCGG GCGGCGGCTG TGGCTACAGC
      481 GCCAGCCTGC ACAGTGAGCC TCCGGTCTAC GCCAACCTCA GCAACTTCAA CCCGGGTGCG
      541 CTGAGCAGCG GCGGTGGGGC GCCCTCCTAT GGCGCGGCCG GCTGGCCTT TCCCTCGCAG
      601 CCGCAGCAGC AGCAGCAGC GCCTGCAAGC CCGGCACCCG CCGCACCACT GATCCCGGTG
      661 CAGCCCCGC GGCTGCAGCC CCTGTCCCC CCTGAAGGAA CCGTGCCCGA GATGCCGGGA
      721 GAGACGCCGC CCCTGTCCCC TATCGACATG GAGTCTCAGG AGCGGATCAA GGCAGAGAGG
      781 AAGCGCATGA GGAACCGCAT TGCCGCCTCC AAGTGCCGGA AAAGGAAGCT GGAGCGGATC
      841 GCTCGGCTAG AGGAAAAAGT GAAAACCTTG AAAGCGCAAA ACTCCGAGCT GGCATCCACG
      901 GCCAACATGC TCAGGGAACA GGTGGCACAG CTTAAGCAGA AGTCATGAA CCACGTTAAC
      961 AGTGGGTGCC AACTCATGCT AACGCAGCAG TTGCAAACGT TTTGA
```

FIG. 28H

```
LOCUS       MUSDJUNX       1026 bp    DNA                       19-DEC-1991
BASE COUNT       172 A      382 C      343 G      129 T
ORIGIN
    1 ATGGAAACGC CCTTCTATGG CGAGGAGGCG CTGAGCGGCC TGGCTGCCGG TGCCGTCGAGC
   61 GTCGCTGGTG CTACTGGGGC CCCCGGCGGT GGTGGCTTCG CGCCCCCGGG CCGCGCTTTC
  121 CCCGGGCGCC CCCGACGAG CAGCATGCTG AAGAAAGACG CGCTGACGCT CAGCCTGCCG
  181 GAGCAGGGAG CGGCGGGATT GAAACCAGGG TCGGCCACTG GCTGCGCCCC
  241 GACGGCGCCC CCGACGGGCT GCTGGCTTCG CCGGATCTTG GGCTGCTCAA ACTCGCGTCG
  301 CCGGAGCTGG AGAGGCTGAT CATCCAGTCC AACGGGCTGG TGACCACTAC CCCGACCAGT
  361 ACGCAGTTCC TCTACCCGAA GGTGGCAGCC GCACAAGCAA AGCGAGGAGC CGAAGGCTTC
  421 GTCAAGGCGC TGGAGGACCT GCACAAGCAA AGCCAGCTGG CGCGGCCACC
  481 TCAGGGGCTC CCGGCGCCTCC CGCGCCCCGCC GACCTGGCCG GGCCACGGAG
  541 ACCCCGGTCT ACGCCAACCT GAGCAGTTTC GCGGTGGCG CCACCCCCGG TGGGGGCGCG
  601 GCCACCGTGG CTTTCGCCGC GGAGCCAGTG CCCTTCCCGC CCGGGCCCCG CGCGCTGGGG
  661 CCGCCGCCAC CTCCGCCATCC ACCGCGCCTG GCCGCGCTCA AGGACGAGCC GCAGACCGTG
  721 CCGGACGTGC CGAGCTTCGG CGACAGCCCT CGCTGTCGC CCATCGACAT GGACACGCAA
  781 GAACGCCATCA AGGCGGAGCG CAAGAGGCTG CGCAACCGCA TCGCCGCCTC CAAATGCCGC
  841 AAGCCCAAGC TGGAGCGTAT CTCGCGCCTG GAGGAGAAAG TCAAGACCCT CAAAAGCCAG
  901 AACACCGAGC TGGCGTCCAC CGCCAGCCTG CTGCGCGAGC AGGTGGCGCA GCTCAAACAG
  961 AAAGTCCTCA GCCACGTCAA CAGCGGCTGC CAGCTGCTGC CCCAGCACCA GGTCCCGGCG
 1021 TACTGA
```

OLIGOPROBE DESIGNSTATION: A COMPUTERIZED METHOD FOR DESIGNING OPTIMAL DNA PROBES

Microfiche Appendix

This patent application includes a microfiche appendix consisting of three sheets of microfiche with a total number of 175 frames. This microfiche appendix contains the source code for the software incorporated into this invention.

A portion of the disclosure of this patent document contains material which is subject to copyright protection. The copyright owner has no objection to the facsimile reproduction by anyone of the patent disclosure, as it appears in the Patent and Trademark Office patent files or records, but otherwise reserves all copyright rights whatsoever.

References

These publications are cited hereinabove and they are incorporated by reference:

1. Benner, T. I., Brenner, C. J., Neufeld, B. R., and Britten, R. J. "Reduction in the Rate of DNA Reassociation by Sequence Divergence," 81 Journal of Molecular Biology 123 (1973).
2. Bolton, E. T. and McCarthy, B. J., "A General Method for the Isolation of RNA Complementary to DNA," 48 Proceedings of the National Academy of Science 1390 (1962).
3. Grossi, R. and Luccio, F., "Simple and Efficient String Matching with k Mismatches", 33 Information Processing Letters 113 (Nov. 30, 1989).
4. Hume, A. and Sunday, D., "Fast String Searching," 21(11) Sofware—Practice and Experience 1221 (1991).
5. Itakura, K., Rossi, J. J., and Wallace, R. B., "Synthesis and Use of Synthetic Oligonnucleotides," 53 Annual Review of Biochemistry 323 (1984).
6. Landau, G. M. and Vishkin, U. "Efficient String Matching with k Mismatches," 43 Theoretical Computer Science 239 (1986).
7. Landau, G. M., Vishkin, U., and Nussinov, R., "Alignments with k Differences for Nucleotide and Amino Acid Sequences," 4 CABIOS 19 (1988).
8. Landau, G. M., Vishkin, U., and Nussinov, R., "Fast Alignment of DNA and Protein Sequences," 183 Methods in Enzymology 487 (1990).
9. Lewis, R. M., "PROBFIND: A Computer Program for Selecting Oligonucleotide Probes from Peptide Sequences," 14 NUCLEIC ACIDS RES. 567 (1986).
10. Martin, F. H. and Castro, M. M., "Base Pairing Involving Deoxyinosine: Implications for Probe Design," 13 NUCLEIC ACIDS RES. 8927 (1985).
11. Raupach, R. E., "Computer Programs Used to Aid in the Selection of DNA Hybidization Probes," 12 NUCLEIC ACIDS RES. 833 (1984).
12. Rosenberg, J. M., DICTIONARY OF COMPUTERS, DATA PROCESSING AND TELECOMMUNICATIONS (1984).
13. Southern, E. M., "Detection of Specific Sequences Among DNA Fragments Separated by Gel Electrophoresis," 98 JOURNAL OF MOLECULAR BIOLOGY 503 (1975).
14. Ukkonen, E., "Approximate String-Matching with q:Grams and Maximal Matches," 92 Theoretical Computer Science 191 (1992).
15. von Heijne, G., Sequence Analysis in Molecular Biology (1987) (available at the University of California at Los Angeles and California State University at Northridge).
16. Yang, J., Ye, J., and Wallace, D. C., "Computer Selection of Oligonucleotide Probes from Amino Acid Sequences for Use in Gene Library Screening," 12 Nucleic Acids Res. 837 (1984).

BACKGROUND OF THE INVENTION

This invention relates to the fields of genetic engineering, microbiology, and computer science, and more specifically to an invention that helps the user, whether they be a molecular biologist or a clinical diagnostician, to calculate and design extremely accurate oligonucleotide probes for DNA and mRNA hybridization procedures. These probes may then be used to test for the presence of precursors of specific proteins in living tissues. The oligonucleotide probes designed with this invention may be used for medical diagnostic kits, DNA identification, and potentially continuous monitoring of metabolic processes in human beings. The present implementation of this computerized design tool runs under Microsoft® Windows™ v. 3.1 (made by Microsoft Corporation of Redmond, Wash.) on IBM® compatible personal computers (PC's).

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference.

To isolate a specific gene for any particular purpose, a researcher first has to have some idea of what he or she is looking for. To do this, the researcher needs to have a probe, which acts like a molecular hook that can identify and latch onto (i.e., bind to or hybridize with) the desired gene in a crowd of many other genes. A researcher who can obtain an entire strand of mRNA can eventually find the gene from which it was copied, using complementary DNA (cDNA, which is a cloned equivalent to RNA and somewhat equivalent to mRNA) as a probe to search through the great mass of genetic material and locate the desired original gene. cDNA essentially is manufactured or non-naturally occurring DNA from which all of the nonessential DNA has been removed. cDNA allows the researcher to concentrate entirely on the important portions of the gene being examined. The nonessential DNA regions are easy to recognize because when the gene is translated into protein, these regions do not wind up reflected in the protein sequence. These regions are called introns, or intervening regions. mRNA has no introns because they have been "spliced" out of the mRNA before translation. Thus, mRNA and cDNA contain only the essential information from a gene (called the exons). cDNA is the equivalent of mRNA with a complementary sequence, only the exons are present. cDNA may be produced by reverse transcription of mRNA.

The procedure of using cDNA from known mRNA as a probe to search through genetic material and locate the original gene is called molecular hybridization, and is currently one method of identifying specific genes. However, this method is less than perfect, can be extremely time consuming, and often is not even feasible because the researcher actually has to have an entire strand of cDNA from the desired gene before he or she can attempt to use this cDNA to locate and identify the particular gene. Thus, it is something of a circular problem. If the researcher cannot obtain an entire strand of mRNA or cDNA from the desired gene, then he or she must somehow design a probe from scratch to be used to identify that gene.

Oligonucleotide probes (that is, probes made up of a small number of nucleotides, such as 17 to 100), are increasingly being used to identify specific genes from genomic or cDNA libraries when the partial amino acid sequences is known. (von Heijne 1987, Ref. 15). This is a second method of determining a proper probe. Although the present implementation of this invention does not deal with cases in which the proteins have been sequenced, but rather only the DNA or mRNA, it is possible that this invention or a future implementation of it might be used with protein sequences. Such probes can also be used as primers which, when annealed to mRNAs, can be selectively extended into cDNAs. (von Heijne 1987, Ref. 15).

Because of these situations, the problem that the researcher faces is to discover or design a probe or mixture of probes that maximizes the researchers chances of successful hybridization while at the same time minimizing the amount of time and money that has to be spent on discovering or designing the probes. (von Heijne 1987, Ref. 15). Researchers in the field have determined that computer analysis can greatly expedite and simplify the search for optimal probe sequences. (von Heijne 1987, Ref. 15). However, all of the search strategies known to the present inventors are time consuming (both CPU and user time) and may be somewhat inaccurate. As stated in von Heijne, "a true optimization of the probe in terms not only of degeneracy but in terms of length, codon usage, Guanine-Cytosine (GC) avoidance, and expected signal-to-noise ratio (hybridization to target over background) is a fairly complex problem, however, and does not seem to have been automated so far." (von Heijne 1987, Ref. 15). Various search strategies known and used in the field to identify and design probes are outlined in the following sources: Lewis (1986, Ref. 9), Raupach (1984, Ref. 11), Yang et al. (1984, Ref. 16), and Martin and Castro (1984, Ref. 10).

In the simplest version of a protein-related search strategy, the search procedure is limited to finding a set of probes of given lengths with the least possible degeneracy simply by scanning the amino acid sequence and noting the number of alternative codons in the corresponding oligonucleotide as the scan moves along the chain of nucleotides. (Lewis 1986). The researcher can also include codon usage statistics (because more than one codon can translate to the same amino acid), which would attach a probability-of-occurrence value to each probe. (Raupach 1984, Ref. 11).

A more advanced algorithm would allow the researcher to specify the way in which he or she plans to synthesize the probes (for example, by adding toohomers or mixtures of monomers). It would also be easy for a researcher to add a rough estimate of the disassociation (or melting) temperatures of each probe to a program such as this.

One way to solve the problem of finding local similarities between two proteins being compared that has been discussed in the relevant literature is to use list-sorting or hashing routines. (von Heijne 1987, Ref. 15). These routines are based on the construction of a list or lookup table of k-letter words or k-tuples (i.e., all possible di- or trinucleotides), and the positions where they appear in the sequences being compared. This method is employed in some of the most extensively used "fast search" programs (see examples identified in von Heijne 1987, Ref. 15).

Two general methods of designing probes are common in the field, depending upon whether the researcher is trying to design a common probe or a specific probe. Common probes attempt to find common or consensus sequences among various species and among family genes. The first step in designing such a probe is to find the genes of interest. This may be done by performing a keyword or homology search against the GenBank (a genome database available from IntelliGenics of Mountain View, Calif.) or a keyword search against MEDLINE (the database currently available from the U.S. National Library of Medicine under the data access system known as Dialog of Dialog Information Service, Inc., Palo Alto, Calif.) or by performing a homology analysis between one of the genes of interest and whole GenBank sequences. The next step is to retrieve all of the relevant genes of interest. In the third step, multiple alignment analysis can be done using a commercially available software package such as DNASIS (from Hitachi Software of Brisbane, Calif.), which is an autoconnect program. In this step, the computer identifies which nucleotides are common among the requested sequences:

```
A1   A G G C C T C G G T T A G T T G G C C G T T G C C G A A A A A

A2   A G G C G T C G G T T A T T T G G G C C T T C C C A A T G T G

A3   A G G C G T C G G T T C T G T G G A A C T T C C C G A G G A A
     * * * *   * * * * * *         * * *       * *   * *     *
* = common among A1, A2, and A3
```

Alternatively, after homology analyses between two sequences are carried out, data from the multiple homology analyses can be combined. The researcher then manually has to find the common or consensus region:

```
A1   A G G C C T C G G T T A G T T G G C C G T T G C C G A A A A A

A2   A G G C G T C G G T T A T T T G G G C C T T C C C A A T G T G

A2   A G G C G T C G G T T A T T T G G G C C T T C C C A A T G T G

A3   A G G C G T C G G T T C T G T G G A A C T T C C C G A G G A A
     * * * *   * * * * * *         * * *       * *   * *     *
* = common among A1, A2, and A3
```

Next, the researcher would input the sequence of the common region into the program and then analyze the secondary structure (i.e., the stacking site and the hairpin structure). After this, the researcher manually would select several candidate probes (from five to ten) which contain the minimal hairpin structure and specific length according to the user's interest. A hairpin is an area in which a probe has "folded back" and one portion of the probe has hybridized with another portion of the same probe. The researcher would then perform a homology analysis between each candidate probe and all sequences in the GenBank to find all possible cross-hybridizable genes. Lastly, the researcher manually would decide which is the best candidate probe by determining which probe is highly homologous among the group of interest, but quite different from other unrelated sequences in the GenBank.

The conventional methods for designing common oligonucleotide probes using currently available computer software have at least five problems: (1) they involve time consuming multiple processes; (2) it is difficult to control a significant variable, the melting temperature Tm of the oligonucleotide probes; (3) the methods do not recognize exons and introns and differentiate (thereby making it possible to have a designed probe that is identical to unrelated mRNA sequences); (4) the methods may miss short pieces of identical sequences; and (5) it is difficult to recognize multiple pieces of identical sequences in the gene.

The second method of designing probes that is common in the field involves designing specific probes. Specific probes attempt to find unique sequences among various species and among family genes and among published sequences in the GenBank. A specific probe is a probe that hybridizes with only one particular gene, thereby identifying the presence of that gene for the researcher. The procedure involves first finding the genes of interest (by performing a keyword search against the GenBank or against MEDLINE) and then retrieving all of the relevant genes of interest. A manual homology analysis between the gene of interest and whole sequences in the GenBank can be performed to find common and unique regions.

```
A1  A GG C C T C GG T T A GT T GG C C GT T GC C GA A A A A
    . . . .   . . . . . . . . .   .   .     .     . . . . .
B1  A GG C GT C GG T T A T T GT GG T C T C C C C A A T GT G
    - - - - - - - - - - - -   * * * * * * * * * * * * * * *
           common                         unique
```

Next, the researcher would input the sequence of the unique region into the program and then analyze the secondary structure. After this, the researcher would manually select several candidate probes which contain the minimal hairpin structure and specific length according to the user's interest. The researcher would then perform a homology analysis between each candidate probe and all sequences in the GenBank to find all possible cross-hybridizable genes. Lastly, the researcher manually would decide which is the best candidate probe by determining which probe does not have identical sequences in unrelated sequences in the GenBank.

All of the conventional methods for designing specific oligonucleotide probes known to the inventors using currently available computer software have at least four problems: (1) they involve time consuming multiple processes; (2) it is difficult to control the melting temperature Tm of the oligonucleotide probes; (3) the methods do not allow for quantification of uniqueness; and (4) there is no guarantee that the method will design the best possible probe.

None of the methods discussed in the literature discloses a system that may be used to design both common probes and extremely specific probes, especially a method that minimizes user and CPU time and is exceptionally accurate.

Programs currently used for rapid database similarity searches use either hashing strategies or statistical strategies. The hashing strategy is now being used for the detection of relatively short regions of similarity, while the statistical strategy is now being used for the detection of weaker and longer similarity regions. The Mismatch Model of this invention can be used for very strong similarity searches with running times faster than current hashing strategies.

The basic technologies behind the Mismatch Model used in this invention are hashing and continuous seed filtration, each general technology being known in the public domain and having been previously applied separately to non-genetic applications. To the best of the inventors' knowledge, these methods, used together, have never been suggested in other studies on optimal probe selection. The inventors' methods have a program performance of tens of seconds (CPU+I/O time) with a 1000 nucleotide query and all mammalian DNA on a SPARC station, and are even faster on the more common personal computer proposed herein.

The H-Site Model of this invention likewise is unique in that it offers a multitude of information on selected probes and original and distinctive means of visualizing, analyzing and selecting among candidate probes designed with the invention. Candidate probes are analyzed using the H-Site Model for their binding specificity relative to some known set of mRNA or DNA sequences, collected in a database such as the GenBank database. The first step involves selection of candidate probes at some or all the positions along a given target. Next, a melting temperature model is selected, and an accounting is made of how many false hybridizations each candidate probe will produce and what the melting temperature of each will be. Lastly, the results are presented to the researcher along with a unique set of tools for visualizing, analyzing and selecting among the candidate probes.

This invention is both much faster and much more accurate than the methods that are currently in use. It is unique because it is the only method that can find not only the most specific and unique sequence, but also the common sequences. Further, it allows the user to perform many types of analysis on the candidate probes, in addition to comparing those probes in various ways to the target sequences and to each other.

Therefore, it is the object of this invention to provide a practical and user-friendly system that will allow a researcher to design both specific and common oligonucleotide probes, and to do this in less time and with much more accuracy than currently done. For example, the current version of the GenBank contains over ninety (90) million nucleotides. It is thought that the human genome alone consists of three billion base pairs, and scientists have so far managed to decode the base sequence of only about 500 human genes, less than one percent of the total. Currently available searching strategies are limited in how many of the GenBank's sequences can be accessed and successfully searched, and how convenient and feasible such a search would be (in terms of both computer processor and human user time). It is also an object of this invention to allow the user to be able to run the program on more readily available and far less expensive computer hardware (i.e., a PC rather than a mainframe). This invention will remove those limits and allow genetic research to take a giant leap forward.

These and other advantages and objects of this invention will become apparent from the following detailed descriptions, drawings, and appended claims.

BRIEF DESCRIPTION OF THE INVENTION

There is disclosed herein a system which allows the user to calculate and design extremely accurate oligonucleotide probes for DNA and mRNA hybridization procedures. The invention runs under Microsoft® Windows on IBM® compatible personal computers (PC's). Its key features design oligonucleotide probes based on the GenBank database of DNA and mRNA sequences and examine probes for specificity or commonality with respect to a user-selected experimental preparation of gene sequences. Hybridization strength between a probe and a subsequence of DNA or mRNA can be estimated through a hybridization strength model. Quantitatively, hybridization strength is given as the melting temperature Tm. Currently, two hybridization strength models are supported by this invention: 1) the Mismatch Model and 2) the H-Site Model. The user is allowed to select from the following calculations for each probe, results of which are available for display and analysis: 1) Sequence, Melting Temperature (Tm) and Hairpin characteristics; 2) Hybridization with other species within the preparation mixture; and (3) Location and Tm for the strongest hybridizations. The results of the invention's calculations are then displayed on the Mitsuhashi Probe Selection Diagram (MPSD), which is a graphic display of all of the hybridizations of probes for the target mRNA with all sequences in the preparation.

The Main Dialog Window of the present implementation of this invention controls all user-definable settings. The user is offered a number of options at this window. The File option allows the user to print, print in color, save selected probes, and exit the program. The Preparation option allows the user to open and create preparation (PRP) files. The Models option allows the user to chose between the two hybridization models currently supported by the invention: 1) the H-Site Model and 2) the Mismatch Model. If the user selects the H-Site Model option, the user normally sets the following model parameters: 1) the melting temperature Tm for which probes are being designed (i.e., the melting temperature that corresponds to a particular experiment or condition the user desires to simulate); and 2) the nucleation threshold, which is the number of base pairs constituting a nucleation site. If the user selects the Mismatch Model option, the user normally sets the following model parameters: 1) probe length, which is the number of bases in probes to be considered; and 2) mismatch N, which is the maximum number of mismatches constituting a hybridization.

The Mismatch Model program is used to design DNA and mRNA probes, utilizing sequence database information from sources such as GenBank and other databases with similar file formats. In the Mismatch Model, hybridization strength is related only to the number of base pair mismatches between a probe and its binding site. Generally, the more mismatches a user allows, the more probes will be found. The Mismatch Model does not take into account the Guanine-Cytosine (GC) content of candidate probes, as does the H-Site Model, discussed below, so there is no reflection or indication of the probe's binding strength. The basic technologies employed by this model are hashing and continuous seed filtration. Hashing involves the application of an algorithm or process to the records in a set of data to obtain a symmetric grouping of the records. When using an indexed set of data, hashing is the process of transforming a record key to an index value for storing and retrieving a record. Rosenberg (1984, Ref. 12)). The concept of continuous seed filtration is discussed in detail below.

The essence of the Mismatch Model is a fast process for doing exact and inexact matching between DNA and mRNA sequences to support the Mitsuhashi Probe Selection Diagram (MPSD) and other types of analysis discussed above. The process used by the Mismatch Model is the Waterman-Pevzner Algorithm (the WPALG, which is named for two of the inventors), which is a computer-based probe selection process. Essentially, this is a combination of new and improved pattern matching processes. See Hume and Sunday (1991, Ref. 4), Landau et al (1986–1990, Refs. 6, 7, 8), Grossi and Luccio (1989, Ref. 3), and Ukkonen (1982, Ref. 14).

There are three principal programs that make up the Mismatch Model in this implementation of the invention. The first is designated by the inventors as "k_diff." WPALG is used in k_diff to find all locations of matches of length greater than or equal to one (1) (length is user-specified) with less than or equal to k number of mismatches (k is also user-specified) between the two sequences. If a candidate oligonucleotide probe fails to match that well, it is considered unique. k_diff uses hashing and continuous seed filtration, and looks for homologs in GenBank and other databases with similar file formats. The technique of continuous seed filtration allows for much more efficient searching than previously implemented techniques. A seed is defined in this invention to be a subsequence of length equal to the longest exact match in the worst case scenario. For example, suppose the user selects a probe length (1) of 18, with 2 or fewer mismatches (k). If a match exists with 2 mismatches, then there must be a perfectly matching subsequence of length equal to 6. Once the seed length has been determined, the Mismatch Model looks at all substrings of that seed length (in this example, that seed length would be 6), finds the perfectly matched base pair subsequence of length equals 6, and then looks to see if this subsequence extends to a sequence of length equal to the user selected probe length (i.e., 20 in this example). If so, a candidate probe has been found that meets the user's criteria.

Where the seed size is large, the program allocates a relatively large amount of memory for the hash table. This invention has an option that allows memory allocation for GenBank entries just once at the beginning of the program, instead of reallocating memory for each GenBank entry. This reduces input time for GenBank entries by as much as a factor of two (2), but the user needs to know the maximum GenBank entry size in advance to do this.

A probe is defined to hybridize if it has k or fewer mismatches in comparison with a target sequence from the database or file searched. Otherwise, it is non-hybridizing. The hit extension time for all appropriate parameters of the Mismatch Model has been found by experimentation to be less than thirty-five (35) seconds, except in one case where the minimum probe length (1) was set to 24 and the maximum number of mismatches (k) was set to four (4), which is a situation that is never used in real gene localization experiments because the hybridization conditions are too weak.

In this invention, the second hybridization strength model is termed the H-Site Model. One aspect of the H-Site Model uses a generalization of an experimental formula in general usage. The basic formula on which this aspect of the model is built is as follows:

$Tm=81.5-16.6(\log[Na]) -0.63$ %(formamide) $+0.41$ (%(G+C)) $-600 / N$ In this formula, log[Na] is the sodium concentration, %(G+C) is the fraction of matched base pairs which are G-C complementary, and N is the probe length. In other words, this formula is an expression of the fact that melting temperature Tm is a function of both probe length and percent of Guanine-Cytosine (GC) content. This basic formula has been modified in this invention to account for the presence of mismatches. Each percent of mismatch reduces the melting temperature Tm by an average of 1.25 degrees (2 degrees C. for an Adenine-Thymine mismatch, and 4 degrees C. for a Guanine-Cytosine mismatch). This formula is, however, an approximation. The actual melting temperature might differ significantly from this approximation, especially for short probes or for probes with a relatively large number of mismatches.

Hybridization strength in the H-Site Model is related to each of the following factors: 1) "binding region"; 2) type of mismatch (GC or AT substitution); 3) length of the probe; 4) GC content of the binding region (since GC pairs have a stronger bond than AT pairs, thus requiring a higher melting temperature); and 5) existence of a "nucleation site" (an exactly matching subsequence). The type of mismatch and the GC content of the binding region each contribute to a candidate probe's binding strength, which can be compared to other candidate probes' binding strengths to enable the user to select the optimal probe.

The fundamental assumption of the H-Site Model is that binding strength is determined by a paired subsequence of the probe-species combination, called the binding region. If the binding region contains more GC pairs than AT pairs, the binding strength will be higher since the G and. C bases (connected with three bonds) form a tighter bond than the A and T bases (connected with two bonds). Thus, G and C bases, and probes that are GC rich, require a higher melting temperature Tm and subsequently form a stronger bond. In the H-Site Model, and one of its unique features, the program designs optimal probes, ideally ones that do not have any mismatches, but if there are mismatches the H-Site Model takes these into account. With this model, a candidate probe can afford to have more mismatches involving the AT bases if there are more GC bases than AT bases in the probe. This is because this model looks primarily at regions of the candidate probe and target sequence that match and does not "penalize" the probe for areas that do not match. If the mismatches are located at either or both of the ends of the binding region, this has little effect. It is much more deleterious to have mismatches in the middle of the binding region, as this will significantly lower the binding strength of the probe.

The formula cited above for Tm applies within the binding region. The length of the probe is used to calculate percentages, but all other parameters of the formula are applied to the binding region only. The H-Site Model further assumes the existence of a nucleation site, which is a region of exact match. The length of this nucleation site may be set by the user. Typically, a value of 8 to 10 base pairs is used. To complete the H-Site Model, the binding region is chosen so as to maximize the melting temperature Tm among all regions containing a nucleation site, assuming one exists (otherwise, Tm=0).

The H-Site Model is more complex than the Mismatch Model discussed above in that hybridization strength is modeled as a sum of signed contributions, with matches generally providing positive binding energy and mismatches generally providing negative binding energy. The exact coefficients to be used depend only on the matched or mismatched pair. These coefficients may be specified by the user, although in the current version of this invention these coefficients are not explicitly user-selectable, but rather are selected to best fit the hybridization strength formulas developed by Itakura et al (1984, Ref. 5), Bolton and McCarthy (1962, Ref. 2), Benner et al (1973, Ref. 1), and Southern (1975, Ref. 13).

A unique aspect of the H-Site Model is that hybridization strength is defined to be determined by whatever the optimal binding region between the candidate probe and binding locus. This binding region is called the hybridization site, or h-site, and is selected so as to maximize overall hybridization strength, so that mismatches outside the binding region do not detract from the estimated hybridization strength. Several other unique features of the H-Site Model include the fact that it is more oriented toward RNA and especially cDNA sequences than DNA sequences, and the fact that the user has control over preparation and environmental variables. The first feature allows the user to concentrate on "meaningful" sequences, rather than having to sort through all of a DNA sequence (including the introns). The second feature allows the user to more accurately simulate laboratory conditions and more closely correspond with any experiments he or she is conducting. Further, this implementation of the invention does some preliminary preprocessing of the GenBank database to sort out and select the cDNA sequences. This is done by locating a keyword (in this case CDS) in each GenBank record, thereby eliminating any sequences containing introns.

The Mitsuhashi Probe Selection Diagram (MPSD), FIG. 4, is the third key feature of this invention, as it is a unique way of visualizing the results of the probe designing performed by the Mismatch and H-Site Models. It is a graphic display of all of the hybridizations of candidate oligonucleotide probes for the target mRNA with all sequences in the preparation. Given a gene sequence database and a target mRNA sequence, the MPSD graphically displays all of the candidate probes and their hybridization strengths with all sequences from the database. In the present implementation, each melting temperature Tm is displayed as a different color, from red (highest Tm) to blue (lowest Tm). The MPSD allows the user to see visually the number of false hybridizations at various temperatures for all candidate probes, and the sources of these false hybridizations (with a loci and sequence comparison). A locus may be a specific site or place, or, in the genetic sense, a locus is any of the homologous parts of a pair of chromosomes that may be occupied by allelic genes.

BRIEF DESCRIPTION OF THE DRAWING

This invention may be more clearly understood from the following detailed description and by reference to the drawing in which:

FIG. 5 is a display screen representation of the probeinfo and matchinfo window;

FIG. 6 is a display screen representation of the probesedit window;

FIG. 6a is a printout of the probesedit output file;

FIG. 20 is a printout of a sample file containing the output of the Mismatch Model program of this invention;

FIG. 24a is a printout of a sample file containing output of the Mismatch Model program;

FIG. 24b is a printout of a sample file containing output of the H-Site Model program;

FIG. 27 is a printout of a sample target species file;

FIG. 28 is a printout of a sample preparation file.

DETAILED DESCRIPTION OF THE INVENTION

Figure 1:
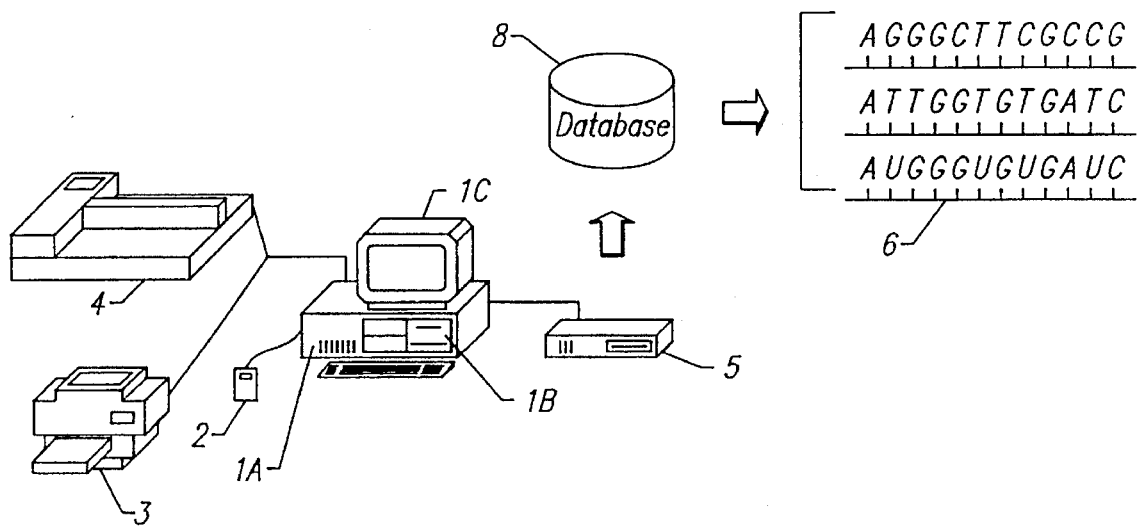
FIG. 1 is a simplified block diagram of a computer system illustrating the overall design of this invention.

This invention is employed in the form best seen in FIG. 1. There, the combination of this invention consists of an IBM® compatible personal computer (PC), running software specific to this invention, and having access to a distributed database with the file formats found in the GenBank database and other related databases.

The preferred computer hardware capable of operating this invention involves of a system with at least the following specifications (FIG. 1): 1) an IBM® compatible PC, generally designated 1A, 1B, and 1C, with an 80486 coprocessor, running at 33 Mhz or faster; 2) 8 or more MB of RAM, 1A; 3) a hard disk 1B with at least 200 MB of storage space, but preferably 1 GB; 4) a VGA color monitor 1C with graphics capabilities of a size sufficient to display the invention's output in readable format, preferably with a resolution of 1024×768; and 5) a 580 MB CD ROM drive 5 (1B of FIG. 1 generally refers to the internal storage systems included in this PC, clockwise from upper right, two floppy drives, and a hard disk). Because the software of this invention preferably has a Microsoft® Windows™ interface, the user will also need a mouse 2, or some other type of pointing device.

The preferred embodiment of this invention would also include a laser printer 3 and/or a color plotter 4. The invention may also require a modem (which can be internal or external) if the user does not have access to the CD ROM versions of the GenBank database 8 (containing a variable number of gene sequences 6). If a modem is used, information and instructions are transmitted via telephone lines to and from the GenBank database 8. If a CD ROM drive 5 is used, the GenBank database (or specific portions of it) is stored on a number of CDs.

The computer system should have at least the Microsoft® DOS v. 5.0 operating system running Microsoft® Windows™ v. 3.1. All of the programs in the preferred embodiment of the invention are written in the Borland® C++ (made by Borland International, Inc., of Scotts Valley, Calif.) computer language. It must be recognized that subsequently developed computers, storage systems, and languages may be adapted to utilize this invention and vice versa.

This invention is designed to enable the user to access DNA, mRNA and cDNA sequences stored either in the GenBank or in databases with similar file formats. GenBank is a distributed flat file database made up of records, each record containing a variable number of fields in ASCII file format. The stored database itself is distributed, and there is no one database management system (DBMS) common to even a majority of its users. One general format, called the line type format, is used both for the distributed database and for all of GenBank's internal record keeping. All data and system files and indexes for GenBank are kept in text files in this line type format.

The primary GenBank database is currently distributed in a multitude of files or divisions, each of which represents the genome of a particular species (or at least as much of it as is currently known and sequenced and publicly available). The GenBank provides a collection of nucleotide sequences as well as relevant bibliographic and biological annotation. Release 72.0 (Jun. 6/1992) of the GenBank CD distribution contains over 71,000 loci with a total of over ninety-two (92) million nucleotides. GenBank is distributed by IntelliGenetics, of Mountain View, Calif., in cooperation with the National Center for Biotechnology Information, National Library of Medecinge, in Bethesda, Md.

1. Overall Description of the Invention a. General Theory

The intent of this invention is to provide one or more fast processes for performing exact and inexact matching between DNA sequences to support the Mitsuhashi Probe Selection Diagram (MPSD), discussed below, and other analysis with interactive graphical analysis tools. Hybridization strength between a candidate oligonucleotide probe and a subsequence of DNA, mRNA or cDNA can be estimated through a hybridization strength model. Quantitatively, hybridization strength is given as the melting temperature Tm. Currently, two hybridization strength models are supported by the invention: 1) the Mismatch Model and 2) the H-Site Model.

b. Inputs i. Main Dialog Window

Figure 2A:
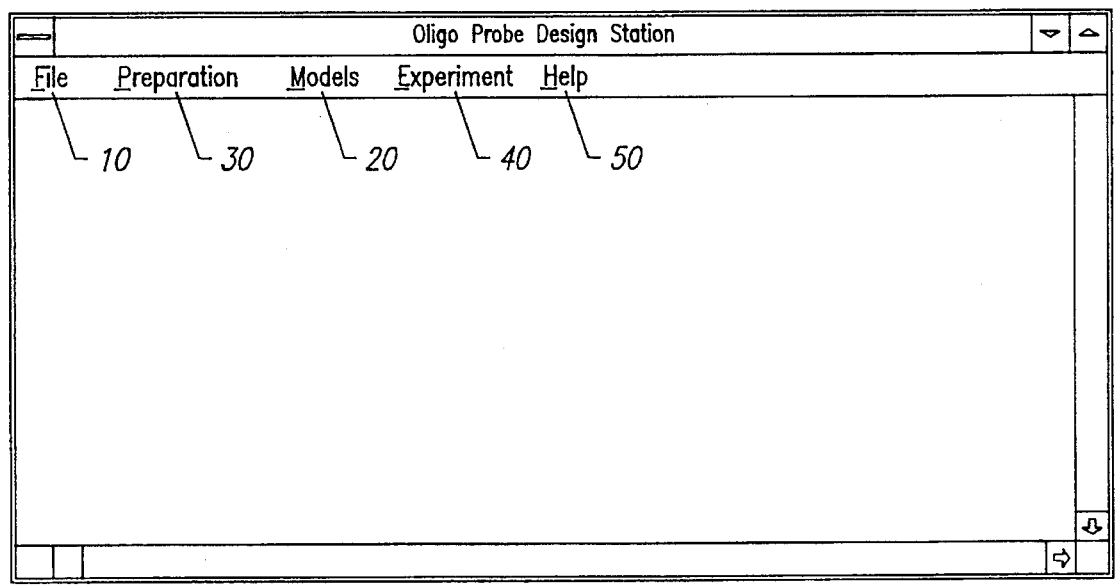
FIG. 2 is a display screen representation of the main dialog window of this invention.

The Main Dialog Window, FIG. 2, controls all user-definable settings. This window has a menu bar offering five options: 1) File 10; 2) Preparation 30; 3) Models 20; 4) Experiment 40; and 5) Help 50. The File 10 option allows the user to print, print in color, save selected probes, and exit the program. The Preparation 30 option allows the user to open and create preparation (PRP) files.

The Models 20 option allows the user to chose between the two hybridization models currently supported by the invention: 1) the H-Site Model 21 and 2) the Mismatch Model 25. If the user selects the H-Site Model 21 option, the left hand menu of FIG. 2C is displayed and the user sets the following model parameters: 1) the meeting temperature Tm 22 for which probes are being designed (i.e., the melting temperature that corresponds to a particular experiment or condition the user desires to simulate); and 2) the nucleation threshold 23, which is the number of base pairs constituting a nucleation site. If the user selects the Mismatch Model 25 option, the right hand menu of FIG. 2C is displayed and the user sets the following model parameters: 1) probe length 26, which is the number of base pairs in probes to be considered; and 2) mismatch N 27, which is the maximum number of mismatches constituting a hybridization. Computation of the user's request will take longer with the H-Site Model if the threshold 23 setting is decreased and with the Mismatch Model if the number of mismatches K 27 is increased.

In addition, for both Model options the user chooses the target species 11 DNA or mRNA for which probes are being designed and the preparation 12, a file of all sequences with which hybridizations are to be calculated. A sample of a target species file is shown in FIG. 27 (humbjunx.cds), while a sample of a preparation file is shown in FIG. 28 (junmix-.seq). Each of these inputs is represented by a file name and extension in general DOS format. In the target species and preparation fields, the file format follows the GenBank format, and each of the fields includes a default file extension. Pressing the "OK" button 41 of FIG. 2C will cause the processing to begin, and pressing the "Cancel" button 43 will cause it to stop.

The Experiment 40 option and the Help 50 option are expansion options not yet available in the current implementation of the invention.

c. Processing

Figure 3:
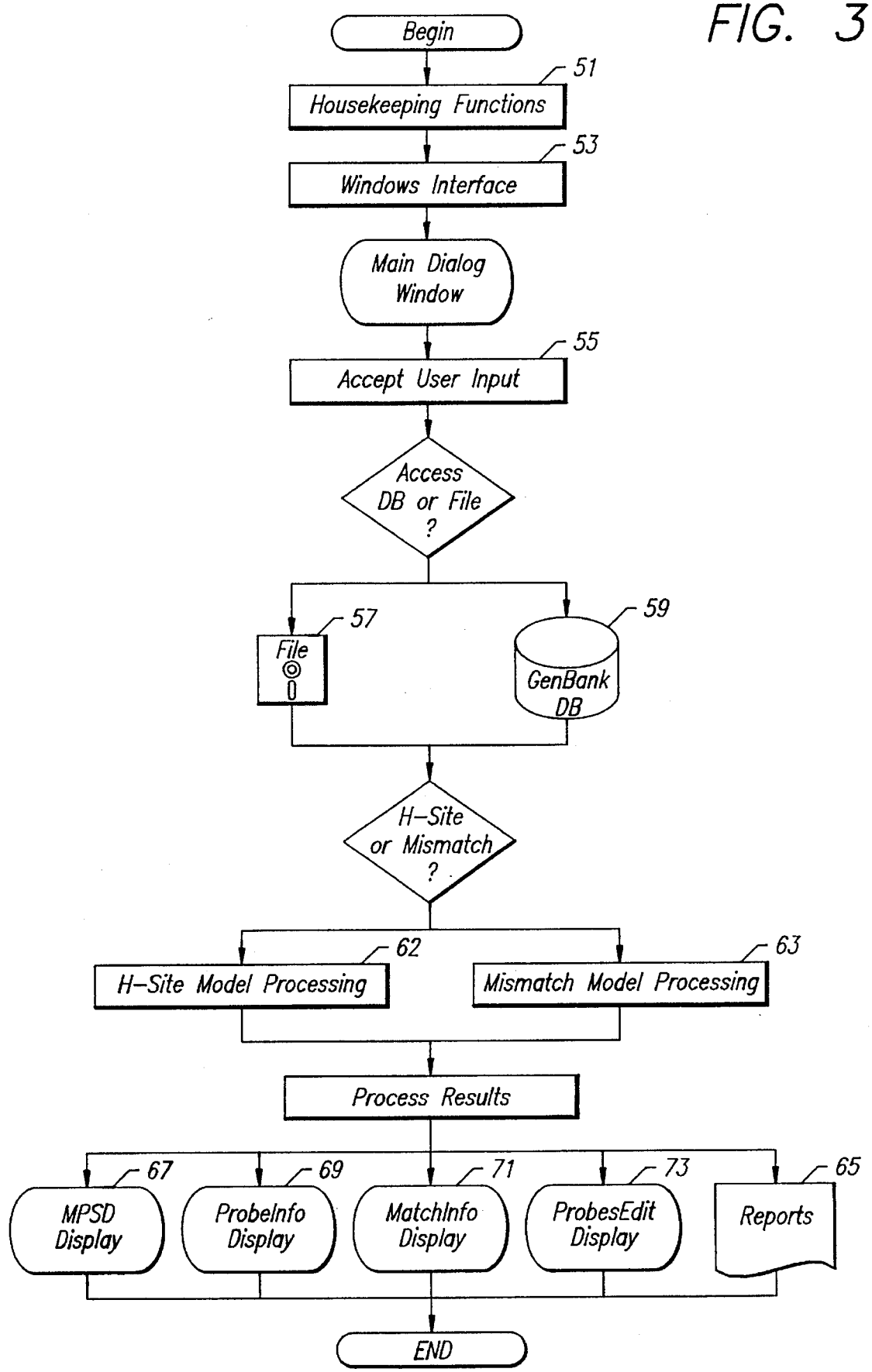
FIG. 3 is a flow chart of the overall invention illustrating the program, and the invention's sequence and structure.

FIG. 3 is a flow chart of the overall program, illustrating its sequence and structure. Generally, the main or "control" program of the invention basically performs overall maintenance and control functions. This program, as illustrated in FIG. 3, accomplishes the general housekeeping functions 51, such as defining global variables. The user-friendly interface 53, carries out the user-input procedures 55, the file 57 or database 59 access procedures, calling of the model program 62 or 63 selected by the user, and the user-selected report 65 or display 67, 69, 71 and 73 features. Each of these features is discussed in more detail in later sections, with the exception of the input procedures, which involves capturing the user's set-up and control inputs.

d. Outputs i. The Mitsuhashi Probe Selection Diagram Window

Figure 4:
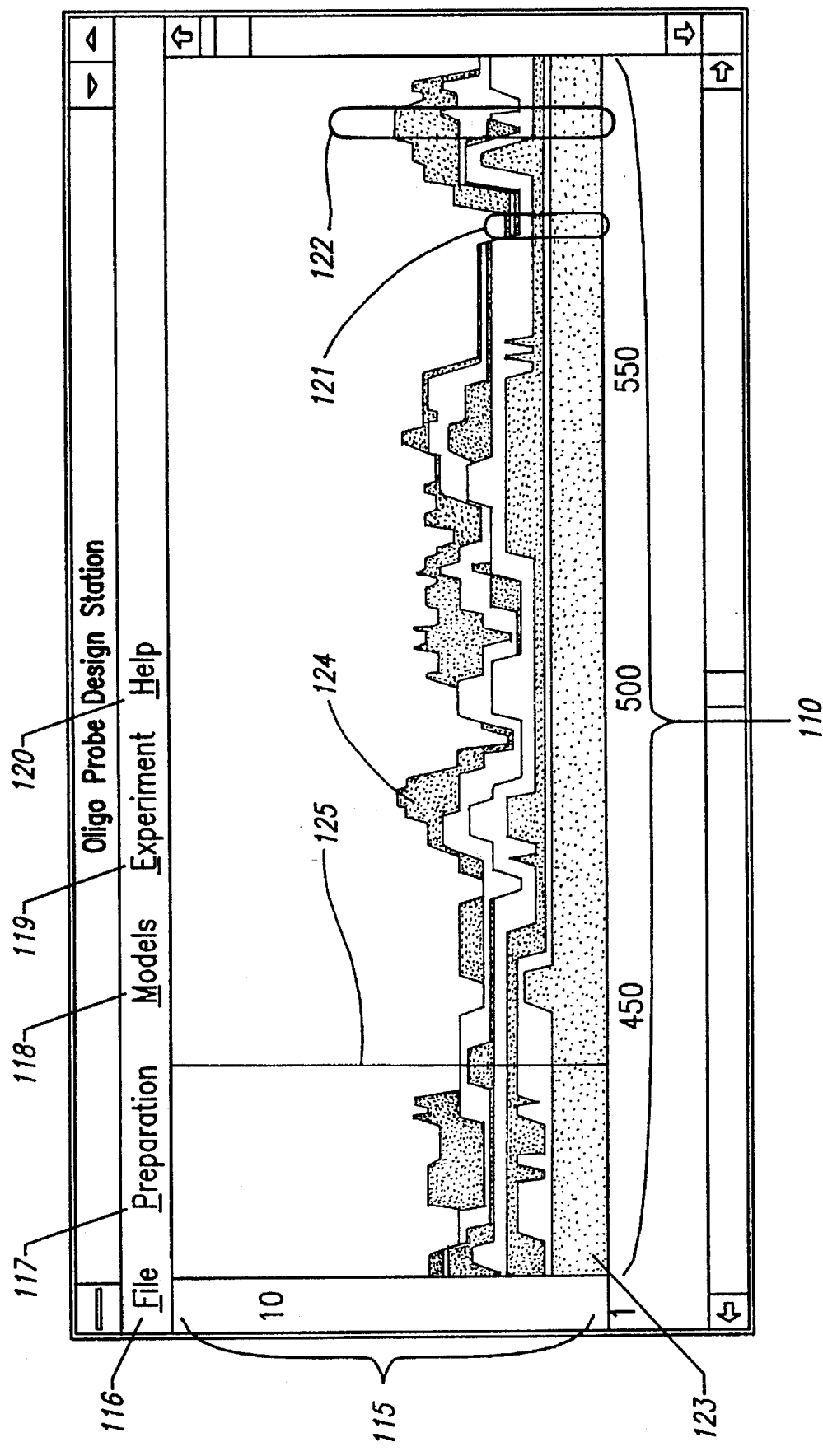
FIG. 4 is a display screen representation of the Mitsuhashi probe selection diagram.

The Mitsuhashi Probe Selection Diagram (MPSD), FIG. 4, is a key feature of the invention as it is a unique way of visualizing the results of the program's calculations. It is a graphic display of all of the hybridizations of probes for the target mRNA with all sequences in the preparation. In other words, given a sequence database and a target mRNA, the MPSD graphically displays all of the candidate probes and their hybridization strengths with all sequences from the sequence database. The MPSD allows the user to see visually the number of false hybridizations at various temperatures for all candidate probes, and the sources of these false hybridizations (with a loci and sequence comparison).

For each melting temperature Tm of interest, a graphical representation of the number of hybridizations for each probe is displayed. In the preferred embodiment, this representation is color coded. In this implementation of the invention, the color red 123 identifies the highest melting temperature Tm and the color blue 124 identifies the lowest melting temperature Tm. Each mismatch results in a reduction in Tm. Tm is also a function of probe length and percent content of GC bases. Within the window, the cursor 125 shape is changed from a vertical line bisecting the screen to a small rectangle when the user selects a particular probe. The current probe is defined to be that probe under the cursor position (whether it be a line or a rectangle) in the MPSD window. More detailed information about the current probe is given in the ProbeInfo and MatchInfo windows, discussed below. Clicking the mouse 2 once at the cursor 125 selects the current probe. Clicking the mouse 2 a second time deselects the current probe. Moving the cursor across the screen causes the display to change to reflect the candidate probe under the current cursor position.

The x-axis 110 of the MPSD, FIG. 4, shows the candidate probes' starting positions along the given mRNA sequence. The user may "slide" the display to the left or right in order to display other probe starting positions. The y-axis 115 of the MPSD displays the probe specificity, which is calculated by the program.

The menu options 116, 117, 118, 119, and 120 available to the user while in the MPSD, FIG. 4, are displayed along a menu bar at the top of the screen. The user can click the mouse 2 on the preferred option to briefly display the option choices, or can click and hold the mouse button on the option to allow an option to be selected. The user may also type a combination of keystrokes in order to display an option in accordance with well-known computer desk top interface operations. This combination usually involves holding down the ALT key while pressing the key representing the first letter of the desired option (i.e, F, P, M, E or H).

The File option 116 allows the user to specify input files and databases. The Preparation option 117 allows the user to create a preparation file summarizing the sequence database. The Models option 118 allows the user to specify the hybridization model (i.e., H-Site or Mismatch) and its parameters. The Experiment option 119 and the Help option 120 are not available in the current implementation of this invention. These options are part of the original Main Dialog Window, FIG. 2.

Areas on the graphical display of the MPSD, FIG. 4, where the hybridizations for the optimal probes are displayed are lowest and most similar, such as shown at 121, indicate that the particular sequence displayed is common to all sequences. Areas on the graphical display of the MPSD where the hybridizations for the optimal probes are displayed are highest and most dissimilar, such as shown at 122, indicate that the particular sequence displayed is extremely specific to that particular gene fragment. The high points on the MPSD show many loci in the database, to which the candidate probe will hybridize (i.e., many false hybridizations). The low points show few hybridizations, at least relative to the given database. In other words, the sequence shown at 121 would reflect a probe common to all of the gene fragments tested, such that this probe could be used to detect each of these genes. The sequence shown at 122 would reflect a probe specific to the particular gene fragment, such that this probe could be used to detect this particular gene and no others.

ii. The ProbeInfo and MatchInfo Window

The combined ProbeInfo and MatchInfo Window, FIG. 5, displays detailed information about the current candidate probe. The upper portion of the window is the ProbeInfo window, and the lower portion is the MatchInfo window. The ProbeInfo window portion displays the following types of information: the target locus (i.e., the mRNA, cDNA, or DNA from which the user is looking for probes) is displayed at 131, while the preparation used for hybridizations is displayed at 132. In the example shown in FIG. 5, the target locus 131 is the file named HUMBJUNX.CDS, which is shown as being located on drive F in the subdirectory MILAN. The preparation 132 is shown as being the file designated JUNMIX.PRP, which is also shown as being located on drive F in the subdirectory MILAN. The JUNMIX.PRP preparation in this example is a mixture of human and mouse jun loci.

The current and optimal probe's starting position is shown at 135. The current candidate oligonucleotide probe is defined at 136, and is listed at 137 as having a length of 21 bases. The melting temperature for the probe 136 as hybridized with the targets is shown in column 140. The melting temperature for the optimal probe is given as 61.7 degrees C. at 138. The ProbeInfo Window FIG. 5 also displays hairpin characteristics of the probe at 139. In the example shown, the ProbeInfo Window shows that there are four (4) base pairs involved in the worst hairpin, and that the worst hairpin has a length of one (1) (see FIG. 5, at 139).

The MatchInfo Window portion displays a list of hybridizations between the current probe and species within the preparation file, including hybridization loci and hybridization temperatures. The hybridizations are listed in descending order by melting temperature. The display shows the locus with which the hybridization occurs, the position within the locus, and the hybridization sequence.

In the MatchInfo window portion, the candidate probe 136 is shown at 150 as hybridizing completely with a high binding strength. This is because the target DNA is itself represented in the database in this case, so the candidate probe is seen at 150 to hybridize with itself (a perfect hybridization). The locus of each hybridization from the preparation 132 are displayed in column 141, while the starting position of each hybridization is given in column 142. The calculated hybridizations are shown at 145.

iii. The ProbesEdit Window

The ProbesEdit Window, FIG. 6, is a text editing window provided for convenient editing and annotation of the invention's text file output. It is also used to accumulate probes selected from the MPSD, FIG. 4, by mouse 2 clicks. Standard text editing capabilities are available within the ProbesEdit Window. The user may accumulate selected probes in this window (see 155 for an example) and then save them to a file (which will bear the name of the preparation sequence with the file extension of "prb" 156, or may be another file name selected by the user). A sample of this file is shown in FIG. 6A.

iv. Miscellaneous Output

The present embodiment of this invention also creates two output files, currently named "test.out" and "test1.out", depending upon. which model the user has selected. The first file, "test.out", is created with both the Mismatch Model and the H-Site Model. This file is a textual representation of the Mitsuhashi Probe Selection Diagram (MPSD). It breaks the probe sequence down by position, length, delta Tm, screensN, and the actual probe sequence (i.e., nucleotides). An example of this file created by the Mismatch Model is shown in FIG. 20, and example created by the H-Site Model is shown in FIG. 24A. The second file, "test1.out", is created only by the H-Site Model. This file is a textual representation of the ProbeInfo and MatchInfo window that captures all hybridizations, along with their locus, starting position, melting temperature, and possible other hybridizations. A partial example of this file is shown in FIG. 24B (10 pages out of a total of 190 pages created by the H-Site Model).

2. Description of the Mismatch Model Program a. Overview

In this invention, one of the hybridization strength models is termed the Mismatch Model (see FIG. 2 for selection of this model). The basic operation of this model involves the techniques of hashing and continuous seed filtration, as defined earlier and described in more detail below. The essence of the Mismatch Model is a fast process for doing exact and inexact matching between DNA and mRNA sequences to support the Mitsuhashi Probe Selection Diagram (MPSD). There are a number of modules in the present implementation of the Mismatch Model contained in this invention, the most significant of which are shown in the flow chart in FIG. 7 and in more detail in FIGS. 8 through 18. The main k_diff module shown in the flow chart in FIG. 8 is a structured program that provides overall control of the Mismatch Model, calling various submodules that perform different functions.

b. Inputs

The user-selected input variables for this model are minimum probe length 26 (which is generally from 18 to 30) and maximum number of mismatches 27 (which generally is from 1 to 5). These inputs are entered by the user in the Main Dialog Window, FIG. 2C.

c. Processing i. k_diff Program

Some terms of art need to be defined before the processing performed by this module can be explained. A hash table basically is an array or table of data. A linked list is a classical data structure which is a chain of linked entries and involves pointers to other entry structures. Entries in a linked list do not have to be stored sequentially in memory, as is the case with elements contained in an array. Usually there is a pointer to the list associated with the list, which is often initially set to point to the start of the list. A pointer to a list is useful for sequencing through the entries in the list. A null pointer (i.e., a pointer with a value of zero) is used to mark the end of the list.

Figure 7:
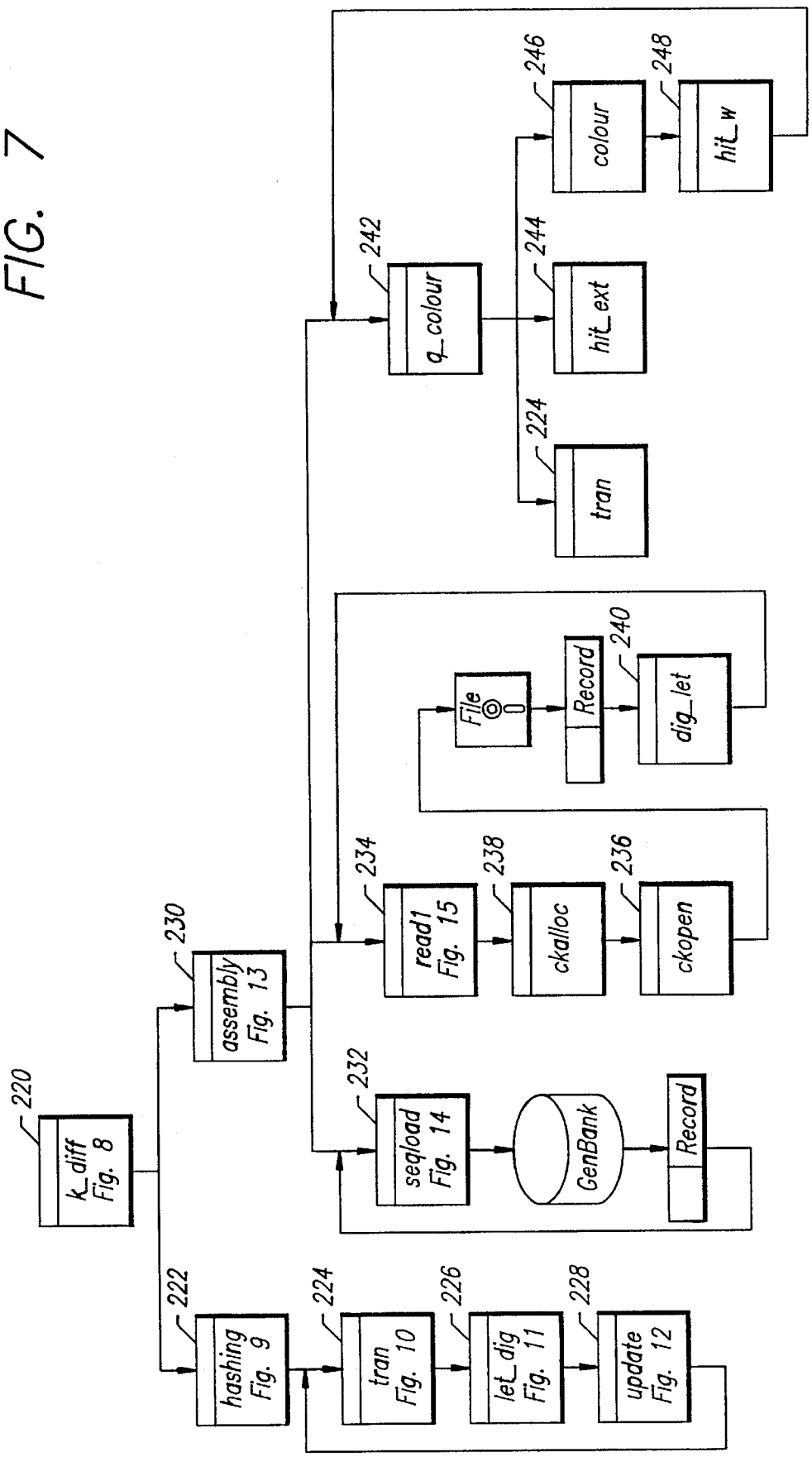
FIG. 7 is a flow chart of the overall k_diff program of the Mismatch Model of this invention, including its sequence and structure.
Figure 8A:
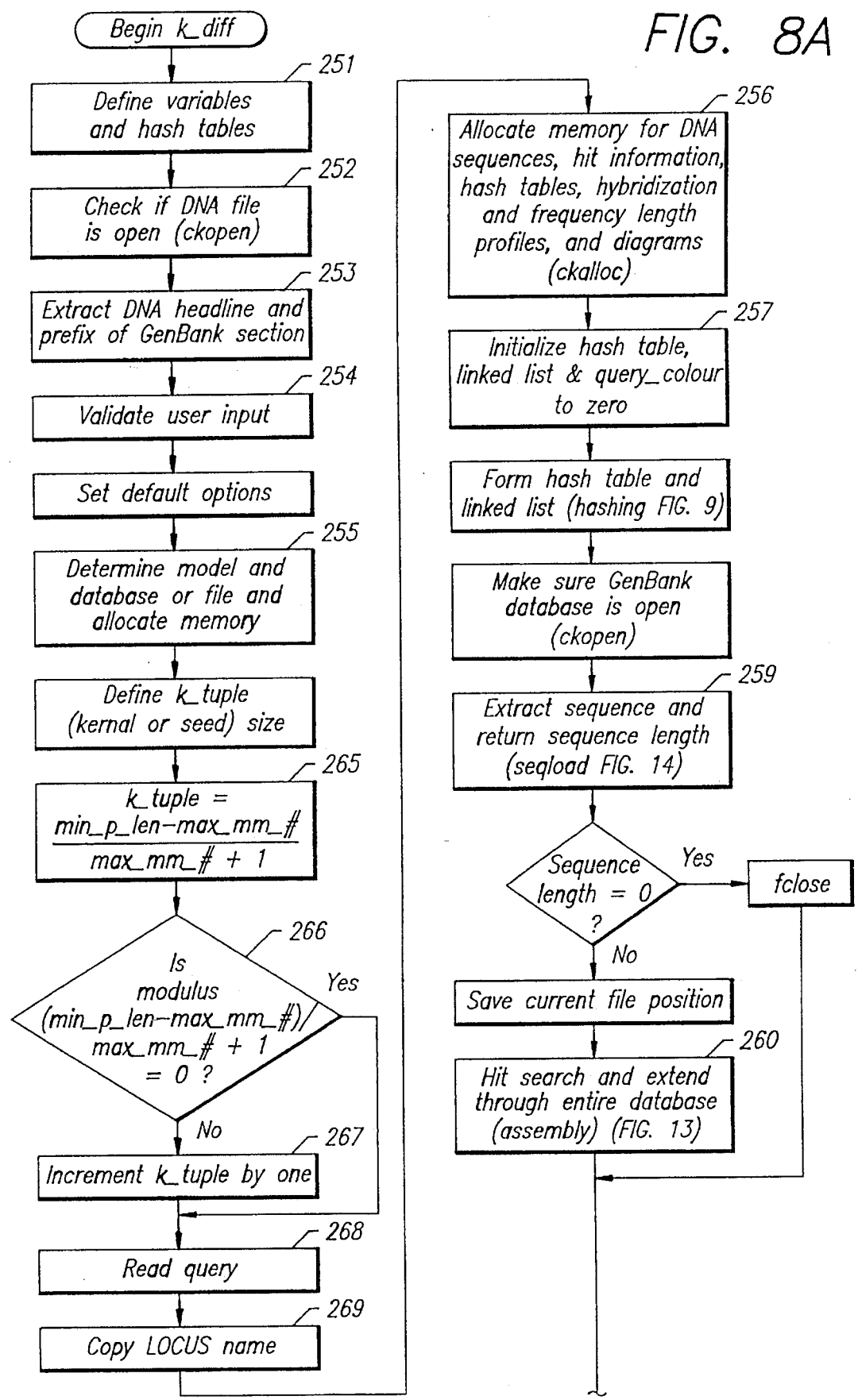
FIG. 8 is a flow chart of the k_diff module of this invention.
Figure 8B:
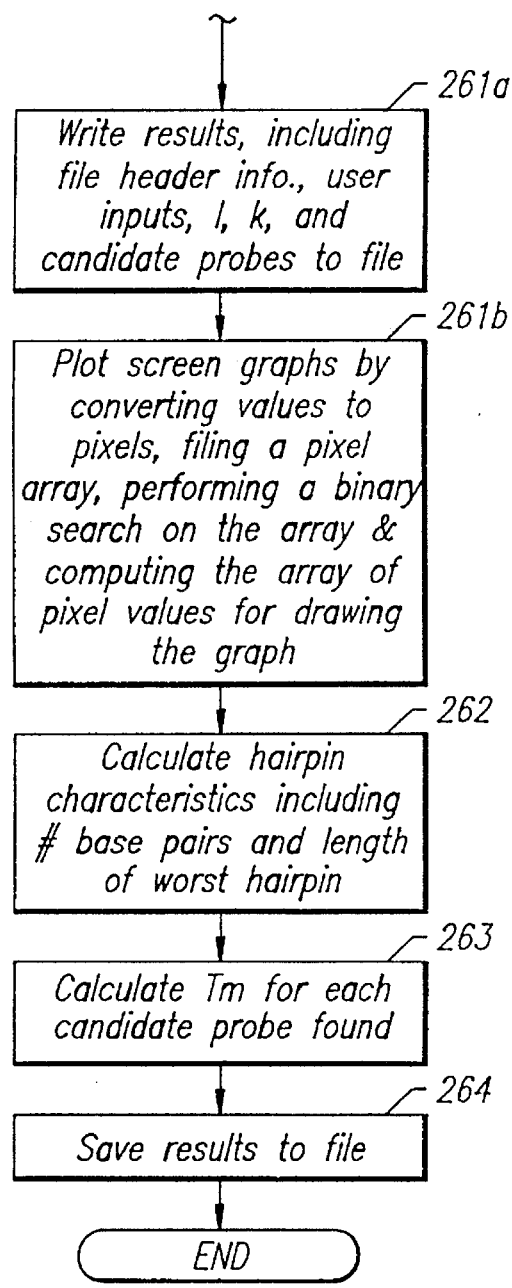

As the flow charts in FIGS. 7 and 8 illustrate, the general process steps and implemented functions of this model can be outlined as follows:

Step 1: First, create a hash table and linked list from the query (FIG. 7, hashing module 222).

Step 2: Next, while there are still GenBank entries available for searching (FIG. 7, assembly module 230):

Step 2a: Read the current GenBank entry (record) sequence of user-specified length (FIG. 7, seqload module 232), or read the current sequence (record) from the file selected by the user (FIG. 7, read1 module 234).

Step 2b: For the current sequence for each position of the sequence from the first position (or nucleotide) to the last position (or nucleotide) (incrementing the position number once each iteration of the loop) (FIG. 7, q_colour module 242), Step 2c: set the variable dna_hash equal to the hash of the current position of the current sequence (FIG. 7, q_colour module 242).

Step 2d: While not at the end of the linked list for dna_hash (FIG. 7, q_colour module 242), Step 2e: set the query_pos equal to the current position of dna_hash in the linked list (FIG. 7, q_colour module 242) and Step 2f: Extend the hit with the coordinates (query_pos, dna_pos) (FIG. 7, hit_ext module 244), Step 2g: If there exists a k_mismatch in the current extended hit (FIG. 7, colour module 246), then Step 2h: print the current hit (FIG. 7, q_colour module 242), and repeat from Step 2. As this illustrates, there are three (3) basic looping or iteration processes with functions being performed based on variables such as whether the GenBank section end has been reached (the first "WHILE" loop, Step 2), whether the end of the current DNA entry has been reached (the "FOR" loop, Step 2b), and whether the end of the dna_hash linked list has been reached (the second "WHILE" loop, Step 2d). A "hit" will only be printed if there are k_mismatches in the current extended hit.

FIGS. 8 through 18 illustrate the functions of each of the modules of the present embodiment of this invention, all of which were generalized and summarized in the description above. FIG. 8, which outlines the main "k_diff" module, shows that this module is primarily a program organization and direction module, in addition to performing routine "housekeeping" functions, such as defining the variables and hash tables 251, checking if the user-selected gene sequence file is open 252, extracting needed identification information from the GenBank 253, and ensuring valid user input 254. This module also performs a one-time allocation of memory for the gene sequences, and allocates memory for hit information, hashing, hybridization and frequency length profiles and output displays, 255 & 256. The "k_diff" module also initializes or "zeros out" the hashing table, the linked hashing list and the various other variables 257 in preparation for the hashing function. In addition, this module forms the hash tables 258 and extracts a sequence and finds the sequence length 259.

One of the most important functions performed by the "k_diff" module is to define the seed (or kernel or k_tuple) size. This is done by setting the variable k_tuple equal to (min.probe_length-max_mismatch_#)/(max_mismatch+#+1) FIG. 8 at 265. Next, if the remainder of the aforementioned process is not equal to zero 266, then the value of the variable k_tuple is incremented by one 267. The resulting value is the size of the seed. The module then reads the query 268 and copies the LOCUS name 269 for identification purposes (a definition of the term locus is given earlier in the specification).

The "k_diff" module FIG. 8 also calls the "assembly" module 260, writes the results to a file 261a, plots the results 261b (discussed below), calculates the hairpin characteristics 262 (i.e., the number of base pairs and the length of the worst hairpin) and the melting temperature (Tm) for each candidate probe 263, and saves the results to a file 264.

The screen graphs are plotted 261b by converting the result values to pixels, filing a pixel array and performing a binary search into the pixel array. Next, given the number of pixels per probe position and which function is of interest to the user (i.e., the three mismatch match numbers), the program interpolates the values at the value of (pixelsPerPositionN-1) and computes the array of pixel values for drawing the graph. These values are then plotted on the MPSD.

Figure 9:
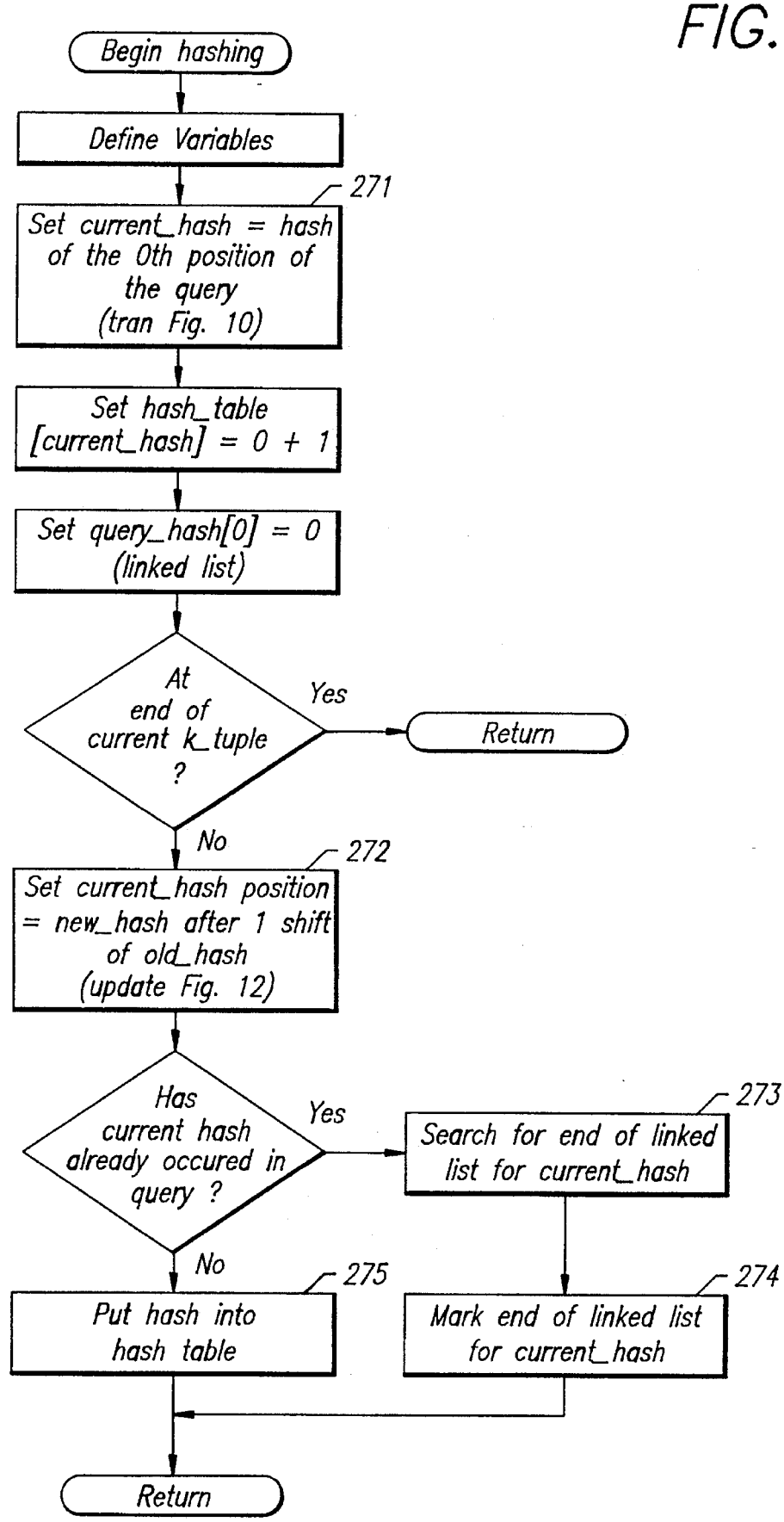
FIG. 9 is a flow chart of the hashing module of this invention.

The "hashing" module, FIG. 9, performs hashing of the query. In other words, it creates the hash table and linked list of query positions with the same hash. The variable has_table[i] equals the position of the first occurrence of hash i in the query. If i does not appear in the query, hash_table[i] is set to zero.

Figure 10:
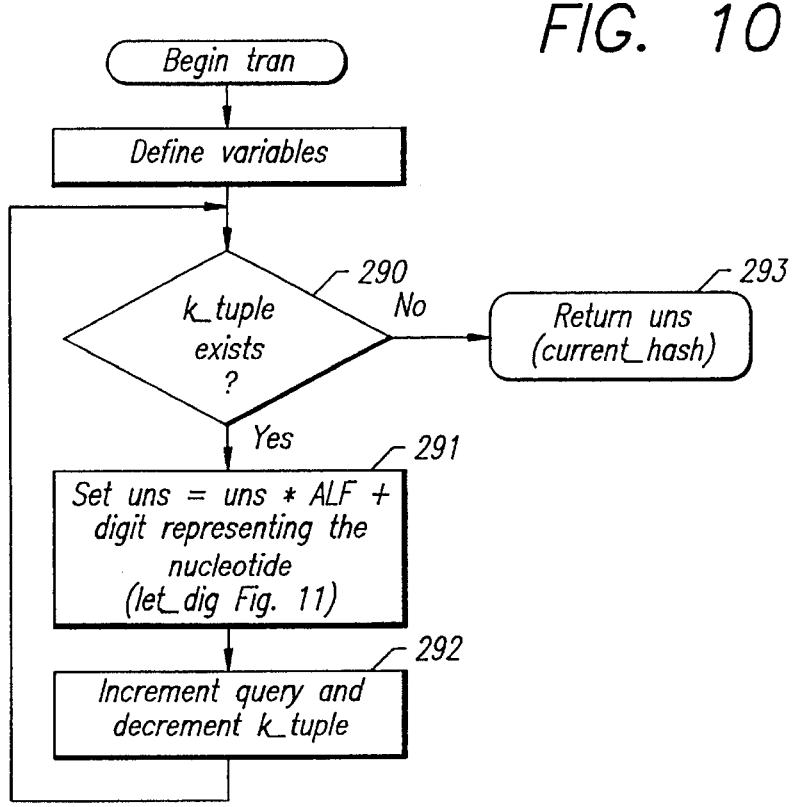
FIG. 10 is a flow chart of the tran module of this invention.
Figure 12:
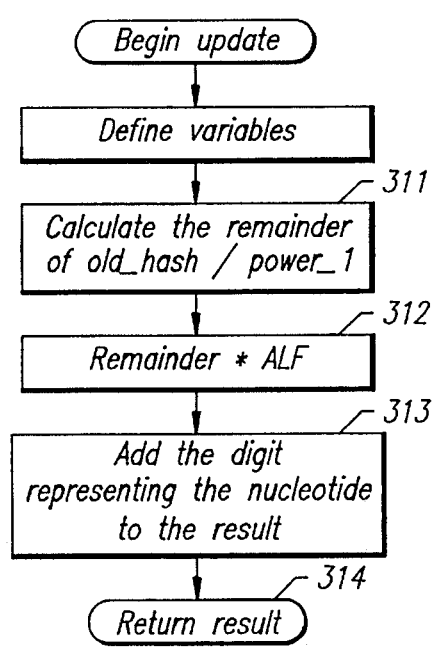
FIG. 12 is a flow chart of the update module of this invention.

The "tran" module, FIG. 10, is called by the "hashing" module 271, and performs the hashing of the sequence of k_tuple (kernel or seed) size. If the k_tuple exists (i.e., its length is greater than zero), the variable uns is set equal to uns*ALF+p 291. The variable p represents the digit returned by the "let_dig" module FIG. 11 that represents the nucleotide being examined. ALF is a constant that is set by the program in this implementation to equal four. The query pointer is then incremented, while the size of k_tuple (the seed) is decremented 292. This process is repeated until the sequence of k_tuple has been entirely hashed. Then the "tran" module returns the variable current_hash 293 to the "hashing" module FIG. 9.

Figure 11:
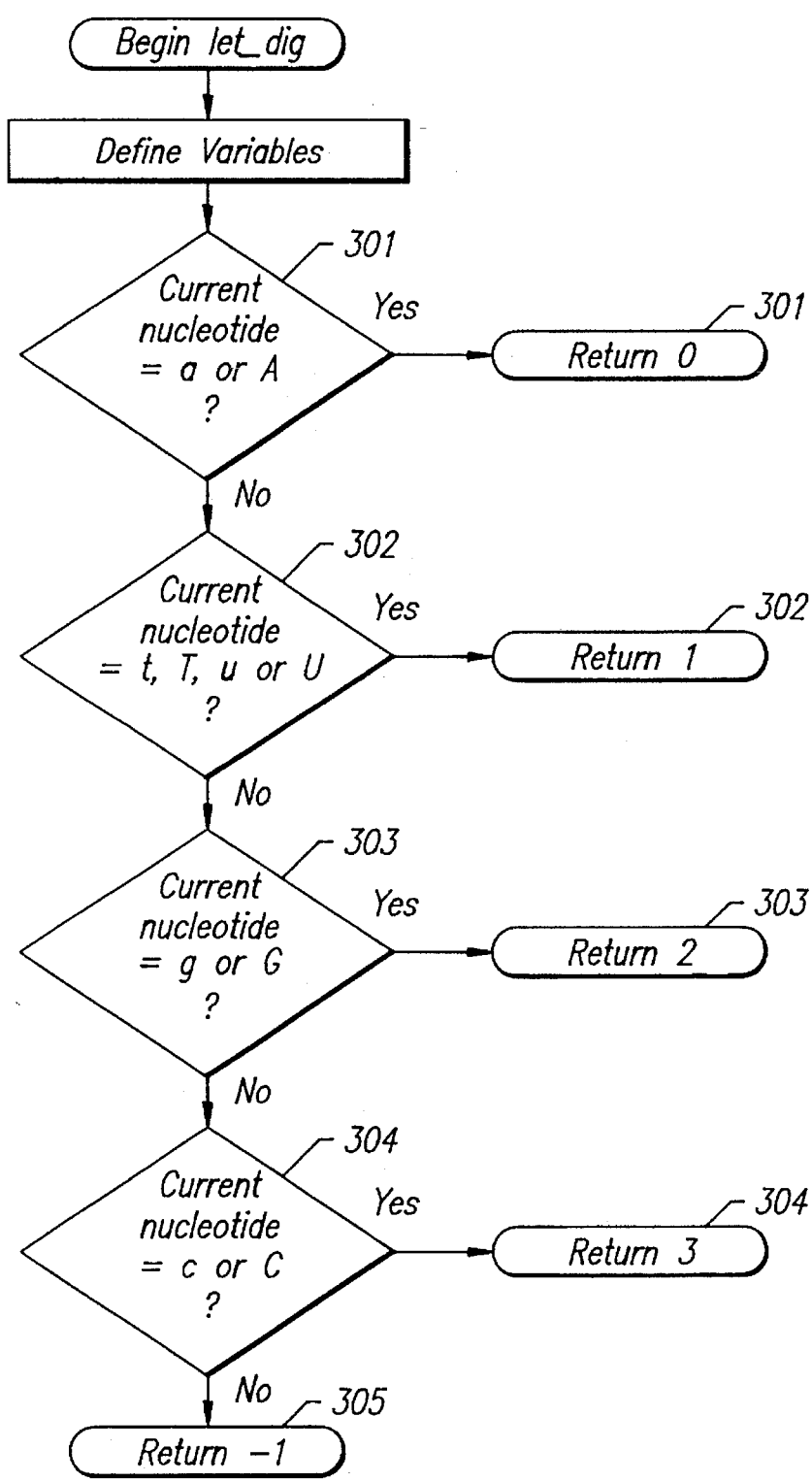
FIG. 11 is a flow chart of the let_dig module of this invention.

The "let_dig" module, FIG. 11, is called by the "tran" module 291, and transforms the nucleotides represented as the characters "A", "T", "U", "G" and "C" in the GenBank and the user's query into numeric digits for easier processing by the program. This module transforms "a" and "A" into "0" 301, "t", "T", "u" and "U" into "1" 302, "g" and "G" into "2" 303, and "c" and "C" into "3" 305. If the character to be transformed does not match any one of those listed above, the module returns "-1" 305. The "hashing" module, FIG. 9, then calls the "update" module 272, FIG. 12, which updates the hash with a sliding window (i.e., it forms a new hash after shifting the old hash by "1"). The remainder of old_hash divided by power_1 is calculated 311 (a modulus operation), the remainder is multiplied by ALF 312 (i.e., four), and then the digit representing the nucleotide is added to the result 313. The "update" module then returns the result 314 to the "hashing" module FIG. 9.

If the current hash has already occurred in the query, the program searches for the end of the linked list for the current hash 273 and marks the end of the linked list for the current hash 274. If the current hash has not already occurred in the query, the program puts the hash into the hash table 275. The resulting hash table and linked list are then returned to the "k_diff" module, FIG. 8 at 258.

Figure 13:
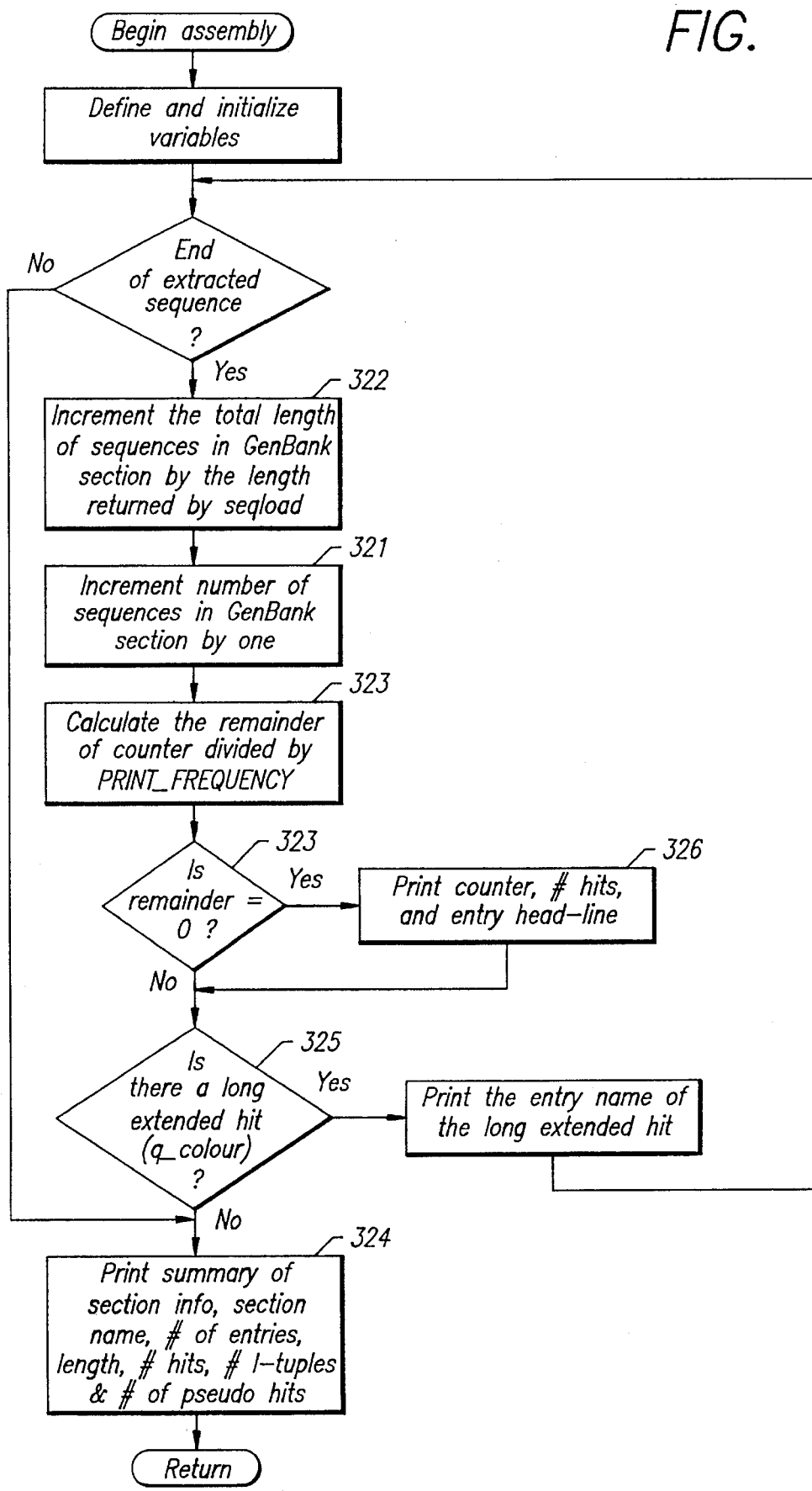
FIG. 13 is a flow chart of the assembly module of this invention.

The "assembly" module, FIG. 13, extracts sequences from the GenBank and performs hit locating and extending functions. This module is called by the "k_diff" module FIG. 8 at 260 if the user has chosen to use the database to locate matches. The output from the "assembly" module (FIG. 13) tells the user that the section of the database searched contains E number of entries 321 of S summary length 322 with H number of hits 323. Further, the program tells the user that the number of considered 1-tuples equals T 324. The entry head line is also printed 326.

Figure 14:
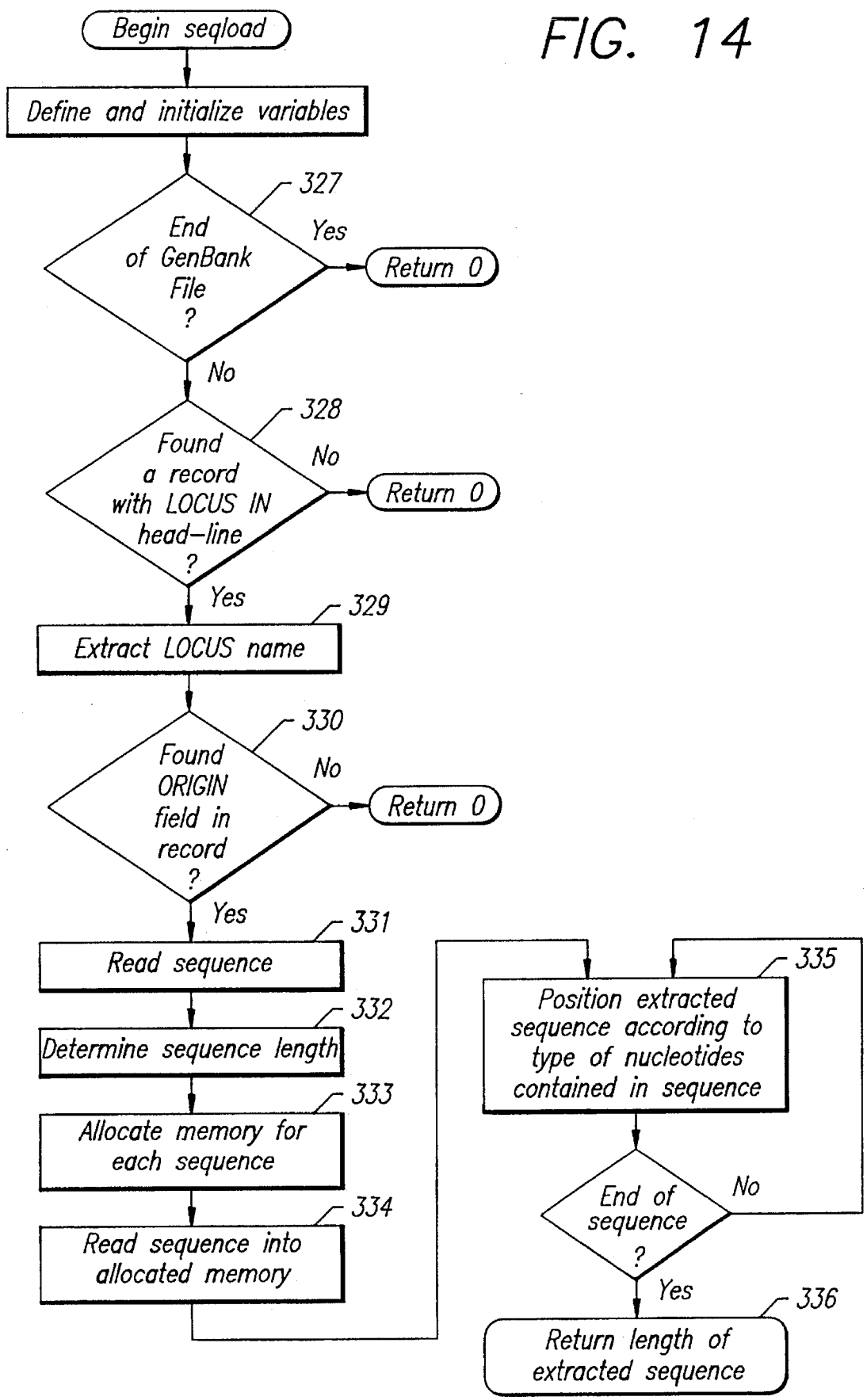
FIG. 14 is a flow chart of the seqload module of this invention.

The "seqload" module, FIG. 14, is called by the "k_diff" module FIG. 8 at 259 once the query hash table and linked list have been formed by the "hashing" module FIG. 9. The "seqload" module FIG. 14 checks to see if the end of the GenBank file has been reached 327, and, if not, searches until a record is found with LOCUS in the head-line 328. Next, the LOCUS name is extracted 329 for identification purposes, and the program searches for the ORIGIN field in the record 330.

The program then extracts the current sequence 331 from the GertBank and performs two passes on each sequence. The first is to determine the sequence length 332 and allocate memory for each sequence 333, and the second pass is to read the sequence into the allocated memory 334. Since the sequences being extracted can contain either DNA nucleotides or protein nucleotides, the "seqload" module can recognize the characters "A", "T", "U", "G", and "C". The bases "A", "T", "G" and "C" are used in DNA sequences, while the bases "A", "U", "G" and "C" are used in RNA and mRNA sequences. The extracted sequence is then positioned according to the type of nucleotides contained in the sequence 335, and the process is repeated. Once the end of the sequence has been reached, the "seqload" module returns the sequence length 336 to the "k_diff" module FIG. 8.

Figure 15:
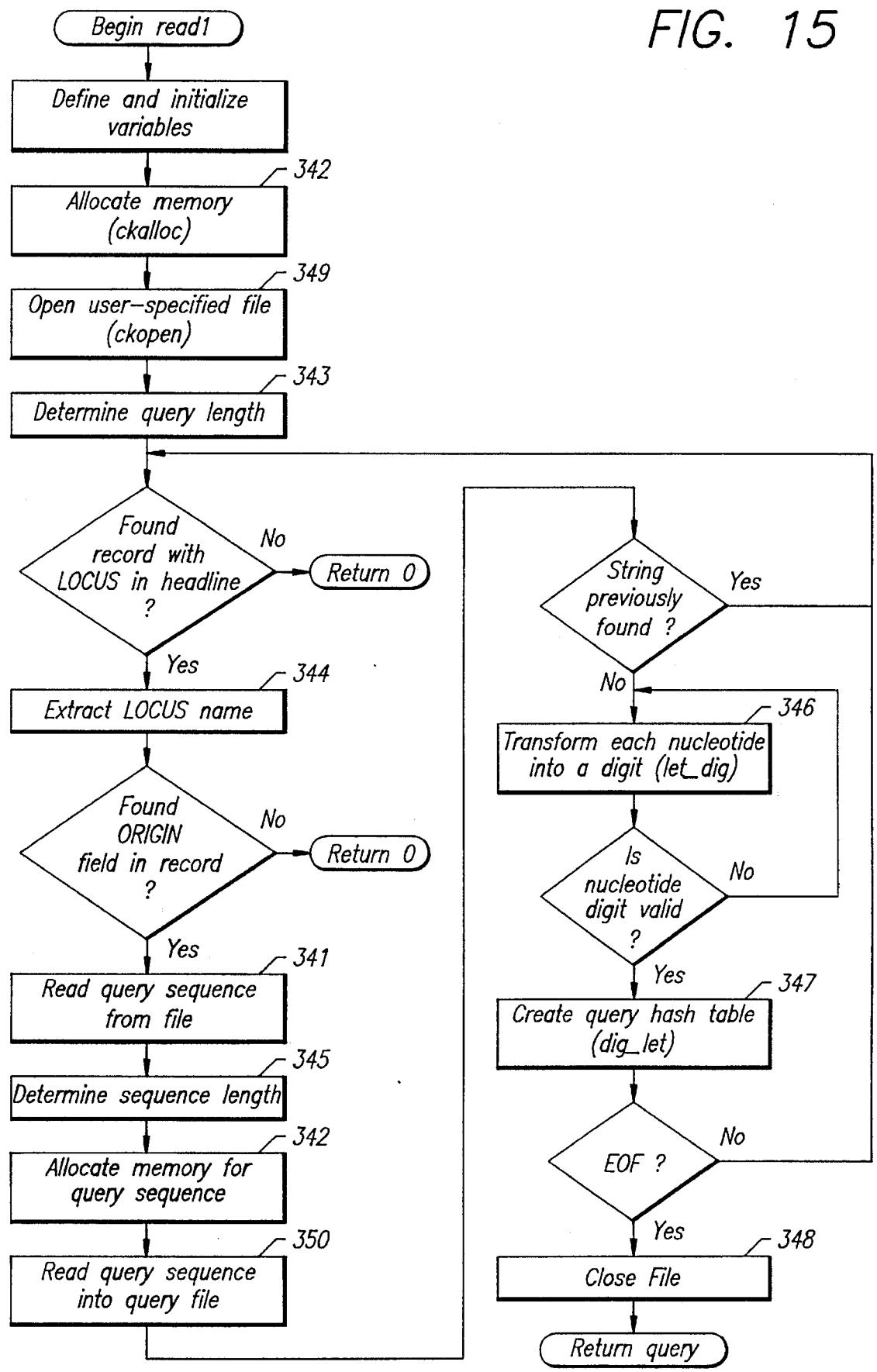
FIG. 15 is a flow chart of the read 1 module of this invention.

If the user has chosen to use one or more files to locate matches, rather than the database, the "read1" module, FIG. 15, rather than the "seqload" module FIG. 14, is called by the "k_diff" module FIG. 8. The "read1" module, FIG. 15, reads the sequence from the user specified query file 341 and allocates memory 342. This module also determines the query length 343, extracts sequence identification information 344, determines the sequence length 345, transforms each nucleotide into a digit 346 by calling the "let_dig" module FIG. 11, creates the query hash table 347 by calling the "dig_let: module FIG. 16, and closes the file 348 once everything has been read in.

First, the "read1" module FIG. 15 allocates space for the query 342. To do this, the "ckalloc" module, FIG. 15 at 342, is called. This module allocates space and checks whether this allocation is successful (i.e., is there enough memory or has the program run out of memory). After allocating space, the "read1" module FIG. 15 opens the user-specified file 349 (the "ckopen" module, FIG. 15 at 349, is called to ensure that the query file can be successfully opened 349), determines the query length 343, locates a record with LOCUS in the head-line and extracts the LOCUS name 344 for identification purposes, locates the ORIGIN field in the record and then reads the query sequence from the file 341. Next, the sequence length is determined 345, memory is allocated for the sequence 342, and the sequence is read into the query file 350. If the string has previously been found, processing is returned to 344. If not, then each character in the query file is read into memory 350.

Figure 16:
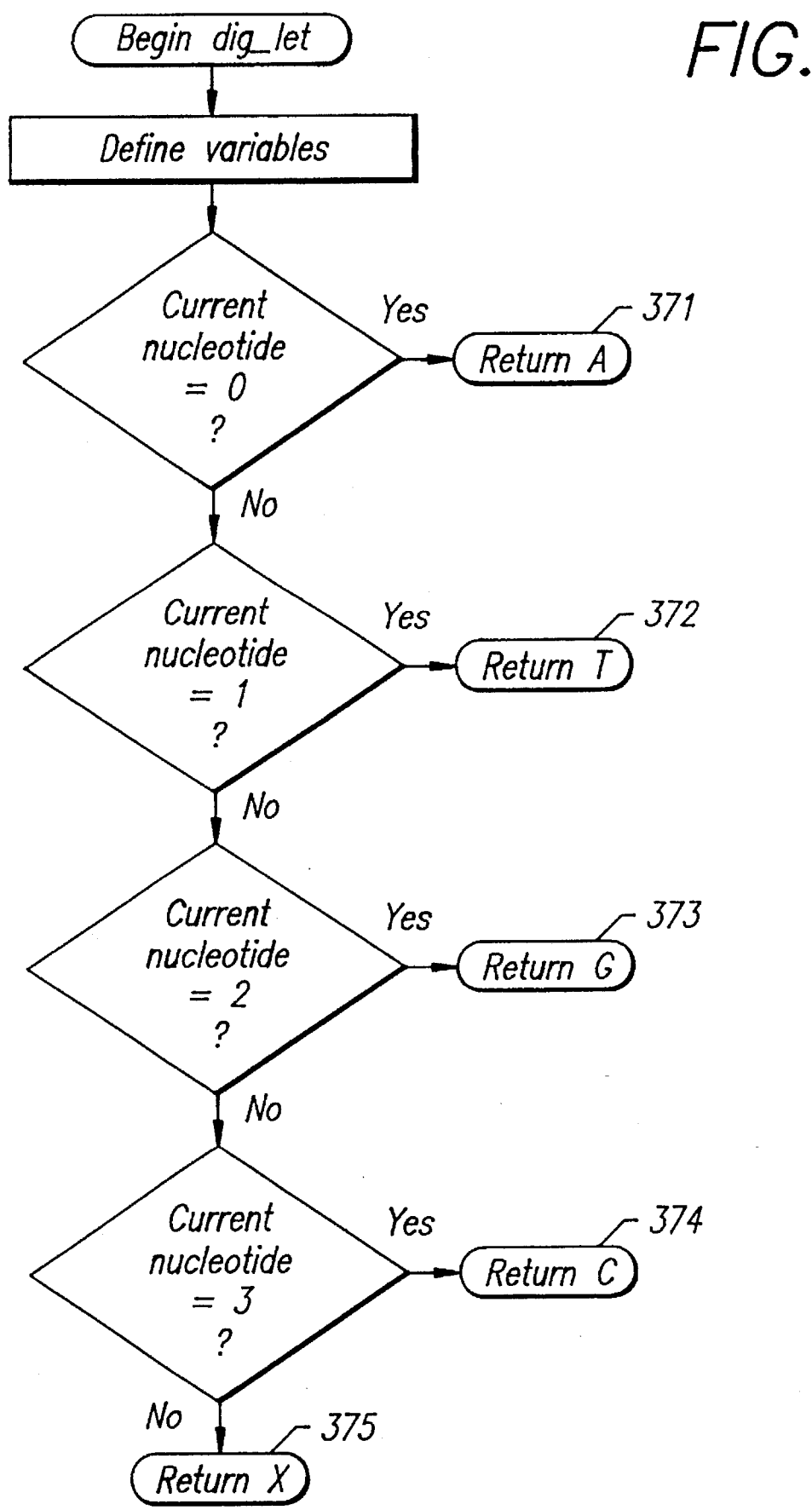
FIG. 16 is a flow chart of the dig_let module of this invention.

The characters are transformed into digits 346 using the "let_dig" module, FIG. 11, until a valid digit has been found, and then the hash table containing the query is set up 347 using the module "dig_let", FIG. 16, which transforms the digits into nucleotides represented by the characters "A" 371, "T" 371, "G" 373, "C" 374, and "X" 375 as a default. If the end of the file has not been reached, processing is returned to 344. If it has, the file is closed 348 and the query is then returned to the "read1" module FIG. 15 at 347.

Figure 17:
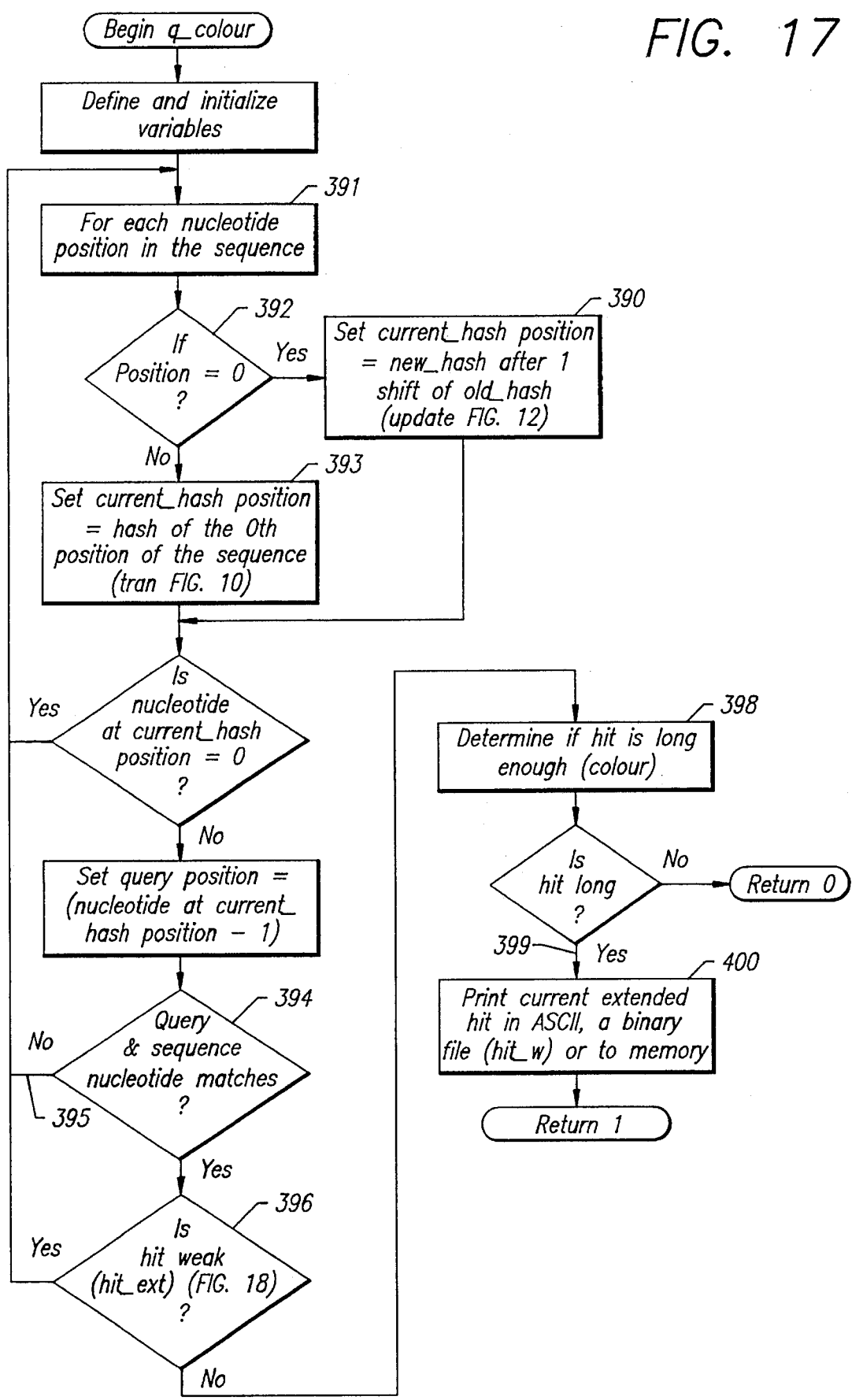
FIG. 17 is a flow chart of the q_colour module of this invention.

The "q_colour" module, FIG. 17 (FIG. 13 at 325), is called by the "assembly" module FIG. 13 after the current sequence has been extracted from the GenBank. The "q_colour" module FIG. 17 performs the heart of the Mismatch Model process in that it performs the comparison between the query and the database or file sequences. If the module finds that there exists a long (i.e., greater than the min_hit_length) extended hit, it returns a "1" to the "assembly" module FIG. 14. Otherwise, the "q_colour" module, FIG. 17, returns a "0".

In the "q_colour" module, FIG. 17, all DNA positions are analyzed in the following manner. First, the entire DNA sequence is analyzed 391 to see whether each position is equal to zero 392 (i.e., whether it is empty or the sequence is finished). If it is not equal to zero 393, the "q_colour" module FIG. 20 calls the "tran" module, FIG. 10 described above, which performs the hashing of k_tuples. The "tran" module FIG. 10 calls other modules which transform the nucleotides represented by characters into digits for easier processing by the program and then updates the hash with a sliding window. If the position is equal to zero, the current_hash position is set to new_has after one shift of old_hash 390 by calling the "update" module FIG. 12.

If the nucleotide at the current_hash position is equal to zero, processing is returned to 391. If not, the query position is set equal to (nucleotide at current hash position - 1). Next, the "q_colour" module FIG. 17 looks for the current_hash in the hash table 394. If the current k_tuple does not match the query 395, then the next k_tuple is considered 395, and processing is returned to 391. If the current k_tuple does match the query, then the program checks the hit's (i.e., the match's) vicinity 396 by calling the "hit_ext" module, FIG. 18 to determine if the hit is weak. The inventors have found that if the code for the module "hit_ext" is included within the module "q_colour", rather than being a separate module utilizing the parameter transfer machinery, 25% of CPU time can be saved.

Figure 18:
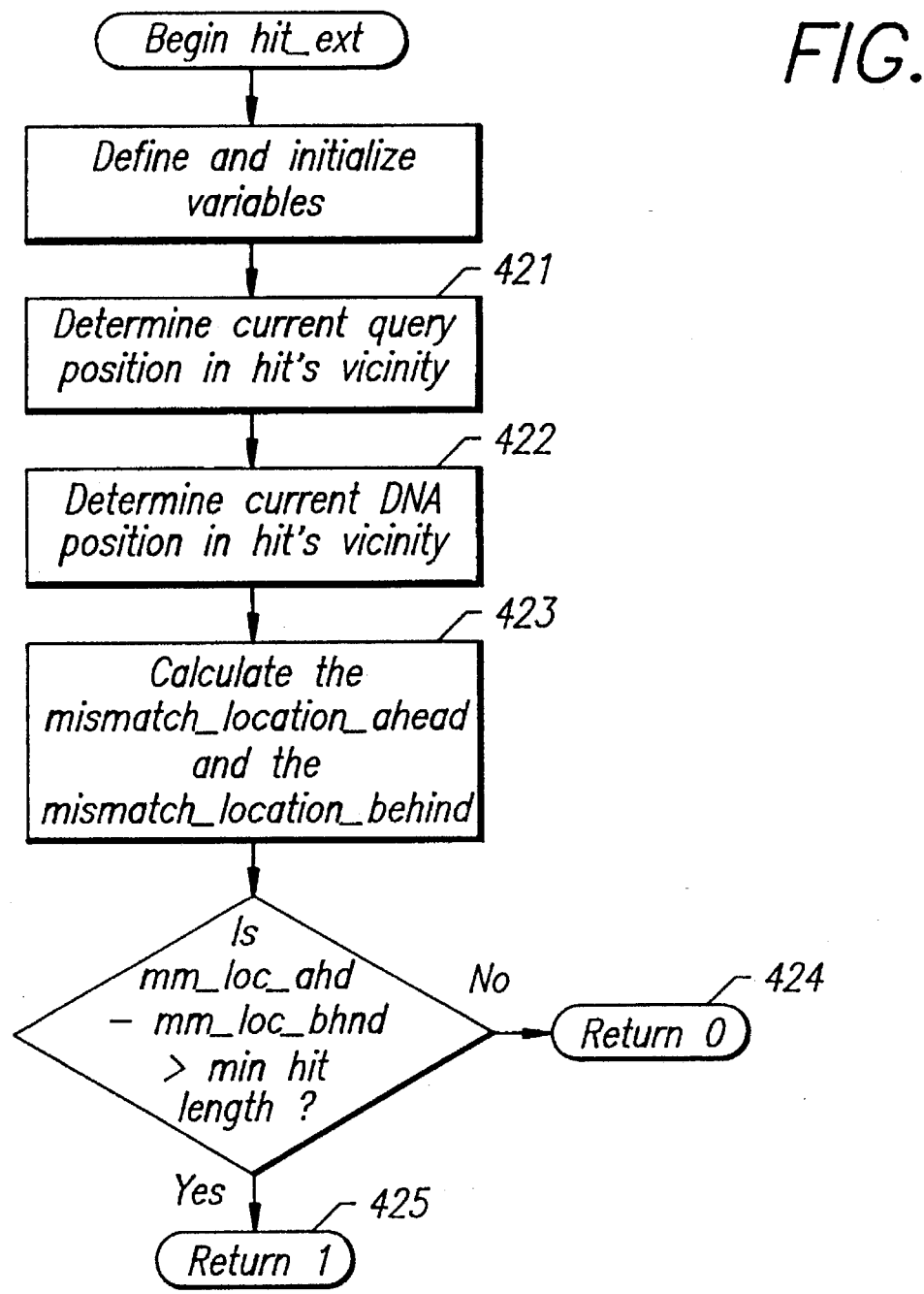
FIG. 18 is a flow chart of the hit_ext module of this invention.

The "hit_ext" module FIG. 18 determines the current query position in the hit's vicinity 421, determines the current DNA position in the hit's vicinity 422, and creates the list of mismatch positions (i.e., the mismatch_location_ahead 423, the mismatch_location_behind 423 and the kernel match location). If the hit is weak 424, the "hit_ext" module FIG. 18 returns "0" to the "q_colour" module FIG. 17. If the hit has a chance to contain 425, the module returns "1" to the "q_colour" module FIG. 17. A hit has a chance to contain, and is therefore not considered weak, if the mismatch_location_ahead the mismatch_location_behind is greater than the min_hit_length. If not, it is a short hit and is too weak.

Figure 19:
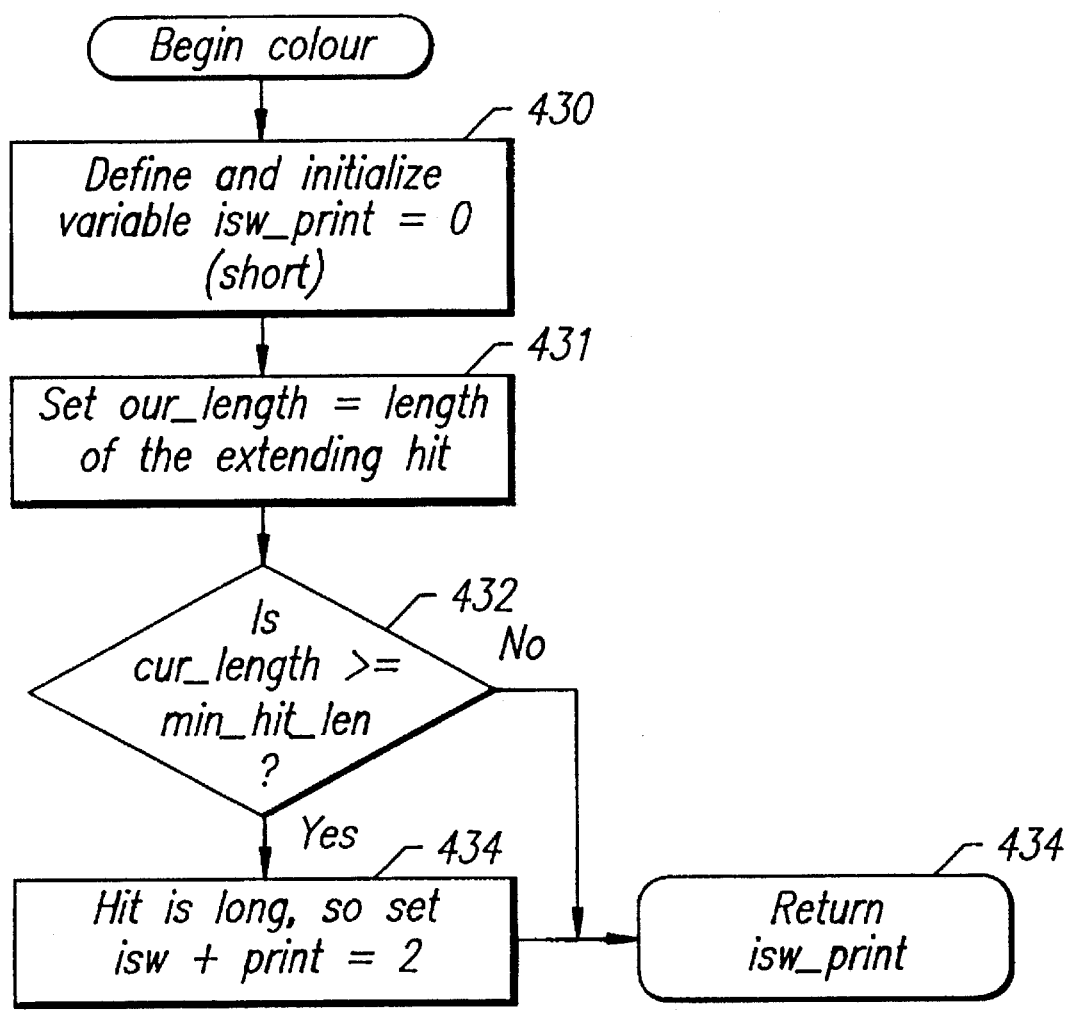
FIG. 19 is a flow chart of the colour module of this invention.

If the "hit_ext" module FIG. 18 tells the "q_colour" module FIG. 17 that the hit was not a weak one, then the "q_colour" module determines whether the current hit is long enough 398 by calling the "colour" module FIG. 19. The "colour" module FIG. 19 performs query_colour modification by the hit data, starting at pos_query and described by mismatch_location_ahead and mismatch_location_behind. After the variables to be used in this module are defined, variable isw_print (which is the switch indicating the hit length) is initialized to zero 430. The cur_length is then set equal to the length of the extending hit 431 (mismatch_location_behind[i]+mismatch_location_ahead[j]-1 ). Next, if cur_length is greater than or equal to the min_hit_length 432 (i.e., the minimum considered probe size), the hit is considered long and isw_print is set equal to two 433. The value of isw_print is then returned 434 to the "q_colour" module FIG. 17.

If the length of the extending hit is longer than the min_hit_length, the hit is considered long 399. Otherwise, the hit is considered short. If the hit is short, nothing more is done to the current hit and the module begins again. If, on the other hand, the hit is considered long 399, the "q_colour" module FIG. 17 prints the current extended hit 400. The current extended hit can be printed in ASCII, printed in a binary file, or printed to a memory file. The "q_colour" module FIG. 17 then repeats until the end of the linked list is reached.

d. Outputs

The output of the k_diff program in the current implementation of this invention may be either a binary file containing the number of extended hits and the k_mismatch hit locations (see FIG. 20), or the output may be kept in memory without writing it to a file. See Section 1(d)(iv) for more detail.

3. Description of the H-Site Model Program a. Overview

In this invention, the second hybridization strength model is termed the H-Site Model (see FIG. 2 for user selection of this model). One aspect of the H-Site Model uses a generalization of an experimental formula in general usage. The formula used in the H-Site Model is an expression of the fact that melting temperature Tm is a function of both probe length and percent of GC content. This basic formula has been modified in this invention to account for the presence of mismatches. Each percent of mismatch reduces the melting temperature Tm by an average of 1.25 degrees (2 degrees C. for an AT mismatch, and 4 degrees C. for a GC mismatch).

In addition, this implementation of the invention does some preliminary preprocessing of the GenBank database to sort out and select the cDNA sequences. This is done by locating a keyword (in this case CDS) in each GenBank record. No other programs currently available allow for this combination of functions as far as the inventors are aware.

There are a number of modules in the present embodiment of the H-Site Model contained in this invention. Each step of the processing involved in the H-Site Model is more fully explained below, and is accompanied by detailed flow charts.

b. Inputs

There are two basic user-selected inputs for the H-Site Model (see FIG. 2C): 1) the melting temperature Tm 22 for which probes are being designed (i.e., the melting temperature that corresponds to a particular experiment or condition the user desires to simulate); and 2) the nucleation threshold 23, which is the number of base pairs constituting a nucleation site. The user is also required to select the 1) target species 11 gene sequence(s) (DNA, mRNA or cDNA) for which probes are being designed; 2) the preparation 12 of all sequences with which hybridizations are to be calculated; and 3) the probe output file 13. The preparation file is the most important, as discussed below.

c. Organization of the H-Site Model Program

The current implementation of the H-Site Model program of this invention is distributed between five files containing numerous modules. The main file is designated by the inventors as "ds.cpp" in its uncompiled version. This file provides overall control to the entire invention. It is divided into six sections. Section 0 defines and manipulates global variables. Section 1 controls general variable definition and initialization (including the arrays and memory blocks). It also reads and writes buffers for user input selections, and constructs multi buffers.

Section 2 sets up and initializes various "snippet" variables (see section below for a complete definition of the term snippet), converts base pair characters to a representation that is 96 base pairs long and to ASCII base pair strings, and performs other sequence file manipulation such as comparing snippets. This section also reads the sequence format file, reads base pairs, checks for and extracts sequence identification information (such as ORIGIN and LOCUS) and filters out sequences beginning with :numbers.

Section 3 involves preparation file manipulation. This section performs the preprocessing on the PRP file discussed above. It also merges and sorts the snippet files, creates a PRP file and sorts it, and outputs the sorted snippets. Next, this section streams through the PRP file.

Section 4 contains the essential code for H-Site Model processing (see FIGS. 21 through 23 for details, discussed below). Streams are set up, and then RIBI comparisons are performed for hybridizations (see file "ribi.cpp" for definitions of RIBI search techniques). Next, probes are generated, binding strength is converted to melting temperature, and hybridizations are calculated and stored (including hybridization strength). Lastly, other H-Site calculations are performed.

Section 5 is concerned with formatting and presenting diagnostic and user file (test.out, test1.out, and test2.out files) output. This section also handles the graphing functions (the MPSD diagram in particular). In addition, this section calculates the hairpin characteristics for the H-Site Model candidate probes.

The second H-Site Model file, designated as "ds.h" defines data variables and structures. Section 1 of this file concerns generic data structures (including memory blocks and arrays, and file inputs and outputs). Section 2 defines the variables and structures used with sequences, probes and hybridizations. Section 3 defines variables and structures concerned with protocols (i.e., function prototypes, graphing, etc.).

The third H-Site Model file, designated as "funcdoc.txt", contains very detailed documentation for this implementation of the H-Site Model program. Numerous variables and structures are also defined. The flow of the program is clearly shown in this file.

The fourth H-Site Model file, designated as "ribi.h" handles the sequence comparisons. The fifth and last H-Site Model file, designated as "ribi.cpp", performs internal B-Tree indexing. Definitions of Red-black Internal Binary Index (RIBI) searching are found in this file. Definitions are also included for the concepts keyed set, index, binary tree, internal binary index, paths, and red-black trees. Implementation notes are also included in this file.

d. Processing

Implementation of the H-Site Model in this invention is done in three stages. First, the invention creates the preparation (PRP) file, which contains all relevant information from the sequence database. This is the preprocessing stage discussed above. Next, the target is prepared by the program. Lastly, the invention calculates the MPSD data using the PRP file and target sequence to find probes.

i. Creation of the Preprocessed Preparation File

Figure 21:
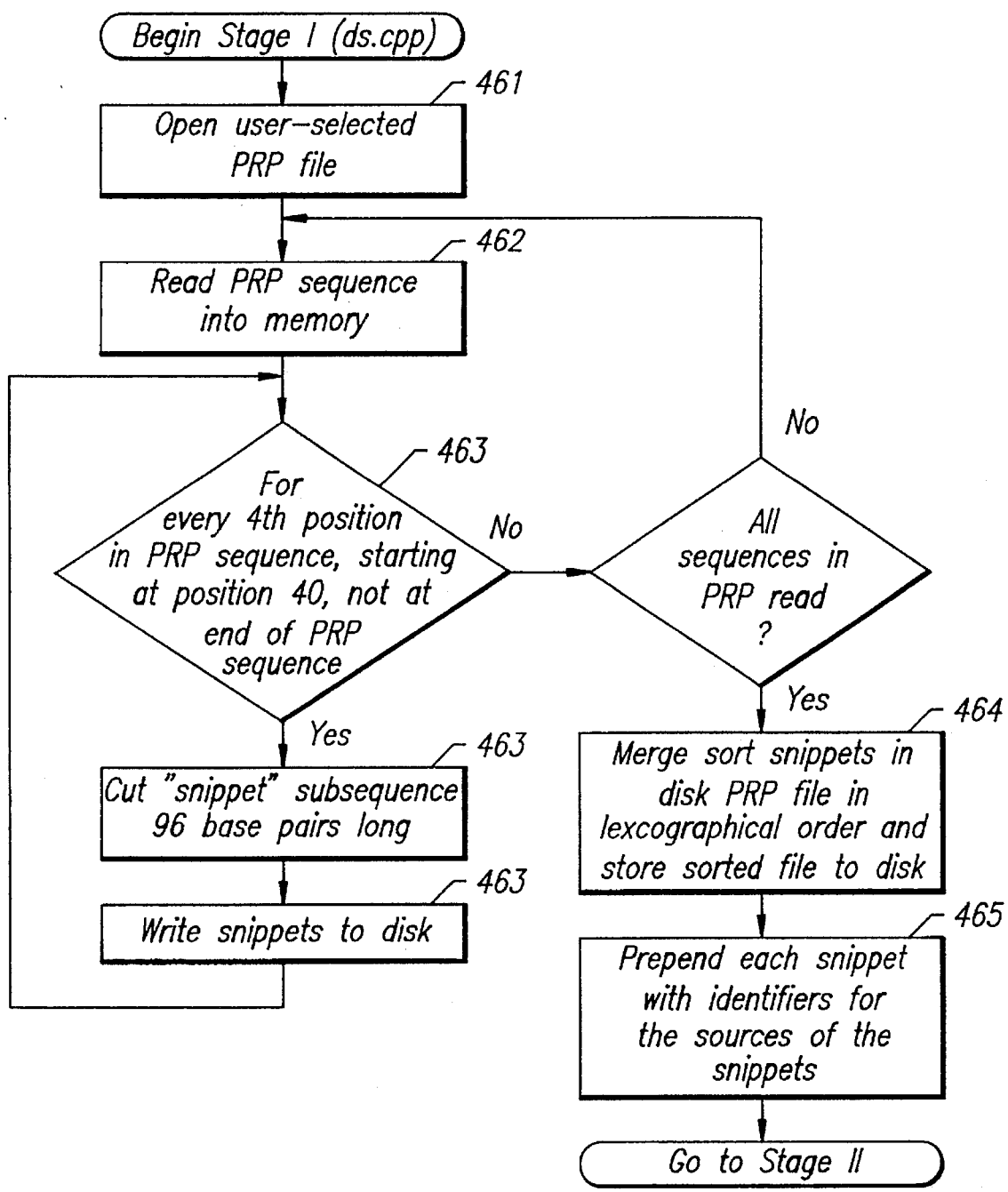
FIG. 21 is a flow chart of the H-Site Model, stage I, covering the creation of a preprocessed preparation file of this invention.

FIG. 21. Step 1: The program first opens the sequence database for reading into memory 461, 462. Step 2: Next, as sequence base pairs are read in 462, "snippets" are saved to disk 463, along with loci information. A snippet is a fixed-length subsequence of a preparation sequence. The purpose of snippets is to allow the user to examine a small portion of a preparation sequence together with its surrounding base pairs. Snippets in the implementation of this invention are 96 base pairs long (except for snippets near the end or beginning of a sequence, which may have fewer base pairs). The "origin" of the snippet is in position 40. For snippets taken near the beginning of a sequence, some of the initial 40 bases are undefined. For snippets near the end of a sequence, some of the final 55 bases are undefined. Snippets are arranged in the preparation file (PRP) in sorted order (lexicographical order beginning at position 40). In this invention, the term "lexicographical order" means a preselected order, such as alphabetical, numeric or alphanumeric. In order to conserve space, snippets are only taken at every 4th position of the preparation sequence.

Step 3: The snippets are merge sorted 464 to be able to search quickly for sequences which pass the "screen", discussed below. Step 4: The merged file is prepended with identifiers for the sources of the snippets 465. This is done to identify the loci from which hybridizations arise.

ii. Target Preparation

Figure 22:
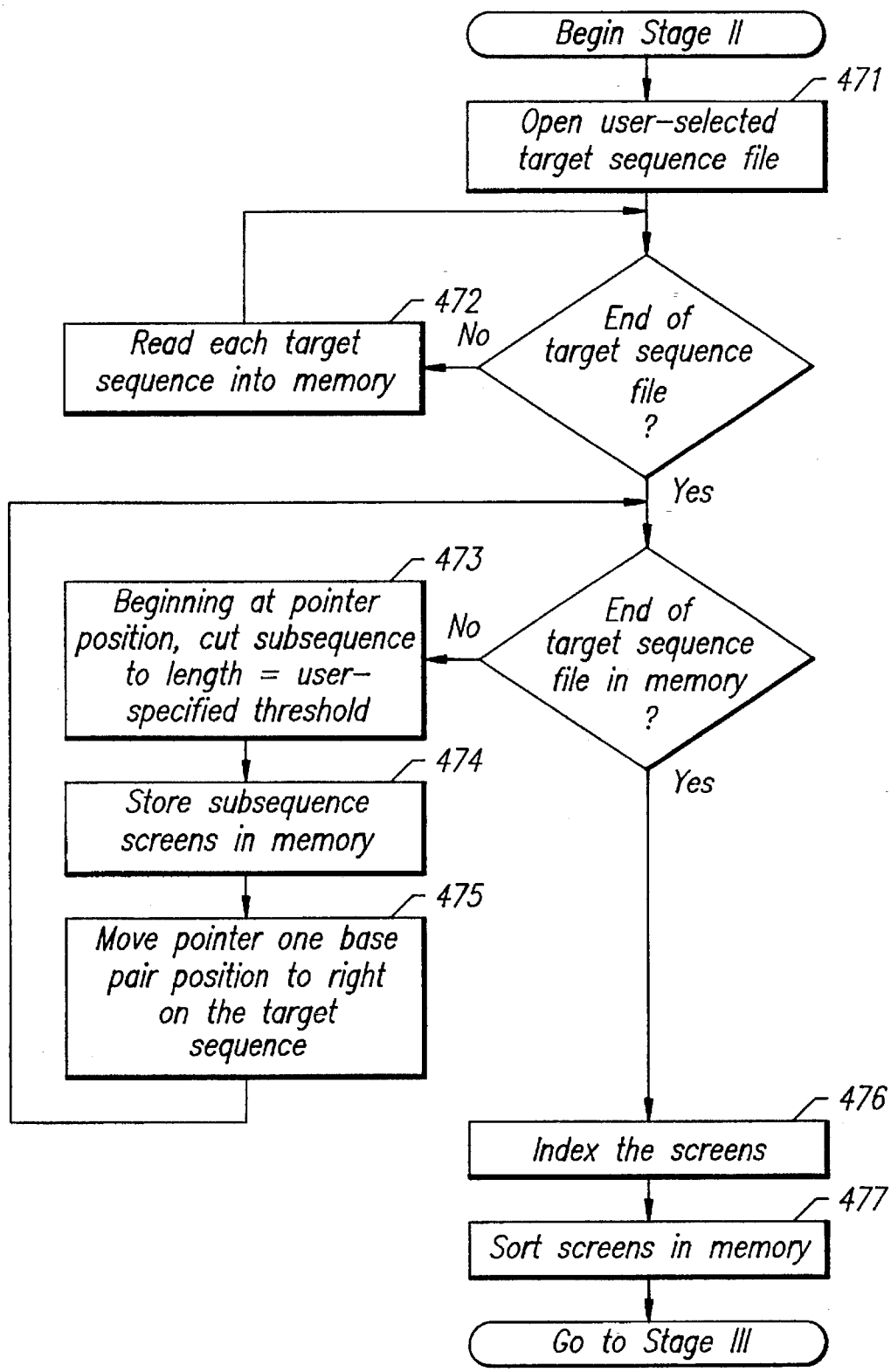
FIG. 22 is a flow chart of the H-Site Model, stage II, covering the preparation of the target sequence(s)

FIG. 22. Step 1: The target sequence file is opened 471 and read into memory 472. For each position in the target mRNA, the probe defined at that starting position is the shortest subsequence starting at that position whose hybridization strength is greater than the user specified melting temperature Tm. Typically, the probes are of length 18 to 50. Step 2: Four lists of "screens" are formed 473, 474, 475, each shifted by one base pair 475 to correspond to the fact that snippets are only taken at every four base pairs. A screen is a subsequence of the target mRNA of length equal to the screening threshold specified by the user. The screens are then indexed 476 and sorted in memory 477.

iii. Calculation of the MPSD Data

Figure 23A:
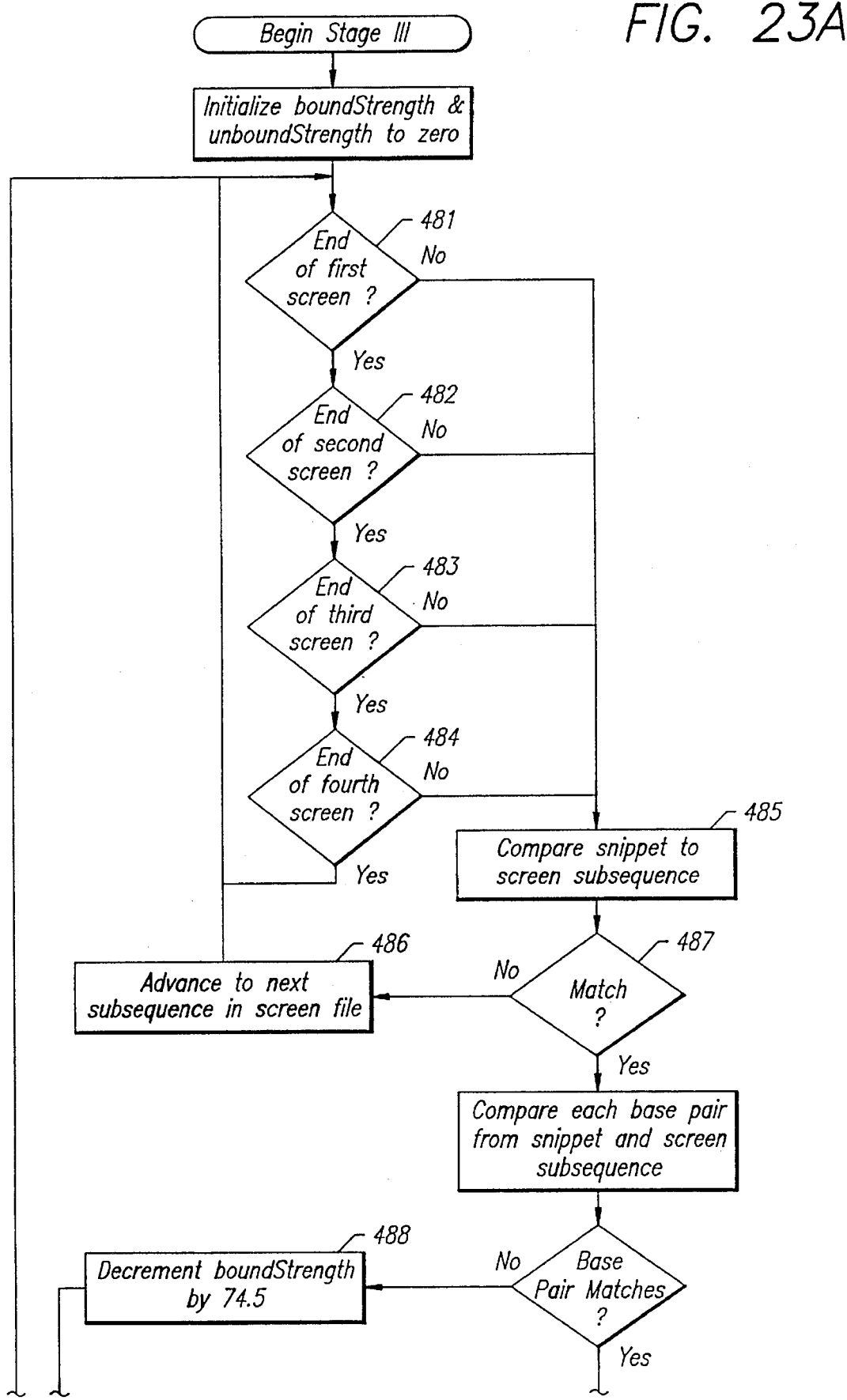
FIG. 23 is a flow chart of the H-Site Model, stage III, covering the calculation of MPSD data.
Figure 23B:
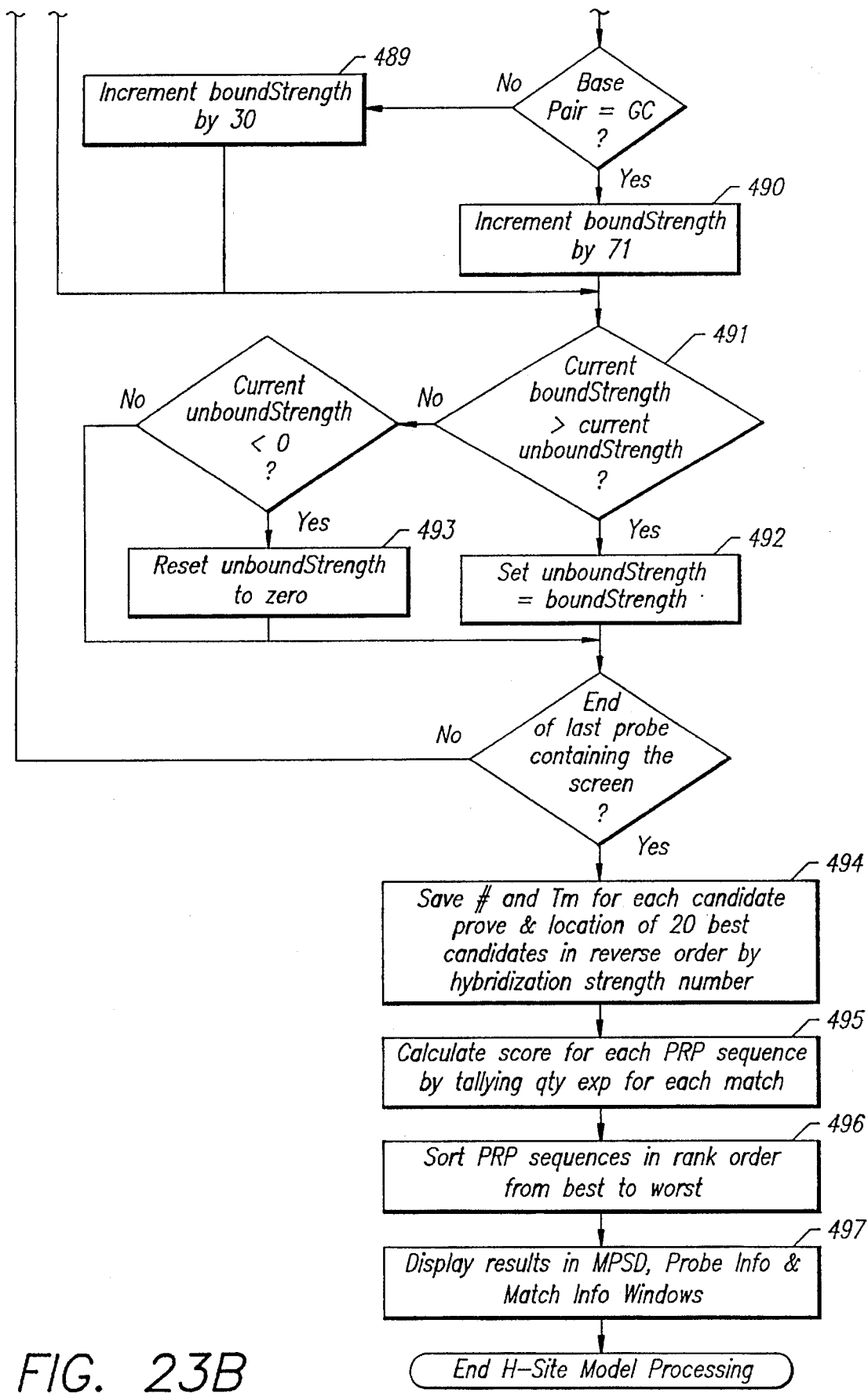

FIG. 23. Step 3: This step is the heart of the process. Step 3*a*: The program streams through the following five items in sync, examining them in sequential order: the snippet file and the four lists of screens 481–484. Step 3*b*: Each snippet is compared to a screen 485. Step 3*c*: If the shipper does not match, whichever stream is behind is advanced 486 and Step 3*b* is repeated. If the snippet does match, Step 4 is performed.

Step 4: If a snippet and a matching screen were found in Step 3*b* 487, the hybridization strength of the binding between the sequence containing the snippet and all of the probes containing the screen is calculated (see Step 5). Double counting is avoided by doing this only for the first matched screen containing the probe. Each pair of bases is examined and assigned a numerical binding strength. An AT pair would be assigned a lower binding strength than a GC pair because AT pairs have a lower melting temperature Tm. The process is explained more fully below at Step 5*b*.

Step 5: The hybridization strengths between sequence and all the probes containing it are calculated using a dynamic programming process. The process is as follows: Step 5*a*: Begin at the position of the first probe containing the given screen but not containing any other screens which start at an earlier position and also match the sequence. This is done to avoid double counting. Two running totals are maintained: a) boundStrength, which represents the hybridization strength contribution which would result if the sequence and probe were to match exactly for all base pairs to the right of the current position, and b) unboundStrength, which represents the strength of the maximally binding region. Step 5*b*: *At each new base pair, the variable bound Strength is incremented by* 71 if the sequence and probe match and the matched base pair is GC 489, incremented by 30 if the matched base pair is AT 490 (i.e., this number is about 42.25% of the first number 71), and decremented by 74.5 if there is not a match 488 (i.e., this number is about 5% larger than the first number 71). Step 5*c*: If the current boundStrength exceeds the current unboundStrength 491 (which was originally initialized to zero), a new binding region has been found, and unboundStrength is set equal to boundStrength 492. Step 5*d*: If the current boundStrength is negative, boundStrength is reset to zero 493. Step 5*e*: If the current position is at the end of a probe, the results (the hybridization strengths) are tallied for that probe. Step 5*f*: If the current position is at the end of the last probe containing the screen, the process stops.

Step 6: A tally is kept of the number and melting temperature of the matches for each candidate probe, and the location of the best 20 candidates, using a priority queue (reverse order by hybridization strength number) 494. Step 7: A numerical "score" is kept for each preparation sequence by tallying the quantity exp (which can be expressed as $Ee^{-Tm}$) for each match 495, where Tm is the melting temperature for the "perfect" match, the probe itself. In other words, the probe hybridizes "perfectly" to its target.

Step 8: Hairpins are calculated by first calculating the complementary probe. In other words, the order of the bases in the candidate probe are reversed (CTATAG to GATATC), and complementary base pairs are substituted (A for T, T for A, G for C, and C for G, changing GATATC to CTATAG in the above example). Next, the variable representing the maximum hairpin length for a candidate probe is initialized to zero, as is the variable representing a hairpin's distance. For each offset, the original candidate probe and the complementary probe just created are then aligned with each other and compared. The longest match is then found. If any two matches have the same length, the one with the longest hairpin distance (i.e., the number of base pairs separating the match) is then saved.

Step 9: The preparation sequences are then sorted 496 and displayed in rank order, from best to worst 497. Step 10: The resulting MPSD, which includes all candidate probes, is then displayed on the screen. Step 11: The best 20 matches are also printed or displayed in rank order, as the user requests 497.

e. Outputs

The outputs of the H-Site Model as currently implemented in this invention are fully described in Section 1(d)(iv), above, and illustrated in FIGS. 4 through 6. Samples of the two output files created by the H-Site Model are shown in FIGS. 24A and 24B.

4. Description of the Mitsuhashi Probe Selection Diagram Processing

Figure 25:
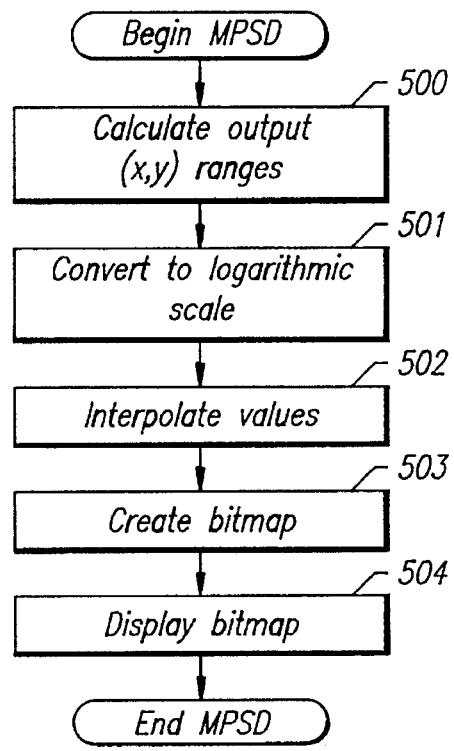
FIG. 25 is a flow chart of the processing used to create the Mitsuhashi probe selection diagram (MPSD)

Once the Mitsuhashi Probe Selection Diagram (MPSD) data has been calculated by the H-Site Model program (see stage three and FIG. 23, discussed above), it is necessary to convert this data to pixel format and plot a graph. An overview of this process is shown in FIG. 25. First, the program calculates the output (x,y) ranges 500. Next, these are converted to a logarithmic scale 501. The values are then interpolated 502, and a bitmap is created 503. Lastly, the bitmap is displayed on the screen 504 in MPSD format (discussed above in section 1(e)(i)). A sample MPSD is shown in FIG. 4.

5. Description of the Matchinfo Window Processing

Figure 26:
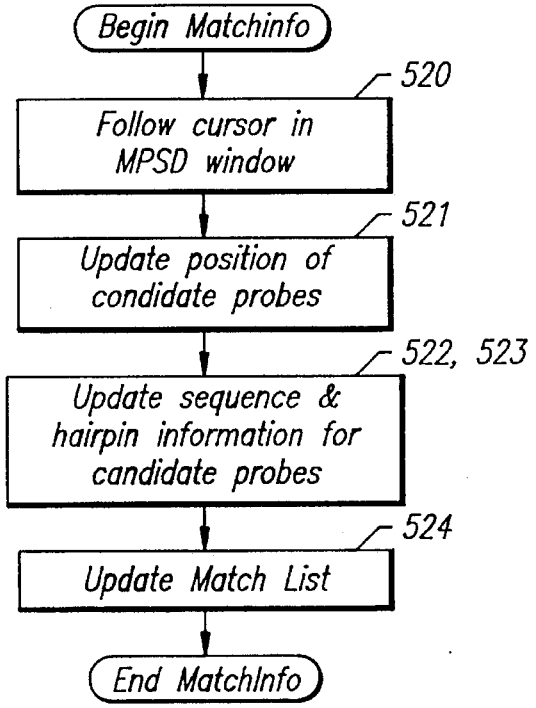
FIG. 26 is a flow chart of processing used to create the matchinfo window.

The ProbeInfo and MatchInfo windows are discussed in great detail in Section 1(e)(ii), and a sample of these windows is shown in FIG. 5. An overview of the processing involved in creating the MatchInfo portion of the window is given in the flow chart in FIG. 26. First, as the user moves the MPSD cursor 520 (seen as a vertical line bisecting the MPSD window), the program updates the position of the candidate probe shown under that cursor position 521. Next, based upon the candidate probe's position, the program updates the sequence 522 and hairpin information 523 for that probe. This updated information is then displayed in an updated match list 524, shown in the MatchInfo window.

The above described embodiments of the present invention are merely descriptive of its principles and are not to be considered limiting. The scope of the present invention instead shall be determined from the scope of the following claims including their equivalents.

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
        ( A ) LENGTH: 1044 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: NO ( i v ) ANTI-SENSE: NO ( v i i ) IMMEDIATE SOURCE:
        ( B ) CLONE: HUMBJUNX ( x i ) SEQUENCE DESCRIPTION: SEQ ID NO:1:

```
ATGTGCACTA AAATGGAACA GCCCTTCTAC CACGACGACT CATACACAGC TACGGGATAC      60
GGCCGGGCCC CTGGTGGCCT CTCTCTACAC GACTACAAAC TCCTGAAACC GAGCCTGGCG     120
GTCAACCTGG CCGACCCCTA CCGGAGTCTC AAAGCGCCTG GGGCTCGCGG ACCCGGCCCA     180
GAGGGCGGCG GTGGCGGCAG CTACTTTTCT GGTCAGGGCT CGGACACCGG CGCGTCTCTC     240
AAGCTCGCCT CTTCGGAGCT GGAACGCCTG ATTGTCCCCA ACAGCAACGG CGTGATCACG     300
ACGACGCCTA CACCCCCGGG ACAGTACTTT TACCCCCGCG GGGTGGCAG CGGTGGAGGT      360
GCAGGGGGCG CAGGGGGCGG CGTCACCGAG GAGCAGGAGG CTTCGCCGA CGGCTTTGTC      420
AAAGCCCTGG ACGATCTGCA CAAGATGAAC CACGTGACAC CCCCCAACGT GTCCCTGGGC     480
GCTACCGGGG GGCCCCCGGC TGGGCCCGGG GGCGTCTACG CCGGCCCGGA GCCACCTCCC     540
GTTTACACCA ACCTCAGCAG CTACTCCCCA GCCTCTGCGT CCTCGGGAGG CGCCGGGGCT     600
GCCGTCGGGA CCGGGAGCTC GTACCCGACG ACCACCATCA GCTACCTCCC ACACGCGCCG     660
CCCTTCGCCG GTGGCCACCC GGCGCAGCTG GGCTTGGGCC GCGGCGCCTC CACCTTCAAG     720
GAGGAACCGC AGACCGTGCC GGAGGCGCGC AGCCGGGACG CCACGCCGCC GGTGTCCCCC     780
ATCAACATGG AAGACCAAGA GCGCATCAAA GTGGAGCGCA AGCGGCTGCG GAACCGGCTG     840
GCGGCCACCA AGTGCCGGAA GCGGAAGCTG GAGCGCATCG CGCGCCTGGA GGACAAGGTG     900
AAGACGCTCA AGGCCGAGAA CGCGGGGCTG TCGAGTACCG CCGGCCTCCT CCGGGAGCAG     960
GTGGCCCAGC TCAAACAGAA GGTCATGACC CACGTCAGCA ACGGCTGTCA GCTGCTGCTT    1020
GGGGTCAAGG GACACGCCTT CTGA                                          1044
```

( 2 ) INFORMATION FOR SEQ ID NO:2:

( i ) SEQUENCE CHARACTERISTICS:
        ( A ) LENGTH: 996 base pairs
        ( B ) TYPE: nucleic acid
        ( C ) STRANDEDNESS: single
        ( D ) TOPOLOGY: linear (i i) MOLECULE TYPE: cDNA to mRNA (i i i) HYPOTHETICAL: NO (i v) ANTI-SENSE: NO (v i i) IMMEDIATE SOURCE:
  (B) CLONE: HUMCJUNX (x i) SEQUENCE DESCRIPTION: SEQ ID NO:2:

| | | | | | |
|---|---|---|---|---|---|
| ATGACTGCAA | AGATGGAAAC | GACCTTCTAT | GACGATGCCC | TCAACGCCTC | GTTCCTCCCG | 60 |
| TCCGAGAGCG | GACCTTATGG | CTACAGTAAC | CCCAAGATCC | TGAAACAGAG | CATGACCCTG | 120 |
| AACCTGGCCG | ACCCAGTGGG | GAGCCTGAAG | CCGCACCTCC | GCGCCAAGAA | CTCGGACCTC | 180 |
| CTCACCTCGC | CCGACGTGGG | GCTGCTCAAG | CTGGCGTCGC | CCGAGCTGGA | GCGCCTGATA | 240 |
| ATCCAGTCCA | GCAACGGGCA | CATCACCACC | ACGCCGACCC | CCACCCAGTT | CCTGTGCCCC | 300 |
| AAGAACGTGA | CAGATGAGCA | GGAGGGGTTC | GCCGAGGGCT | TCGTGCGCGC | CCTGGCCGAA | 360 |
| CTGCACAGCC | AGAACACGCT | GCCCAGCGTC | ACGTCGGCGG | CGCAGCCGGT | CAACGGGGCA | 420 |
| GGCATGGTGG | CTCCCGCGGT | AGCCTCGGTG | GCAGGGGGCA | GCGGCAGCGG | CGGCTTCAGC | 480 |
| GCCAGCCTGC | ACAGCGAGCC | GCCGGTCTAC | GCAAACCTCA | GCAACTTCAA | CCCAGGCGCG | 540 |
| CTGAGCAGCG | GCGGCGGGGC | GCCCTCCTAC | GGCGCGGCCG | GCCTGGCCTT | TCCCGCGCAA | 600 |
| CCCCAGCAGC | AGCAGCAGCC | GCCGCACCAC | CTGCCCCAGC | AGATGCCCGT | GCAGCACCCG | 660 |
| CGGCTGCAGG | CCCTGAAGGA | GGAGCCTCAG | ACAGTGCCCG | AGATGCCCGG | CGAGACACCG | 720 |
| CCCCTGTCCC | CCATCGACAT | GGAGTCCCAG | GAGCGGATCA | AGGCGGAGAG | GAAGCGCATG | 780 |
| AGGAACCGCA | TCGCTGCCTC | CAAGTGCCGA | AAAAGGAAGC | TGGAGAGAAT | CGCCCGGCTG | 840 |
| GAGGAAAAAG | TGAAAACCTT | GAAAGCTCAG | AACTCGGAGC | TGGCGTCCAC | GGCCAACATG | 900 |
| CTCAGGGAAC | AGGTGGCACA | GCTTAAACAG | AAAGTCATGA | CCACGTTAA | CAGTGGGTGC | 960 |
| CAACTCATGC | TAACGCAGCA | GTTGCAAACA | TTTTGA | | | 996 |

(2) INFORMATION FOR SEQ ID NO:3:

(i) SEQUENCE CHARACTERISTICS:
    (A) LENGTH: 1044 base pairs
    (B) TYPE: nucleic acid
    (C) STRANDEDNESS: single
    (D) TOPOLOGY: linear (i i) MOLECULE TYPE: cDNA to mRNA (i i i) HYPOTHETICAL: NO (i v) ANTI-SENSE: NO (v i i) IMMEDIATE SOURCE:
    (B) CLONE: HSJUNDR (x i) SEQUENCE DESCRIPTION: SEQ ID NO:3:

| | | | | | |
|---|---|---|---|---|---|
| ATGGAAACAC | CCTTCTACGG | CGATGAGGCG | CTGAGCGGCC | TGGGCGGCGG | CGCCAGTGGC | 60 |
| AGCGGCGGCA | CGTTCGCGTC | CCCGGGCCGC | TTGTTCCCCG | GGGCGCCCCC | GACGGCCGCG | 120 |
| GCCGGCAGCA | TGATGAAGAA | GGACGCGCTG | ACGCTGAGCC | TGAGTGAGCA | GGTGGCGGCA | 180 |
| GCGCTCAAGC | CTGCGCCCGC | GCCCGCCTCC | TACCCCCCTG | CCGCCGACGG | CGCCCCCAGC | 240 |
| GCGGCACCCC | CCGACGGCCT | GCTCGCCTCT | CCCGACCTGG | GCTGCTGAA | CTGGCCTCC | 300 |
| CCCGAGCTCG | AGCGCCTCAT | CATCCAGTCC | AACGGGCTGG | TCACCACCAC | GCCGACGAGC | 360 |
| TCACAGTTCC | TCTACCCCAA | GGTGGCGGCC | AGCGAGGAGC | AGGAGTTCGC | CGAGGGCTTC | 420 |
| GTCAAGGCCC | TGGAGGATTT | ACACAAGCAG | AACCAGCTCG | GCGCGGGCCG | GGCCGCTGCC | 480 |

| | | | | | | |
|---|---|---|---|---|---|---|
| GCCGCCGCCG | CCGCCGCCGG | GGGGCCCTCG | GGCACGGCCA | CGGGCTCCGC | GCCCCCCGGC | 540 |
| GAGCTGGCCC | CGGCGGCGGC | CGCGCCCGAA | GCGCCTGTCT | ACGCGAACCT | GAGCAGCTAC | 600 |
| GCGGGCGGCG | CCGGGGGCGC | GGGGGGCGCC | GCGACGGTCG | CCTTCGCTGC | CGAACCTGTG | 660 |
| CCCTTCCCGC | CGCCGCCACC | CCCAGGCGCG | TTGGGGCCGC | CGCGCCTGGC | TGCGCTCAAG | 720 |
| GACGAGCCAC | AGACGGTGCC | CGACGTGCCG | AGCTTCGGCG | AGAGCCCGCC | GTTGTCGCCC | 780 |
| ATCGACATGG | ACACGCAGGA | GCGCATCAAG | GCGGAGCGCA | AGCGGCTGCG | CAACCGCATC | 840 |
| GCCGCCTCCA | AGTGCCGCAA | GCGCAAGCTG | GAGCGCATCT | CGCGCCTGGA | AGAGAAAGTG | 900 |
| AAGACCCTCA | AGAGTCAGAA | CACGGAGCTG | GCGTCCACGG | CGAGCCTGCT | GCGCGAGCAG | 960 |
| GTGGCGCAGC | TCAAGCAGAA | AGTCCTCAGC | CACGTCAACA | GCGGCTGCCA | GCTGCTGCCC | 1020 |
| CAGCACCAGG | TCCCGGCGTA | CTGA | | | | 1044 |

( 2 ) INFORMATION FOR SEQ ID NO:4:

( i ) SEQUENCE CHARACTERISTICS:
        ( A ) LENGTH: 1035 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: NO ( i v ) ANTI-SENSE: NO ( v i i ) IMMEDIATE SOURCE:
        ( A ) LIBRARY: MUSBJUNX ( x i ) SEQUENCE DESCRIPTION: SEQ ID NO:4:

| | | | | | | |
|---|---|---|---|---|---|---|
| ATGTGCACGA | AAATGGAACA | GCCTTTCTAT | CACGACGACT | CTTACGCAGC | GGCGGGATAC | 60 |
| GGTCGGAGCC | CTGGCAGCCT | GTCTCTACAC | GACTACAAAC | TCCTGAAACC | CACCTTGGCG | 120 |
| CTCAACCTGG | CGGATCCCTA | TCGGGGTCTC | AAGGGTCCTG | GGCGCGGGG | TCCAGGCCCG | 180 |
| GAGGGCAGTG | GGGCAGGCAG | CTACTTTTCG | GGTCAGGGAT | CAGACACAGG | CGCATCTCTG | 240 |
| AAGCTAGCCT | CCACGGAACT | GGAGCGCTTG | ATCGTCCCCA | ACAGCAACGG | CGTGATCACG | 300 |
| ACGACGCCCA | CGCCTCCGGG | ACAGTACTTT | TACCCCCGTG | GGGTGGCAG | CGGTGGAGGT | 360 |
| ACAGGGGGCG | GCGTCACCGA | GGAGCAGGAG | GGCTTTGCGG | ACGGTTTTGT | CAAAGCCCTG | 420 |
| GACGACCTGC | ACAAGATGAA | CCACGTGACG | CCCCCCAACG | TGTCCCTGGG | CGCCAGCGGG | 480 |
| GGTCCCCAGG | CCGGCCCAGG | GGGCGTCTAT | GCTGGTCCGG | AGCCGCCTCC | CGTCTACACC | 540 |
| AACCTCAGCA | GTTACTCTCC | AGCCTCTGCA | CCCTCTGGAG | GCTCCGGGAC | CGCCGTCGGG | 600 |
| ACTGGGAGCT | CATACCCGAC | GGCCACCATC | AGCTACCTCC | ACATGCACC | ACCCTTTGCG | 660 |
| GGCGGCCACC | CGGCACAGCT | GGGTTTGAGT | CGTGGCGCTT | CCGCCTTTAA | AGAGGAACCG | 720 |
| CAGACCGTAC | CGGAGGCACG | CAGCCGCGAC | GCCACGCCGC | CTGTGTCCCC | CATCAACATG | 780 |
| GAAGACCAGG | AGCGCATCAA | AGTGGAGCGA | AAGCGGCTGC | GGAACAGGCT | GGCGGCCACC | 840 |
| AAGTGCCGGA | AGCGGAAGCT | GGAGCGCATC | GCGCGCCTGG | AGGACAAGGT | GAAGACACTC | 900 |
| AAGGCTGAGA | ACGCGGGGCT | GTCGAGTGCT | GCCGGTCTCC | TAAGGGAGCA | AGTGGCGCAG | 960 |
| CTCAAGCAGA | AGGTCATGAC | CCATGTCAGC | AACGGCTGCC | AGTTGCTGCT | AGGGGTCAAG | 1020 |
| GGACACGCCT | TCTGA | | | | | 1035 |

( 2 ) INFORMATION FOR SEQ ID NO:5:

(i) SEQUENCE CHARACTERISTICS:
    (A) LENGTH: 1005 base pairs
    (B) TYPE: nucleic acid
    (C) STRANDEDNESS: single
    (D) TOPOLOGY: linear (ii) MOLECULE TYPE: cDNA to mRNA (iii) HYPOTHETICAL: NO (iv) ANTI-SENSE: NO (vii) IMMEDIATE SOURCE:
    (B) CLONE: MUSCJUNX (xi) SEQUENCE DESCRIPTION: SEQ ID NO:5:

| | | | | | | |
|---|---|---|---|---|---|---|
| ATGACTGCAA | AGATGGAAAC | GACCTTCTAC | GACGATGCCC | TCAACGCCTC | GTTCCTCCAG | 60 |
| TCCGAGAGCG | GTGCCTACGG | CTACAGTAAC | CCTAAGATCC | TAAAACAGAG | CATGACCTTG | 120 |
| AACCTGGCCG | ACCCGGTGGG | CAGTCTGAAG | CCGCACCTCC | GCGCCAAGAA | CTCGGACCTT | 180 |
| CTCACGTCGC | CCGACGTCGG | GCTGCTCAAG | CTGGCGTCGC | CGGAGCTGGA | GCGCCTGATC | 240 |
| ATCCAGTCCA | GCAATGGGCA | CATCACCACT | ACACCGACCC | CCACCCAGTT | CTTGTGCCCC | 300 |
| AAGAACGTGA | CCGACGAGCA | GGAGGGCTTC | GCCGAGGGCT | TCGTGCGCGC | CCTGGCTGAA | 360 |
| CTGCATAGCC | AGAACACGCT | TCCCAGTGTC | ACCTCCGCGG | CACAGCCGGT | CAGCGGGGCG | 420 |
| GGCATGGTGG | CTCCCGCGGT | GGCCTCAGTA | GCAGGCGCTG | GCGGCGGTGG | TGGCTACAGC | 480 |
| GCCAGCCTGC | ACAGTGAGCC | TCCGGTCTAC | GCCAACCTCA | GCAACTTCAA | CCCGGGTGCG | 540 |
| CTGAGCAGCG | GCGGTGGGGC | GCCCTCCTAT | GGCGCGGCCG | GCTGGCCTT | TCCCTCGCAG | 600 |
| CCGCAGCAGC | AGCAGCAGCC | GCCTCAGCCG | CCGCACCACT | TGCCCCAACA | GATCCCGGTG | 660 |
| CAGCACCCGC | GGCTGCAAGC | CCTGAAGGAA | GAGCCGCAGA | CCGTGCCGGA | GATGCCGGGA | 720 |
| GAGACGCCGC | CCCTGTCCCC | TATCGACATG | GAGTCTCAGG | AGCGGATCAA | GGCAGAGAGG | 780 |
| AAGCGCATGA | GGAACCGCAT | TGCCGCCTCC | AAGTGCCGGA | AAAGGAAGCT | GGAGCGGATC | 840 |
| GCTCGGCTAG | AGGAAAAAGT | GAAAACCTTG | AAAGCGCAAA | ACTCCGAGCT | GGCATCCACG | 900 |
| GCCAACATGC | TCAGGGAACA | GGTGGCACAG | CTTAAGCAGA | AAGTCATGAA | CCACGTTAAC | 960 |
| AGTGGGTGCC | AACTCATGCT | AACGCAGCAG | TTGCAAACGT | TTTGA | | 1005 |

(2) INFORMATION FOR SEQ ID NO:6:

(i) SEQUENCE CHARACTERISTICS:
    (A) LENGTH: 1026 base pairs
    (B) TYPE: nucleic acid
    (C) STRANDEDNESS: single
    (D) TOPOLOGY: linear (ii) MOLECULE TYPE: cDNA to mRNA (iii) HYPOTHETICAL: NO (iv) ANTI-SENSE: NO (vii) IMMEDIATE SOURCE:
    (B) CLONE: MUSDJUNX (xi) SEQUENCE DESCRIPTION: SEQ ID NO:6:

| | | | | | | |
|---|---|---|---|---|---|---|
| ATGGAAACGC | CCTTCTATGG | CGAGGAGGCG | CTGAGCGGCC | TGGCTGCGGG | TGCGTCGAGC | 60 |
| GTCGCTGGTG | CTACTGGGGC | CCCCGGCGGT | GGTGGCTTCG | CGCCCCGGG | CCGCGCTTTC | 120 |
| CCCGGGGCGC | CCCCGACGAG | CAGCATGCTG | AAGAAAGACG | CGCTGACGCT | CAGCCTGGCG | 180 |
| GAGCAGGGAG | CGGCGGGATT | GAAACCAGGG | TCGGCCACTG | CACCTTCTGC | GCTGCGCCCC | 240 |
| GACGGCGCCC | CCGACGGGCT | GCTGGCTTCG | CCGGATCTTG | GGCTGCTCAA | ACTCGCGTCG | 300 |

| | | | | | |
|---|---|---|---|---|---|
| CCGGAGCTGG | AGAGGCTGAT | CATCCAGTCC | AACGGGCTGG | TGACCACTAC | CCCGACCAGT | 360 |
| ACGCAGTTCC | TCTACCCGAA | GGTGGCAGCC | AGCGAGGAGC | AGGAGTTCGC | CGAAGGCTTC | 420 |
| GTCAAGGCGC | TGGAGGACCT | GCACAAGCAA | AGCCAGCTGG | GTGCGGCCAC | CGCGGCCACC | 480 |
| TCAGGGGCTC | CCGCGCCTCC | CGCGCCCGCC | GACCTGGCCG | CCACCCCCGG | GGCCACGGAG | 540 |
| ACCCCGGTCT | ACGCCAACCT | GAGCAGTTTC | GCGGGTGGCG | CCGGGCCCCC | TGGGGGCGCG | 600 |
| GCCACCGTGG | CTTTCGCCGC | GGAGCCAGTG | CCCTTCCCGC | CGCCCCCGGG | CGCGCTGGGG | 660 |
| CCGCCGCCAC | CTCCGCATCC | ACCGCGCCTG | GCCGCGCTCA | AGGACGAGCC | GCAGACCGTG | 720 |
| CCGGACGTGC | CGAGCTTCGG | CGACAGCCCT | CCGCTGTCGC | CCATCGACAT | GGACACGCAA | 780 |
| GAACGCATCA | AGGCGGAGCG | CAAGAGGCTG | CGCAACCGCA | TCGCCGCCTC | CAAATGCCGC | 840 |
| AAGCGCAAGC | TGGAGCGTAT | CTCGCGCCTG | GAGGAGAAAG | TCAAGACCCT | CAAAAGCCAG | 900 |
| AACACCGAGC | TGGCGTCCAC | CGCCAGCCTG | CTGCGCGAGC | AGGTGGCGCA | GCTCAAACAG | 960 |
| AAAGTCCTCA | GCCACGTCAA | CAGCGGCTGC | CAGCTGCTGC | CCCAGCACCA | GGTCCCGGCG | 1020 |
| TACTGA | | | | | | 1026 |

( 2 ) INFORMATION FOR SEQ ID NO:7:

( i ) SEQUENCE CHARACTERISTICS:
    ( A ) LENGTH: 31 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:7:

AGGCCTCGGT TAGTTGGCCG TTGCCGAAAA A      31

( 2 ) INFORMATION FOR SEQ ID NO:8:

( i ) SEQUENCE CHARACTERISTICS:
    ( A ) LENGTH: 31 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:8:

AGGCGTCGGT TATTTGGGCC TTCCCAATGT G      31

( 2 ) INFORMATION FOR SEQ ID NO:9:

( i ) SEQUENCE CHARACTERISTICS:
    ( A ) LENGTH: 31 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:9:

AGGCGTCGGT TCTGTGGAAC TTCCCGAGGA A                                          31

( 2 ) INFORMATION FOR SEQ ID NO:10:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:10:

AGGCCTCGGT TAGTTGGCCG TTGCCGAAAA A                                          31

( 2 ) INFORMATION FOR SEQ ID NO:11:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:11:

AGGCGTCGGT TATTTGGGCC TTCCCAATGT G                                          31

( 2 ) INFORMATION FOR SEQ ID NO:12:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:12:

AGGCGTCGGT TATTTGGGCC TTCCCAATGT G                                          31

( 2 ) INFORMATION FOR SEQ ID NO:13:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:13:

AGGCGTCGGT TCTGTGGAAC TTCCCGAGGA A                                          31

(2) INFORMATION FOR SEQ ID NO:14:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:14:

AGGCCTCGGT TAGTTGGCCG TTGCCGAAAA A                     31

(2) INFORMATION FOR SEQ ID NO:15:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:15:

AGGCGTCGGT TATTGTGGTC TCCCCAATGT G                     31

What is claimed is:

1. A programmed computer system for designing optimal oligonucleotide probes for use with a gene sequence data source comprising:

first input means for introducing user-selected gene sequences into the computer system;

memory means for storing user-selected gene sequences;

means for accessing gene sequence data from said gene sequence data source;

means for performing hybridization strength modeling on gene sequences which is determined by numbers of matching between gene sequences;

means for performing hybridization strength modeling on gene sequences which is determined by melting temperature (Tm);

means for selecting either of said modeling means; and means for presenting the results of said modeling to present candidate oligonucleotide probes with a candidate oligonucleotide probe hybridization shown as numbers of hybridizations as compared to said gene sequence data from said gene sequence data source.

2. A programmed computer system in accordance with claim 1 wherein said means for performing hybridization strengt modeling on gene sequences which is determined by numbers of matching sequences utilizes said accessing means to introduce a user-selected set of gene sequence data and a user-selected set of target gene sequence data from said gene sequence data source into the computer system and said memory means to store said gene sequence data and said target gene sequence data and wherein said means for performing hybridization strength modeling on gene sequences which is determined by numbers of matching sequences includes:

means for determining a minimum oligonucleotide probe length;

means for creating a look-up hash table and linked list in memory for each gene sequence in said gene sequence data and each of said target gene sequences;

means for calculating the minimum length of any matching gene subsequence of said gene sequence data and said target gene sequence data;

means for transforming base characters in each said target sequence and in each said gene sequence into numeric digits;

means for comparing each base pair digit in each said target sequence stored in a hash table in memory to each base pair digit of said gene sequence stored in a hash table in memory;

means for finding a matching seed by determining if said comparison results in a matching gene subsequence of length equal to said calculated minimum length;

means for comparing base pair digits behind and ahead of said seed to determine if there exists an extended match of a subsequence of base pair digits of length greater than the calculated minimum length, resulting in a current hit sequence;

means for calculating whether said current hit sequence is longer than said minimum oligonucleotide probe length, resulting in a current candidate oligonucleotide probe;

means for storing said current candidate oligonucleotide probe;

wherein said presenting means provides said current candidate oligonucleotide probe to the user.

3. A programmed computer system for designing optimal oligonucleotide probes for use with a gene sequence data source comprising:

first input means for introducing user-selected gene sequences into the computer system;

memory means for storing user-selected gene sequences;

means for accessing gene sequence data from said gene sequence data source;

means for performing hybridization strength modeling on gene sequences which is determined by numbers of matching between gene sequences;

means for presenting the results of said modeling to present candidate oligonucleotide probes with a candidate oligonucleotide probes hybridization shown as numbers of hybridizations as compared to gene sequence data from said gene sequence data source;

wherein said means for performing hybridization strength modeling on gene sequences which is determined by numbers of matching utilizes said accessing means to introduce a user-selected set of gene sequence data and a user-selected set of target gene sequence data from said gene sequence data source into the computer system and said memory means to store said gene sequence data and said target gene sequence data;

wherein said means for performing said hybridization strength modeling on gene sequences which is determined by numbers of matching includes:

means for determining a minimum oligonucleotide probe length;

means for creating a look-up hash table and linked list in memory for each gene sequence in said gene sequence data and each of said target gene sequences;

means for calculating the minimum length of any matching gene subsequence of said gene sequence data and said target gene sequence data;

means for comparing each base pair character in each said target sequence stored in a hash table in memory to each base pair character of said gene sequence stored in a hash table in memory;

means for finding a matching seed by determining if said comparison results in a matching seed subsequence of length equal to said calculated minimum length;

means for comparing base pair characters behind and ahead of said seed to determine if there exists an extended match of a subsequence of base pair characters of length greater than the calculated minimum length, resulting in a current hit sequence;

means for calculating whether said current hit sequence is longer than said minimum oligonucleotide probe length, resulting in a current candidate oligonucleotide probe;

means for storing said current candidate oligonucleotide probe;

wherein said presenting means provides said current candidate oligonucleotide probe to the user.

4. A programmed computer system in accordance with claim 3 wherein said computer system further includes:

means for calculating the melting temperature for each candidate oligonucleotide probe;

means for tracking the number and melting temperature of the matches for each candidate oligonucleotide probe;

means for tracking the location of a set number of the best candidate oligonucleotide probes; and wherein said presenting means is operative to present said additional results to the user; and wherein said presenting means provides said melting temperature to the user.

5. A programmed computer system in accordance with claim 3 wherein said computer system further includes:

means for determining the length of sequences from said target gene sequence data.

6. A programmed computer system in accordance with claim 3 wherein said computer system further includes:

means for determining the length of sequences from said set of gene sequence data.

7. A programmed computer system in accordance with claim 3 wherein said computer system further includes:

means for copying the LOCUS name for each said gene sequences into said memory means; and means for linking said LOCUS name with each said gene sequence.

8. A programmed computer system in accordance with claim 3 wherein said means for performing hybridization strength modeling on gene sequences which is determined by numbers of matching utilizes said accessing means to introduce a user-selected minimum oligonucleotide probe length from said gene sequence data source into the computer system and said memory means to store said minimum oligonucleotide probe length.

9. A programmed computer system in accordance with claim 3 wherein said computer system further includes:

means for calculating the melting temperature for each candidate oligonucleotide probe;

means for tracking the number and melting temperature of the matches for each candidate oligonucleotide probe;

means for tracking the location of a set number of the best candidate oligonucleotide probes employing a priority queue by sorting said candidate oligonucleotide probes in reverse order and sorting said candidate oligonucleotide probes by hybridization strength;

wherein said presenting means is operative to present said additional results to the user; and wherein said presenting means provides said melting temperature to the user.

10. A programmed computer system in accordance with claim 3 wherein said first input means is operative to introduce a user-selected maximum number of mismatches and a user-selected minimum candidate oligonucleotide probe length into the computer system, and wherein said means for calculating the minimum length of any matching gene subsequence of said gene sequence data and said target gene sequence data comprises:

means for subtracting said maximum number of mismatches from said minimum candidate oligonucletide probe length to give a first result;

means for dividing said first result by said maximum number of mismatches plus one to give a second result;

means for incrementing said second result by one if the remainder is not equal to zero to give a third result; and means for truncating said third result to an integer.

11. A programmed computer system in accordance with claim 10 wherein a further means for calculating the hairpin characteristics of said candidate oligonucleotide probe comprises the steps of:

calculating a complementary oligonucleotide probe to the candidate oligonucleotide probe by reversing the base pair order of the candidate oligonucleotide probe and substituting complementary base pairs;

comparing each character of said original cnadidate oligonucleotide probe and said complementary oligonucleotide probe;

finding the longest match between said original candidate oligonucleotide probe and said complementary oligonucleotide probe; and saving the match with the longest hairpin distancew if any two matches have the same length;

means for storing hairpin characteristics; and wherein said presenting means provides said hairpin characteristics to the user.

12. A programmed computer system in accordance with claim 3 wherein said computer system includes a further means for calculating the hairpin characteristics of said candidate oligonucleotide probe.

13. A programmed computer system in accordance with claim 3 wherein said computer system includes a further means for preprocessing said set of target gene sequence data and said set of gene sequence data comprises the steps of:

searching for sequences without introns in said target gene sequences and said gene sequences;

extracting target gene sequences and gene sequences that do not contain introns; and storing said extracted target gene sequences and gene sequences in memory.

14. A programmed computer system in accordance with claim 3 wherein said presenting means to provide the results of said matching and modeling to display candidate oligonucleotide probes includes means for displaying in multiple dimensions the gene sequences which result from the comparisons and calculations characterized in that said display format exhibits the starting position of each candidate oligonucleotide probe in one dimension;

the specificity of a candidate oligonucleotide probe's hybridization with the target gene sequence in a second dimension; and superimposed melting temperature of gene sequenes in contrasting presentations in at least an apparent third dimension.

15. A programmed computer system in accordance with claim 14 wherein said display further includes a cursor moveable along one dimension of said display that selects a position for an expansion of data representing the homology between the candidate oligonucleotide probes and said gene sequence data; and wherein said display is operative to display in alphanumeric form the homology between the candidate oligonucleotide probes and said gene sequence data.

16. A programmed computer system in accordance with claim 14 wherein said display is further operative to provide an expansion of data including presenting false hybridization at various melting temperatures for all candidate oligonucleotide probes;

the location of each false hybridization;

a candidate oligonucleotide probes starting position; and hairpin characteristics of each candidate oligonucleotide probe.

17. A programmed computer system in accordance with claim 14 wherein said display format data is outputted to a printing means.

18. A programmed computer system in accordance with claim 14 wherein said display format data is saved to a data file.

19. A programmed computer system in accordance with claim 14 wherein said display format data is exported to another computer system.

20. A programmed computer system in accordance with claim 14 wherein said display further includes a cursor moveable along one dimension of said display that selects a position for an expansion of data representing the homology between the candidate oligonucleotide probes and said gene sequence data; and wherein said moveable cursor may be positioned by the user to select and save particular candidate oligonucleotide probe information; and wherein said display is operative to display in alphanumeric form the homology between the candidate oligonucleotide probes and said gene sequence data.

21. A programmed computer system in accordance with claim 20 wherein said method of selecting and saving particular candidate oligonucleotide probe information comprises capturing candidate oligonucleotide probe information at the user-selected point and storing said information in said memory means.

22. A programmed computer system in accordance with claim 21 wherein said user-selected candidate oligonucleotide probe information is exported to another computer system.

23. A programmed computer system in accordance with claim 14 wherein said means for displaying comprises the steps of:

calculating display output ranges;

converting said output ranges to a logarithmic scale;

interpolating said converted values;

creating a bitmap of said interpolations; and displaying said bitmap on a display device.

24. A programmed computer system in accordance with claim 14 wherein said means for displaying comprises the steps of:

converting said result values to pixels;

filling a pixel array with said pixels;

performing a binary search into said pixel array;

determining the number of pixels per candidate oligonucleotide probe to be displayed;

interpolating said pixels at the value of pixels per position minus one;

computing an array of said pixel array; and plotting the results on a display device.

25. A programmed computer system for designing optimal oligonucleotide probes for use with a gene sequence data source comprising:

first input means for introducing user-selected gene sequences into the computer system;

memory means for storing user-selected gene sequences;

means for accessing gene sequence data from said gene sequence data source;

means for performing hybridization strength modeling on gene sequences which is determined by melting temperature (Tm);

means for selecting either of said modeling means;

means for presenting the results of said modeling to present candidate oligonucleotide probes;

wherein said means for performing hybridization strength modeling utilizes said first input means to introduce a user-selected screening threshold into the computer system and said accessing means to introduce a user-selected set of gene sequence data and a user-selected set of target gene sequence data from said gene sequence data source into the computer system and said memory means to store said gene sequence data, said target gene sequence data and said screening threshold and wherein said means for performing hybridization strength modeling comprises:

means for preprocessing said target gene sequence data and said gene sequence data by selecting only those sequences without introns;

means for forming a preparation file of gene sequence fragments by cutting said target gene sequences into fixed length target gene subsequences and sorting said subsequences in lexicographical order;

means for merge sorting said gene sequences;

means for forming multiple lists of screens by forming lists of subsequences of the preparation file of length equal to said screening threshold;

means for indexing, sorting and storing said screens in said memory means;

means for sequentially comparing said preparation file gene sequences with each of said screens to design candidate oligonucleotide probes;

means for calculating the hybridization strengths between a gene sequence and all candidate oligonucleotides probes containing that gene sequence by accounting for Guanine-Cytosine (GC) and Adenine-Thymine (AT) base pair content of the gene sequence and the number of mismatches between said preparation file sequences and a said screen when said comparison results in a match;

means for preparing the candidate oligonucleotide probe and hybridization strength for presentation to the user;

wherein said presenting means provides the candidate oligonucleotide probe and hybridization strength to the user.

26. A programmed computer system in accordance with claim 25 wherein said computer system further includes:

means for calculating the melting temperature for each candidate oligonucleotide probe;

means for tracking the number and melting temperature of the matches for each candidate oligonucleotide probe;

means for tracking the location of a set number of the best candidate oligonucleotide probes;

means for preparing the melting temperature for presentation to the user; and wherein said presenting means provides the melting temperature to the user.

27. A progammed computer system in accordance with claim 26 wherein said means for calculating said candidate oligonucleotide probes melting temperature comprises:

solving the formula Tm=81.5−16.6(log)[NA])−0.63% (formamide)+((0.41 (%(G+C))−600N), wherein log [NA] is the sodium concentration, %(G+C) is the fraction of matched base pairs which are G-C complementary, N is the probe length and wherein the number of mismatches is equal to zero.

28. A programmed computer system in accordance with claim 27 wherein said computer system further includes:

means for reducing a candidate oligonucleotide probe's calculated melting temperature by a certain amount for each percent of mismatch between the candidate oligonucleotide probe and a user-selected target gene sequence base upon the assumption that ther are an equal number of GC and AT base pair mismatches.

29. A programmed computer system in accordance with claim 28 wherein said means for reducing a candidate oligonucleotide probes calculated melting temperature comprises the steps of:

reducing said calculated melting temperature by 2 degrees Celsius if an AT mismatch exists; and reducing said calculated melting temperature by 4 degrees Celsius if a GC mismatch exists.

30. A programmed computer system in accordance with claim 25 wherein said computer system further includes:

means for assigning a numerical score to each said gene sequence; and mans for sorting said gene sequences in accordance with said numerical score.

31. A programmed computer system in accordance with claim 25 wherein said means for performing hybridization strength modeling utilizes said accessing means for copying the LOCUS name for each said gene squence into said memory means; and means for prepending said gene sequence with said LOCUS name.

32. A programmed computer system in accordance with claim 25 wherein four lists of screens are formed by said list forming means.

33. A programmed computer system in accordance with claim 25 wherein said computer system includes a means of shifting each screen by at least one base pair as it is formed by said list forming means.

34. A programmed computer system in accordance with claim 25 wherein said computer system further includes:

means for calculating the melting temperature for each candidate oligonucleotide probe;

means for tracking the number and melting temperature of the matches for each candidate oligonucleotide probe;

means for tracking the location of a set number of the best candidate oligonucleotide probes employing a priority queue by sorting said candidate oligonucleotide probes in reverse order and sorting said candidate oligonucleotide probes by hybridization strength;

means for presenting the melting temperature for presentation to the user; and wherein said presenting means provides the melting temperature to the user.

35. A programmed computer system in accordance with claim 25 wherein said computer system further includes:

means for assigning a numerical score to each said gene sequence by tallying the quantity "exp" where "exp"= $\Sigma e^{-Tm}$ and wherein Tm is the melting temperature for the said gene sequence; and means for sorting said gene sequences in accordance with said numerical score.

36. A programmed computer system in accordance with claim 25 wherein said means for calculating the hybridization strengths between a gene sequence and all candidate oligonuclestide probes containing that gene sequence comprises the steps of:

accessing gene sequence data from said gene sequence data source;

comparing base pairs of a first gene sequence and a second gene sequence to determine if a match exists;

incrementing said first gene sequence's bound strength by some first number if a base pair character in said first gene sequence and said second gene sequence match and the matched base pair is equal to a combination of the bases Guanine (G) and Cytosine (C);

incrementing said first gene sequence's bound strength by some second number if a base pair character in said first gene sequence and said second gene sequence match and the matched base pair is equal to a combination of the bases Adenine (A) and Thymine (T);

decrementing said first gene sequence's bound strength by a third number if there is no match in base pairs between said first gene sequence and said second gene sequence;

comparing said first gene sequence's bound strength to said first gene sequence's unbound strength;

setting said first gene sequence's unbound strength equal to its bound strength if said first gene sequence's bound strength is greater than said first gene sequence's unbound strength; and resetting said first gene sequence's bound strength to zero if said first gene sequence's unbound strength is less than zero.

37. A programmed computer system in accordance with claim 36 wherein said first and second numbers are greater than zero.

38. A programmed computer system in accordance with claim 36 wherein said second number is in the order of 42% of said first number.

39. A programmed computer system in accordance with claim 36 wherein said third number is in the order of 5% larger than said first number.

40. A programmed computer system in accordance with claim 25 wherein said computer system further includes a means for calculating the hairpin characteristics of said candidate oligonucleotide probe;

means for preparing the hairpin characteristics for presentation to the user; and wherein said presenting means provides the hairpin characteristics to the user.

41. A programmed computer system in accordance with claim 40 wherein said means for calculating the hairpin characteristics of said candidate oligonucleotide probe comprises the steps of:

calculating a complementary oligonucleotide probe to the candidate oligonucleotide probe by reversing the base pair order of the candidate oligonucleotide probe and substituting complementary base pairs;

comparing each character of said original candidate oligonucleotide probe and said complementary probe oligonucleotide probe;

finding the longest match between said original candidate oligonucleotide probe and said complementary oligonucleotide probe; and saving the match with the longest hairpin distance if any two matches have the same length; and means for preparing the hairpin characteristics for presentation to the user;

wherein said presenting means provides the hairpin characteristics to the user.

42. A programmed computer system in accordance with claim 25 wherein said fixed-length subsequences are calculated by a method comprising the steps of:

locating the origin of said subsequence in a set position of said target gene sequence in said preparation file;

cutting a subsequence that is a fixed-length long every preselected number of positions of said target gene sequence in said preparation file; and sorting said subsequences in said preparation file in lexicographical order beginning at a set position.

43. A programmed computer system in accordance with claim 42 wherein the origin of said subsequence is located at position 40 of said target sequence in said preparation file.

44. A programmed computer system in accordance with claim 25 wherein said fixed-length subsequences are calculated by a method comprising the steps of: locating the origin of said subsequence in the 40th position of said target gene sequence in said preparation file;

cutting a subsequence that is 96 base pairs long of said target gene sequence in said preparation file; and sorting said subsequences in said preparation file in lexicographical order beginning at a set position.

45. A programmed computer system in accordance with claim 25 wherein said computer system further includes means for prepending said preparation file subsequences with identifiers for the sources of each subsequence.

46. A programmed computer system for designing optimal oligonucleotide probes for use with a gene sequence data source comprising:

first input means for introducing user-selected gene sequences into the computer system;

memory means for storing user-selected gene sequences;

means for accessing gene sequence data from said gene sequence data source;

means for performing hybridization strength modeling on gene sequences which is determined by numbers of matching sequences between gene sequences; and means for presenting the results of said modeling to present candidate oligonucleotide probes with a candidate oligonucleotide hybridization shown as numbers of hybridized probe's gene sequences from said gene sequence data source and numbers of matched nucleotides.

47. A programmed computer system for designing optimal oligonucleotide probes for use with a gene sequence data source comprising:

first input means for introducing user-selected gene sequences into the computer system;

memory means for storing user-selected gene sequences;

means for accessing gene sequence data from said gene sequence data source;

means for performing hybridization strength modeling on gene sequences which is determined by melting temperature (Tm); and means for presenting the results of said modeling to present candidate oligonucleotide probes with a candidate oligonucleotide probe hybridization shown as numbers of hybridization to gene sequence data from said gene sequence data source.

48. A programmed computer system in accordance with claims 1, 3 or 46, wherein hybridization strength modeling on gene sequences which is determined by numbers of matching sequences between gene sequences includes use of both hashing and continuous seed filtration.

49. A programmed computer system in accordance with claims 1, 3, 46 or 47, wherein said presenting means to provide the results of modeling to display candidate oligonucleotide probes includes means for displaying in at least two dimensions the gene sequences which result from the comparisons and calculations characterized in that said display format exhibits:

the starting position of each candidate oligonucleotide in one dimension; and a candidate oligonucleotide probes' hybridization with the target gene sequence in a second dimension.

50. A programmed computer system in accordance with claims 1, 3, 46 or 47, wherein said user-selected gene sequences are user-selected oligonucleotide sequences.

51. A programmed computer system for designing candidate oligonucleotide probes for use with a gene sequence data source including:

first input means for introducing user-selected gene sequence, design, model and presentation criteria and a user-specified oligonucleotide probe length into the computer system;

memory means for storing said gene sequence, design, model and presentation criteria and said oligonucleotide probe length;

means for accessing gene sequence data from said gene sequence data source;

wherein said accessing means is operative to introduce a user-selected set of gene sequence data and a user-selected set of target gene sequence data from said gene sequence data source into the computer system;

wherein said criteria are used for comparison of gene sequence data and target gene sequence data;

means for comparing said gene sequences against said target gene sequences employing said criteria;

means for calculating candidate oligonucleotide probes of said oligonucleotide probe length that are either common to a pool of user-specified gene sequences or specific to a particular user-specified gene sequence;

means for calculating the homology between the candidate oligonucleotide probes and said gene sequence data;

means for calculating a candidate oligonucleotide probe's hairpin characteristics;

means for displaying in multiple dimensions the gene sequences which result from the comparisons and calculations characterized in that said display format exhibits:

the starting position of each candidate oligonucleotide probe in one dimension;

a candidate oligonucleotide probe's specificity to the target gene sequence in a second dimension; and superimposed melting temperatures of gene sequences in contrasting presentations in at least an apparent third dimension;

wherein said display further includes a cursor moveable along one dimension of said display that selects a position for an expansion of data representing the homology between the candidate oligonucleotide probes and said gene sequence data;

wherein said display means displays in alphanumeric form the homology between the candidate oligonucleotide probes and said gene sequence data;

wherein said display provides an expansion of data including presenting hybridizations at various melting temperatures for all candidate oligonucleotide probes;

the location of each hybridization;

a candidate oligonucleotide probe's starting position; and hairpin characteristics of each candidate oligonucleotide probe.

52. A method for designing candidate oligonucleotide probes by performing hybridization strength modeling on gene sequences which is determined by numbers of matching sequences for use with a gene sequence data source comprising the steps of:

introducing user-selected gene sequences into a computer system;

accessing gene sequence data from said gene sequence data source;

storing said user-selected gene sequence in the memory of the computer system;

accessing the gene sequence source to introduce the user-selected set of gene sequence data and a user-selected set of target gene sequence data from said gene sequence data source into the computer system;

storing said gene sequence data and said target gene sequence data in the memory of the computer system;

determining a minimum oligonucleotide probe length;

creating a look-up hash table and linked list in memory for each gene sequence in said gene sequence data and each of said target gene sequences;

calculating the minimum length of any matching gene subsequence of said gene sequence data and said target gene sequence data;

comparing each base pair character in each said target sequence stored in a hash table in memory to each base pair character of said gene sequence stored in a hash table in memory;

determining a matching seed by determining if the said comparison results in a matching gene subsequence of length equal to said calculated minimum length;

comparing base pair characters behind and ahead of said seed to determine if there exists an extended match of a subsequence of base pair characters of length greater than the calculated minimum length, resulting in a current hit sequence;

calculating whether said current hit sequence is longer than said minimum oligonucleotide probe length, resulting in a current candidate oligonucleotide probe;

storing said current candidate oligonucleotide probe in the memory of the computer system; and presenting a representation of said current candidate oligonucleotide probe to the user.

53. A method in accordance with claim 52 wherein said method includes the steps for performing additional calculations for each candidate oligonucleotide probe said additional calculations comprising:

calculating the melting temperature for each candidate oligonucleotide probe tracking the number and melting temperature of the matches for each candidate oligonucleotide probe;

tracking the location of a set number of the best candidate oligonucleotide probes; and presenting said additional results to the user.

54. A method in accordance with claim 52 wherein said method includes the step of transforming base characters into numeric digits.

55. A method in accordance with claim 52 wherein said method further includes a step of determining the length of sequences from said target gene sequence data.

56. A method in accordance with claim 52 wherein said method includes the step of determining the length of sequences from said set of gene sequence data.

57. A method in accordance with claim 52 wherein said method includes the steps of:

copying the LOCUS name for each said gene sequence into the memory of the computer system; and linking said LOCUS name with each said gene sequence.

58. A method in accordance with claim 52 wherein said method includes the steps of:

introducing a user-selected minimum probe length into the computer system; and storing said minimum oligonucleotide probe length in the memory of the computer system.

59. A method in accordance with claim 52 wherein said method further includes a step for performing additional calculations for each candidate oligonucleotide probe, said additional calculations comprising:

calculating the melting temperature for each candidate oligonucleotide probe;

tracking the number and melting temperature of the matches for each candidate oligonucleotide probe;

tracking the location of a set number of the best candidate oligonucleotide probes employing a priority queue by sorting said candidate oligonucleotide probes in reverse order and sorting said candidate oligonucleotide probes by hybridization strength; and presenting said additional results to the user.

60. A method in accordance with claim 52 wherein said step for calculating the minimum length of any matching gene subsequence comprises:

introducing a user-selected maximum number of mismatches and a user-selected minimum candidate oligonucleotide probe length into the computer system;

subtracting said maximum number of mismatches from said minimum candidate oligonucleotide probe length to give a first result;

dividing said first result by said maximum number of mismatches plus one to give a second result;

incrementing said second result by one if the remainder is not equal to zero to give a third result; and truncating said third result to an integer.

61. A method in accordance with claim 52 wherein said method further includes a step of calculating the hairpin characteristics of said candidate oligonucleotide probes.

62. A method in accordance with claim 52 wherein said method further includes a step of calculating the hairpin characteristics of said candidate oligonucleotide probe comprising:

calculating a complementary oligonucleotide probe to the candidate oligonucleotide probe by reversing the base pair order of the candidate oligonucleotide probe and substituting complementary base pairs;

comparing each character of said original candidate oligonucleotide probe and said complementary oligonucleotide probe;

finding the longest match between said original candidate oligonucleotide probe and said complementary oligonucleotide probe; and saving the match with the longest hairpin distance if any two matches have the same length.

63. A method for designing candidate oligonucleotide probes by performing hybridization strength modeling which is determined by melting temperature (Tm) for use with a gene sequence data source comprising the steps of:

introducing user-selected gene sequence and a user-selected screening threshold into a computer system;

storing user-selected gene sequence and said screening threshold in the memory of the computer system;

accessing the gene sequence source to introduce the user-selected set of gene sequence data and a user-selected set of target gene sequence data from said gene sequence data source into the computer system;

storing said gene sequence data and said target gene sequence data in the memory of the computer system;

preprocessing said target gene sequence data and said gene sequence data by selecting only those sequences without introns;

forming a preparation file of gene sequence fragments by cutting said target gene sequences into fixed length target gene subsequences and sorting said subsequences in lexicographical order;

merge sorting said gene sequences;

forming multiple lists of screens by forming lists of subsequences of the preparation file of length equal to said screening threshold;

indexing and sorting said screens in memory; storing said screens in the memory of the computer system;

sequentially comparing said preparation file gene sequences with each of said screens to design candidate oligonucleotide probes;

calculating the hybridization strengths between a gene sequence and all candidate oligonucleotide probes containing that gene sequence by accounting for Guanine-Cytosine (GC) and Adenine-Thymine (AT) base pair content of the gene sequence and the number of mismatches between said preparation file sequences and a said screen when said comparison results in a match;

preparing the candidate oligonucleotide probe and hybridization strength for presentation to the user; and presenting the candidate oligonucleotide probe and hybridization strength to the user.

64. A method in accordance with claim 63 wherein said method further includes a step for performing additional calculations for each candidate oligonucleotide probe, said additional calculations comprising:

calculating the melting temperature for each candidate oligonucleotide probe;

tracking the number and melting temperature of the matches for each candidate oligonucleotide probe;

tracking the location of a set number of the best candidate oligonucleotide probes; and presenting said additional results to the user.

65. A method in accordance with claim 63 wherein the step for preparing the candidate oligonucleotide probe for presenting to the user comprises:

assigning a numerical score to each said gene sequence;

sorting said gene sequences in accordance with said numerical score; and displaying a representation of the resulting candidate oligonucleotide and said gene sequences.

66. A method in accordance with claim 63 wherein said method includes the steps of:

copying the LOCUS name for each said gene sequence into the memory of the computer system; and prepending said gene sequence with said LOCUS name.

67. A method in accordance with claim 63 wherein the step for forming lists of screens produces four lists of screens.

68. A method in accordance with claim 63 wherein said method further includes a step of shifting each screen by one base pair as it is formed.

69. A method in accordance with claim 63 wherein said method further includes a step for performing additional calculations for each candidate oligonucleotide probe, said additional calculations comprising:

calculating the melting temperature for each candidate oligonucleotide probe;

tracking the number and melting temperature of the matches for each candidate oligonucleotide probe;

tracking the location of a set number of the best candidate oligonucleotide probes employing a priority queue by sorting said candidate oligonucleotide probes in reverse order and sorting said candidate oligonucleotide probes by hybridization strength; and presenting said additional results to the user.

70. A method in accordance with claim 63 wherein said steps for preparing the results for presenting to the user comprises: assigning a numerical score to each said gene sequence by tallying the quantity "exp" where "exp"=$\Sigma e^{-Tm}$ and wherein Tm is the melting temperature for the said gene sequence;

sorting said gene sequences in order of the numerical score; and displaying a representation of the resulting candidate oligonucleotide probe and said gene sequences.

71. A method in accordance with claim 63 for use with a gene sequence data source, programmed to determine hybridization strength comprising the steps of:

comparing base pairs of a first gene sequence and a second gene sequence to determine if a match exists;

incrementing said first gene sequence's bound strength by some first number if a base pair character in said first gene sequence and said second gene sequence match and the matched base pair is equal to a combination of the bases Guanine (G) and Cytosine ( C);

incrementing said first gene sequence's bound strength by some second number if a base pair character in said first gene sequence and said second gene sequence match and the matched base pair is equal to a combination of the bases Adenine (A) and Thymine (T);

decrementing said first gene sequence's bound strength by a third number if there is no match in base pairs between said first gene sequence and said second gene sequence;

comparing said first gene sequence's bound strength to said first gene sequence's unbound strength;

setting said first gene sequence's unbound strength equal to its bound strength if said first gene sequence's bound strength is greater than said first gene sequence's unbound strength; and resetting said first gene sequence's bound strength to zero if said first gene sequence's unbound strength is less than zero.

72. A method in accordance with claim 71 wherein said first and second numbers are greater than zero.

73. A method in accordance with claim 71 wherein said second number is in the order of 42% of said first number.

74. A method in accordance with claim 71 wherein said third number is in the order of 5% larger than said first number.

75. A method in accordance with claim 63 wherein said method further includes a step of calculating the hairpin characteristics of said candidate oligonucleotide probe.

76. A method in accordance with claim 75 wherein the step of calculating the hairpin characteristics of said candidate oligonucleotide probe includes the steps of:

calculating a complementary oligonucleotide probe to the candidate oligonucleotide probe by reversing the base pair order of the candidate oligonuOleotide probe and substituting complementary base pairs;

comparing each character of said original candidate oligonucleotide probe and said complementary oligonucleotide probe;

finding the longest match between said original candidate oligonucleotide probe and said complementary oligonucleotide probe; and saving the match with the longest hairpin distance if any two matches have the same length.

77. A method in accordance with claim 63 wherein said fixed-length target gene subsequences are calculated by a method comprising the steps of:

locating the origin of said subsequence in a set position of said target gene sequence in said preparation file;

cutting a subsequence that is a fixed-length long every preselected number of positions of said target gene sequence in said preparation file; and sorting said subsequences in said preparation file in lexicographical order beginning at a set position.

78. A method in accordance with claim 77 wherein the origin of said subsequence is located at position 40 of said target sequence in said preparation file.

79. A method in accordance with claim 63 wherein said fixed-length subsequences are calculated by a method comprising the steps of:

locating the origin of said subsequence in the 40th position of said target gene sequence in said preparation file;

cutting a subsequence that is 96 base pairs long of said target gene sequence in said preparation file; and sorting said subsequences in said preparation file in lexicographical order beginning at a set position.

80. A method in accordance with claim 63 wherein said method further includes a step of prepending said preparation file subsequences with identifiers for the sources of each subsequence.

81. A method in accordance with claim 63 wherein said method includes the step of calculating an candidate oligonucleotide probe's melting temperature comprising:

solving the formula $Tm=81.5-16.6(\log[Na])-0.63\%(\text{formamide})+((0.41\ (\%(G+C))-600/N)$;

wherein $\log[Na]$ is the sodium concentration, $\%(G+C)$ is the fraction of matched base pairs which are G-C complementary, N is the probe length; and wherein the number of mismatches is equal to zero.

82. A method in accordance with claim 63 wherein said method further includes a step for reducing a candidate oligonucleotide probe's calculated melting temperature by a preselected amount for each percent of mismatch between the candidate oligonucleotide probe and a user-selected target gene sequence based upon the assumption that there are an equal number of GC and AT base pair mismatches.

83. A method in accordance with claim 63 wherein said method includes the step for reducing a candidate oligonucleotide probe's calculated melting temperature by a preselected amount comprising the steps of:

reducing said calculated melting temperature by 2 degrees Celsius if an AT mismatch exists; and reducing said calculated melting temperature by 4 degrees Celsius if a GC mismatch exists.

84. A method for designing candidate oligonucleotide probes for use with a gene sequence data source comprising the steps of:

introducing user-selected gene sequence and a user-specified oligonucleotide probe length into a computer system;

storing said gene sequence and said oligonucleotide probe length in the memory of the computer system;

accessing gene sequence data from said gene sequence data source;

accessing the gene sequence source to introduce the user-selected set of gene sequence data and a user-selected set of target gene sequence data from said gene sequence data source into the computer system;

comparing said gene sequences against said target gene sequences employing said criteria;

calculating candidate oligonucleotide probes of said probe length that are either common to a pool of user-specified gene sequences or specific to a particular user-specified gene sequence;

calculating the homology between the candidate oligonucleotide probes and said gene sequence data;

displaying in multiple dimensions the gene sequences which result from the comparisons and calculations characterized in that said display format exhibits:

the starting position of each candidate oligonucleotide probe in one dimension;

a candidate oligonucleotide probe's specificity to the target gene sequence in a second dimension; and superimposed melting temperatures of gene sequences in contrasting presentations in at least an apparent third dimension.

85. A method in accordance with claim 84 wherein said method further includes the step of calculating a candidate oligonucleotide probe's hairpin characteristics.

86. A method in accordance with claim 85 wherein said step of calculating hairpin characteristics for a gene sequence comprises:

calculating a complementary probe to the said gene sequence by reversing the base pair order of the gene sequence and substituting complementary base pairs;

comparing each character of said original gene sequence and said complementary probe;

finding the longest match between said original gene sequence and said complementary oligonucleotide; and saving the match with the longest hairpin distance if any two matches have the same length.

87. A method in accordance with claim 84 wherein the step of displaying further includes producing a cursor moveable along one dimension of said display that selects a position for an expansion of data representing the homology between the candidate oligonucleotide probes and said gene sequence data; and displaying in alphanumeric form the homology between the candidate oligonucleotide probes and said gene sequence data.

88. A method in accordance with claim 84 wherein said display format data is outputted to a printing means.

89. A method in accordance with claim 84 wherein said display format data is saved to a data file.

90. A method in accordance with claim 84 wherein said display format data is exported to another computer system.

91. A method in accordance with claim 84 wherein the step of displaying further includes producing a cursor moveable along one dimension of said display that selects a position for an expansion of data representing the homology between the candidate oligonucleotide probe and said gene sequence data;

positioning said moveable cursor to select and save particular candidate oligonucleotide probe information; and displaying in alphanumeric form the homology between the candidate oligonucleotide probes and said gene sequence data.

92. A method in accordance with claim 84 wherein the step of displaying further includes producing a cursor moveable along one dimension of said display that selects a position for an expansion of data representing the homology between the candidate oligonucleotide probes and said gene sequence data;

positioning said moveable cursor to select and save particular candidate oligonucleotide probe information;

capturing candidate oligonucleotide probe information at the user-selected point and storing said information in said memory means; and displaying in alphanumeric form the homology between the candidate oligonucleotide probes and said gene sequence data.

93. A method in accordance with claim 84 wherein said method of displaying comprises:

calculating display output ranges;

converting said output ranges to a logarithmic scale;

interpolating said converted values;

creating a bitmap of said interpolations; and displaying said bitmap on a display device.

94. A method in accordance with claim 84 wherein said method of displaying comprises:

converting said result values to pixels;

filling a pixel array with said pixels;

performing a binary search into said pixel array;

determining the number of pixels per candidate oligonucleotide probe to be displayed;

interpolating said pixels at the value of pixels per position minus one;

computing an array of said pixel array; and plotting the results on a display device.

95. A method of creating a preparation file from a user-selected set of target gene sequence data comprising:

locating the origin of subsequences in a set position of said target gene sequence in a preparation file;

cutting said target gene sequence data into fixed-length subsequences;

said subsequences beginning every preselected number of positions of said target gene sequence in said preparation file;

sorting said subsequences in said preparation file in lexicographical order beginning at a set position; and storing said subsequences in a preparation file.

96. A method of creating a preparation file from a user-selected set of target gene sequence data comprising:

locating the origin of a subsequence in a set position of said target gene sequence in said preparation file wherein the origin of said subsequence is located at position 40 of said target sequence in said preparation file;

cutting a subsequence of said target gene sequence data into fixed-length subsequence in the order of 96 base pairs in of length;

cutting successive sequences that are a fixed length long every preselected number of positions of said target gene sequence in said preparation file; and sorting said subsequences in said preparation file in lexicographical order beginning at a set position; and storing said subsequences in a preparation file.

97. A method in accordance with claim 96 wherein said fixed-length subsequences are calculated by a method comprising the steps of:

locating the origin of said subsequence the 40th position of said target gene sequence in said preparation file;

cutting a subsequence that is 96 base pairs long of said target gene sequence in said preparation file; and sorting said subsequences in said preparation file in lexicographical order beginning at a set position.

* * * * *